US00RE50631E

(19) United States
(12) Reissued Patent
Lannutti et al.

(10) Patent Number: US RE50,631 E
(45) Date of Reissued Patent: *Oct. 14, 2025

(54) ROR1 ANTIBODY IMMUNOCONJUGATES

(71) Applicant: VelosBio Inc., Rahway, NJ (US)

(72) Inventors: Brian Lannutti, Solana Beach, CA (US); Katti Jessen, San Diego, CA (US); Thanh-Trang Vo, San Diego, CA (US); Jeffry Dean Watkins, Encinitas, CA (US)

(73) Assignee: VelosBio Inc.

( * ) Notice: This patent is subject to a terminal disclaimer.

(21) Appl. No.: 17/365,293

(22) Filed: Jul. 1, 2021

Related U.S. Patent Documents

Reissue of:
(64) Patent No.: 10,335,496
Issued: Jul. 2, 2019
Appl. No.: 16/027,967
Filed: Jul. 5, 2018

U.S. Applications:
(63) Continuation of application No. 16/016,238, filed on Jun. 22, 2018, now abandoned.

(60) Provisional application No. 62/524,386, filed on Jun. 23, 2017, provisional application No. 62/524,388, filed on Jun. 23, 2017, provisional application No. 62/524,382, filed on Jun. 23, 2017.

(51) Int. Cl.

| | |
|---|---|
| ***A61K 47/68*** | (2017.01) |
| ***A61K 38/05*** | (2006.01) |
| ***A61K 39/00*** | (2006.01) |
| ***A61K 39/395*** | (2006.01) |
| ***A61K 45/06*** | (2006.01) |
| ***A61P 35/00*** | (2006.01) |
| ***C07K 16/28*** | (2006.01) |

(52) U.S. Cl.
CPC ..... *A61K 47/6849* (2017.08); *A61K 38/05* (2013.01); *A61K 39/3955* (2013.01); *A61K 45/06* (2013.01); *A61K 47/6803* (2017.08); *A61K 47/6811* (2017.08); *A61K 47/6871* (2017.08); *A61P 35/00* (2018.01); *C07K 16/2803* (2013.01); *A61K 2039/505* (2013.01); *A61K 2039/572* (2013.01); *C07K 2317/24* (2013.01); *C07K 2317/56* (2013.01); *C07K 2317/565* (2013.01); *C07K 2317/732* (2013.01); *C07K 2317/734* (2013.01); *C07K 2317/76* (2013.01); *C07K 2317/92* (2013.01)

(58) Field of Classification Search
CPC ..... A61K 47/6849; C07K 16/2803
See application file for complete search history.

(56) References Cited

U.S. PATENT DOCUMENTS

| | | | |
|---|---|---|---|
| 6,821,783 | B1 | 11/2004 | Comely et al. |
| 6,884,869 | B2 | 1/2005 | Senter et al. |
| 7,498,298 | B2 | 3/2009 | Doronina et al. |
| 7,659,241 | B2 | 2/2010 | Senter et al. |
| 7,829,531 | B2 | 11/2010 | Senter et al. |
| 7,851,437 | B2 | 12/2010 | Senter et al. |
| 8,212,009 | B2 | 7/2012 | Kipps et al. |
| 8,288,352 | B2 | 10/2012 | Doronina et al. |
| 8,609,105 | B2 | 12/2013 | Senter et al. |
| 8,697,688 | B2 | 4/2014 | Howard et al. |
| 8,742,076 | B2 | 6/2014 | Cohen et al. |
| 8,900,589 | B2 | 12/2014 | Beria et al. |
| 8,936,910 | B2 | 1/2015 | Mitsch et al. |
| 9,150,647 | B2 | 6/2015 | Mellstedt et al. |
| 9,089,614 | B2 | 7/2015 | Lin et al. |
| 9,217,040 | B2 | 12/2015 | Kipps et al. |
| 9,228,023 | B2 | 1/2016 | Rohlff et al. |
| 9,242,014 | B2 | 1/2016 | Kipps et al. |
| 9,266,952 | B2 | 2/2016 | Teige |
| 9,316,646 | B2 | 4/2016 | Rader et al. |
| 9,523,695 | B2 | 12/2016 | Kipps et al. |
| 9,758,591 | B2 | 9/2017 | Kipps et al. |
| 9,933,434 | B2 | 4/2018 | Kipps et al. |
| 9,938,350 | B2 | 4/2018 | Kipps et al. |
| 10,316,080 | B2 | 6/2019 | Smith et al. |
| 2008/0050310 | A1* | 2/2008 | Ebens, Jr. ..... C07K 16/2803 424/1.49 |
| 2009/0258442 | A1 | 10/2009 | Polakiewicz et al. |
| 2009/0311249 | A1 | 12/2009 | Gianni et al. |
| 2011/0178070 | A1* | 7/2011 | Gong ..... C07D 513/04 514/221 |
| 2012/0058051 | A1 | 3/2012 | Rader et al. |
| 2012/0282177 | A1 | 11/2012 | Rohlff et al. |
| 2013/0028919 | A1 | 1/2013 | Howard et al. |

(Continued)

FOREIGN PATENT DOCUMENTS

| | | | |
|---|---|---|---|
| CN | 103429618 | A | 12/2013 |
| CN | 105473616 | A | 4/2016 |

(Continued)

OTHER PUBLICATIONS

Li et al. Cancef Biology & Therapy. vol. 17, No. 4, 346-354. (Year: 2016).*

Karvonen. Biochemical Society Transactions (Apr. 2017) 45 457-464 (Year: 2017).*

Agarwal, Paresh et al., A Pictet-Spengler ligation for protein chemical modification, Proc Natl Acad Sci USA, 2013, 46-51, 110(1).

Axup et al., Synthesis of site-specific antibody-drug conjugates using unnatural amino acids, Proc. Natl. Acad. Sci. USA, 2012, Issue 40, pp. 16101-16106, 109.

Balakrishnan, Ashwini et al., Analysis of ROR1 protein expression in human cancer and normal tissues, Clinical Cancer Research, 2017, 3061-3071, 23(12).

(Continued)

*Primary Examiner* — Padmashri Ponnaluri
(74) *Attorney, Agent, or Firm* — Jeffrey Bergman; Catherine Fitch

(57) ABSTRACT

Provided herein are immunoconjugates comprising an anti-ROR-1 antibody or an antigen-fragment [fragment] thereof and a drug moiety. These immunoconjugates are useful for treating ROR-1 expressing cancers.

20 Claims, 29 Drawing Sheets

Specification includes a Sequence Listing.

(56) References Cited

U.S. PATENT DOCUMENTS

| | | | | |
|---|---|---|---|---|
| 2013/0101607 | A1 | 4/2013 | Kipps et al. | |
| 2013/0131139 | A1 | 5/2013 | Tyner et al. | |
| 2013/0251642 | A1 | 9/2013 | Rader et al. | |
| 2013/0309256 | A1 | 11/2013 | Lyon et al. | |
| 2014/0127239 | A1 | 5/2014 | Howard | |
| 2014/0286970 | A1 | 9/2014 | Jeffrey et al. | |
| 2014/0294851 | A1 | 10/2014 | Nguyen | |
| 2015/0037360 | A1 | 2/2015 | Smith | |
| 2015/0232569 | A1* | 8/2015 | Kipps | C07K 16/2803 424/139.1 |
| 2016/0022833 | A1 | 1/2016 | Bregeon | |
| 2016/0193355 | A1 | 7/2016 | Qin et al. | |
| 2016/0208018 | A1 | 7/2016 | Chen et al. | |
| 2017/0014311 | A1 | 1/2017 | Ishizuka et al. | |
| 2017/0319709 | A1 | 11/2017 | Tikhomirov | |
| 2017/0368173 | A1 | 12/2017 | Kipps et al. | |
| 2022/0133901 | A1* | 5/2022 | Lannutti | A61K 45/06 424/181.1 |
| 2022/0152214 | A1* | 5/2022 | Miller | A61K 47/6803 |

FOREIGN PATENT DOCUMENTS

| | | | |
|---|---|---|---|
| CN | 105813655 | A | 7/2016 |
| EP | 154613 | B9 | 1/2012 |
| EP | 1545613 | B9 | 1/2012 |
| EP | 2353611 | B1 | 5/2015 |
| JP | 2019509021 | A | 4/2019 |
| JP | 7245239 | B2 | 3/2023 |
| WO | WO 2010/124188 | A1 | 10/2010 |
| WO | WO 2011/159847 | A2 | 12/2011 |
| WO | WO 2012/045085 | A1 | 4/2012 |
| WO | 2014031174 | A1 | 2/2014 |
| WO | WO 2014/031171 | A1 | 2/2014 |
| WO | WO 2014/080251 | A1 | 5/2014 |
| WO | WO 2014/145090 | A1 | 9/2014 |
| WO | WO 2014/167022 | A1 | 10/2014 |
| WO | WO 2014/177042 | A1 | 11/2014 |
| WO | WO 2014/197854 | A1 | 12/2014 |
| WO | WO 2015/038426 | A1 | 3/2015 |
| WO | WO 2015/057699 | A2 | 4/2015 |
| WO | 2015198332 | A1 | 12/2015 |
| WO | WO 2015/198332 | | 12/2015 |
| WO | WO 2016/055592 | A1 | 4/2016 |
| WO | WO 2016/055593 | A1 | 4/2016 |
| WO | 2016094873 | A2 | 6/2016 |
| WO | WO 2016/094873 | | 6/2016 |
| WO | WO 2016/115559 | A1 | 7/2016 |
| WO | 2016187220 | A2 | 11/2016 |
| WO | WO 2016/187220 | | 11/2016 |
| WO | WO 2017/072361 | A1 | 5/2017 |
| WO | 2017127664 | A1 | 7/2017 |
| WO | WO 2017/127499 | A1 | 7/2017 |
| WO | WO 2017/127664 | | 7/2017 |
| WO | WO 2018/119314 | A1 | 6/2018 |
| WO | 2018237335 | A1 | 12/2018 |
| WO | 2020160527 | A1 | 8/2020 |

OTHER PUBLICATIONS

Berger, Carolina et al., Safety of targeting ROR1 in primates with chimeric antigen receptor-modified T cells, Cancer Immunology Research, 2015, 206-216, 3.

Bicocca, Vincent T. et al., Crosstalk between ROR1 and the Pre-B cell receptor promotes survival of t(1;19) acute lymphoblastic leukemia, Cancer Cell, 2012, 656-667, 22(5).

Blaney, Paul et al., Traceless solid-phase organic synthesis, Chem Rev, 2002, 2607-2624, 102(7).

Bulmus, Volga et al., A new pH-responsive and glutathione-reactive, endosomal membrane-disruptive polymeric carrier for intracellular delivery of biomolecular drugs, Journal of Controlled Release, 2003, 105-120, 93(2).

Casi, Giulio et al., Site-specific traceless coupling of potent cytotoxic drugs to recombinant antibodies for pharmacodelivery, J Am Chem Soc, 2012, 5887-5892, 134(13).

Castaneda, Lourdes et al., Acid-cleavable thiomaleamic acid linker for homogeneous antibody-drug conjugation, Chem Commun (Camb), 2013, 8187-8189, 49(74).

Cheson, Bruce D. et al., Recommendations for initial evaluation, staging, and response assessment of Hodgkin and non-Hodgkin lymphoma: the Lugano classification, Journal of Clinical Oncology, 2014, 3059-3068, 32(27).

Choi, Michael et al., Durable and specific inhibition of ROR1 signaling associates with prolonged progression free survival in patients with chronic lymphocytic leukemia treated with cirmluzumab, Blood, 2017, 3 pages, 130 (Suppl. 1): 829.

Choi, Michael Y. et al., Pre-clinical specificity and safety of UC 961, a first-in-class monoclonal antibody targeting ROR1, Clinical Lymphoma, Myeloma & Leukemia, 2015, S167-S169, 15.

Cui, Bing et al., Cirmtuzumab Vedotin (UC-961ADC3), An Anti-ROR1-Monomethyl Auristatin E Antibody-Drug Conjugate, Is a Potential Treatment For ROR1-Positive Leukemia and Solid Tumors, Blood, 2013, 1637, 122(21).

Cui, Bing et al., High-level ROR1 associates with accelerated disease progression in chronic lymphocytic leukemia, Blood, 2016, 2931-2940, 128(25).

Cui, Bing et al., Targeting ROR1 inhibits epithelial-mesenchymal transition and metastasis, Cancer Research, 2013, 3649-3660, 73(12).

Daneshmanesh, A.H. et al., Monoclonal antibodies against ROR1 induce apoptosis of chronic lymphocytic leukemia (CLL) cells, Leukemia, 2012, 1348-1355, 26(6).

Daneshmanesh, Amir Hossein et al., Orphan receptor tyrosine kinases ROR1 and ROR2 in hematological malignancies, Leukemia & Lymphoma, 2013, 843-850, 54(4).

Dawson, Philip E. et al., Modulation of reactivity in native chemical ligation through the use of thiol additives, Journal of the American Chemical Society, 1997, 4325-4329, 119(19).

Dawson, Philip E. et al., Synthesis of proteins by native chemical ligation, Science, 1994, 776-779, 266.

Dennler, Patrick et al., Transglutaminase-based chemo-enzymatic conjugation approach yields homogeneous antibody-drug conjugates, Bioconjugate Chemistry, 2014, 569-578, 25(3).

El-Sayed, Mohamed E.H. et al., Rational design of composition and activity correlations for pH-responsive and glutathione-reactive polymer therapeutics, Journal of Controlled Release, 2005, 417-427, 104(2).

Flanary, Suzanne et al., Antigen delivery with poly(propylacrylic acid) conjugation enhances MHC-1 presentation and T-cell activation, Bioconjugate Chemistry, 2009, 241-248, 20(2).

Fukuda, Tetsuya et al., Antisera induced by infusions of autologous Ad-CD154-leukemia B cells identify ROR1 as an oncofetal antigen and receptor for Wnt5a, Proc. Natl. Acad. Sci. USA, 2008, 3047-3052, 105(8).

Gentile, Alessandra et al., Ror1 is a pseudokinase that is crucial for Met-driven tumorigenesis, Cancer Research, 2011, 3132-3141, 71(8).

Gong, Xing et al., LGR5-targeted antibody-drug conjugate eradicates gastrointestinal tumors and prevents recurrence, Molecular Cancer Therapeutics, 2016, 1580-1590, 15(7).

Grawunder, Ulf, Antibody drug conjugates with anthracycline payload induce tumor-selective antitumor immunity and exhibit a favorable safety profile in cynomolgus monkey toxicology studies, Proc Amer Assoc Cancer Res, 2018, 4 pages, Abstract CT737/4.

Hackeng, Tilman M. et al., Protein synthesis by native chemical ligation: expanded scope by using straightforward methodology, Proc Natl Acad Sci USA, 1999, 10068-10073, 96(18).

Hejesen, Christian et al., A traceless aryl-triazene linker for DNA-directed chemistry, Organic & Biomolecular Chemistry, 2013, 2493-2497, 11(15).

Henry, Scott M. et al., pH-responsive poly(styrene-alt-maleic anhydride) alkylamide copolymers for intracellular drug delivery, Biomacromolecules, 2006, 2407-2414, 7(8).

Hojjat-Farsangi, Mohammad et al., Inhibition of the receptor tyrosine kinase ROR1 by anti-ROR1 monoclonal antibodies and siRNA induced apoptosis of melanoma cells, PLoS One, 2013, 1-10, 8(4):e61167.

(56) References Cited

OTHER PUBLICATIONS

Hojjat-Farsangi, Mohammad et al., The tyrosine kinase receptor ROR1 is constitutively phosphorylated in chronic lymphocytic leukemia (CLL) cells, PLoS One, 2013, 1-9, 8(10):e78339.
Ida, Lisa et al., Receptor tyrosine kinase-like orphan receptor 1, a target of NKX2-1/TTF-1 lineage-survival oncogene, inhibits apoptosis signal-regulating kinase 1-mediated pro-apoptotic signaling in lung adenocarcinoma, Cancer Science, 2016, 155-161, 107(2).
Janovska, Pavlina et al., Autocrine Signaling by Wnt-5a Deregulates Chemotaxis of Leukemic Cells and Predicts Clinical Outcome in Chronic Lymphocytic Leukemia, Clinical Cancer Research, 2016, 459-469, 22(2).
Jones, Rachel A. et al., Poly(2-alkylacrylic acid) polymers deliver molecules to the cytosol by pH-sensitive disruption of endosomal vesicles, Biochem. J., 2003, 65-75, 372 (Pt 1).
Kamath, Amrita V. et al., Preclinical pharmacokinetic considerations for the development of antibody drug conjugates, Pharm. Res., 2015, 3470-3479, 32.
Kolb, Ryan et al., ROR1 is an intriguing target for cancer therapy, Molecular Enzymology and Drug Targets, 2016, 1-3, 2 (1:4).
Kovtun, Yelena V. et al., Antibody-drug conjugates designed to eradicate tumors with homogeneous and heterogeneous expression of the target antigen, Cancer Research, 2006, 3214-3221, 66(6).
Li, Fu et al., Intracellular released payload influences potency and bystander-killing effects of antibody-drug conjugates in preclinical models, Cancer Research, 2016, 2710-2719, 76(9).
Li, Ping et al., Stat3 activates the receptor tyrosine kinase like orphan receptor-1 gene in chronic lymphocytic leukemia cells, PLoS One, 2010, 1-11, 5(7):e11859.
Loganzo, Frank et al., Mechanisms of resistance to antibody-drug conjugates, Molecular Cancer Therapeutics, 2016, 2825-2834, 15(12).
Lyon, Robert P. et al., Self-hydrolyzing maleimides improve the stability and pharmacological properties of antibody-drug conjugates, Nature Biotechnology, 2014, 1059-1062, 32(10).
Mao, Zhengrong et al., IgVH mutational status and clonality analysis of Richter's transformation: diffuse large B-cell lymphoma and Hodgkin lymphoma in association with B-cell chronic lymphocytic leukemia (B-CLL) represent 2 different pathways of disease evolution, Am J Surg Pathol, 2007, 1605-1614, 31(10).
O'Connell, Michael P. et al., Hypoxia induces phenotypic plasticity and therapy resistance in melanoma via the tyrosine kinase receptors ROR1 and ROR2, Cancer Discovery, 2013, 1378-1393, 3(12).
Okeley, Nicole M. et al., Correction: Intracellular activation of SGN-35, a potent anti-CD30 antibody-drug conjugate, Clinical Cancer Research, 2011, 5524, 17(16).
Okeley, Nicole M. et al., Intracellular activation of SGN-35, a potent anti-CD30 antibody-drug conjugate, Clinical Cancer Research, 2010, 888-897, 16(3).
Patterson, James T. et al., Improving the serum stability of site-specific antibody conjugates with sulfone linkers, Bioconjugate Chemistry, 2014, 1402-1407, 25.
Saber, Haleh et al., An FDA oncology analysis of antibody-drug conjugates, Regulatory Toxicology and Pharmacology, 2015, 444-452, 71(3).
Sochaj, Alicja M. et al., Current methods for the synthesis of homogeneous antibody-drug conjugate, Biotechnology Advances, 2015, 775-784, 33 (6 Pt 1).
Specht, Jennifer M. et al., A phase I study of adoptive immunotherapy for advanced ROR1+ malignancies with defined subsets of autologous T cells expressing a ROR1-specific chimeric antigen receptor (ROR1-CAR), Proc Amer Assoc Cancer Res, 2018, 5 pages, Abstract CT131.
Strop, Pavel et al., Location matters: site of conjugation modulates stability and pharmacokinetics of antibody drug conjugates, Chemistry & Biology, 2013, 161-167, 20(2).
Van Der Weyden, Ca et al., Understanding CD30 biology and therapeutic targeting: a historical perspective providing insight into future directions, Blood Cancer Journal, 2017, 1-10, 7(9):e603.
Widhopf, George F. et al., ROR1 can interact with TCL 1 and enhance leukemogenesis in Eμ-TCL 1 transgenic mice, Proc Natl Acad Sci USA, 2014, 793-798, 111(2).
Wu, Bin et al., Building complex glycopeptides: Development of a cysteine-free native chemical ligation protocol, Angew Chem Int Ed Engl, 2006, 4116-4125, 45(25).
Wu, Peng et al., Site-specific chemical modification of recombinant proteins produced in mammalian cells by using the genetically encoded aldehyde tag, Proc Natl Acad Sci USA, 2009, 3000-3005, 106(9).
Yamaguchi, Tomoya et al., NKX2-1/TITF1/TTF-1-Induced ROR1 is required to sustain EGFR survival signaling in lung adenocarcinoma, Cancer Cell, 2012, 348-361, 21(3).
Yang, Jiahui et al., Therapeutic potential and challenges of targeting receptor tyrosine kinase ROR1 with monoclonal antibodies in B-cell malignancies, PLoS One, 2011, 1-15, 6(6):e21018.
Yessine, Marie-Andree et al., Characterization of the membrane-destabilizing properties of different pH-sensitive methacrylic acid copolymers, Biochimica et Biophysica Acta, 2003, 28-38, 1613(1-2).
Yu, J. et al., Cirmtuzumab inhibits Wnt5a-induced Rac1-activation in chronic lymphocytic leukemia treated with ibrutinib, Leukemia, 2017, 1333-1339, 31(6).
Yu, Jian et al., Cirmtuzumab inhibits ibrutinib-resistant, Wnt5a-induced Rac1 activation and proliferation in mantle cell lymphoma, Oncotarget, 2018, 24731-24736, 9(37).
Yu, Jian et al., Wnt5a induces ROR1/ROR2 heterooligomerization to enhance leukemia chemotaxis and proliferation, The Journal of Clinical Investigation, 2016, 585-598, 126(2).
Zhang, Huilin et al., ROR1 expression correlated with poor clinical outcome in human ovarian cancer, Scientific Reports, 2014, 1-7, 4:5811.
Zhang, Suping et al., ROR1 is expressed in human breast cancer and associated with enhanced tumor-cell growth, PLoS One, 2012, 1-12, 7(3):e31127.
Zhang, Suping et al., The onco-embryonic antigen ROR1 is expressed by a variety of human cancer, The American Journal of Pathology, 2018, 1903-19010, 181(6).
Dillon, Thomas M. et al., Structural and Functional Characterization of Disulfide Isoforms of the Human IgG2 Subclass, Journal of Biological Chemistry, 2008, 16206-16215, 283(23).
Keating, Gillian M., Idelalisib: a review of its use in chronic lymphocytic leukaemia and indolent non-Hodgkin's lymphoma, Targeted Oncology, vol. 10, p. 141-151, 2015.
Dillon et al. (Journal of Biological Chemistry, 283(23): 16206-16215, 2008, Supplementary Material.*
Grawunder et al., "Development of best-in-class, homogeneous Antibody Drug Conjugates (ADCs) for highly effective and safer cancer therapy," presented at World ADC Congress, Berlin, Feb. 8-9, (2016).
Grawunder et al., "Preclinical validation of site-specically conjugated ADCs with potent anthracycline payloads in solid and hematological tumor models," presented at World ADC Congress, Berlin, Mar. 27, 2018.

* cited by examiner

| | Ab1 | ADC-A |
|---|---|---|
| EC50 | 13.61 | 17.01 |

| | Ab1 | ADC-A |
|---|---|---|
| EC50 | 32.81 | 48.53 |

| | Ab1 | ADC-A | 4A5 | ADC-T |
|---|---|---|---|---|
| EC50 | 16.39 | 21.57 | 120.6 | 192.7 |

| | Ab1 | ADC-A | D10 | ADC-S |
|---|---|---|---|---|
| EC50 | 16.49 | 22.12 | 250.2 | 150.3 |

| | ADC-A | ADC-S |
|---|---|---|
| IC50 | 4.462e-008 | 8.331e-008 |

ROR1 ANTIBODY IMMUNOCONJUGATES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application is a continuation of U.S. patent application Ser. No. 16/016,238, filed on Jun. 22, 2018, which claims priority from U.S. Patent Applications 62/524,382, 62/524,386, and 62/524,388, all of which were filed on Jun. 23, 2017. The disclosures of these priority applications are incorporated by reference herein in their entirety.

SEQUENCE LISTING

The instant application contains a Sequence Listing which has been submitted electronically in ASCII format and is hereby incorporated by reference in its entirety. Said ASCII copy, created on Jul. 5, 2018, is named 024651_C1002_SL.txt and is 56,687 bytes in size.

BACKGROUND OF THE INVENTION

Cancer is the second leading cause of human death next to coronary artery disease. Receptor tyrosine kinases (RTKs) play a key role in oncogenic transformation, growth and metastases. RTKs regulate cell differentiation, proliferation, migration, angiogenesis, and survival. The receptor tyrosine kinase-like orphan receptor 1 (ROR1) is an evolutionarily-conserved type I membrane protein that belongs to the ROR subfamily and has extracellular domains that contain immunoglobulin (Ig)-like, Frizzled, and Kringle domains. ROR1-deficient mice display a variety of phenotypic defects within the skeletal and urogenital systems, as well as postnatal growth retardation. ROR1 is expressed during embryogenesis and by a variety of different cancers, but not by normal post-partum tissues, and can be considered an onco-embryonic surface antigen. Functional data suggest that ROR1 may function in non-canonical WNT-signaling to promote the survival of malignant cells.

ROR1 expression and activation appears to be correlated with features of tumor aggressiveness in models of chronic lymphocytic leukemia (CLL), breast cancer, lung cancer, gastric cancer, and melanoma (Li et al., PLoS One 5(7): e11859 (2010); Gentile et al., Cancer Res. 71(8):3132-41 (2011); Zhang et al., PLoS One 7(3):e31127 (2012); Yamaguchi et al., Cancer Cell. 21(3):348-61 (2012); Daneshmanesh et al., Leukemia 26(6):1348-55 (2012); Daneshmanesh et al., Leuk Lymphoma 54(4):843-50 (2013); O'Connell et al., Cancer Discov. 3(12):1378-93 (2013); Hojjat-Farsangi et al., PLoS One 8(4):e61167 (2013); Hojjat-Farsangi et al., PLoS One 8(10):e78339 (2013); Ida et al., Cancer Sci. 107(2):155-61 (2016); and Janovska et al., Clin Cancer Res. 22(2):459-69 (2016)). Elevated levels of ROR1 expression in patients and cell lines are associated with genes involved in epithelial-mesenchymal transition (EMT) (Cui et al., Cancer Res. 73(12):3649-60 (2013)). In patients with CLL, high levels of ROR1 expression are associated with shorter treatment-free survival and overall survival (OS) (Cui et al., Blood 128(25):2931-2940 (2016)).

Similarly, in patients with ovarian cancer, high ROR1 expression is associated with poor clinical outcomes (Zhang et al., Sci Rep. 4:5811 (2014)).

In view of the role of ROR1 in cancer, there is a need for new and improved therapies that target ROR1-positive cancer cells.

SUMMARY OF THE INVENTION

Provided herein is an immunoconjugate having the formula of Ab-((L)m-(D))n, wherein: Ab is an antibody or an antigen-binding fragment thereof that specifically binds to human receptor tyrosine kinase like orphan receptor 1 (ROR1); L is a linker, and m is 0 or 1; D is a cytotoxic drug moiety; and n is an integer from 1 to 10.

The cytotoxic drug moiety may be selected from the group consisting of, for example, an anti-tubulin agent, a DNA alkylating agent, a DNA cross-linking agent, a DNA intercalating agent, and an RNA polymerase II inhibitor. In some embodiments, the cytotoxic drug moiety is selected from the group consisting of monomethyl auristatin E (MMAE), azonafide, α-amanitin, duocarmycin TM, pyrrolobenzodiazepine (PBD), PNU-159682, and pharmaceutically acceptable salts, esters, and analogs thereof.

The linker in the immunoconjugate may comprise a cleavable moiety. It may be cleaved inside a target cell. Alternatively, the linker is not cleavable. The linker can be branched or unbranched. In some embodiments, the linker comprises one or more moieties selected from valine-citrulline (VC), valine-alanine (VA), para-aminobenzyloxycarbonyl (PAB), polyethylene glycol (PEG), diaminopropionic acid (DPR), Phe-$C_4$, $C_2$-$Gly_3$, $C_6$ alkyl, dimethylethylamine (DMEA), and ethylene diamine (EDA). In certain embodiments, the linker is covalently bonded to the antibody or antigen-binding fragment at a succinimide, a carbonyl, or a cyclooctene, or a triazole group of the linker.

In certain embodiments, the antibody or fragment in the immunoconjugate is covalently bonded to the linker by reaction with a moiety selected from the group consisting of 6-maleimidocaproyl (MC)-VC-PAB; 6-MC-$C_6$; 6-MC-PEG4-VC-PAB-DMEA; 6-MC-PEG4-VA; 6-MC-DPR-VC-PAB; 6-MC-Phe-$C_4$-VC-PAB; 6-MC-Phe-$C_4$-VC-PAB-DMEA; 6-MC-$C_2$-$Gly_3$-EDA; dibenzylcyclooctyne (DBCO)-(PEG2-VC-PAB)$_2$; DBCO-PEG4-VC-PAB-DMEA; and N-succinimidyl 4-(N-maleimidomethyl)cyclohexane-1-carboxylate-VC-PAB. As used herein, VC represents a valine-citrulline dipeptide; VA represents a valine-alanine dipeptide; PEG represents polyethylene glycol; PAB represents para-amino-benzyloxycarbonyl; DMEA represents dimethylethylamine; Phe represents a benzyl group; and EDA represents ethylene diamine.

Provided herein also is an immunoconjugate having the formula of Ab-((L)m-(D))n, wherein: Ab is an antibody or an antigen-binding fragment thereof that specifically binds to human receptor tyrosine kinase like orphan receptor 1 (ROR1); L is a cleavable linker, and m is 0 or 1; D is an auristatin (e.g., MMAE); and n is an integer from 1 to 10.

In an immunoconjugate of the present disclosure, the linker may comprise, for example, a heterocycle or carbonyl covalently bonded to the antibody or antigen-binding fragment, a spacer group covalently bonded to the heterocycle or carbonyl, and an ester, thioester, amide, carbonate, thiocarbonate or carbamate covalently bonded to the cytotoxic drug moiety. In some embodiments, the spacer group comprises an amino acid, a polyamino acid, or an amino benzyl group, or a combination thereof. In some embodiments, the linker in an immunoconjugate of the present disclosure forms a covalent bond with a cysteine or lysine residue on the antibody or fragment.

The Ab (antibody or fragment thereof) component of an immunoconjugate of the present disclosure may bind to the same ROR1 epitope as an antibody comprising the heavy chain and light chain amino acid sequences of SEQ ID NOs: 3 and 4, respectively. The antibody or fragment may comprise the heavy chain complementarity-determining region (CDR) 1-3 (HCDR1-3) in SEQ ID NO: 3 and the light chain CDR1-3 (LCDR1-3) in SEQ ID NO: 4. In some embodiments, the antibody or fragment comprises the amino acid sequences of SEQ ID NOs: 7-9, and the light chain of the antibody comprises the amino acid sequences of SEQ ID NOs: 10-12. The antibody or fragment may be humanized. The antibody or fragment may have one or more of the following properties: a) facilitates ROR1 internalization in a human cell; b) binds to human ROR1 with a $K_D$ of less than 100 nM (e.g., less than 50, 40, 30, 20, or 10 nM); and c) inhibits growth of $ROR1^+$ human cancer cells in vitro with an $EC_{50}$ of 500 nM or less (e.g., 400 nM or less, 300 nM or less, 200 nM or less, or 100 nM or less).

In some embodiments, the heavy chain variable domain ($V_H$) and light chain variable domain ($V_L$) of the antibody in the immunoconjugate comprise the amino acid sequences of: a) SEQ ID NOs: 5 and 6, respectively; b) SEQ ID NOs: 5 and 50, respectively; c) SEQ ID NOs: 48 and 6, respectively; or d) SEQ ID NOs: 48 and 50, respectively. The antibody may comprise a human $IgG_1$ constant region and optionally also a human κ light chain constant region. In further embodiments, the heavy chain and light chain of the antibody comprise the amino acid sequences of: a) SEQ ID NOs: 3 and 4, respectively; b) SEQ ID NOs: 3 and 49, respectively; c) SEQ ID NOs: 47 and 4, respectively; or d) SEQ ID NOs: 47 and 49, respectively.

In some embodiments, the Ab component of the immunoconjugate is an Fab, $F(ab)_2$, or scFv, e.g., an Fab, $F(ab)_2$, or scFv.

Specific embodiments of the present disclosure include an immunoconjugate comprising an antibody conjugated to a cytotoxic drug moiety, wherein the $V_H$ and $V_L$ of the antibody comprise the amino acid sequences of SEQ ID NOs: 5 and 6, respectively. Examples of such an immunoconjugate are shown in Tables 2 and 3 below, and include Antibody-Drug Conjugates (ADC)-A, E, H, I, J, K, L, M, N, O, P, Q, and R. In further embodiments, the heavy chain and light chain of the antibody comprise the amino acid sequences of SEQ ID NOs: 3 and 4, respectively.

In the immunoconjugate of the present disclosure, the number of the drug moiety to per antibody or fragment, or the ratio of the cytotoxic drug moiety to the antibody or fragment (DAR), may be 1 to 10, for example, 1 to 7, 1 to 6, 1 to 5, 2 to 7, 2 to 6, or 2 to 5.

Also provided herein are pharmaceutical compositions comprising an immunoconjugate of the present disclosure and a pharmaceutically acceptable excipient. The pharmaceutical compositions may further comprise an additional therapeutic agent selected from the group consisting of a Bruton's tyrosine kinase (BTK) inhibitor, a B-cell lymphoma 2 (Bcl-2) inhibitor, a mammalian target of [rapamycine] *rapamycin* (mTOR) inhibitor, and a phosphoinositide 3-kinase (PI3K) inhibitor. For example, the additional therapeutic agent is selected from ibrutinib, acalabrutinib, venetoclax, everolimus, sapanisertib, and idelalisib.

Also provided herein is a therapy or method for treating cancer in a patient in need thereof, comprising administering to the patient a therapeutically effective amount of an immunoconjugate of the present invention. The cancer may be homogenous or heterogeneous for ROR1 expression and may be, for example, a leukemia, a lymphoma, or a solid tumor. In some embodiments, the cancer is chronic lymphocytic leukemia (CLL), T-cell leukemia (TCL), mantle cell lymphoma (MCL), diffuse large B-cell lymphoma (DLBCL), Burkitt's lymphoma, multiple myeloma (MM), marginal zone lymphoma (MZL), small lymphocytic lymphoma (SLL), or a non-Hodgkin lymphoma (NHL) that has undergone Richter's transformation. In some embodiments, the cancer is non-small cell lung cancer (NSCLC), hepatocellular carcinoma, pancreatic cancer, osteosarcoma, head and neck cancer, ovarian cancer, breast cancer, or triple negative breast cancer (TNBC).

The therapy or treatment method of the present disclosure may further comprise administering to the patient an additional anti-cancer therapeutic agent, which may be, for example, a Bruton's tyrosine kinase (BTK) inhibitor, a B-cell lymphoma 2 (Bcl-2) inhibitor, a mammalian target of [rapamycine] *rapamycin* (mTOR) inhibitor, and a phosphoinositide 3-kinase (PI3K) inhibitor. In some embodiments, the additional therapeutic agent is selected from ibrutinib, acalabrutinib, venetoclax, everolimus, sapanisertib, and idelalisib.

In certain embodiments of the present therapy or treatment method, the cancer is CLL, MCL, or an NHL that has undergone Richter's transformation.

Provided herein also are immunoconjugates and pharmaceutical compositions as described herein for use in treating cancer in the therapy or treatment methods described herein. For example, provided herein is an immunoconjugate having the formula of Ab-((L)m-(D))n for use in treating cancer in a patient in need thereof, wherein: Ab is an antibody or an antigen-binding fragment thereof that specifically binds to human receptor tyrosine kinase like orphan receptor 1 (ROR1); L is a linker, and m is 0 or 1; D is a cytotoxic drug moiety; and n is an integer from 1 to 10. Exemplary embodiments of the immunoconjugate and the treatment are described above and will be further described below.

Provided herein also are the use of an immunoconjugate herein for the manufacture of a medicament for use in treating cancer in a patient in need thereof. For example, provided herein is the use of is an immunoconjugate having the formula of Ab-((L)m-(D))n for the manufacture of a medicament in treating cancer in a patient in need thereof, wherein: Ab is an antibody or an antigen-binding fragment thereof that specifically binds to human receptor tyrosine kinase like orphan receptor 1 (ROR1); L is a linker, and m is 0 or 1; D is a cytotoxic drug moiety; and n is an integer from 1 to 10. Exemplary embodiments of the immunoconjugate and the treatment are described above and will be further described below.

The present disclosure also provides a method of making an immunoconjugate, comprising: providing an antibody or an antigen-binding fragment thereof that specifically binds to human receptor tyrosine kinase like orphan receptor 1 (ROR1); conjugating to the antibody a cytotoxic drug moiety selected from the group consisting of an anti-tubulin agent, a DNA alkylating agent, a DNA cross-linking agent, a DNA intercalating agent, and an RNA polymerase II inhibitor; wherein the heavy chain of the antibody comprises the amino acid sequences of SEQ ID NOs: 7-9, and the light chain of the antibody comprises the amino acid sequences of SEQ ID NOs: 10-12. Exemplary embodiments of the immunoconjugate are described above and will be further described below.

Provided herein also are articles of manufactures, such as kits, comprising an immunoconjugate of the present disclosure.

on inhibition of Jeko-1 cell proliferation, and displayed an additive effect with both inhibitors on inhibition of Mino cell proliferation.

Figure 21:
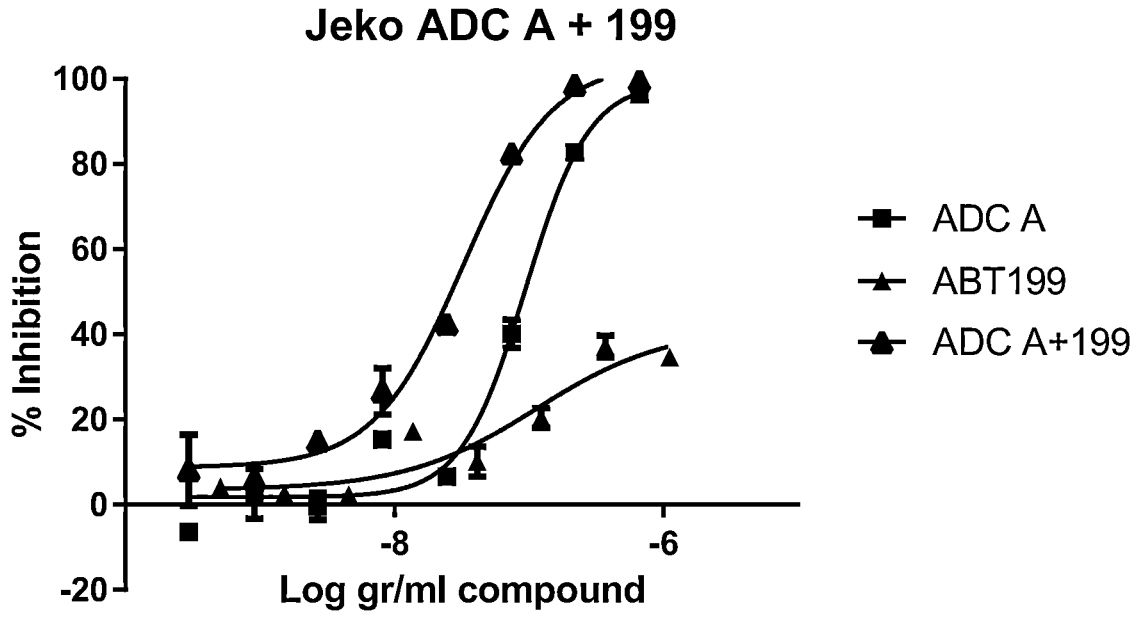

FIG. 21 is a graph illustrating inhibition of Jeko-1 cell proliferation upon treatment with ADC-A, ABT-199, or a combination of ADC-A and ABT-199.

Figure 22:
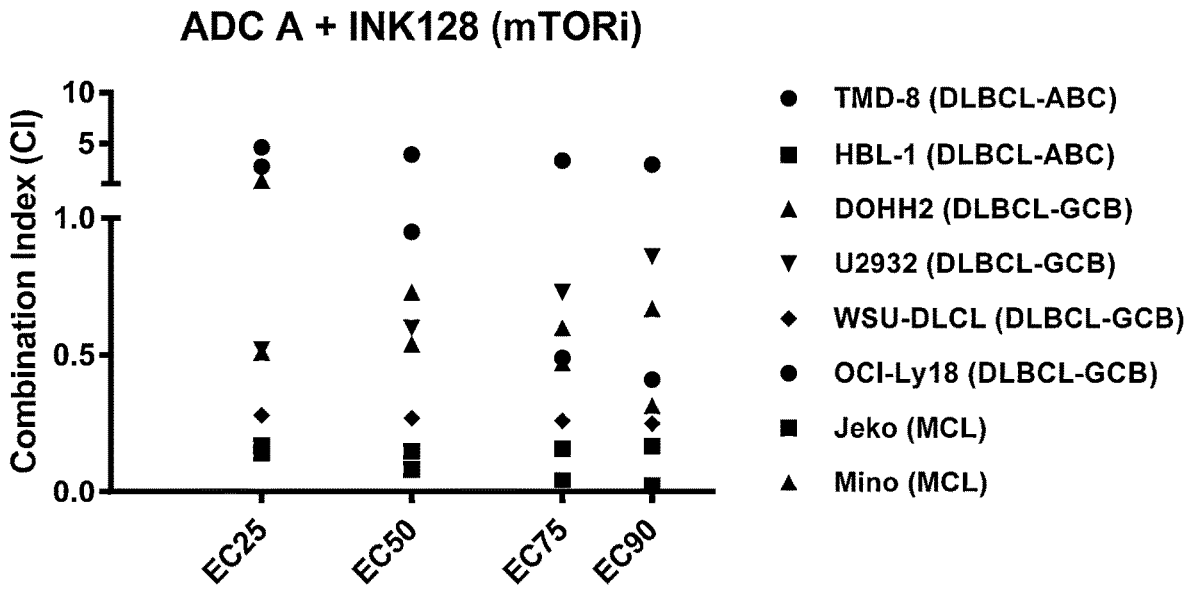

FIG. 22 is a graph illustrating the combination index of treatment with ADC-A and mTOR1/2 inhibitor INK128/sapanisertib ("INK128") in various cell lines. ADC-A displayed a synergistic effect with INK128 on inhibition of both MCL and DLBCL cell proliferation.

Figure 23:
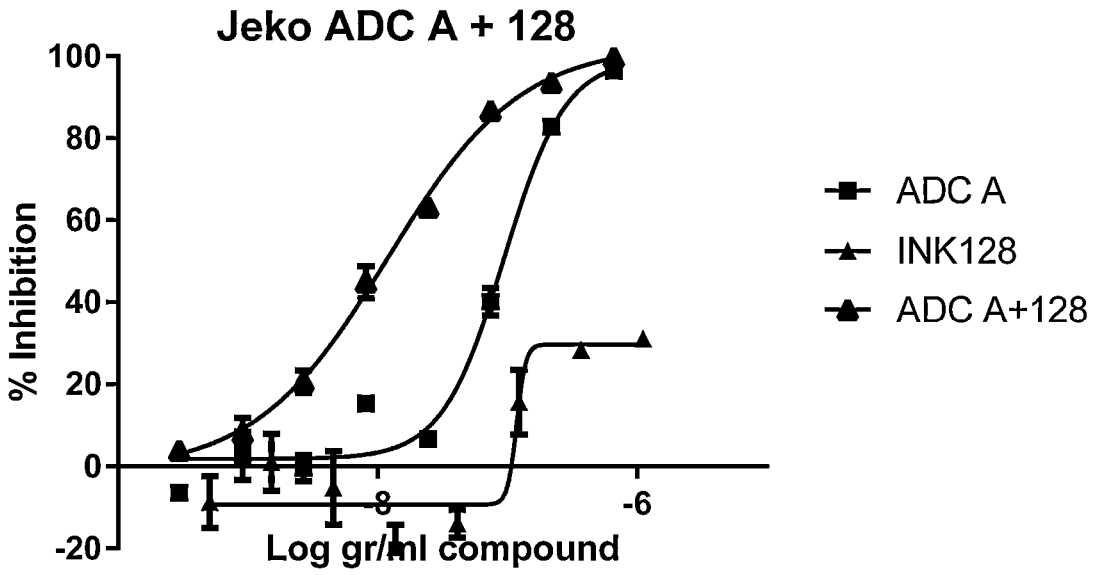

FIG. 23 is a graph illustrating inhibition of Jeko-1 cell proliferation upon treatment with ADC-A, INK128, or a combination of ADC-A and INK128.

Figure 24:
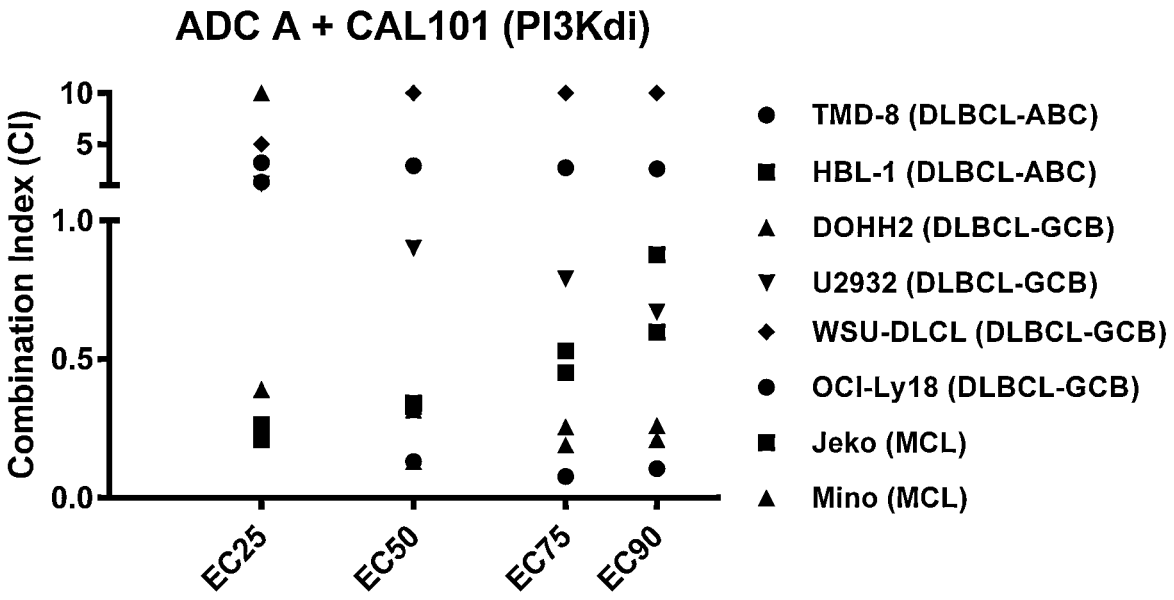

FIG. 24 is a graph illustrating the combination index of treatment with ADC-A and PI3K inhibitor CAL-101/idelalisib ("CAL101") in various cell lines. ADC-A displayed a synergistic effect with CAL101 on inhibition of both MCL and DLBCL cell proliferation.

Figure 25A:
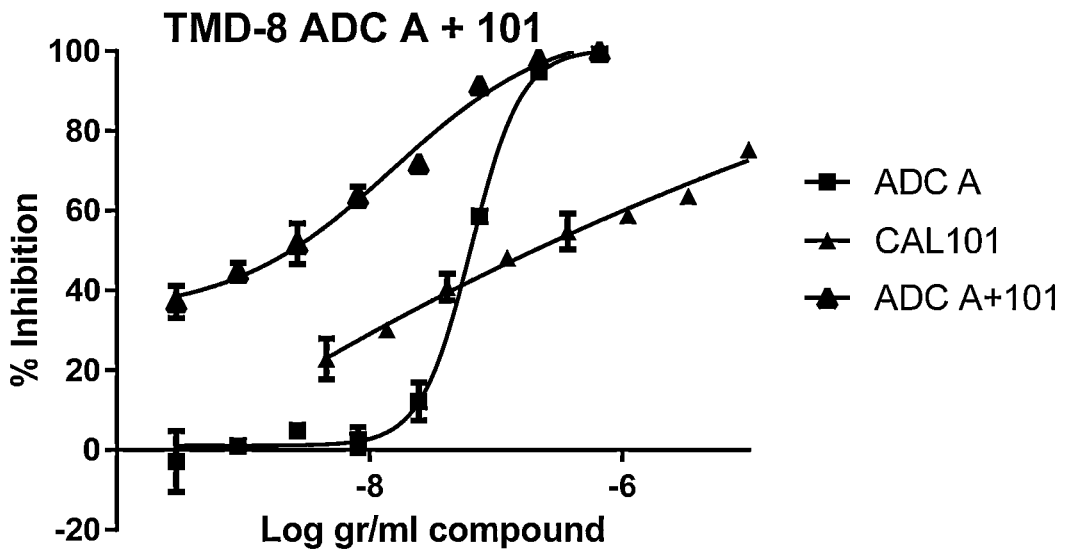
Figure 25B:
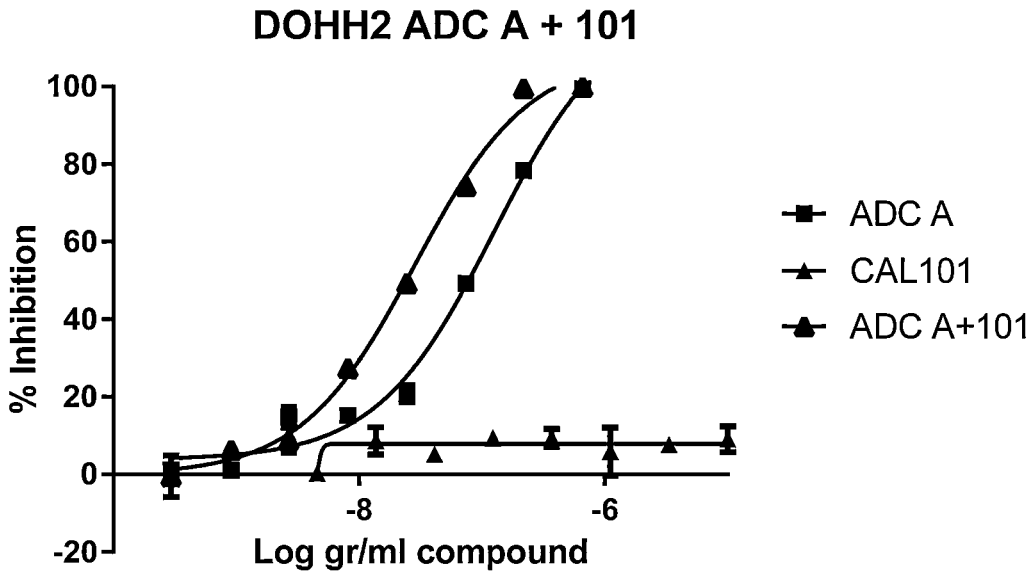

FIGS. 25A and 25B are graphs illustrating inhibition of cell proliferation upon treatment with ADC-A, PI3K inhibitor CAL-101/idelalisib ("CAL101" or "101"), or a combination of ADC-A and CAL101, in DLBCL-ABC cell line TMD-8 (25A) or in DLBCL-GCB cell line DOHH2 (25B).

DETAILED DESCRIPTION OF THE INVENTION

The present invention provides immunoconjugates of the formula Ab-$((L)_m$-$(D))_n$, wherein Ab is an antibody or an antigen-binding fragment thereof that specifically binds to the ROR1 protein; L is a linker; D is a drug moiety that has therapeutic activity in cancer; m is 0 or 1; and n is an integer from 1 to 10. In the formula, the dash "-" denotes a covalent or non-covalent bond. The antibody or fragment includes, but is not limited to, an antibody or antibody fragment that competes with antibody D10 or Ab1 for binding to human ROR1, or binds to the same epitope as D10 or Ab1. The drug moiety includes, but is not limited to, another antibody or an antigen-binding fragment thereof, a polypeptide, a small molecule compound, a nucleic acid molecule such as a small interfering RNA molecule or an antisense molecule. The immunoconjugates of the present invention may be used to treat a variety of cancers such as ROR1-positive cancers.

1. Immunoconiugates

An "antibody-drug conjugate," or "ADC," or "immunoconjugate" refers to an antibody molecule, or an antigen-binding fragment thereof, that is covalently or non-covalently bonded, with or without a linker, to one or more biologically active molecule(s). The present immunoconjugates comprise antibodies or fragments thereof that are specific for human ROR1 and can thus serve as excellent targeting moieties for delivering the conjugated payloads to ROR1-positive cells. In some embodiments, a ROR1 immunoconjugate provided herein has an equilibrium dissociation constant ($K_D$) of about 1 μM, 100 nM, 50 nM, 40 nM, 30 nM, 20 nM, 10 nM, 5 nM, 2 nM, 1 nM, 0.5 nM, 0.1 nM, 0.05 nM, 0.01 nM, or 0.001 nM or less (e.g., $10^{-8}$ M or less, from $10^{-8}$M to $10^{-13}$ M, or from $10^{-9}$M to $10^{-13}$ M) for human ROR1. $K_D$ can be measured by any suitable assay, such as surface plasmon resonance assays (e.g., using a BIACORE®-2000 or a BIACOREg-3000). In certain embodiments, the $K_D$ of an immunoconjugate of the invention is less than the $K_D$ for the D10 antibody. In certain embodiments, the $K_D$ of an immunoconjugate of the invention for human ROR1 is less than about 50, 40, 30, 20, or 10 nM (e.g., 40 nM). In some embodiments, a ROR1 immunoconjugate provided herein inhibits growth of ROR1$^+$ human cancer cells in vitro with an $EC_{50}$ of about 500, 400, 350, 300, or 250 nM or less (e.g., 300 nM or less). As used herein, an antibody is said to bind specifically to an antigen when it binds to the antigen with a $K_D$ of 100 nM or less, such as less than 10 nM or less (e.g., 1-5 nM), as determined by, e.g., surface plasmon resonance or Bio-Layer Interferometry.

In certain embodiments, the immunoconjugate provided herein is internalized by a ROR1-positive cell primarily through the lysosome/endosome pathway. In particular embodiments, the internalization is independent of the ROR1 expression level on the cell surface.

Embodiments of the antibody or fragment thereof, the linker, and the drug moiety used in the immunoconjugates are described in further detail below.

1.1. Types and Structures of Antibodies

The term "antibody" is used herein in the broadest sense and includes polyclonal and monoclonal antibodies, such as intact antibodies and functional (antigen-binding) fragments thereof. The term encompasses genetically engineered and/or otherwise modified forms of immunoglobulins, such as intrabodies, peptibodies, chimeric antibodies, fully human antibodies, humanized antibodies, and heteroconjugate antibodies, multi-specific (e.g., bispecific) antibodies, diabodies, triabodies, and tetrabodies, tandem di-scFv, and tandem tri-scFv. Unless otherwise indicated, the term encompasses intact or full-length antibodies, including antibodies of any class or subclass (e.g., IgG and sub-classes thereof such as $IgG_1$, $IgG_2$, $IgG_3$, and $IgG_4$; IgM; IgE; IgA; and IgD), as well as antibody fragments.

An antibody may include a heavy chain (or a polypeptide sequence derived therefrom) and a light chain (or a polypeptide sequence derived therefrom). The term "variable region" or "variable domain" refers to the domain of an antibody heavy or light chain that is involved in the antibody's binding to an antigen. The variable domains of the heavy chain and light chain ($V_H$ and $V_L$, respectively) of a native antibody generally have similar structures, with each domain comprising four conserved framework regions and three complementarity-determining regions. A single $V_H$ or $V_L$ domain may sometimes be sufficient to confer all or a majority of the antigen-binding specificity of an antibody. Furthermore, antibodies that bind a particular antigen may be isolated by using a $V_H$ or $V_L$ domain from an antibody that binds the antigen to screen a library of complementary $V_L$ or $V_H$ domains, respectively. See, e.g., Portolano et al., J. Immunol. 150:880-887 (1993); Clarkson et al., Nature 352: 624-628 (1991).

The terms "complementarity-determining region" and "CDR," which are synonymous with "hypervariable region" or "HVR," refer to subregions within the antibody variable domains, which confer the antibody's specificity and/or affinity for its antigen. In general, there are three CDRs in each heavy chain variable domain (HCDR1, HCDR2, and HCDR3) and three CDRs in each light chain variable domain (LCDR1, LCDR2, and LCDR3). "Framework regions" ("FRs") refer to the non-CDR portions of the variable domains. In general, there are four FRs in each full-length heavy chain variable domain and four FRs in each full-length light chain variable domain. The precise amino acid sequence boundaries of a given CDR or FR can be readily determined using any of several well-known schemes, including those described by Kabat et al., 5th Ed., Public Health Service, National Institutes of Health, Bethesda, Md. (1991) ("Kabat" numbering scheme); Al-Lazikani et al., IMB 273, 927-948 (1997) ("Chothia" numbering scheme); MacCallum et al., J Mol. Biol. 262:732-745

(1996) ("contact" numbering scheme); Lefranc et al., Dev Comp Immunol. 27(1):55-77 (2003) ("IMGT" numbering scheme); and Honegger and Pluckthun, J Mot Biol, 309(3): 657-70 (2001) ("Aho" numbering scheme).

The boundaries of a given CDR or FR may vary depending on the scheme used for identification. For example, the Kabat scheme is based on sequence alignments, while the Chothia scheme is based on structural information. Numbering for both the Kabat and Chothia schemes is based upon the most common antibody region sequence lengths, with insertions accommodated by insertion letters, for example, "30a." The two schemes place certain insertions and deletions ("indels") at different positions, resulting in differential numbering. The contact scheme is based on analysis of complex crystal structures and is similar in many respects to the Chothia numbering scheme. Unless indicated otherwise, the CDRs of the antibodies referred to herein may be identified according to any of the Kabat, Chothia, IMGT, and contact methods.

An antigen-binding fragment of a full-length antibody may be used in making an immunoconjugate of the present invention. Examples of antibody fragments include, but are not limited to, Fv, Fab, Fab', Fab'-SH, $F(ab')_2$; recombinant IgG (rIgG) fragments; diabodies; linear antibodies; single-chain antibody molecules (e.g., scFv or sFv); single domain antibodies (e.g., sdAb, sdFv, nanobodies); and multi-specific antibodies formed from antibody fragments. In certain embodiments, the fragments are single-chain antibody fragments comprising a variable heavy chain region and/or a variable light chain region, such as scFvs.

1.2 Exemplary ROR1 Antibodies

An immunoconjugate of the invention comprises an antibody or an antigen-binding fragment thereof that specifically binds to ROR1, e.g., human ROR1. The antibody or fragment binds to an extracellular portion of the ROR1 protein such as an epitope in one or more of the immunoglobulin (Ig)-like, Frizzled, and Kringle domains of the ROR1 protein. In certain embodiments, the ROR1-binding antibody or fragment binds to an amino acid sequence of ROR1 shown in SEQ ID NO: 1 or 2 (not including the terminal cysteine, which is added for convenience of conjugation) and can be internalized by a $ROR1^+$ cell; examples of such an antibody are murine antibodies D10 and 99961. See U.S. Pat. Nos. 9,217,040 and 9,758,591, the disclosures of which are incorporated by reference herein in their entirety. In certain embodiments, the antibody or fragment competes with D10 or 99961 for binding to human ROR1. Amino acid sequences of exemplary anti-ROR1 antibodies used in the immunoconjugates of the invention are shown in Table 1 below, where Ab1-Ab4 are humanized variants of antibody 99961.

TABLE 1

SEQ ID NOs of Exemplary Anti-ROR1 Antibodies

| Ab | HCDR1 | HCDR2 | HCDR3 | VH | HC | LCDR1 | LCDR2 | LCDR3 | VL | LC |
|---|---|---|---|---|---|---|---|---|---|---|
| 99961 | 7 | 8 | 9 | 45 | — | 10 | 11 | 12 | 46 | — |
| Ab1 | 7 | 8 | 9 | 5 | 3 | 10 | 11 | 12 | 6 | 4 |
| Ab2 | 7 | 8 | 9 | 5 | 3 | 10 | 11 | 12 | 50 | 49 |
| Ab3 | 7 | 8 | 9 | 48 | 47 | 10 | 11 | 12 | 6 | 4 |
| Ab4 | 7 | 8 | 9 | 48 | 47 | 10 | 11 | 12 | 50 | 49 |
| D10 | 27 | 28 | 29 | 25 | — | 30 | 31 | 32 | 26 | — |

In some embodiments, the antibody or antibody fragment in the immunoconjugate specifically binds human ROR1, and its heavy and light chains respectively comprise:

a) the heavy chain CDR1-3 (HCDR1-3) amino acid sequences in SEQ ID NO: 3, and the light chain CDR1-3 (LCDR1-3) amino acid sequences in SEQ ID NO: 4;

b) HCDR1-3 comprising the amino acid sequences of SEQ ID NO: 7-9, respectively, and LCDR1-3 comprising the amino acid sequences of SEQ ID NOs: 10-12, respectively;

c) the HCDR1-3 amino acid sequences in SEQ ID NO: 13-15, and the LCDR1-3 amino acid sequences in SEQ ID NOs: 16-18;

d) HCDR1-3 comprising the amino acid sequences of SEQ ID NO: 27-29, respectively, and LCDR1-3 comprising the amino acid sequences of SEQ ID NOs: 30-32, respectively;

e) HCDR1-3 comprising the amino acid sequences of SEQ ID NO: 37-39, respectively, and LCDR1-3 comprising the amino acid sequences of SEQ ID NOs: 40-42, respectively;

f) HCDR1-3 comprising residues 26-33, 51-58, and 97-105 of SEQ ID NO: 5, respectively, and LCDR1-3 comprising residues 27-32, 50-52, and 89-97 of SEQ ID NO: 6, respectively;

g) HCDR1-3 comprising residues 26-32, 52-57, and 99-105 of SEQ ID NO: 5, respectively, and LCDR1-3 comprising residues 24-34, 50-56, and 89-97 of SEQ ID NO: 6, respectively;

h) HCDR1-3 comprising residues 31-35, 50-66, and 99-105 of SEQ ID NO: 5, respectively, and LCDR1-3 comprising residues 24-34, 50-56, and 89-97 of SEQ ID NO: 6, respectively;

i) HCDR1-3 comprising residues 26-32, 52-57, and 99-105 of SEQ ID NO: 5, respectively, and LCDR1-3 comprising residues 27-32, 50-52, and 89-97 of SEQ ID NO: 6, respectively; or j) HCDR1-3 comprising residues 31-35, 52-57, and 99-105 of SEQ ID NO: 5, respectively, and LCDR1-3 comprising residues 27-32, 50-52, and 89-97 of SEQ ID NO: 6, respectively.

In some embodiments, the antibody or fragment is humanized, or chimeric with human constant regions. In further embodiments, the antibody or fragment may comprise a human $IgG_1$, $IgG_2$, $IgG_3$, or $IgG_4$ constant region and optionally a human κ constant region.

In certain embodiments, the immunoconjugate of the invention comprises an anti-ROR1 antibody, or an antigen-binding fragment thereof, wherein the antibody comprises:

a) a heavy chain variable domain or region ($V_H$) comprising an amino acid sequence at least 80%, 85%, 90%, 91%, 92%, 93%, 94%, 95%, 96%, 97%, 98%, or 99% (e.g., at least 90%) identical to that of SEQ ID NO: 5, and a light chain variable domain or region ($V_L$) comprising an amino acid sequence at least 80%, 85%, 90%, 91%, 92%, 93%, 94%, 95%, 96%, 97%, 98%, or 99% (e.g., at least 90%) identical to that of SEQ ID NO: 6;

b) a $V_H$ and a $V_L$ comprising the amino acid sequences of SEQ ID NOs: 5 and 6, respectively;

c) a heavy chain (HC) comprising an amino acid sequence at least 80%, 85%, 90%, 91%, 92%, 93%, 94%, 95%, 96%, 97%, 98%, or 99% (e.g., at least 90%) identical to that of SEQ ID NO: 3 and a light chain (LC) comprising an amino acid sequence 80%, 85%, 90%, 91%, 92%, 93%, 94%, 95%, 96%, 97%, 98%, or 99% (e.g., at least 90%) identical to that of SEQ ID NO: 4; or d) an HC and an LC comprising the amino acid sequences of SEQ ID NOs: 3 and 4, respectively.

In certain embodiments, the $V_H$ and $V_L$ of the antibody respectively comprise the amino acid sequences of:

a) SEQ ID NOs: 5 and 50;

b) SEQ ID NOs: 48 and 6; or c) SEQ ID NOs: 48 and 50.

In some embodiments, the antibody or fragment comprises a human $IgG_1$, $IgG_2$, $IgG_3$, or $IgG_4$ constant region and optionally a human κ constant region.

In certain embodiments, the HC and LC of the antibody respectively comprise the amino acid sequences of:

a) SEQ ID NOs: 3 and 49;

b) SEQ ID NOs: 47 and 4; or c) SEQ ID NOs: 47 and 49.

In certain embodiments, the immunoconjugate of the invention comprises an antibody or fragment thereof derived from a murine antibody with the $V_H$ and $V_L$ amino acid sequences of (i) SEQ ID NOs: 25 and 26, respectively; (ii) SEQ ID NOs: 35 and 36, respectively; or (iii) SEQ ID NOs: 45 and 46, respectively. Antibodies derived from these sequences may be, e.g., antibodies that have been humanized or joined to a human Fc region (e.g., chimeric). For example, the antibody or an antigen-binding fragment in the immunoconjugate comprises:

a) a $V_H$ comprising an amino acid sequence at least 80%, 85%, 90%, 91%, 92%, 93%, 94%, 95%, 96%, 97%, 98%, or 99% identical to that of SEQ ID NO: 45 and a $V_L$ comprising an amino acid sequence at least 80%, 85%, 90%, 91%, 92%, 93%, 94%, 95%, 96%, 97%, 98%, or 99% identical to that of SEQ ID NO: 46;

b) a $V_H$ comprising the amino acid sequence of SEQ ID NO: 45 and a $V_L$ comprising the amino acid sequence of SEQ ID NO: 46;

c) a $V_H$ comprising an amino acid sequence at least 80%, 85%, 90%, 91%, 92%, 93%, 94%, 95%, 96%, 97%, 98%, or 99% identical to that of SEQ ID NO: 25 and a $V_L$ comprising an amino acid sequence at least 80%, 85%, 90%, 91%, 92%, 93%, 94%, 95%, 96%, 97%, 98%, or 99% identical to that of SEQ ID NO: 26; or d) a $V_H$ comprising the amino acid sequence of SEQ ID NO: 25 and a $V_L$ comprising the amino acid sequence of SEQ ID NO: 26.

Exemplary coding sequences for the aforementioned antibodies are shown in Table 12 below. For example, the antibody in the immunoconjugate may comprise:

a) a $V_H$ encoded by (i) nucleotides 73-420 of SEQ ID NO: 21, or (ii) SEQ ID NO: 23; and a $V_L$ encoded by SEQ ID NO: 22 or 24;

b) a $V_H$ encoded by SEQ ID NO: 52 and a $V_L$ encoded by SEQ ID NO: 54;

c) a $V_H$ encoded by SEQ ID NO: 33 and a $V_L$ encoded by SEQ ID NO: 34;

d) an HC encoded by nucleotides 73-1,410 of SEQ ID NO: 19 and an LC encoded by nucleotides 73-714 of SEQ ID NO: 20; or e) an HC encoded by SEQ ID NO: 51 and an LC encoded by nucleotides SEQ ID NO: 53.

In certain embodiments, the immunoconjugate of the invention comprises an antigen-binding fragment of an anti-ROR1 antibody, wherein the antigen-binding fragment comprises the sequence of any one of SEQ ID NOs: 64-68. In certain embodiments, the antigen-binding fragment comprises the $V_H$ and $V_L$ amino acid sequences of:

a) SEQ ID NOs: 5 and 6;

b) SEQ ID NOs: 5 and 50;

c) SEQ ID NOs: 48 and 6;

d) SEQ ID NOs: 48 and 50;

e) SEQ ID NOs: 45 and 46; or f) SEQ ID NOs: 25 and 26, wherein the $V_H$ amino acid sequence is optionally linked to the amino acid sequence of SEQ ID NO: 62, and/or the $V_L$ amino acid sequence is optionally linked to the amino acid sequence of SEQ ID NO: 63.

1.3 Antibody Sequence Comparison

Percent (%) sequence identity with respect to a reference polypeptide sequence refers to the percentage of amino acid residues in a candidate sequence that are identical with the amino acid residues in the reference sequence, after aligning the sequences and introducing gaps, if necessary, to achieve the maximum percent sequence identity. Alignment for purposes of determining percent amino acid sequence identity can be achieved in various ways that are known; for instance, using publicly available computer software such as BLAST, BLAST-2, ALIGN, ALIGN-2, or Megalign (DNASTAR). For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparison, the % amino acid sequence identity of a given amino acid sequence A to a given amino acid sequence B is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

In some embodiments, amino acid sequence variants of the antibodies provided herein are contemplated. A variant typically differs from a polypeptide specifically disclosed herein in one or more substitutions, deletions, additions and/or insertions. Such variants can be naturally occurring or can be synthetically generated, for example, by modifying one or more of the above polypeptide sequences of the invention and evaluating one or more biological activities of the polypeptide as described herein and/or using any of a number of known techniques. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

As used herein, the term "substantially identical" refers to two or more sequences having a percentage of sequential units (e.g., amino acid residues) which are the same when compared and aligned for maximum correspondence over a comparison window, or a designated region as measured using comparison algorithms. By way of example, two or more sequences may be "substantially identical" if the sequential units are about 60% identical, about 65% identical, about 70% identical, about 75% identical, about 80% identical, about 85% identical, about 90% identical, about 95% identical, about 96% identical, about 97% identical, about 98% identical, or about 99% identical over a specified region. Such percentages describe the "percent identity" between two sequences.

1.4 Making and Modification of ROR1 Antibodies

Anti-ROR1 antibodies for use in the immunoconjugates of the present invention can be made by immunizing an animal with human ROR1 or a fragment of human ROR1 protein. Antibodies that bind to the immunizing fragment with high affinity (e.g., with a $K_D$ in the nM or lower range) can be screened by using routine methods such as ELISA.

If the antibody is a non-human antibody, it can be humanized. A "humanized" antibody is an antibody in which all or substantially all CDR amino acid residues are derived from a non-human (e.g., mouse or rat) antibody and all or substantially all FR amino acid residues are derived from human FRs. A humanized antibody optionally may include at least a portion of a constant region derived from a human antibody. A "humanized form" of a non-human antibody refers to a variant of the non-human antibody that has undergone humanization, typically to reduce immunogenicity to humans, while retaining the antigen-binding specificity and affinity of the parental non-human antibody. In some embodiments, some FR residues in a humanized antibody are substituted with corresponding residues from the cognate non-human antibody to restore or improve the resultant antibody's antigen-binding specificity and/or affinity.

ROR1 antibodies or fragments may be manufactured recombinantly in mammalian host cells containing coding sequences for the ROR1 antibodies or fragments, wherein the coding sequences are operably linked to transcription-regulatory elements suitable for expression in the host cells. The coding sequences may be introduced into the host cells on one or more vectors. Useful mammalian host cells include, inter alfa, Chinese hamster ovary (CHO) cells, NS0 cells, SP2 cells, HEK-293T cells, 293 Freestyle cells (Invitrogen), NIH-3T3 cells, HeLa cells, baby hamster kidney (BHK) cells, African green monkey kidney cells (COS), human hepatocellular carcinoma cells (e.g., Hep G2), and A549 cells. Cell lines may be selected based on their expression levels. Other cell lines that may be used include insect cell lines, such as Sf9 or Sf21 cells, and yeast cell lines.

In some embodiments, a parent ROR1 antibody may be engineered by introducing one or more amino acid substitutions to improve the antibody's antigen binding, to decrease immunogenicity (e.g., de-immunize; see, e.g., Jones et al., Methods Mot Biol. 525:405-23 (2009)), and/or to improve antibody-dependent cell-mediated cytotoxicity (ADCC) or complement-dependent cytotoxicity (CDC).

In some embodiments, substitutions, insertions, or deletions may be made within one or more CDRs, wherein the mutations do not substantially reduce the antibody's binding to its antigen. For example, conservative substitutions that do not substantially reduce binding affinity may be made.

Alterations (e.g., substitutions) may be made in CDRs to improve antibody affinity. CDR residues involved in antigen binding may be identified by using, e.g., alanine scanning mutagenesis or computer modeling. HCDR3 and LCDR3 in particular are often targeted. A crystal structure of an antigen-antibody complex may also be used to identify contact points between the antibody and its antigen. Such contact residues and their neighboring residues may be targeted for mutations. Variants may be screened to determine whether they obtain the desired properties. In vitro affinity maturation (e.g., using error-prone PCR, chain shuffling, randomization of CDRs, or oligonucleotide-directed mutagenesis) may also be used to improve antibody affinity (see, e.g., Hoogenboom et al., Methods in Molecular Biology 178:1-37 (2001)).

Amino acid sequence insertions and deletions made to an antibody or antibody fragment include amino- and/or carboxyl-terminal fusions ranging in length from one or a few residues to polypeptides containing a hundred or more residues, as well as intra-sequence insertions and deletions of single or multiple amino acid residues. Examples of terminal insertions include an antibody with an N-terminal methionyl residue. Other insertional variants of the antibody molecule include the fusion of the N- or C-terminus of the antibody to an enzyme (e.g., for ADEPT) or a polypeptide that increases the serum half-life of the antibody. Examples of intra-sequence insertion variants of the antibody molecules include an insertion of 3 amino acids in the light chain. Examples of terminal deletions include an antibody with a deletion of 7 or fewer amino acids at an end of the light chain, and the removal of the C-terminal lysine in the heavy chain.

In some embodiments, the ROR1 antibodies are altered to increase or decrease their glycosylation (e.g., by altering the amino acid sequence such that one or more glycosylation sites are created or removed). A carbohydrate attached to an Fc region of an antibody may be altered. Native antibodies from mammalian cells typically comprise a branched, biantennary oligosaccharide attached by an N-linkage to $Asn_{297}$ of the $CH_2$ domain of the Fc region (see, e.g., Wright et al., TIBTECH 15:26-32 (1997)). $Asn_{297}$ refers to the asparagine residue located at about position 297 in the Fc region (EU numbering of Fc region residues; see, e.g., Edelman et al. PNAS 63(1):78-85 (1969)). However, $Asn_{297}$ may also be located about ±3 amino acids upstream or downstream of position 297, i.e., between positions 294 and 300, due to minor sequence variations in antibodies. The oligosaccharide can be any of various carbohydrates, e.g., mannose, N-acetyl glucosamine (GlcNAc), galactose, sialic acid, or fucose attached to a GlcNAc in the stem of the biantennar oligosaccharide structure. Modifications of the oligosaccharide in an antibody can be made, for example, to create antibody variants with certain improved properties. Antibody glycosylation variants can have improved ADCC and/or CDC function.

In some embodiments, antibody variants are provided having a carbohydrate structure that has no or a reduced level of fucose attached (directly or indirectly) to an Fc region. For example, the amount of fucose in such an antibody may be from 1% to 80%, from 1% to 65%, from 5% to 65% or from 20% to 40%. The amount of fucose is determined by calculating the average amount of fucose within the sugar chain at $Asn_{297}$, relative to the sum of all glycostructures attached to $Asn_{297}$ (see, e.g., PCT Patent Publication WO 2008/077546). Such fucosylation variants can have improved ADCC function (see, e.g., Okazaki et al., J. Mol. Biol. 336:1239-1249 (2004); and Yamane-Ohnuki et al., Biotech. Bioeng. 87:614 (2004)). Cell lines (e.g., knockout cell lines) can be used to produce defucosylated antibodies, e.g., Lec13 CHO cells deficient in protein fucosylation and alpha-1,6-fucosyltransferase gene (FUT8) knockout CHO cells (see, e.g., Ripka et al., Arch. Biochem. Biophys. 249:533-545 (1986); Yamane-Ohnuki et al., Biotech. Bioeng. 87:614 (2004); and Kanda et al., Biotechnol. Bioeng. 94(4):680-688 (2006)). Other antibody glycosylation variants as described in, e.g., U.S. Pat. No. 6,602,684) may also be made to the ROR1 antibodies or antibody fragments for use in the present immunoconjugates.

In some embodiments, one or more amino acid modifications may be introduced into the Fc region of a ROR1 antibody to generate a ROR1 antibody with a variant Fc region that confers new properties to the antibody. A variant Fc region may comprise a human Fc region sequence (e.g., a human $IgG_1$, $IgG_2$, $IgG_3$ or $IgG_4$ Fc region) comprising an amino acid modification (e.g., a substitution) at one or more amino acid positions. For example, a ROR1 antibody with a variant Fc region may possess some but not all effector functions, which makes it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. Non-limiting examples of in vitro assays to assess ADCC activity of a molecule of interest are described in U.S. Pat. Nos. 5,500,362 and 5,821,337. Alternatively, non-radioactive assays methods may be employed (e.g., ACTI™ and CytoTox 96® non-radioactive cytotoxicity assays). Useful effector cells for such assays include peripheral blood mononuclear cells (PBMCs), monocytes, macrophages, and natural killer (NK) cells.

Antibodies can have increased half-lives and improved binding to the neonatal Fc receptor (FcRn) (see, e.g., U.S. Patent Publication 2005/0014934). Such antibodies can comprise an Fc region with one or more substitutions therein which improve binding of the Fc region to FcRn, and include those with substitutions at one or more of Fc region residues: 238, 256, 265, 272, 286, 303, 305, 307, 311, 312, 317, 340, 356, 360, 362, 376, 378, 380, 382, 413, 424 and 434 according to the EU numbering system (see, e.g., U.S. Pat. No. 7,371,826). Other examples of Fc region variants are also contemplated (see, e.g., Duncan & Winter, Nature 322:738-40 (1988); U.S. Pat. Nos. 5,648,260 and 5,624,821; and PCT Publication WO 94/29351).

In some embodiments, it may be desirable to create cysteine engineered antibodies, e.g., "thioMAbs," in which one or more residues of an antibody are substituted with cysteine residues. In some embodiments, the substituted residues occur at accessible sites of the antibody. Reactive thiol groups can be positioned at sites for conjugation to other moieties, such as drug moieties or linker drug moieties, to create an immunoconjugate. Any one or more of the following residues may be substituted with cysteine: V205 (Kabat numbering) of the light chain; A118 (EU numbering) of the heavy chain; and 5400 (EU numbering) of the heavy chain Fc region.

An antibody provided herein may be further modified to include non-proteinaceous moieties. The moieties suitable for derivatization of the antibody include but are not limited to water soluble polymers. The term "polymer," as used herein, refers to a molecule composed of repeated subunits; such molecules include, but are not limited to, polypeptides, polynucleotides, or polysaccharides, or polyalkylene glycols. Non-limiting examples of water soluble polymers are polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyamino acids (either homopolymers or random copolymers), and dextran or poly(N-vinyl pyrrolidone)-polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if two or more polymers are attached, they can be the same or different molecules.

1.5 Cytotoxic Drug Moieties

An immunoconjugate of the invention comprises an anti-ROR1 antibody or an antigen-binding fragment thereof conjugated to one or more cytotoxic agents, such as chemotherapeutic agents, growth inhibitory agents, toxins (e.g., protein toxins, enzymatically active toxins of bacterial, fungal, plant, or animal origin, or fragments thereof), or radioactive isotopes. The cytotoxic agent(s) can be conjugated to the anti-ROR1 antibody or fragment by a linker covalently bound to an amino acid residue of the antibody. Many drugs that can serve as a cytotoxic moiety in an immunoconjugate are independently too toxic to be used for cancer treatment, and thus are more effective when specifically targeted to the cancer cell by an antibody or antibody fragment.

The term "cytotoxic drug moiety" or "cytotoxic agent" refers to a compound that can cause harm, disturbances, or death to a cell. Examples of cytotoxic drug moieties that can be used as part of a ROR1 immunoconjugate include, but are not limited to: NCA1, auristatin, auristatin E, DNA minor groove binding agents, DNA minor groove alkylating agents, enediyne, lexitropsin, duocarmycin, taxane, puromycin, dolastatin, maytansinoid, vinca alkaloid, AFP, MMAF, MMAE, AEB, AEVB, taxoids (e.g., paclitaxel and paclitaxel derivatives (TAXOL®, Bristol-Myers Squibb Oncology, Princeton, N.J.), ABRAXANE® (American Pharmaceutical Partners, Schaumberg, Ill.), as well as docetaxel and docetaxel derivatives), CC-1065, SN-38, topotecan, morpholino-doxorubicin, rhizoxin, cyanomorpholino-doxorubicin, dolastatin-10, echinomycin, combretatstatin, chalicheamicin, maytansine, DM-I, netropsin, podophyllotoxin (e.g., etoposide and teniposide), baccatin and its derivatives, anti-tubulin agents, cryptophysin, combretastatin, vincristine, vincristine sulfate, vinblastine, vindesine, vinorelbine, VP-16, camptothecin, epothilone A, epothilone B, nocodazole, colchicines, colcimid, estramustine, cemadotin, discodermolide, eleutherobin, mechlorethamine, cyclophosphamide, melphalan, carmustine, lomustine, semustine, streptozocin, chlorozotocin, uracil mustard, chlormethine, chlorambucil, pipobroman, triethylenemelamine, triethylenethiophosphoramine, busulfan, dacarbazine, temozolomide, ytarabine, cytosine arabinoside, fluorouracil, 5-fluorouracil (5-FU), floxuridine, 6-thioguanine, 6-mercaptopurine, pentostatin, methotrexate, 10-propargyl-5,8-dideazafolate, 5,8-dideazatetrahydrofolic acid, leucovorin, fludarabine phosphate, pentostatine, gemcitabine, Ara-C, deoxycoformycin, mitomycins such as mitomycin-C, L-asparaginase, azathioprine, brequinar, antibiotics (e.g., anthracycline, gentamicin, cefalotin, vancomycin, telavancin, daptomycin, azithromycin, erythromycin, rocithromycin, furazolidone, amoxicillin, ampicillin, carbenicillin, flucloxacillin, methicillin, penicillin, ciprofloxacin, moxifloxacin, ofloxacin, doxycycline, minocycline, oxytetracycline, tetracycline, streptomycin, rifabutin, ethambutol, and rifaximin), enediyne antibiotics (e.g., calicheamicin, calicheamicin gamma1I and calicheamicin omegaI1, and dynemicin, including dynemicin A), antiviral drugs (e.g., abacavir, acyclovir, ampligen, cidofovir, delavirdine, didanosine, efavirenz, entecavir, fosfonet, ganciclovir, ibacitabine, immunovir, idoxuridine, inosine, lopinavir, methisazone, nexavir, nevirapine, oseltamivir, penciclovir, stavudine, trifluridine, truvada, valaciclovir, and zanamivir), daunorubicin hydrochloride, daunoriycin, rubidomycin, cerubidine, idarubicin, doxorubicin, epirubicin and morpholino derivatives, phenoxizone biscyclopeptides (e.g., dactinomycin), basic glycopeptides (e.g., bleomycin), anthraquinone glycosides (e.g., plicamycin and mithramycin), anthracenediones (e.g., mitoxantrone), azirinopyrrolo indolediones (e.g., mitomycin), macrocyclic immunosuppressants (e.g., cyclosporine, FK-506, tacrolimus, prograf, and rapamycin), navelbene, CPT-11, anastrazole, letrazole, capecitabine, reloxafine, droloxafine, allocolchicine, Halichondrin B, colchicine and colchicine derivatives, rhizoxin, thiocolchicine, trityl cysterin, vinblastine sulfate, hydroxyurea, N-methylhydrazine, epidophyllotoxin, procarbazine, mitoxantrone, leucovorin, and tegafur. "Taxanes" include paclitaxel, as well as any active taxane derivative or pro-drug. Chemotherapeutic agents such as erlotinib (TARCEVA®, Genentech/OSI Pharm.), bortezomib (VELCADE®, Millenium Pharm.), fulvestrant (FASLODEX®, AstraZeneca), sunitinib (Sutent®, Pfizer), letrozole (FEMARA®, Novartis), imatinib mesylate (GLEEVEC®, Novartis), PTK787/ZK 222584 (Novartis), oxaliplatin (Eloxatin®, Sanofi), leucovorin, lapatinib (TYKERB®, GSK572016, GlaxoSmithKline), lonafarnib (SCH 66336), sorafenib (BAY43-9006, Bayer Labs.), and gefitinib (IRESSA®, AstraZeneca), AG1478, AG1571 (SU 5271; Sugen), alkylating agents such as thiotepa and cyclosphosphamide (CYTOXAN®); alkyl sulfonates such as busulfan, improsulfan and piposulfan; antifolate antineoplastic such as pemetrexed (ALIMTA® Eli Lilly); aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (such as bullatacin and bullatacinone); a camptothecin (including the synthetic analogue topotecan); bryostatin; callystatin; CC-1065 (including its synthetic analogues adozelesin, carzelesin and bizelesin); cryptophycins (such as cryptophycin 1 and cryptophycin 8); dolastatin; duocarmycin (including its synthetic analogues KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, fotemustine, lomustine, nimustine, and ranimnustine; bisphosphonates, such as clodronate; an esperamicin; as well as neocarzinostatin chromophore and related chromoprotein enediyne antibiotic chromophores, aclacinomysins, actinomycin, anthramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (ADRIAMYCIN®) (including morpholino-doxorubicin, cyanomorpholino-doxorubicin, 2-pyrrolino-doxorubicin and deoxydoxorubicin), epirubicin, esorubicin, idarubicin, marcellomycin, mycophenolic acid, nogalamycin, olivomycins, peplomycin, potfiromycin puromycin, quelamycin, rodorubicin, streptonigrin, streptozocin, tubercidin, ubenimex, zinostatin, zorubicin; anti-metabolites such as methotrexate and 5-FU; folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel (TAXOL®, Bristol-Myers Squibb Oncology, Princeton, N.J.), ABRAXANE™ Cremophor-free, albumin, nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin and carboplatin; vinblastine; platinum; etoposide (VP-16); mitoxantrone; NAVELBINE® vinorelbine; novantrone; teniposide; edatrexate; daunomycin; aminopterin; xeloda; ibandronate; topoisomerase inhibitor RFS 2000; difluoromethylornithine (DMFO); retinoids such as retinoic acid; and pharmaceutically acceptable salts, esters, acids, prodrugs, or derivatives of any of the above.

In some embodiments, a suitable cytotoxic agent for use in the ROR1 immunoconjugate is a) an anti-tubulin agent (e.g., an auristatin or dolastatin such as auristatin E, monomethyl auristatin E (MMAE) or monomethyl auristatin F (MMAF), dimethylvaline-valine-dolaisoleuine-dolaproine-phenylalanine-p-phenylenediamine (AFP), 5-benzoylvaleric acid-auristatin E ester (AEVB), AEB, a maytansinoid, ansamitocin, mertansine/emtansine (DM1), or ravtansine/soravtansine (DM4)), b) a DNA alkylating agent or a DNA minor groove alkylating agent (e.g., duocarmycin), c) a DNA cross-linking agent (e.g., pyrrolobenzodiazepine (PBD)), d) a DNA intercalating agent (e.g., PNU-159682), e) a DNA minor groove binding agent (e.g., CC-1065), or f) an RNA polymerase II inhibitor (e.g., amanitin, such as α-amanitin).

As used herein, the term "intercalating agent" refers to a chemical that can insert into the intramolecular space of a molecule or the intermolecular space between molecules. By way of example, a DNA intercalating agent may be a molecule that inserts into the stacked bases of the DNA double helix.

In some embodiments, the cytotoxic agent used in the ROR1 immunoconjugate is selected from the group consisting of an enediyne, a lexitropsin, a duocarmycin, a taxane, a puromycin, a podophyllotoxin, a baccatin derivative, a cryptophysin, a combrestatin, a dolastatin, a maytansinoid, a vinca alkaloid, paclitaxel, docetaxel, ansamitocin, CC-1065, SN-38, topotecan, morpholino-doxorubicin, rhizoxin, cyanomorpholino-doxorubicin, dolastatin-10, echinomycin, combretatstatin, chalicheamicin, vincristine, vinblastine, vindesine, vinorelbine, VP-16, camptothecin, epothilone A, epothilone B, nocodazole, colchicines, colcimid, estramustine, cemadotin, discodermolide maytansine, eleutherobin, and netropsin.

In some embodiments, the cytotoxic drug moiety in the immunoconjugate is a prodrug. The term "prodrug" or "pharmaceutically acceptable prodrug," as used herein, refers to an agent that is converted into the parent drug in vivo or in vitro and is relatively nontoxic. That is, the immunoconjugate may be administered to a subject without causing undesirable biological effects or interacting in a deleterious manner with any of the components of the composition in which it is contained. Prodrugs are generally drug precursors that, following administration to a subject and subsequent absorption, are converted to an active or a more active species via some process, such as conversion by a metabolic pathway. Some prodrugs have a chemical group present on the prodrug that renders it less active and/or confers solubility or some other property to the drug. Once the chemical group has been cleaved and/or modified from the prodrug, the active drug is generated. Prodrugs may be converted into active drug within the body through enzymatic or non-enzymatic reactions. Prodrugs may provide improved physiochemical properties over their parent drugs such as better solubility, enhanced delivery characteristics (e.g., targeting a particular cell, tissue, organ or ligand), and improved therapeutic value of the drug. The benefits of such prodrugs may include, but are not limited to, (i) ease of administration compared with the parent drug; (ii) the prodrug may be bioavailable by oral administration where the parent is not; and (iii) the prodrug may have improved solubility in pharmaceutical compositions compared with the parent drug. A prodrug includes a pharmacologically inactive or less active derivative of a drug. Prodrugs may be designed to modulate the amount of a drug or biologically active molecule that reaches a desired site of action through the manipulation of the properties of a drug, such as physiochemical, biopharmaceutical, or pharmacokinetic properties.

In some embodiments, the average number of the drug moiety to the antibody in the immunoconjugate (i.e., drug-to-antibody ratio or DAR) is 1; or at least 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 6, 7, 8, 9, or 10. Exemplary methods for measuring DAR are described in the Examples below.

1.6 Linkers

In certain embodiments of an immunoconjugate of the invention, the antibody can be conjugated directly to the cytotoxic agent, or can be conjugated via a linker. Suitable linkers include, for example, cleavable and non-cleavable linkers. In some embodiments, the linker is a cleavable linker. A cleavable linker refers to a linker that comprises a cleavable moiety and is typically susceptible to cleavage under intracellular conditions. Suitable cleavable linkers include, for example, peptide linkers cleavable by an intracellular protease (such as a lysosomal protease or an endosomal protease), and acid-cleavable linkers. In exemplary embodiments, the linker can be a dipeptide, such as a valine-citrulline (val-cit or VC) or a phenylalanine-lysine (phe-lys) linker. The linker may also be a tripeptide or a polypeptide having four or more amino acid residues. Other suitable linkers include linkers hydrolyzable at a pH of less than 5.5, such as a hydrazone linker. Additional suitable cleavable linkers include disulfide linkers. In some embodiments, the linker is a non-polymeric linker. In some cases, the linker is a non-peptide linker or a linker that does not contain an amino acid residue.

In some embodiments, the linker includes a $C_1$-$C_6$ alkyl group (e.g., a $C_5$, $C_4$, $C_3$, $C_2$, or $C_1$ alkyl group). As used herein the term "alkyl" refers to a straight or branched hydrocarbon chain radical consisting solely of carbon and hydrogen atoms, containing no unsaturation. $C_1$-$C_x$ includes $C_1$-$C_2$, $C_1$-$C_3$, . . . , $C_1$-$C_x$, where xis an integer. $C_1$-$C_x$ refers to the number of carbon atoms in the designated group. In some embodiments, an alkyl comprises one to eight carbon atoms ($C_{1-8}$ alkyl). In some embodiments, an alkyl comprises two to six carbon atoms ($C_{2-6}$ alkyl).

As used herein, a linker prior to the chemical reaction to link the Ab (antibody or fragment) and D (payload) components of the immunoconjugate is also called a "linker precursor." It will be apparent to the skilled person in the ADC art whether a certain chemical entity disclosed herein is a linker precursor based on its reactive capabilities, or a linker component in the final immunoconjugate product.

In some embodiments, the linkage between the Ab and D components of the immunoconjugate may be formed through reaction of the components with a homobifuctional linker. Exemplary homobifuctional linkers include, but are not limited to, Lomant's reagent dithiobis (succinimidylpropionate) DSP, 3'3'-dithiobis(sulfosuccinimidyl propionate) (DTSSP), disuccinimidyl suberate (DSS), bis(sulfosuccinimidyl)suberate (BS), disuccinimidyl tartrate (DST), di sulfosuccinimidyl tartrate (sulfo DST), ethylene glycobis (succinimidylsuccinate) (EGS), disuccinimidyl glutarate (DSG), N,N'-disuccinimidyl carbonate (DSC), dimethyl adipimidate (DMA), dimethyl pimelimidate (DMP), dimethyl suberimidate (DMS), dimethyl-3,3'-dithiobispropionimidate (DTBP), 1,4-di-3'-(2'-pyridyldithio)propionamido)butane (DPDPB), bismaleimidohexane (BMH), aryl halide-containing compound (DFDNB), such as, e.g. 1,5-difluoro-2,4-dinitrobenzene or 1,3-difluoro-4,6-dinitrobenzene, 4,4'-difluoro-3,3'-dinitrophenylsulfone (DFDNPS), bis-[β-(4-azidosalicylamido)ethyl]disulfide (BASED), formaldehyde, glutaraldehyde, 1,4-butanediol diglycidyl ether, adipic acid dihydrazide, carbohydrazide, o-toluidine, 3,3'-dimethylbenzidine, benzidine, α,α'-p-diaminodiphenyl, diiodo-p-xylene sulfonic acid, N,N'-ethylene-bis(iodoacetamide), and N,N'-hexamethylene-bis(iodoacetamide).

In some embodiments, the linkage between the Ab and D components of the immunoconjugate may be formed through reaction of the components with a heterobifunctional linker. Exemplary heterobifunctional linkers include, but are not limited to, amine-reactive and sulfhydryl cross-linkers such as N-succinimidyl 3-(2-pyridyldithio)propionate (sPDP), long-chain N-succinimidyl 3-(2-pyridyldithio)propionate (LC-sPDP), water-soluble-long-chain N-succinimidyl 3-(2-pyridyldithio) propionate (sulfo-LC-sPDP), succinimidyloxycarbonyl-a-methyl-α-(2-pyridyldithio)toluene (sMPT), sulfosuccinimidyl-6-[α-methyl-α-(2-pyridyldithio)toluamido]hexanoate (sulfo-LC-sMPT), succinimidyl-4-(N-maleimidomethyl)cyclohexane-1-carboxylate (SMCC), sulfosuccinimidyl-4-(N-maleimidomethyl)cyclohexane-1-carboxylate (sulfo-sMCC), m-maleimidobenzoyl-N-hydroxysuccinimide ester (MBs), m-maleimidobenzoyl-N-hydroxysulfosuccinimide ester (sulfo-MBs), N-succinimidyl(4-iodoacteyl)aminobenzoate (sIAB), sulfosuccinimidyl(4-iodoacteyl)aminobenzoate (sulfo-sIAB), succinimidyl-4-(p-maleimidophenyl)butyrate (sMPB), sulfosuccinimidyl-4-(p-maleimidophenyl)butyrate (sulfo-sMPB), N-(γ-maleimidobutyryloxy)succinimide ester (GMBs), N-(γ-maleimidobutyryloxy)sulfosuccinimide ester (sulfo-GMBs), succinimidyl 6-((iodoacetyl)amino)hexanoate (sIAX), succinimidyl 6-[6-(((iodoacetyl)amino) hexanoyl)amino]hexanoate (sIAXX), succinimidyl 4-(((iodoacetyl)amino)methyl)cyclohexane-1-carboxylate (sIAC), succinimidyl 6-((((4-iodoacetyl)amino)methyl)cyclohexane-1-carbonyl)amino) hexanoate (sIACX), p-nitrophenyl iodoacetate (NPIA), carbonyl-reactive and sulfhydryl-reactive cross-linkers such as 4-(4-N-maleimidophenyl) butyric acid hydrazide (MPBH), 4-(N-maleimidomethyl) cyclohexane-1-carboxyl-hydrazide-8 ($M_2C_2H$), 3-(2-pyridyldithio)propionyl hydrazide (PDPH), amine-reactive and photoreactive cross-linkers such as N-hydroxysuccinimidyl-4-azidosalicylic acid (NHs-AsA), N-hydroxysulfosuccinimidyl-4-azidosalicylic acid (sulfo-NHs-AsA), sulfosuccinimidyl-(4-azidosalicylamido)hexanoate (sulfo-NHs-LC-AsA), sulfosuccinimidyl-2-(p-azidosalicylamido)ethyl-1,3'-dithiopropionate (sAsD), N-hydroxysuccinimidyl-4-azidobenzoate (HsAB), N-hydroxysulfosuccinimidyl-4-azidobenzoate (sulfo-HsAB), N-succinimidyl-6-(4'azido-2'nitrophenylamino)hexanoate (sANPAH), sulfosuccinimidyl-6-(4'azido-2'nitohenylamino)hexanoate (sulfo-sANPAH), N-5-azido-2-nitrobenzoyloxysuccinimide (ANB-NOs), sulfosuccinimidyl-2-(m-azido-o-nitrobenzamido)-ethyl-1,3'dithiopropionate (sAND), N-succinimidyl-4(4-azidophenyl)1,3'dithiopropionate (sADP), N-sulfosuccinimidyl(4-azidophenyl)-1,3'dithiopropionate (sulfo-sADP), sulfosuccinimidyl 4-(p-azidophenyl)butyrate (sulfo-sAPB), sulfosuccinimidyl 2-(7-azido-4-methylcoumarin-3-acetamide)ethyl-1,3'-dithiopropionate (sAED), sulfosuccinimidyl 7-azido-4-methylcoumain-3-acetate (sulfo-sAMCA), p-nitrophenyl diazopyruvate (pNPDP), p-nitrophenyl-2-diazo-3,3,3-trifluoropropionate (PNP-DTP), sulfhydryl-reactive and photoreactive cross-linkers such as1-(p-Azidosalicylamido)-4-(iodoacetamido)butane (AsIB), N-[4-(p-azidosalicylamido)butyl]-3'(2'-pyridyldithio) propionamide (APDP), benzophenone-4-iodoacetamide, benzophenone-4-maleimide carbonyl-reactive and photoreactive cross-linkers such as p-azidobenzoyl hydrazide (ABH), carboxylate-reactive and photoreactive cross-linkers such as 4-(p-azidosalicylamido)butylamine (AsBA), and arginine-reactive and photoreactive cross-linkers such as p-azidophenyl glyoxal (APG).

In some embodiments, the linkage between the Ab and D components of the immunoconjugate may be formed through reaction of the components with a linker having a reactive functional group that may comprise, e.g., a nucleophilic group that is reactive to an electrophilic group present on a binding moiety. Exemplary electrophilic groups include carbonyl groups such as aldehydes, ketones, carboxylic acids, esters, amides, enones, acyl halides, and acid anhydrides. In particular embodiments, the reactive functional group is an aldehyde. Exemplary nucleophilic groups include hydrazide, oxime, amino, hydrazine, thiosemicarbazone, hydrazine carboxylate, and arylhydrazide.

In some embodiments, the conjugation of the linker/payload to the antibody or fragment may be formed through reaction with a maleimide group (which may also be referred to as a maleimide spacer). In certain embodiments, the maleimide group is maleimidocaproyl (mc); thus, the linker/payload is conjugated to the antibody or fragment through reaction between a residue on the antibody or fragment and the mc group in the linker precursor. In some embodiments, the maleimide group comprises a maleimidomethyl group, such as succinimidyl-4-(N-maleimidomethyl)cyclohexane-1-carboxylate (SMCC) or sulfosuccinimidyl-4-(N-maleimidomethyl)cyclohexane-1-carboxylate (sulfo-SMCC), as described herein.

In some embodiments, the maleimide group is a self-stabilizing maleimide. In some embodiments, the self-stabilizing maleimide utilizes diaminopropionic acid (DPR) to incorporate a basic amino group adjacent to the maleimide to provide intramolecular catalysis of thiosuccinimide ring hydrolysis, thereby decreasing the ability of the maleimide to undergo an elimination reaction through a retro-Michael reaction. In some embodiments, the self-stabilizing maleimide is a maleimide group described in Lyon et al., Nat. Biotechnol. 32(10):1059-1062 (2014). In certain embodiments, the linker precursor comprises a self-stabilizing maleimide. In certain embodiments, the linker precursor is a self-stabilizing maleimide.

In some embodiments, the linker may include a peptide moiety. In some embodiments, the peptide moiety comprises at least 2, 3, 4, 5, 6, 7, 8, or more amino acid residues. In some embodiments, the peptide moiety is cleavable (e.g., either enzymatically or chemically). In some embodiments, the peptide moiety is non-cleavable. In some embodiments, the peptide moiety comprises Val-Cit (valine-citrulline), Gly-Gly-Phe-Gly (SEQ ID NO: 55), Phe-Lys, Val-Lys, Gly-Phe-Lys, Phe-Phe-Lys, Ala-Lys, Val-Arg, Phe-Cit, Phe-Arg, Leu-Cit, Ile-Cit, Trp-Cit, Phe-Ala, Ala-Leu-Ala-Leu (SEQ ID NO: 56), or Gly-Phe-Leu-Gly (SEQ ID NO: 57). In certain embodiments, the linker comprises Val-Cit (VC). In certain embodiments, the linker is Val-Cit (VC).

In some embodiments, the linker may include a benzoic acid or benzyloxy group, or a derivative thereof. For example, the linker may comprise para-amino-benzoic acid (PABA). In some embodiments, the linker includes a para-amino-benzyloxycarbonyl (PAB) group. In some embodiments, the linker comprises gamma-amino-butyric acid (GABA).

In some embodiments, the linkage between the Ab and D components of the immunoconjugate may be formed through reaction of the components with a linker comprising a maleimide group, a peptide moiety, and/or a benzoic acid (e.g., PABA) or benzyloxycarbonyl group, in any combination. In certain embodiments, the maleimide group is maleimidocaproyl (mc). In certain embodiments, the peptide group is Val-Cit (VC). In certain embodiments, the linker comprises a Val-Cit-PABA group. In certain embodiments, the conjugation of the linker to the antibody or fragment may be formed from an mc-Val-Cit-PABA group. In certain embodiments, the conjugation of the linker to the antibody or fragment may be formed from an mc-Val-Cit group. In certain embodiments, the linkage between the antibody or fragment and the drug moiety may be formed from an mc-Val-Cit-PAB group.

In some embodiments, the linker is a self-immolative linker or a self-elimination linker (e.g., a cyclization self-elimination linker). In some embodiments, the linker may be a linker described in U.S. Pat. No. 9,089,614 or PCT Publication WO 2015/038426.

In some embodiments, the linker is a dendritic type linker. In certain embodiments, the dendritic type linker comprises a branching, multifunctional linker moiety. The dendritic linker can have two or more branches. In certain embodiments, the dendritic type linker is used to increase the molar ratio of the drug moiety to the antibody or fragment. In certain embodiments, the dendritic type linker comprises PAMAM dendrimers.

In some embodiments, the linker is a traceless linker or a linker which after cleavage does not leave behind a linker moiety (e.g., an atom or a linker group). Exemplary traceless linkers include, but are not limited to, germanium linkers, silicium linkers, sulfur linkers, selenium linkers, nitrogen linkers, phosphorus linkers, boron linkers, chromium linkers, and phenylhydrazide linkers. In some embodiments, the linker is a traceless aryl-triazene linker as described in Hejesen et al., Org Biomol Chem 11(15):2493-2497 (2013). In some embodiments, the linker is a traceless linker described in Blaney et al., Chem. Rev. 102:2607-2024 (2002). In some embodiments, a linker is a traceless linker as described in U.S. Pat. No. 6,821,783.

In some embodiments, the linker comprises a functional group that exerts steric hindrance at the site of bonding between the linker and a conjugating moiety (e.g., any of ADC-A, B, C, E, F, and H-T described herein). In some embodiments, the steric hindrance is a steric hindrance around a disulfide bond. An exemplary linker that exhibits steric hindrance may be, e.g., a heterobifunctional linker (e.g., as described herein). In some embodiments, a linker that exhibits steric hindrance comprises SMCC and SPDB.

In some embodiments, the linker is an acid cleavable linker. In some embodiments, the acid cleavable linker comprises a hydrazone linkage, which is susceptible to hydrolytic cleavage. In some embodiments the acid cleavable linker comprises a thiomaleamic acid linker. In some embodiments, the acid cleavable linker is a thiomaleamic acid linker as described in Castaneda et al., Chem. Commun. 49:8187-8189 (2013).

In some embodiments, the linker is a linker described in any of U.S. Pat. Nos. 6,884,869, 7,498,298, 8,288,352, 8,609,105, and 8,697,688; any of U.S. Patent Publications 2014/0127239, 2013/028919, 2014/286970, 2013/0309256, 2015/037360; and 2014/0294851; or any of PCT Publications WO 2015/057699, WO 2014/080251, WO 2014/197854, WO 2014/145090, and WO 2014/177042.

Suitable linkers for use in the immunoconjugates of the invention may include, e.g., linkers that are intracellularly cleavable with high extracellular stability. In certain embodiments, the linker comprises a functional group that allows for attachment of the linker to any of the antibodies or fragments described herein (e.g., a maleimide derivative). In certain embodiments, the linker (or precursor) comprises 6-maleimidocaproyl (MC), maleimidopropanoyl (MP), valine-citrulline (VC), alanine-phenylalanine (AP), p-aminobenzyloxycarbonyl (PAB), N-succinimidyl 4-(2-pyridylthio) pentanoate (SPP), N-succinimidyl 4-(N-maleimidomethyl) cyclohexane-1-carboxylate (SMCC), N-succinimidyl (4-iodo-acetyl) aminobenzoate (SLAB), 6-maleimidocaproyl-valine-citrulline (MC-VC), 6-maleimidocaproyl-valine-citrulline-p-aminobenzyloxycarbonyl (MC-VC-PAB), N-succinimidyl-1-carboxylate-valine-citrulline-p-aminobenzyloxycarbonyl (SC-VC-PAB), 6-maleimidocaproyl-polyethylene glycol-valine-citrulline (MC-PEG4-VC), 6-maleimidocaproyl-polyethylene glycol-valine-alanine (MC-PEG4-VA), or MC-PEG8-VC-PAB. In some embodiments, the linker prior to conjugation reaction (aka linker precursor) is 6-maleimidocaproyl-valine-citrulline-p-aminobenzyloxycarbonyl (MC-VC-PAB), or N-succinimidyl-1-carboxylate-valine-citrulline-p-aminobenzyloxycarbonyl (SC-VC-PAB). In some embodiments, the linker is a 6-maleimidocaproyl (MC) linker. In some embodiments, the linker is a maleimidopropanoyl (MP) linker. In some embodiments, the linker is a valine-citrulline (VC) linker. In some embodiments, the linker is an alanine-phenylalanine (AP) linker. In some embodiments, the linker is ap-aminobenzyloxycarbonyl (PAB) linker. In some embodiments, the linker is an N-succinimidyl 4-(2-pyridylthio) pentanoate (SPP) linker. In some embodiments, the linker is an N-succinimidyl 4-(N-maleimidomethyl) cyclohexane-1-carboxylate (SMCC) linker. In some embodiments, the linker is an N-succinimidyl (4-iodo-acetyl) aminobenzoate (SIAB) linker. In some embodiments, the linker is a 6-maleimidocaproyl-valine-citrulline (MC-VC) linker. In some embodiments, the linker is a 6-maleimidocaproyl-valine-citrulline-p-aminobenzyloxycarbonyl (MC-VC-PAB) linker. In some embodiments, the linker is an N-succinimidyl-1-carboxylate-valine-citrulline-p-aminobenzyloxycarbonyl (SC-VC-PAB) linker. In some embodiments, the linker further comprises a spacer between the linker and the cytotoxic moiety. In some embodiments, the spacer is a heteroatom. In some embodiments, the spacer is an alkyl chain. In some embodiments, the spacer is an alkyl chain comprising one or more heteroatoms. In some embodiments, the spacer is a carbonyl group. In some embodiments, the linker is a homobifuctional linker or a heterobifunctional linker.

In some embodiments, the linkers described herein may be attached to the antibodies or antigen-binding fragments described herein at a naturally occurring amino acid residue such as a lysine or a reduced cysteine. In some embodiments, the linkers can be attached to a non-natural amino acid (e.g., azidophenylalanine, p-acetylphenylalanine, or p-azidomethylphenylalanine) by way of an alkyne/azide "click" reaction, carbonyl condensations, Michael-type additions, and Mizoroki-Heck substitutions. Additional linker sites can be added genetically and may comprise a polypeptide motif that allows enzymatic addition of the linker. Such polypeptide motifs can comprise, e.g., a glutamine tag (e.g., LLQGA (SEQ ID NO: 58)), an aldehyde tag (e.g., CxPxR, where x is any amino acid), a sortase motif (e.g., LPxTG (SEQ ID NO: 59, where x is any amino acid), NPQTN (SEQ ID NO: 60)), or a BirA tag (e.g., GFEIDKVWYDLDA (SEQ ID NO: 61)). Attaching linkers to a glutamine tag may be achieved by using a bacterial transglutaminase. Attaching linkers to an aldehyde tag is achieved by using formylglycine-generating enzyme (FGE), which oxidizes the cysteine residue of the consensus sequence, creating an aldehyde; this aldehyde can be reacted with an aminooxy group on a linker to form a stable oxime. Attaching linkers to a sortase motif can be achieved by using a bacterial transpeptidase that recognizes a C-terminal LPxTG sequence (SEQ ID NO: 59) or NPQTN sequence (SEQ ID NO: 60), cleaves the TG or TN bond, and facilitates—via a thioacyl enzyme-threonine intermediate—the nucleophilic attack of the incoming protein alpha amine on the threonine. The attacking residue can be a glycine dimer or trimer of a linker or added to a linker. Attaching linkers to a sortase motif or a BirA tag can be achieved by using a biotin ligase. In certain embodiments, the linker is not attached at a lysine residue. In certain embodiments, the linker is only attached to a cysteine residue. In certain embodiments, the cysteine residue has been engineered into the antibody by converting one or more non-cysteine residues on the light chain and/or heavy chain to a cysteine. In certain embodiments, cysteine conversion does not interfere with antigen binding. In certain embodiments, selenocysteine is incorporated into the antibody by genetic modification. See, e.g., Sochaj et al., Biotechnology Advances 33:775-784 (2015).

In some embodiments, the linker is conjugated to the anti-ROR1 antibody or fragment by a chemical ligation process. In some embodiments, the linker is conjugated to the anti-ROR1 antibody or fragment by a native ligation. In some embodiments, the conjugation is as described in Dawson et al., Science 266:776-779 (1994); Dawson et al., J. Am. Chem. Soc. 119:4325-4329 (1997); Hackeng et al., PNAS 96:10068-10073 (1999); or Wu et al., Angew. Chem. Int. Ed. 45:4116-4125 (2006). In some embodiments, the conjugation is as described in U.S. Pat. No. 8,936,910. In some embodiments, the linker is conjugated to the anti-ROR1 antibody or fragment either site-specifically or non-specifically via native ligation chemistry.

In some embodiments, the linker is conjugated to the anti-ROR1 antibody or antigen-binding fragment by a site-directed method utilizing a "traceless" coupling technology (Philochem). In some embodiments, the "traceless" coupling technology utilizes an N-terminal 1,2-aminothiol group on the binding moiety which is then conjugated with the antibody or fragment thereof containing an aldehyde group. See, e.g., Casi et al., JACS 134(13):5887-5892 (2012). In some embodiments, the linker is conjugated to the anti-ROR1 antibody or fragment by a site-directed method utilizing an unnatural amino acid incorporated into the binding moiety. In some embodiments, the unnatural amino acid comprises p-acetylphenylalanine (pAcPhe). In some embodiments, the keto group of pAcPhe is selectively coupled to an alkoxy-amine derivatived conjugating moiety to form an oxime bond. See, e.g., Axup et al., PNAS 109(40):16101-16106 (2012).

In some embodiments, the linker is conjugated to the anti-ROR1 antibody or antigen-binding fragment by a sis conjugated to the anti-ROR1 antibody by a site-directed method utilizing an enzyme-catalyzed process. In some embodiments, the site-directed method utilizes SMARTag™ technology (Redwood). In some embodiments, the SMARTag™ technology comprises generation of a formylglycine (FGly) residue from cysteine by formylglycine-generating enzyme (FGE) through an oxidation process under the presence of an aldehyde tag and the subsequent conjugation of FGly to an alkylhydraine-functionalized amino acid molecule via hydrazino-Pictet-Spengler (HIPS) ligation. See, e.g., Wu et al., PNAS 106(9):3000-3005 (2009) and Agarwal et al., PNAS 110(1):46-51 (2013)).

In some embodiments, the enzyme-catalyzed process comprises microbial transglutaminase (mTG). In certain embodiments, the linker is conjugated to the anti-ROR1 antibody or fragment by utilizing a microbial transglutaminase catalyzed process. In some embodiments, mTG catalyzes the formation of a covalent bond between the amide side chain of a glutamine within the recognition sequence and a primary amine of a functionalized amino acid molecule. In some embodiments, mTG is produced from Streptomyces mobarensis. See, e.g., Strop et al., Chemistry and Biology 20(2):161-167 (2013). In some embodiments, the linker is conjugated to the anti-ROR1 antibody by a carbohydrate-based chemical reaction. In the strategy of carbohydrate-based conjugation, the first step is usually to introduce new bioorthogonal functionalities to facilitate conjugation of the antibody to a drug. Strategies that can be used to introduce bioorthogonal functionalities onto the carbohydrate moiety for bioconjugation (glyco-conjugation) include but are not limited to chemical oxidation of glycans; enzymatic and chemo-enzymatic modification of glycans; and metabolic engineering of the carbohydrate moiety. Chemical approaches may use sodium periodate (NaIO4) to oxidize cis-glycol groups of e.g., galactose or sialic acid to generate aldehydes, which then can be coupled with hydrazide- or primary amine functionalized molecules to create acid-labeled hydrazones or with aminooxy groups to form oximes. Enzymatic and chemo-enzymatic approaches treat the sugar residue with neuraminidase (Neu) and galactose oxidase (Gal Oxi) to formate aldehyde functionalities. Continuous treatment of the antibody with β1,4-galactosyltransferase (Gal T)/α2,6-sialyltransferase (Sial T) can yield homogeneously sialylated antibodies. The resulting antibodies then can be selectively oxidized to the corresponding aldehyde functionalities, and if sialic acid derivatives are used, these antibodies can be used as selective bioorthogonal handles. Similarity, the antibody may be treated with (3-galactosidase (Gal) and a mutant Gal T to mediate the attachment of bioorthogonal azide- or keto-galactoses to generate homogeneous G2 glycan patterns which possess non-natural functionalities. Another method makes non-canonical thiofucose derivatives that can be incorporated into the glycan of antibodies by feeding the cells with the bioorthogonal sugar generating expressed antibodies that display thiol functionalities.

Linkers can be conjugated to the anti-ROR1 antibodies and antigen-binding fragments of the current disclosure in multiple ways. Generally a linker and a cytotoxic moiety are synthesized and conjugated before attachment to an antibody. One method of attaching a linker-drug conjugate to an antibody involves reduction of solvent-exposed disulfides with dithiothreitol (DTT) or tris (2-carboxyethyl)phosphine (TCEP), followed by modification of the resulting thiols with maleimide-containing linker-drug moieties (e.g., 6-maleimidocaproyl-valine-citrulline-p-aminobenzyloxycarbonyl (MC-VC-PAB)). A native antibody contains 4 interchain disulfide bonds and 12 intra-chain disulfide bonds, as well as unpaired cysteines. Thus, antibodies modified in this way can comprise greater than one linker-drug moiety per antibody. In certain embodiments, the immunoconjugates described herein comprise at least 1, 2, 3, 4, 5, 6, 7, or 8, 9, or 10 linker/drug moieties. In certain embodiments, the immunoconjugates described herein comprise 1 to 10, 1 to 9, 1 to 8, 1 to 7, 1 to 6, 1 to 5, 1 to 4, 1 to 3, 1 to 2, linker/drug moieties, or 1 linker/drug moiety. In cases where the linker is branched and can each attach to multiple drug moieties, the ratio of the drug moiety to the antibody will be higher than using an unbranched linker.

In some embodiments, the linker is of the formula:

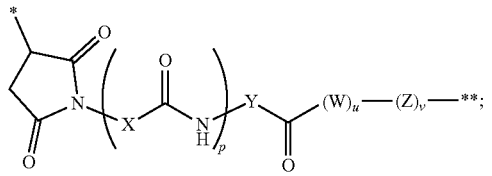

wherein

X is $C_{2-8}$ alkyl;

Y is —$(CH_2CH_2O)_qCH_2CH_2$—;

W is an amino acid unit;

Z is

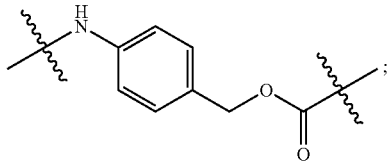

n is 0 or 1;

p is 0 or 1;

q is an integer from 0 to 12;

u is an integer from 0 to 5; and v is 0 or 1; wherein ** indicates the point of attachment to the drug moiety (D); and

* indicates the point of attachment to the antibody or fragment (Ab).

In some embodiments, p is 0. In some embodiments, p is 1. In some embodiments, p is 1 and X is —$(CH_2)_2$—. In some embodiments, p is 1 and X is —$(CH_2)_3$—. In some embodiments, p is 1 and X is —$(CH_2)_4$—. In some embodiments, p is 1 and X is —$(CH_2)_5$—. In some embodiments, p is 1 and X is —$(CH_2)_6$—. In some embodiments, q is an integer from 1 to 12. In some embodiments, q is an integer from 4 to 12. In some embodiments, q is an integer from 4 to 8. In some embodiments, q is 0, 1, 2, 3, 4, 5, 6, 7, 8, 9, 10, 11, or 12. In some embodiments, W is an amino acid unit comprising naturally occurring amino acid residues, as well as minor amino acids and non-naturally occurring amino acid analogs. In some embodiments, W is selected from alanine, valine, leucine, isoleucine, methionine, phenylalanine, tryptophan, proline, lysine protected or not with acetyl or formyl, arginine, arginine protected or not with tosyl or nitro groups, histidine, ornithine, ornithine protected with acetyl or formyl, and citrulline. In some embodiments, u is 1, 2, 3, 4, or 5. In some embodiments, u is 0. In some embodiments, v is 0. In some embodiments, v is 1.

In some embodiments, the linker is of the formula:

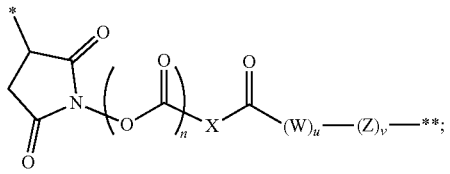

wherein

X is $C_{2-8}$ alkyl;

Y is —$(CH_2CH_2O)_qCH_2CH_2$—;

W is an amino acid unit;

Z is

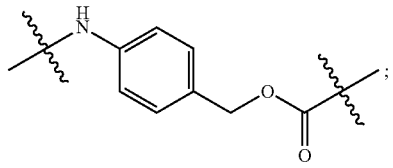

n is 0 or 1;

p is 0 or 1;

q is an integer from 0 to 12;

u is an integer from 0 to 5; and v is 0 or 1; wherein ** indicates the point of attachment to the drug moiety (D); and

* indicates the point of attachment to the antibody or fragment (Ab).

In some embodiments, n is 0. In some embodiments, n is 1. In some embodiments, X is —$(CH_2)_2$—. In some embodiments, X is —$(CH_2)_3$—. In some embodiments, X is —$(CH_2)_4$—. In some embodiments, X is —$(CH_2)_5$—. In some embodiments, X is —$(CH_2)_6$—. In some embodiments, W is an amino acid unit comprising naturally occurring amino acid residues, as well as minor amino acids and non-naturally occurring amino acid analogs. In some embodiments, W is selected from alanine, valine, leucine, isoleucine, methionine, phenylalanine, tryptophan, proline, lysine protected or not with acetyl or formyl, arginine, arginine protected or not with tosyl or nitro groups, histidine, ornithine, ornithine protected with acetyl or formyl, and citrulline. In some embodiments, w is 1, 2, 3, 4, or 5. In some embodiments, w is 0. In some embodiments, v is 0. In some embodiments, v is 1.

In some embodiments, the immunoconjugate optionally further comprises an endosomolytic moiety. In some cases, the endosomolytic moiety is a cellular compartmental release component, such as a compound capable of releasing from any of the cellular compartments known in the art, such as the endosome, lysosome, endoplasmic reticulum (ER), Golgi apparatus, microtubule, peroxisome, or other vesicular bodies with the cell. In some cases, the endosomolytic moiety comprises an endosomolytic polypeptide, an endosomolytic polymer, an endosomolytic lipid, or an endosomolytic small molecule. In some cases, the endosomolytic moiety comprises an endosomolytic polypeptide. In other cases, the endosomolytic moiety comprises an endosomolytic polymer. In some embodiments, an endosomolytic polymer described herein is a pH-responsive endosomolytic polymer. A pH-responsive polymer comprises a polymer that increases in size (swells) or collapses depending on the pH of the environment. Polyacrylic acid and chitosan are examples of pH-responsive polymers. In some embodiments, an endosomolytic moiety described herein is a membrane-disruptive polymer. In some cases, the membrane-disruptive polymer comprises a cationic polymer, a neutral or hydrophobic polymer, or an anionic polymer. In some embodiments, the membrane-disruptive polymer is a hydrophilic polymer. In some embodiments, p(alkylacrylic acids)

include poly(propylacrylic acid) (polyPAA), poly(methacrylic acid) (PMAA), poly(ethylacrylic acid) (PEAA), and poly(propyl acrylic acid) (PPAA). In some embodiments, a p(alkylacrylic acid) described herein may be a p(alkylacrylic acid) described in Jones, et al., Biochemistry Journal 372: 65-75 (2003). In some embodiments, a pH-responsive membrane-disruptive polymer comprises p(butyl acrylate-co-methacrylic acid). See, e.g., Bulmus, et al., Journal of Controlled Release 93:105-120 (2003); and Yessine et al., Biochimica et Biophysica Acta 1613:28-38 (2003). In some embodiments, a pH-responsive membrane-disruptive polymer comprises p(styrene-alt-maleic anhydride). See, e.g., Henry et al., Biomacromolecules 7:2407-2414 (2006). In some embodiments, a pH-responsive membrane-disruptive polymer comprises a pyridyldisulfide acrylate (PDSA) polymer such as poly(MAA-co-PDSA), poly(EAA-co-PDSA), poly(PAA-co-PDSA), poly(MAA-co-BA-co-PDSA), poly (EAA-co-BA-co-PDSA), or poly(PAA-co-BA-co-PDSA) polymer. See, e.g., El-Sayed et al., Journal of Controlled Release 104:417-427 (2005); or Flanary et al., Bioconjugate Chem. 20:241-248 (2009). In some embodiments, the endosomolytic moiety is a lipid (e.g., a fusogenic lipid). In some embodiments, a molecule of Formula (I): A-X-B-Y-C is further conjugated with an endosomolytic lipid (e.g., fusogenic lipid). Exemplary fusogenic lipids include 1,2-dileoyl-sn-3-phosphoethanolamine (DOPE), phosphatidylethanolamine (POPE), palmitoyloleoylphosphatidylcholine (POPC), (6Z,9Z,28Z,31Z)-heptatriaconta-6,9,28,31-tetraen-19-ol (Di-Lin), N-methyl(2,2-di((9Z,12Z)-octadeca-9,12-dienyl)-1,3-dioxolan-4-yl)methanamine (DLin-k-DMA) and N-methyl-2-(2,2-di((9Z,12Z)-octadeca-9,12-dienyl)-1,3-dioxolan-4-yl)ethanamine (XTC). Exemplary small molecules suitable as endosomolytic moieties include, but are not limited to, quinine, chloroquine, hydroxychloroquines, amodiaquins (carnoquines), amopyroquines, primaquines, mefloquines, nivaquines, halofantrines, quinone imines, or any combination thereof.

The term "linkage," as used herein, refer to a bond or chemical moiety formed from a chemical reaction between the functional group of one molecular entity and another molecule entity. Such bonds may include, but are not limited to, covalent and non-covalent bonds, while such chemical moieties may include, but are not limited to, esters, carbonates, carbamates, imines phosphate esters, hydrazones, acetals, orthoesters, peptide linkages, and oligonucleotide linkages. Hydrolytically stable linkage means that the linkage is substantially stable in water and does not react with water at useful pH values, including but not limited to under physiological conditions, for an extended period of time, perhaps even indefinitely. Hydrolytically unstable or degradable linkage means that the linkage is degradable in water or in aqueous solutions, including, for example, blood. Enzymatically unstable or degradable linkage means that the linkage can be degraded by one or more enzymes. By way of example only, PEG and related polymers may include degradable linkages in the polymer backbone or in the linker group between the polymer backbone and one or more of the terminal functional groups of the polymer molecule. Such degradable linkages include, but are not limited to, ester linkages formed by the reaction of PEG carboxylic acids or activated PEG carboxylic acids with alcohol groups on a biologically active agent, wherein such ester groups generally hydrolyze under physiological conditions to release the biologically active agent. Other hydrolytically degradable linkages include but are not limited to carbonate linkages; imine linkages resulted from reaction of an amine and an aldehyde; phosphate ester linkages formed by reacting an alcohol with a phosphate group; hydrazone linkages which are reaction product of a hydrazide and an aldehyde; acetal linkages that are the reaction product of an aldehyde and an alcohol; orthoester linkages that are the reaction product of a formate and an alcohol; peptide linkages formed by an amine group, including but not limited to, at an end of a polymer such as PEG, and a carboxyl group of a peptide; and oligonucleotide linkages formed by a phosphoramidite group, including but not limited to, at the end of a polymer, and a 5' hydroxyl group of an oligonucleotide.

1.7 Exemplary ROR1 Immunoconjugates

In some embodiments, the ADC of the present invention has the structure:

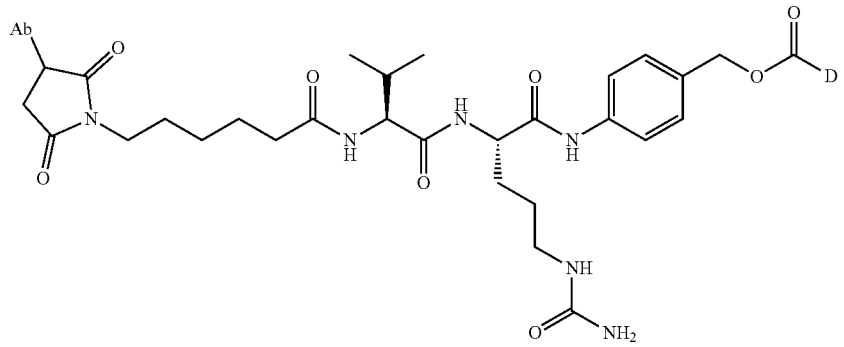

wherein Ab is an antibody and D is a drug moiety. In some embodiments, the ADC has the structure:
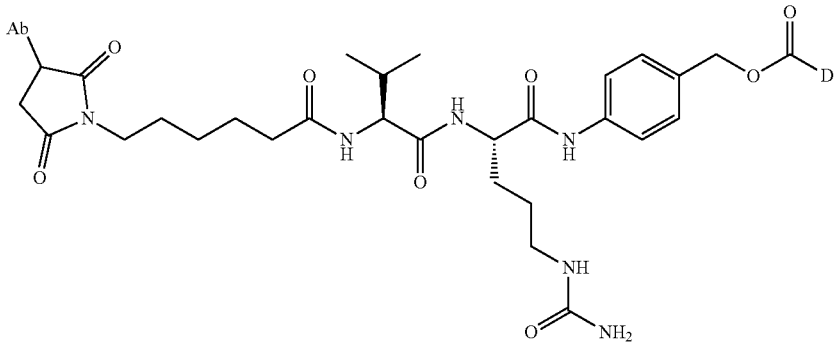
wherein Ab is an antibody and D is monomethyl auristatin E (MMAE). In some embodiments, the ADC has the structure:
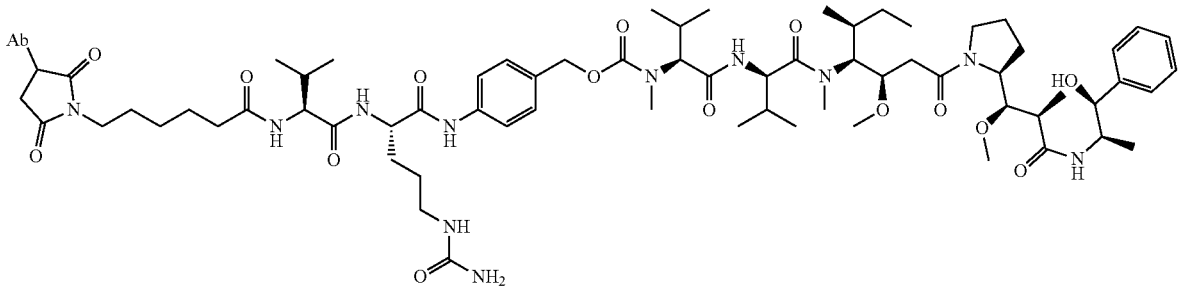
wherein Ab is an antibody. In some embodiments, the ADC has the structure:
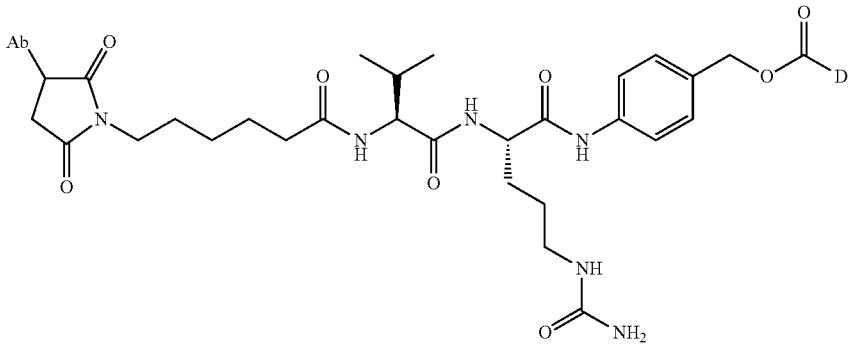

wherein Ab is an antibody and D is mertansine (also called DM1). In some embodiments, the ADC has the structure:

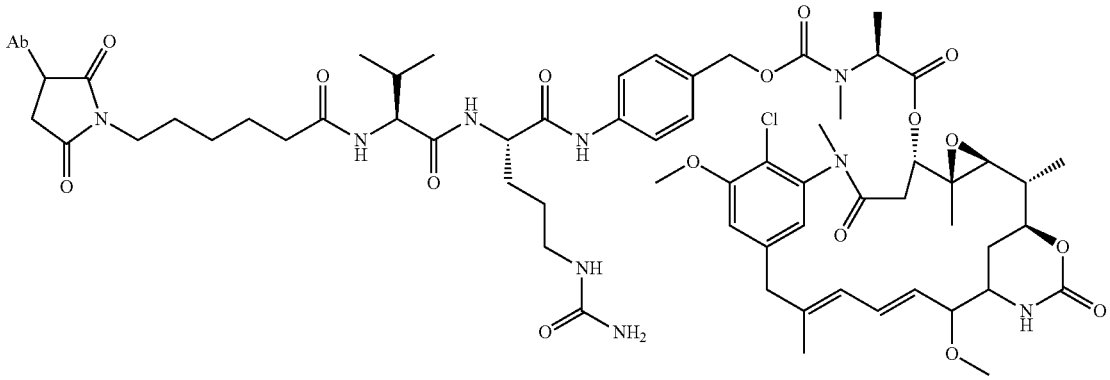

wherein Ab is an antibody.

In some embodiments, the ADC has the structure:

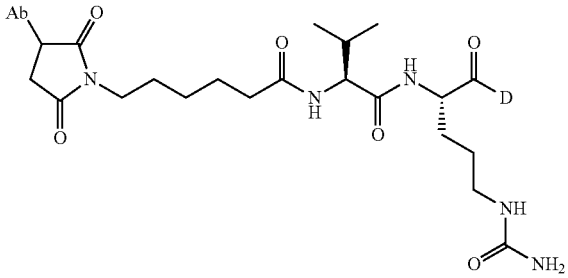

wherein Ab is an antibody and D is a drug moiety. In some embodiments, the ADC has the structure:

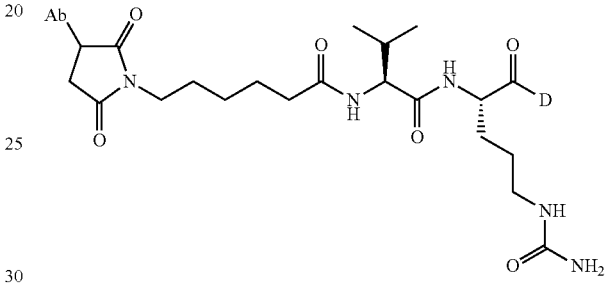

wherein Ab is an antibody and D is mertansine. In some embodiments, the ADC has the structure:

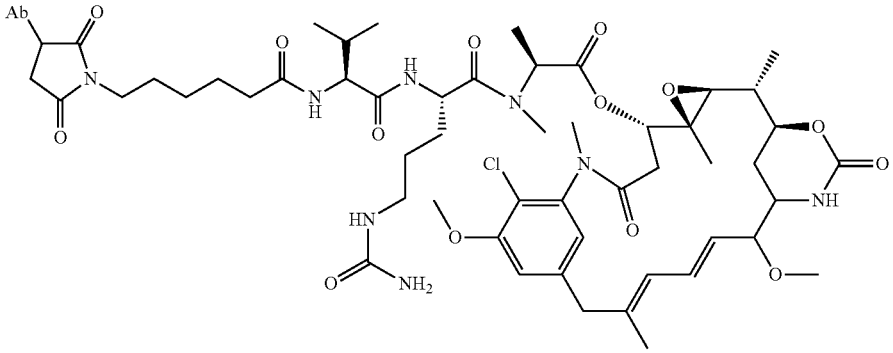

wherein Ab is an antibody.

In some embodiments, the ADC has the structure:

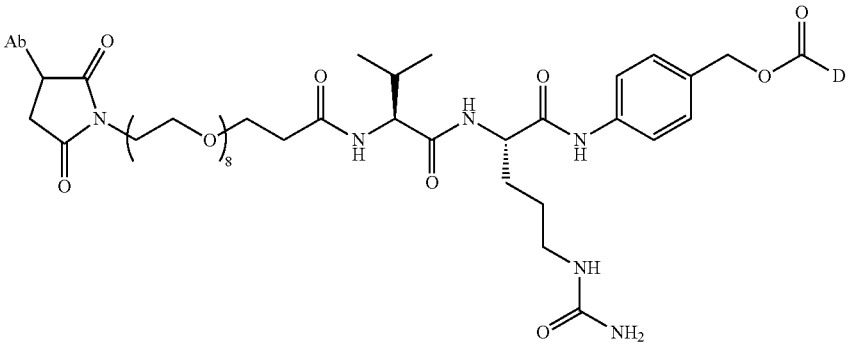

wherein Ab is an antibody and D is a drug moiety. In some embodiments, the ADC has the structure:

wherein Ab is an antibody and D is a dimeric pyrrolobenzodiazepine (PBD). In some embodiments, the ADC has the structure:

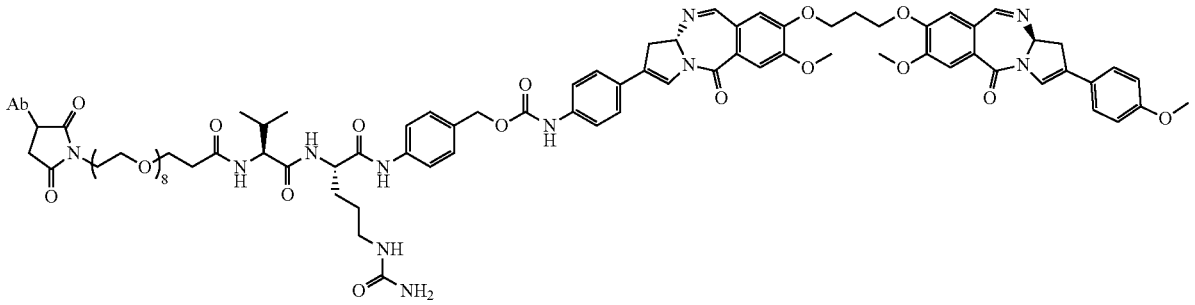

wherein Ab is an antibody.

In some embodiments, the ADC has the structure:

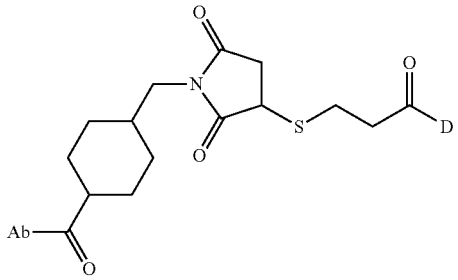

wherein Ab is an antibody and D is a drug moiety. In some embodiments, the ADC has the structure:

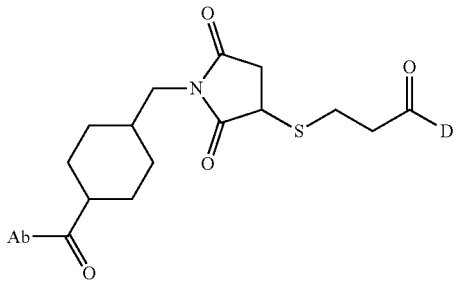

wherein Ab is an antibody and D is mertansine. In some embodiments, the ADC has the structure:

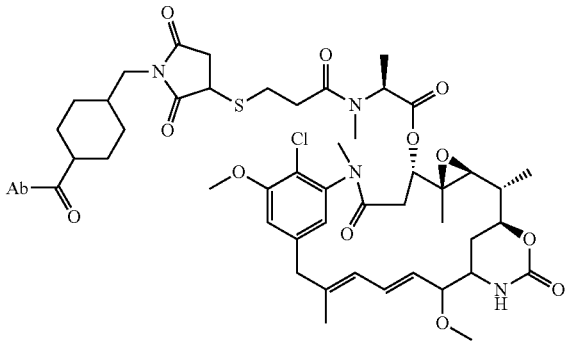

wherein Ab is an antibody.

In some embodiments, the ADC has the structure:

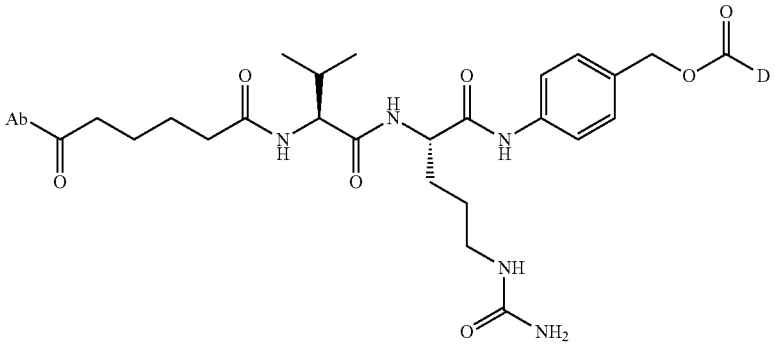

wherein Ab is an antibody and D is a drug moiety. In some embodiments, the ADC has the structure:
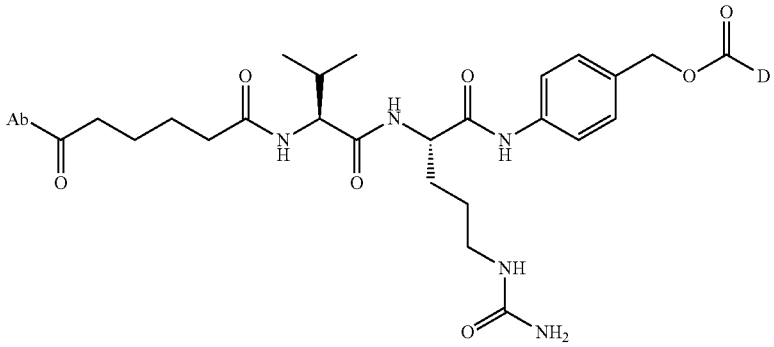
wherein Ab is an antibody and D is MMAE. In some embodiments, the ADC has the structure:
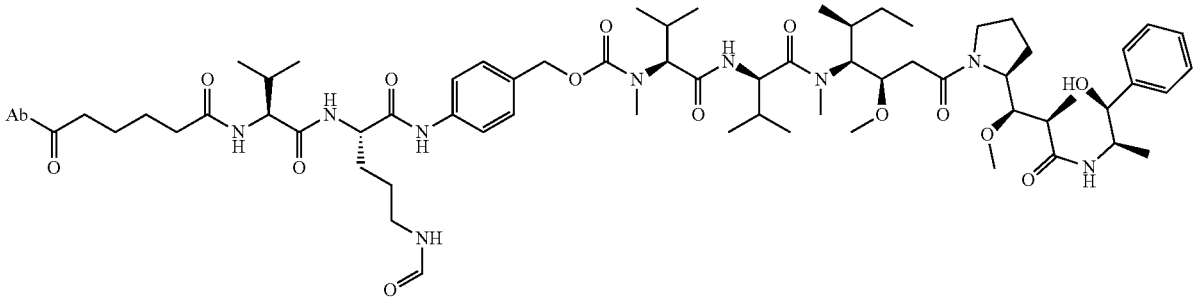
wherein Ab is an antibody. In some embodiments, the ADC has the structure:
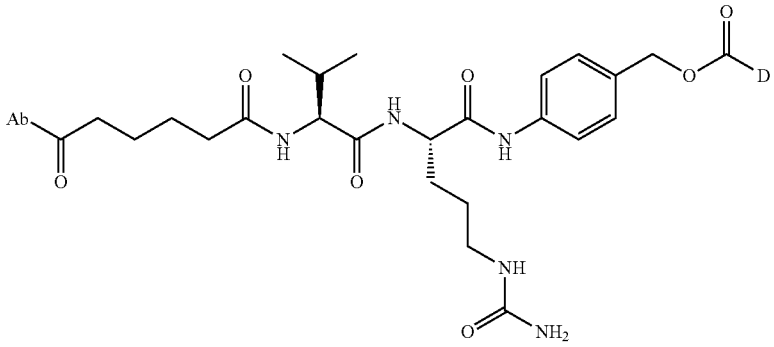

wherein Ab is an antibody and D is mertansine. In some embodiments, the ADC has the structure:

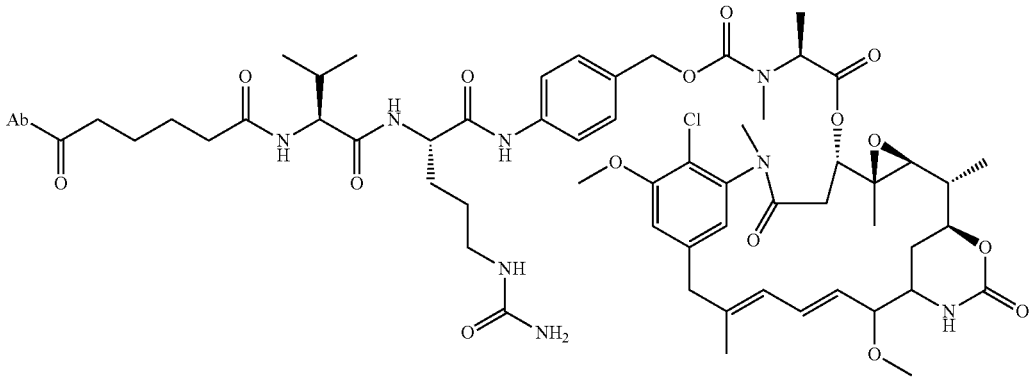

wherein Ab is an antibody.

In some embodiments, the ADC has the structure:

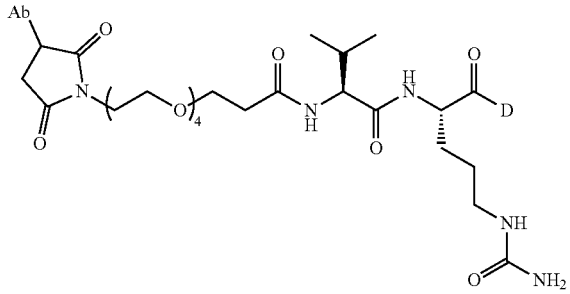

wherein Ab is an antibody and D is a drug moiety. In some embodiments, the ADC has the structure:

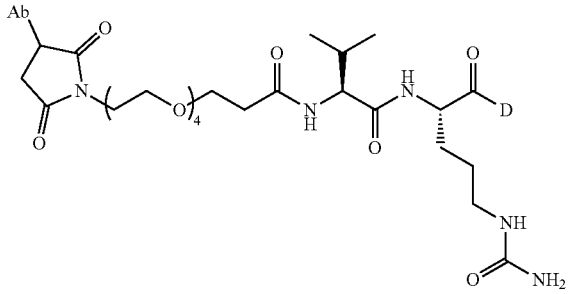

wherein Ab is an antibody and D is a duocarmycin. In some embodiments, the ADC has the structure:

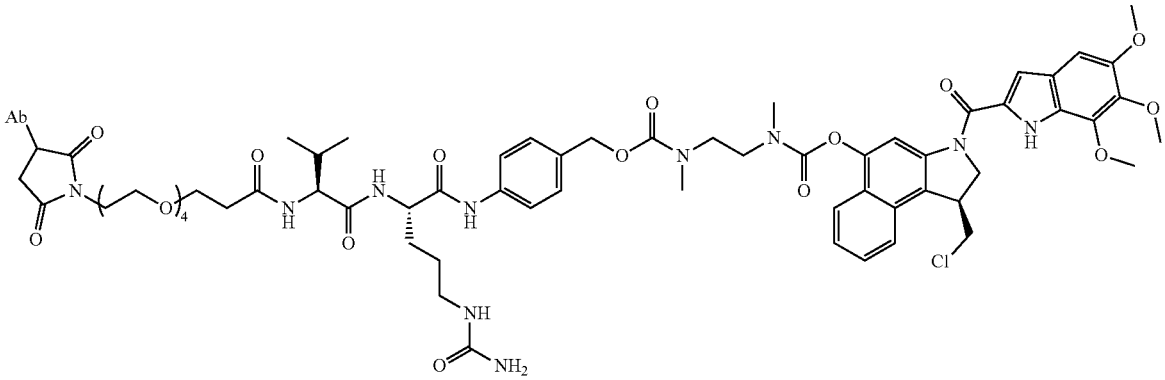

wherein Ab is an antibody.

In some embodiments, the ADC has the structure:
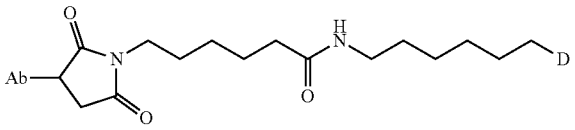
wherein Ab is an antibody and D is a drug moiety. In some embodiments, the ADC has the structure:
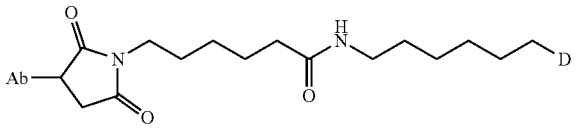
wherein Ab is an antibody and D is an amanitin, such as a-amanitin. In some embodiments, the ADC has the structure:
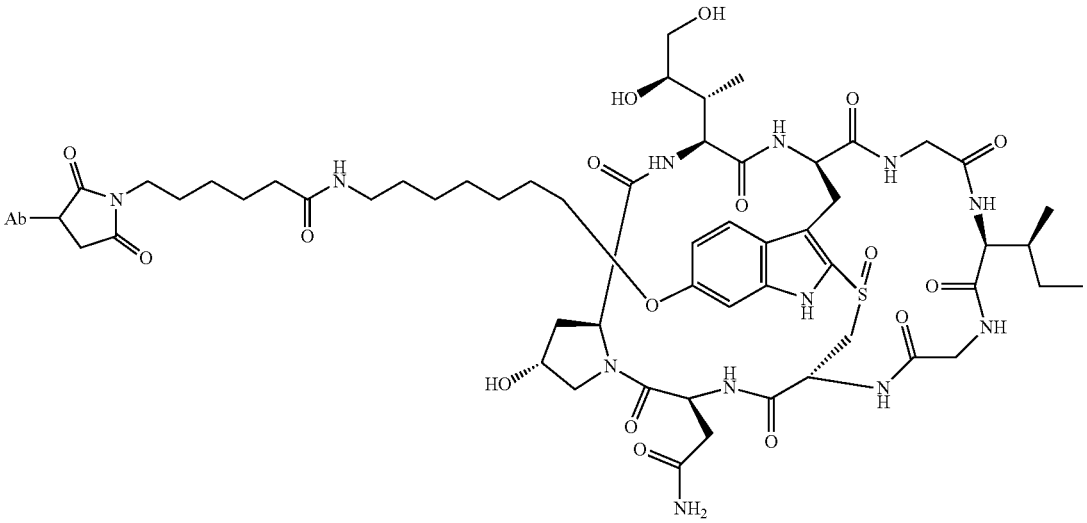
wherein Ab is an antibody.
In some embodiments, the ADC has the structure:
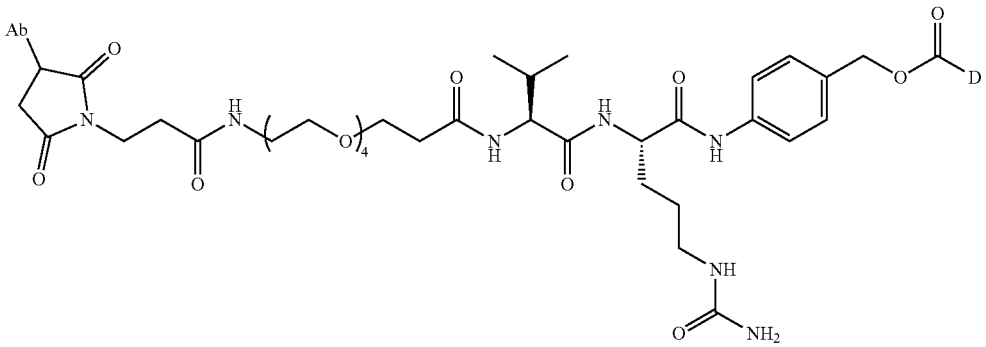

wherein Ab is an antibody and D is a drug moiety. In some embodiments, the ADC has the structure:
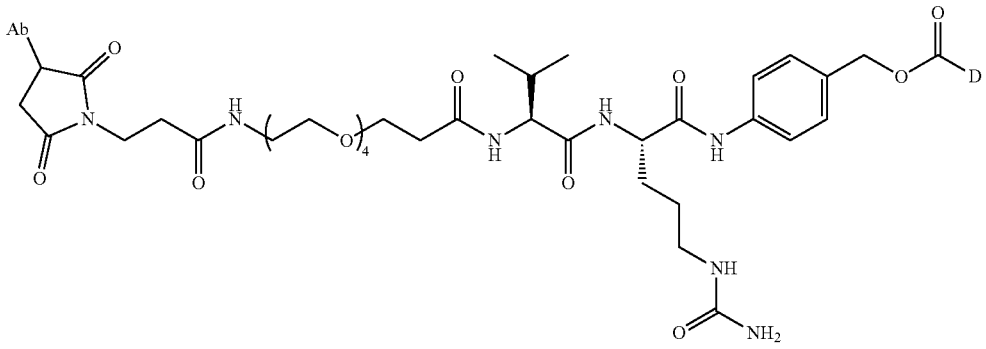
wherein Ab is an antibody and D is PNU159682. In some embodiments, the ADC has the structure:

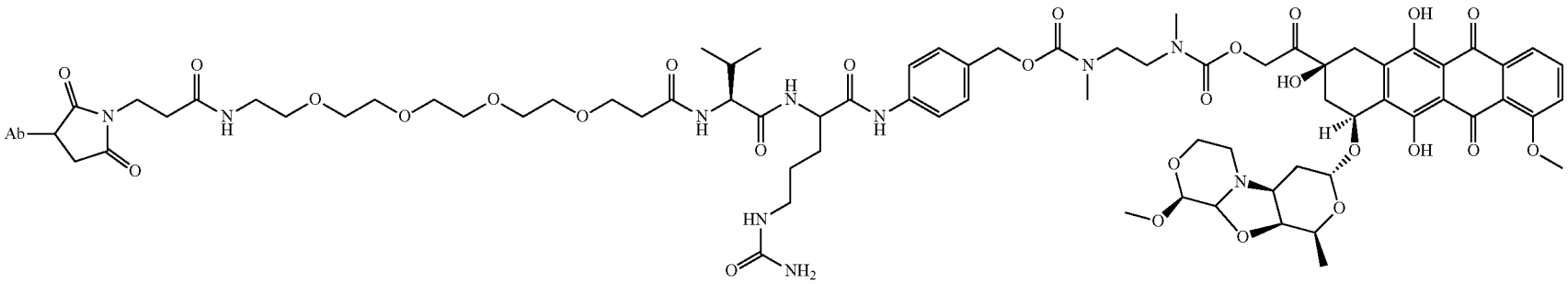

wherein Ab is an antibody.
In some embodiments, the ADC has the structure:
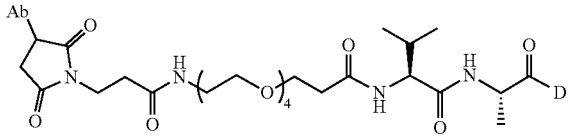
wherein Ab is an antibody and D is a drug moiety. In some embodiments, the ADC has the structure:
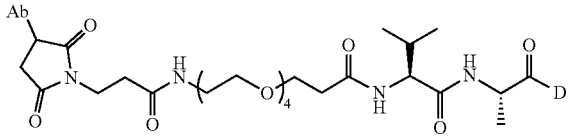
wherein Ab is an antibody and D is PBD. In some embodiments, the ADC has the structure:

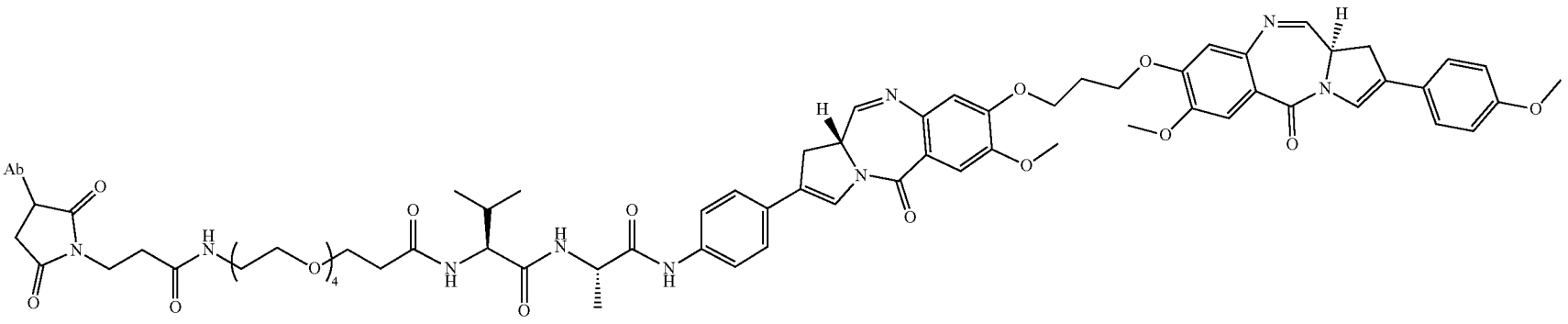

wherein Ab is an antibody.

Exemplary immunoconjugates of the present invention are shown in the table below:

TABLE 2

Exemplary Immunoconjugates

| Construct ID | mAb | Conjugation | Linker Components | | | | Payload |
|---|---|---|---|---|---|---|---|
| ADC-A | Ab1 | MAL (mc) | | VC | PAB | | MMAE |
| ADC-E | Ab1 | SC | | VC | PAB | | MMAE |
| ADC-B | Ab1 | SMCC | | | | | DM1 |
| ADC-C | Ab1 | MAL | | VC | PAB | | DM1 |
| ADC-F | Ab1 | SC | | VC | PAB | | DM1 |
| ADC-H | Ab1 | MAL | | VC | PAB | | azonafide |
| ADC-I | Ab1 | MAL (mc) | | | | C6 | α-amanitin |
| ADC-J | Ab1 | MAL | PEG4 | VC | PAB | DMEA | Duocarmycin TM |
| ADC-K | Ab1 | MAL | PEG4 | VA | | | PBD |
| ADC-L | Ab1 | MAL | DPR | VC | PAB | | MMAE |
| ADC-M | Ab1 | MAL | Phe-C4 | VC | PAB | | MMAE |
| ADC-N | Ab1 | MAL | PEG4 | VC | PAB | DMEA | PNU-159682 |
| ADC-O | Ab1 | MAL | C2-Gly3 | | | EDA | PNU-159682 |
| ADC-P | Ab1 | MAL | Phe-C4 | VC | PAB | DMEA | PNU-159682 |
| ADC-Q# | Ab1* | DBCO | (PEG2 | VC | PAB | | MMAE)2 |
| ADC-R | Ab1* | DBCO | PEG4 | VC | PAB | DMEA | PNU-159682 |
| ADC-S | D10 | MAL | | VC | PAB | | MMAE |
| ADC-T | 4A5 | MAL | | VC | PAB | | MMAE |

#Branched linker-payload.

*Site-specific conjugation using microbial transglutaminase.

In the above table, the abbreviations are used as follows: maleimide chemistry (MAL); maleimidocaproyl (mc); succinimide chemistry (SC); succinimidyl 4-(N-maleimidomethyl)cyclohexane-1-carboxylate) (SMCC); dibenzylcyclooctyne (DBCO); diaminopropionic acid (DPR); benzyl (Phe); polyethylene glycol (PEG); valine-citrulline (VC); valine-alanine (VA); para-amino-benzyloxycarbonyl (self immolative moiety) (PAB); dimethylethylamine (DMEA); ethylene diamine (EDA); monomethyl auristatin E (MMAE); N2'-Deacetyl-N2'-(3-mercaptol-oxopropyl)maytansine (DM1); and pyrrolobenzodiazepine (PBD), [1,2] Diazepino[3,4-e]indole. For ADC-Q and ADC-R, site-specific conjugation of the payload may be made by using microbial transglutaminase.

The chemical structures of immunoconjugates in Table 2 are shown in the table below:

TABLE 3
| Chemical Structures of Exemplary Immunoconjugates | |
|---|---|
| ADC | Structure |
| A | 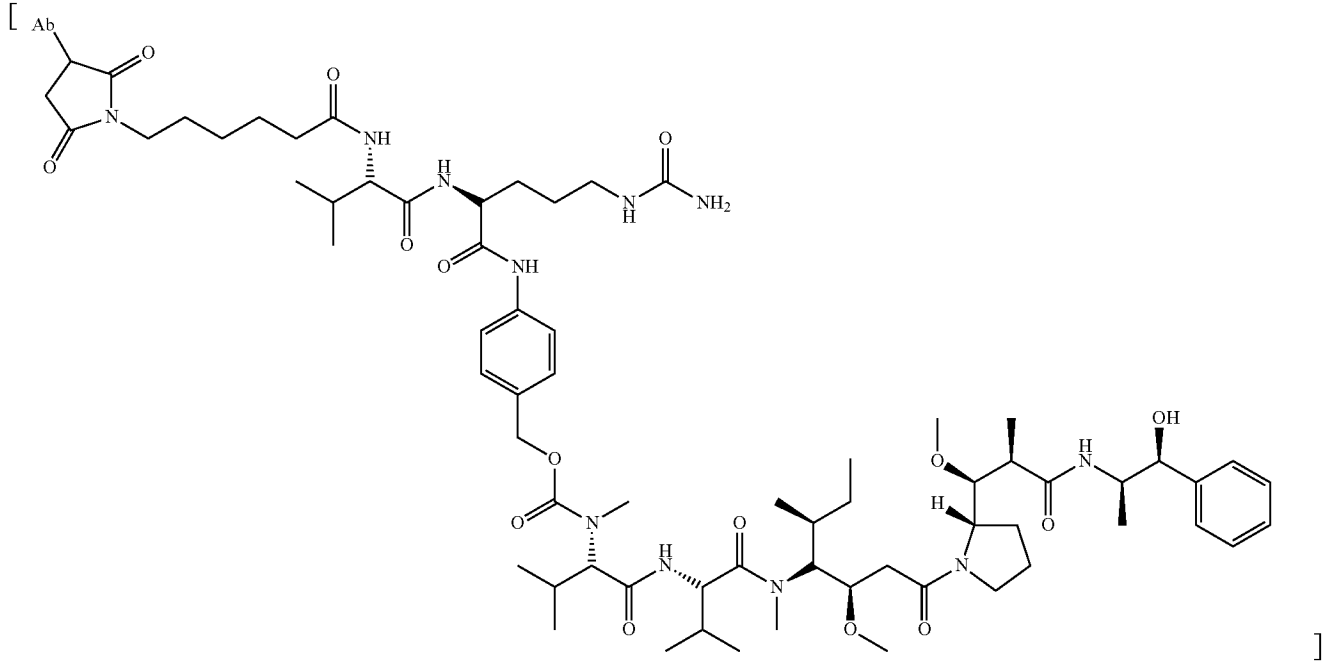 |

TABLE 3-continued
Chemical Structures of Exemplary Immunoconjugates
| ADC | Structure |
|---|---|
| | 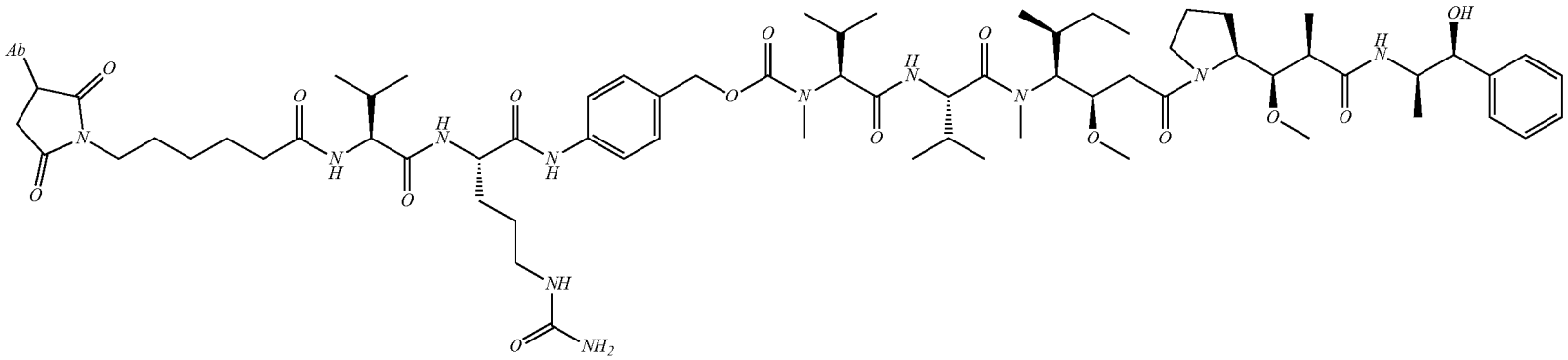 |
| E | 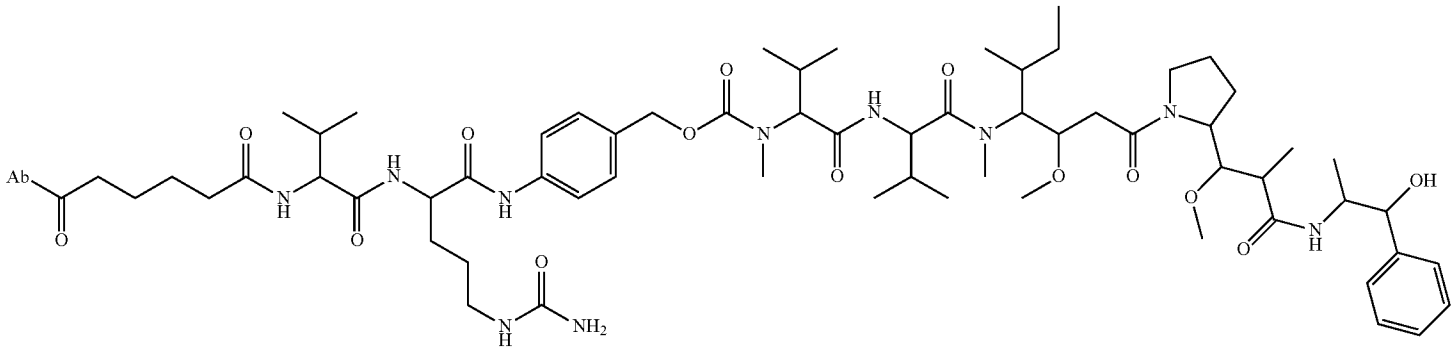 |

TABLE 3-continued
| Chemical Structures of Exemplary Immunoconjugates | |
|---|---|
| ADC | Structure |
| B | 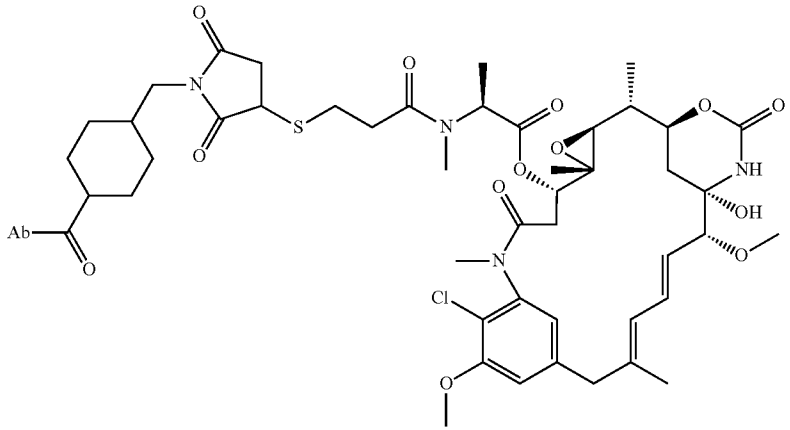 |
| C | 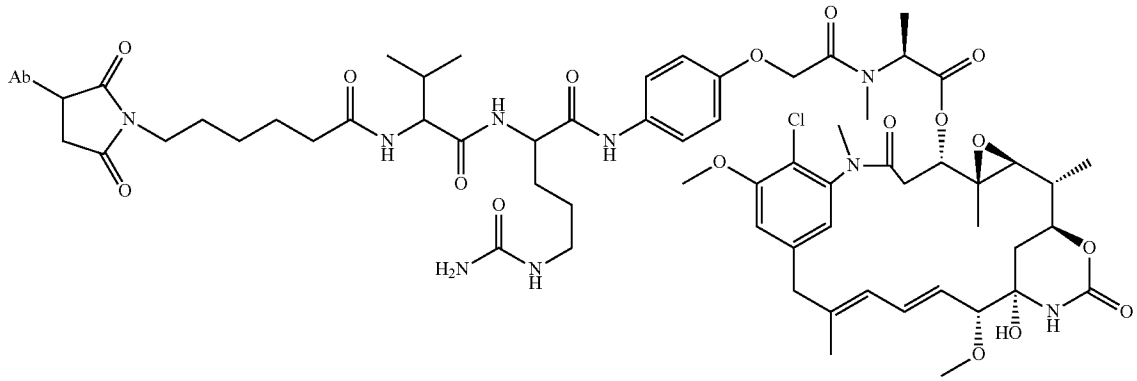 |

TABLE 3-continued
Chemical Structures of Exemplary Immunoconjugates
| ADC | Structure |
|---|---|
| F | 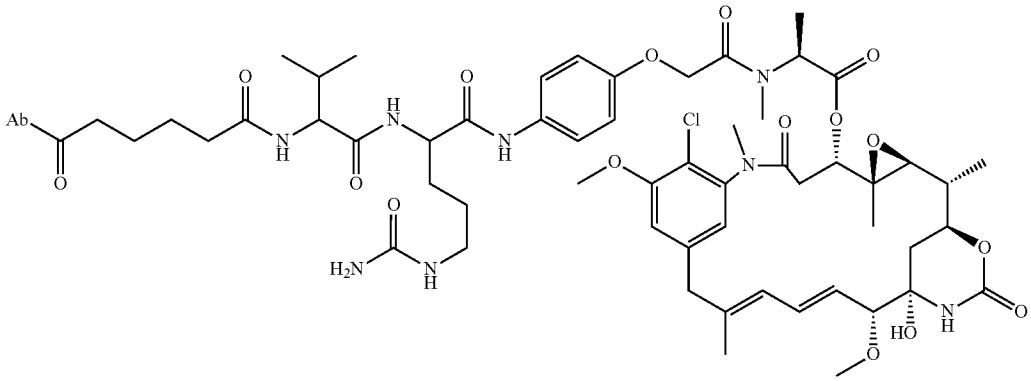 |

TABLE 3-continued
Chemical Structures of Exemplary Immunoconjugates
| ADC | Structure |
|---|---|
| H | 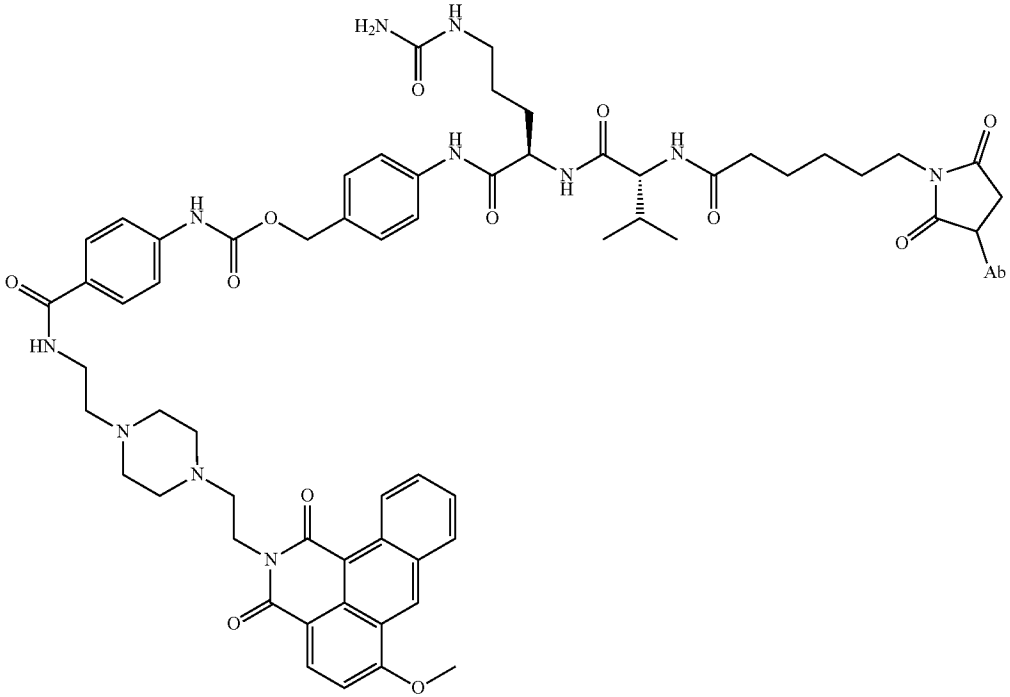 |

TABLE 3-continued
Chemical Structures of Exemplary Immunoconjugates
| ADC | Structure |
|---|---|
| I | 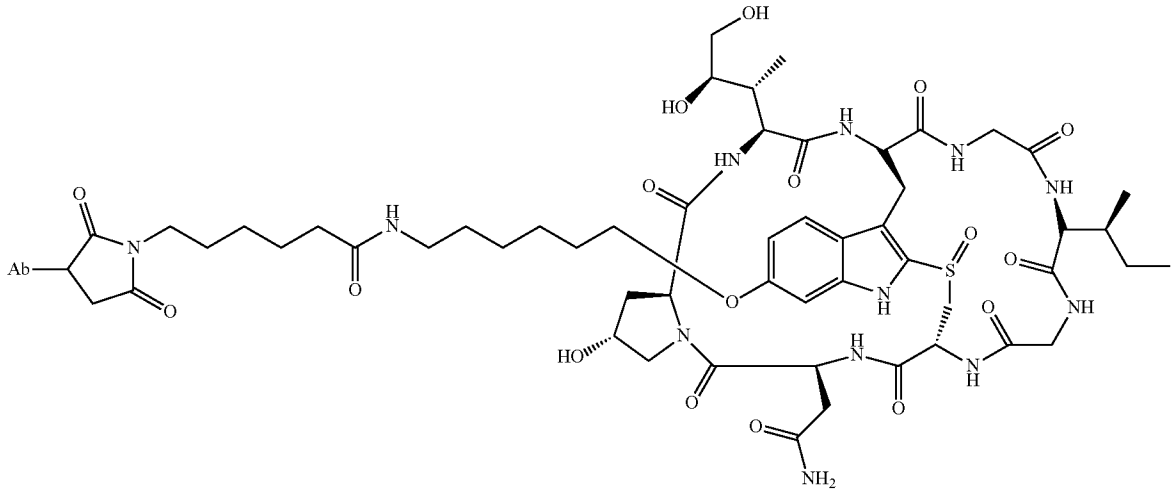 |
| J | 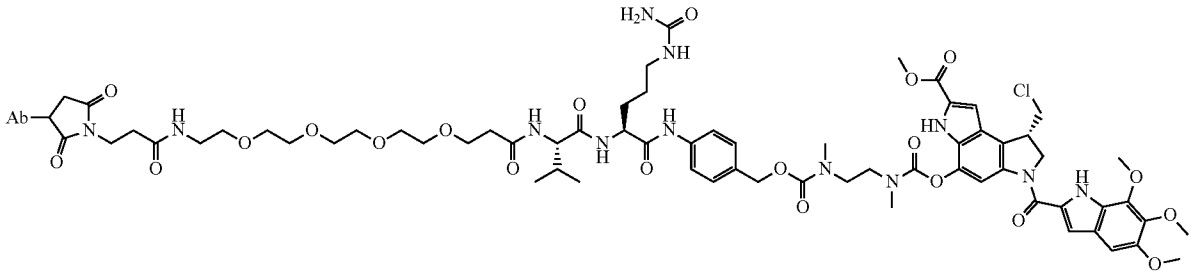 |
| K | 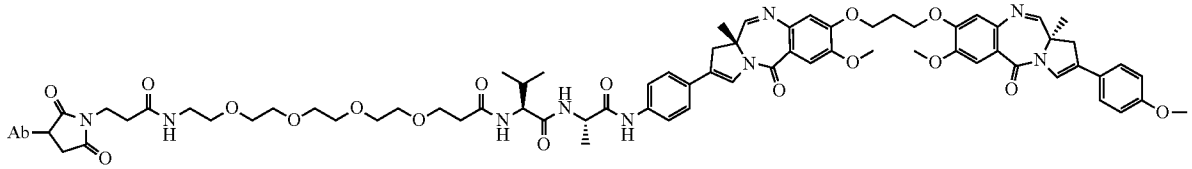 |

TABLE 3-continued
Chemical Structures of Exemplary Immunoconjugates
| ADC | Structure |
|---|---|
| L | 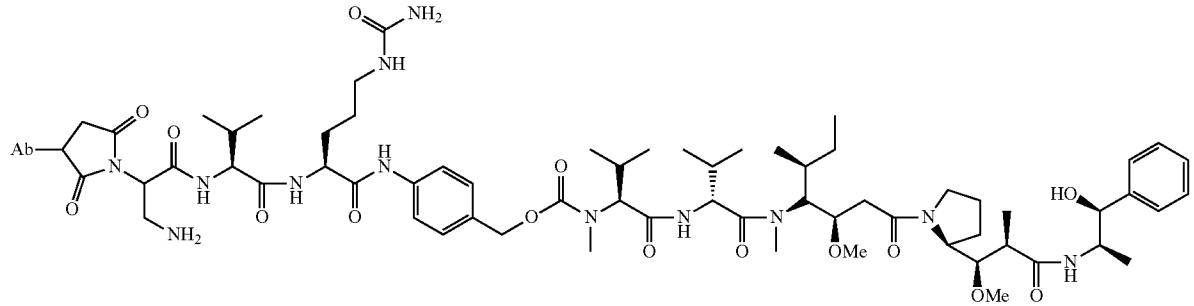 |
| M | 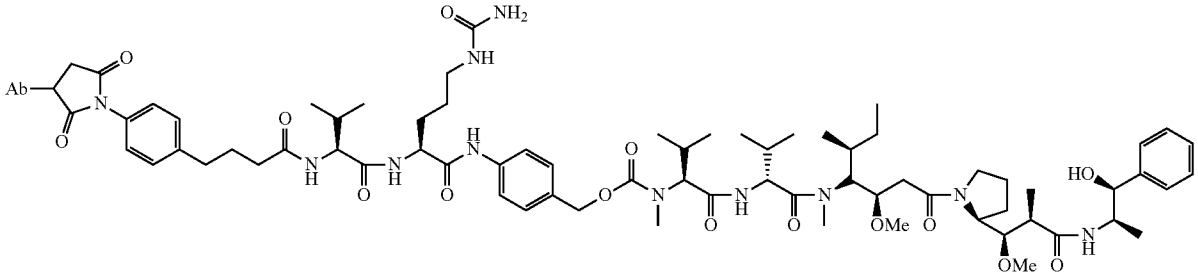 |
| N | 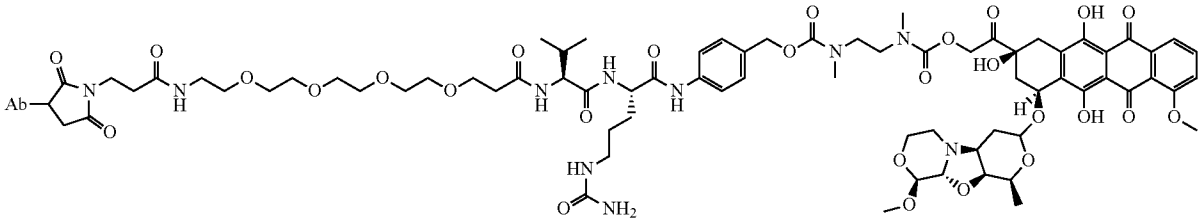 |

TABLE 3-continued
| Chemical Structures of Exemplary Immunoconjugates | |
|---|---|
| ADC | Structure |
| O | 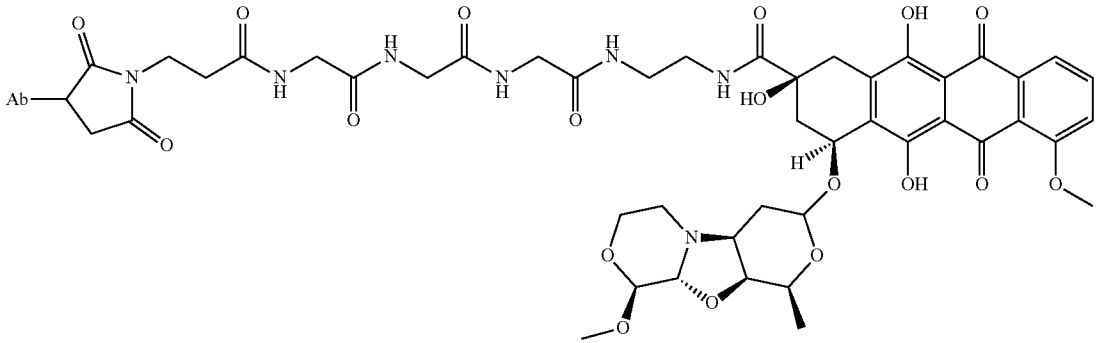 |
| P | 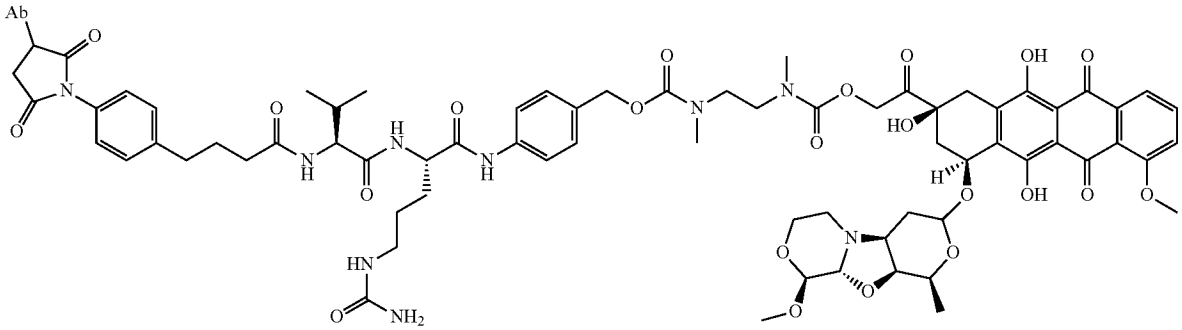 |

TABLE 3-continued
Chemical Structures of Exemplary Immunoconjugates
| ADC | Structure |
|---|---|
| Q | 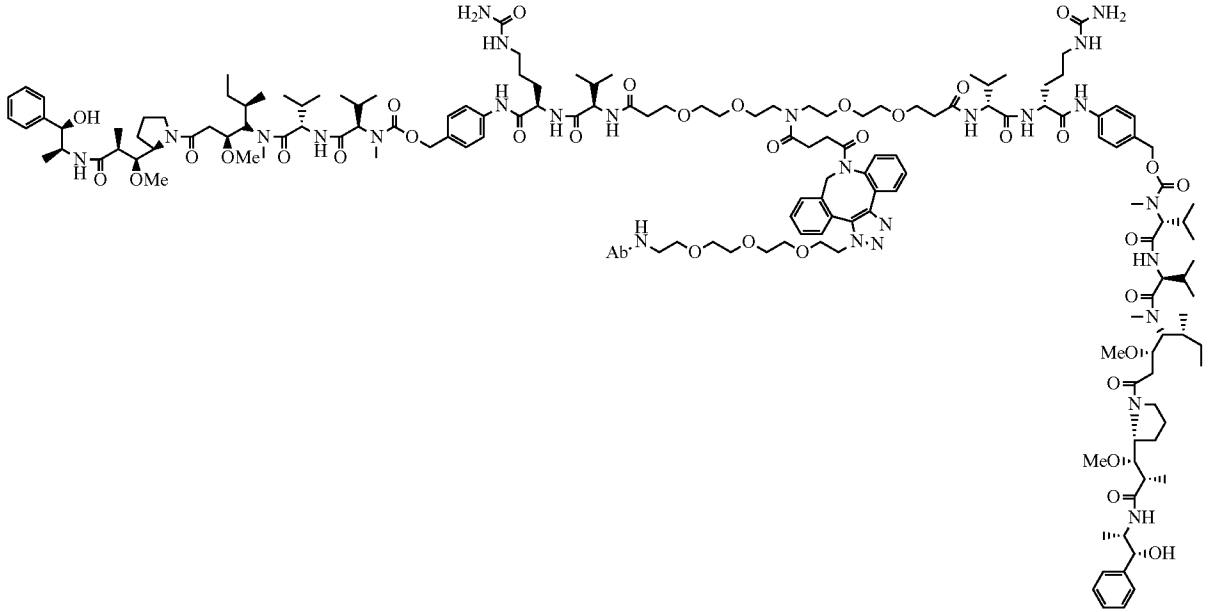 |

TABLE 3-continued
| Chemical Structures of Exemplary Immunoconjugates | |
|---|---|
| ADC | Structure |
| R | 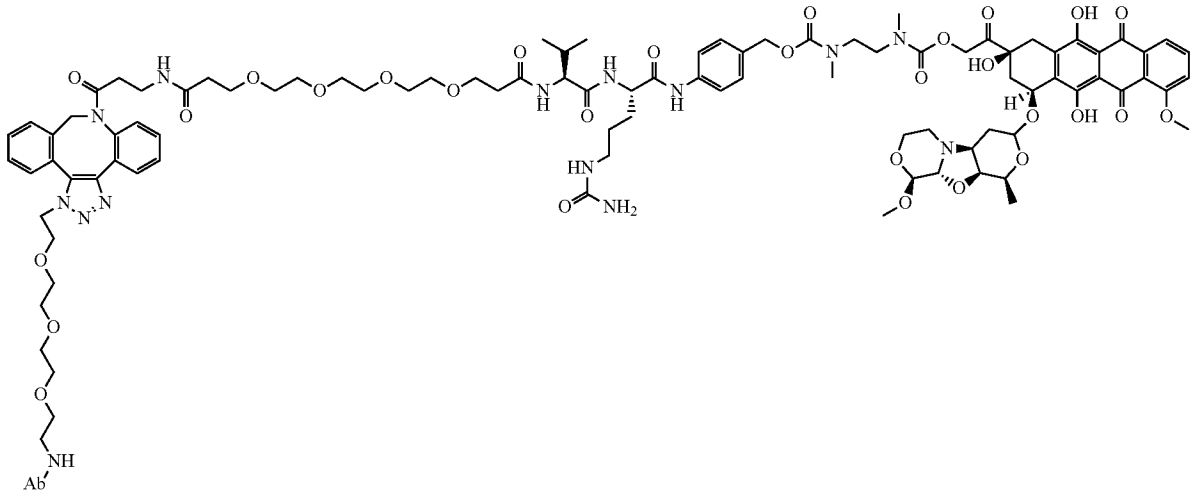 |

TABLE 3-continued
Chemical Structures of Exemplary Immunoconjugates
| ADC | Structure |
|---|---|
| S | 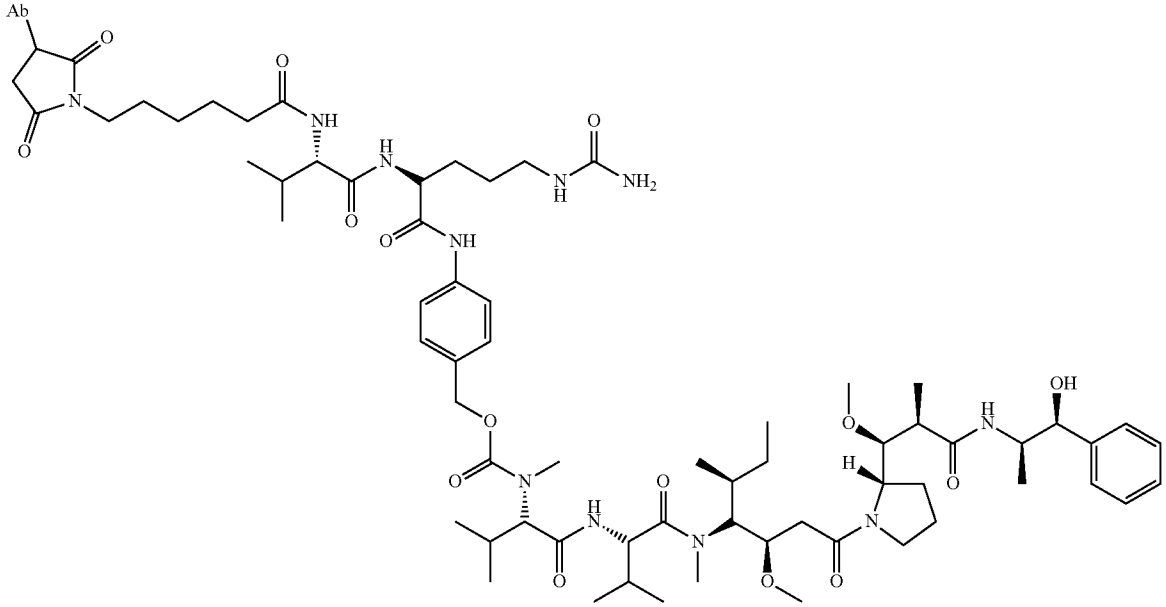 |

TABLE 3-continued
Chemical Structures of Exemplary Immunoconjugates
| ADC | Structure |
|---|---|
| T | 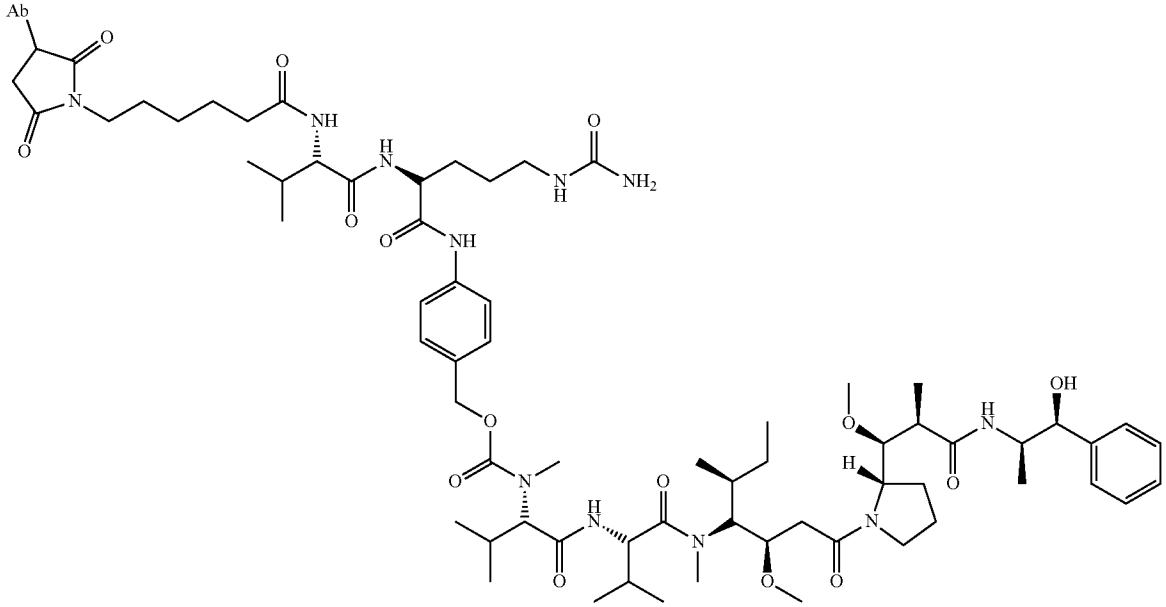 |

2. Synthesis of Immunoconjugates

In some embodiments, the immunoconjugates described herein are prepared as shown in Schemes 1 and 2. MMAE is prepared in 12 steps starting from L-isoleucine as outlined in Scheme 1. As shown in Scheme 2, MMAE prepared in Scheme 1 is coupled with the 4-nitrophenyl carbonate of a FMOC protected valine-citrulline-p-aminobenzyloxycarbonyl (VC-PAB) linker. Deprotection of the FMOC group gives the VC-PAB-MMAE linker-MMAE construct.

Scheme 1

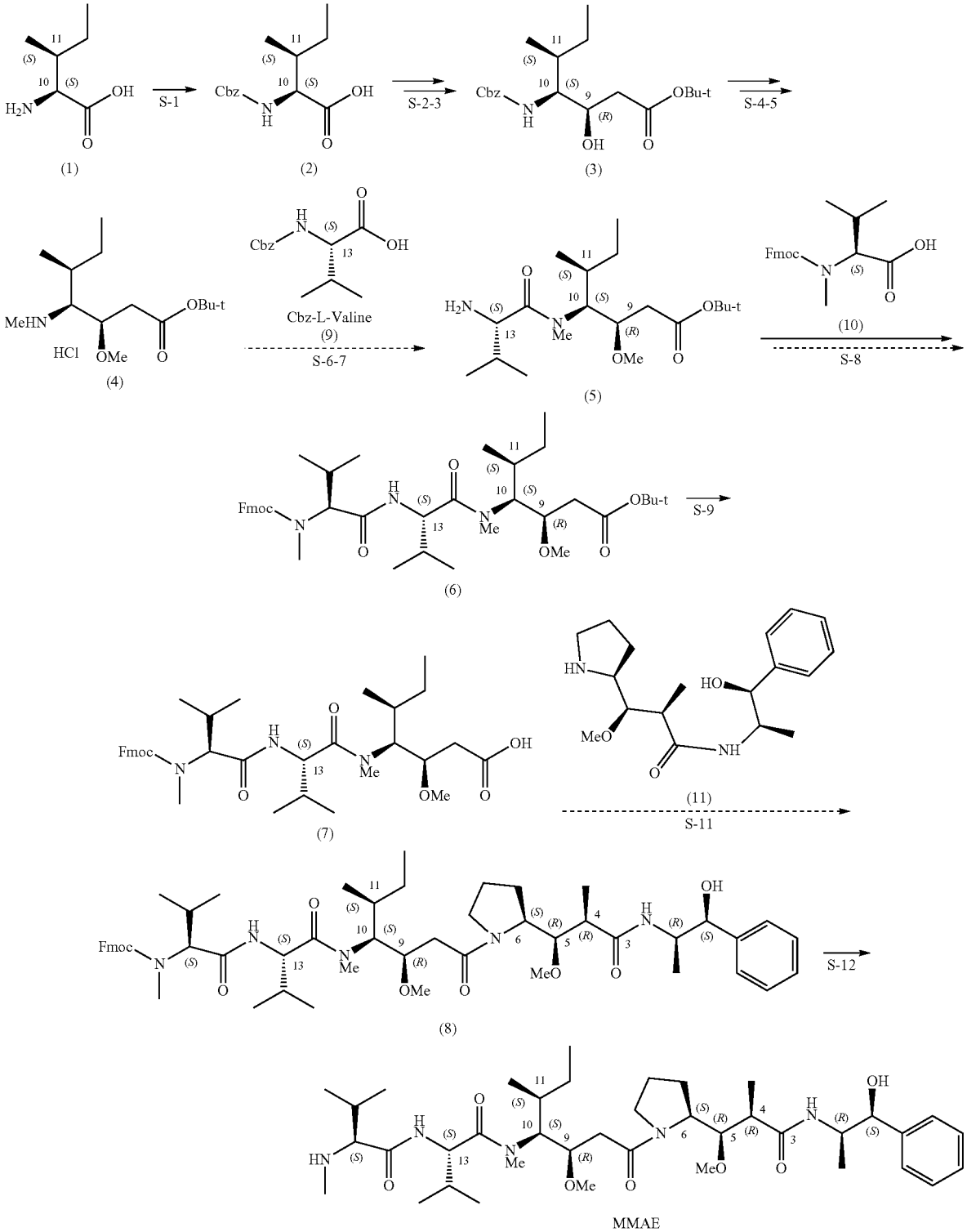

Scheme 2

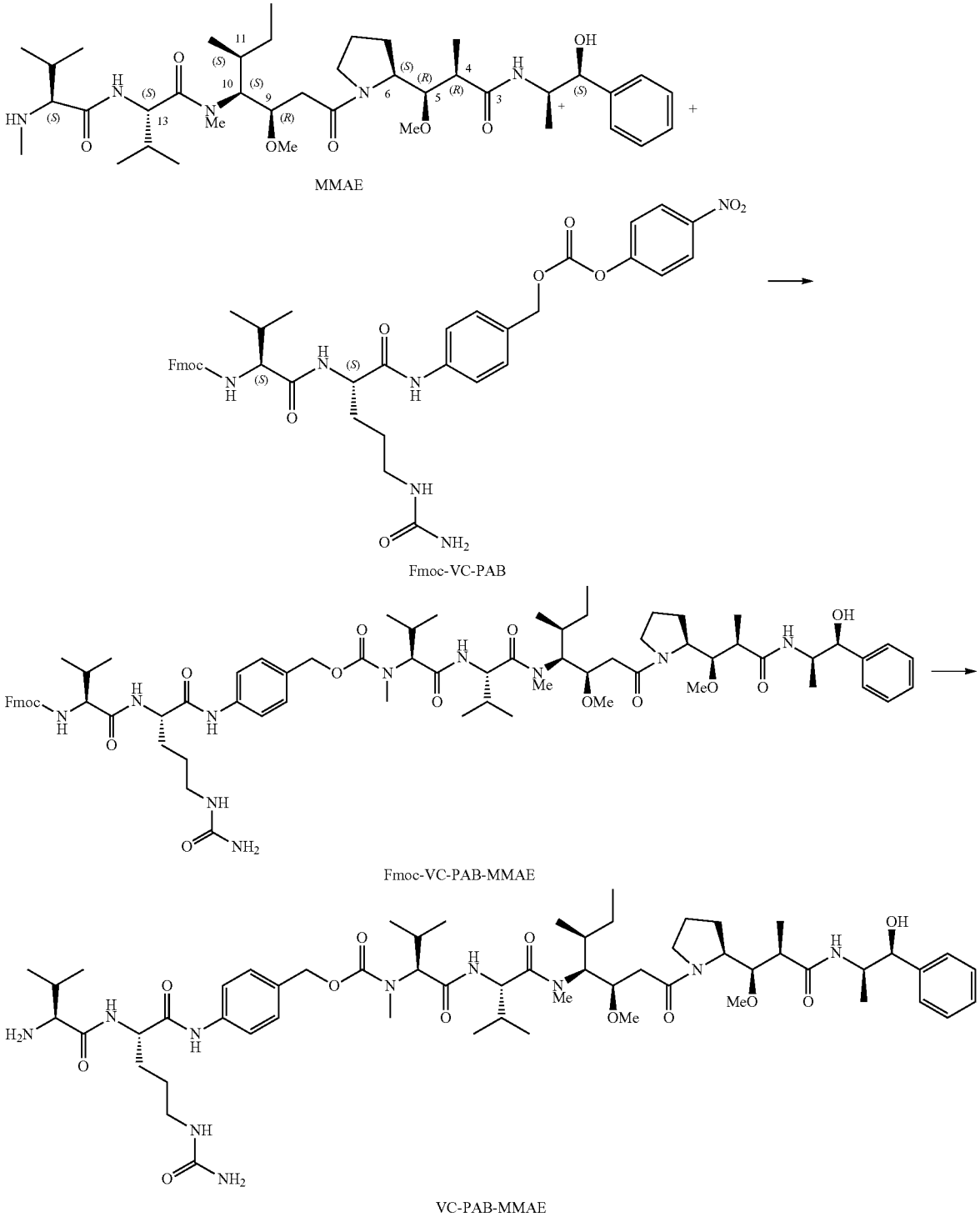

Exemplary synthesis methods for the ADCs shown in Table 3 are illustrated in Example 1 below. In ADC-A, C, H through P, S and T, the antibody is covalently bonded to the linker/payload moiety via cysteine residues. In ADC-B, E, and F, the antibody is covalently bonded to the linker/payload moiety (or to the payload for B) via lysine residues. In ADC-Q and R, the antibody is covalently bonded to the linker/payload via glutamine residues.

3. Immunoconjugate Therapy

The immunoconjugates described herein are useful for treating a variety of cancers. ROR1 has been shown to express across many types of tumors, including lymphomas and solid tumors. High proportions of human cancers express ROR1. For example, Zhang et al. showed that 54% ovarian cancers, 57% colon cancers, 77% lung cancers, 90% lymphomas, 89% skin cancers, 83% pancreatic cancers, 73% testicular cancers, 43% bladder cancers, 96% uterus cancers, 90% prostate cancers, and 83% adrenal cancers that they examined had moderate-to-strong staining with the anti-ROR1 antibody 4A5 (Zhang et al., Am J Pathol. 181 (6):1903-10 (2012)). Daneshmanesh et al. similarly found near universal expression of ROR1 in CLL and hairy cell leukemia (HCL) and varying degrees of expression in other lymphoid cancers such as mantle cell lymphoma (MCL), diffuse large B-cell lymphoma (DLBCL)/marginal zone lymphoma (MZL), follicular lymphoma (FL), chronic myeloid leukemia (CML), acute myeloid lymphoma (AML), and myeloma (Daneshmanesh et al., Leuk Lymphoma 54(4):843-50 (2013)). Our own studies similarly have shown that substantial proportions of patients with hepatocellular cancers (HCC) or non-small-cell lung cancer (NSCLC) are ROR1-positive. This broad tumor expression pattern of ROR1 renders the immunoconjugates of the present invention useful in treating many hematological cancers and solid tumors, such as those aforementioned. Further, it has been shown that ROR1 expression increases in aggressive cancers and correlates with poor prognosis; thus, immunoconjugates of the present invention are particularly well suited to treat aggressive or advanced cancers. In some embodiments, the immunoconjugates of the invention lead to partial or complete tumor regression. In particular embodiments, the partial or complete tumor regression may be sustained beyond the final dose of immunoconjugate treatment.

The ROR1 immunoconjugates of the invention, such as those made with an antibody that binds to a ROR1 epitope set forth in SEQ ID NO:1 or 2 (e.g., Ab1, Ab2, Ab3, or Ab4), are effective in treating cancers such as solid tumors that are heterogeneous in ROR1 expression. Tumors having as little as 20% of their cells expressing ROR1 can be treated effectively by the ROR1 immunoconjugates; for example, the tumors may have 20% or more, 30% or more, 40% or more, 50% or more, 60% or more, or 70% or more of their cells expressing ROR1. Without wishing to be bound by theory, it is contemplated that the ROR1 immunoconjugates of the invention may cause cell death in ROR1-negative tumor cells through bystander toxicity effect (i.e., the payload released from a dead tumor cell causes cytotoxicity to a neighboring tumor cell), or by enhancing the anti-tumor immunity of the immune system, or both.

"Treat", "treating" and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment. Treatment of cancer encompasses inhibiting cancer growth (including causing partial or complete cancer regression), inhibiting cancer progression or metastasis, preventing cancer recurrence or residual disease, and/or prolonging the patient's survival.

In some embodiments, the cancer treatable by the immunoconjugates described herein is a ROR1-expressing cancer. The ROR1-expressing cancer can be determined by any suitable method of determining gene or protein expression, for example, by histology, flow cytometry, RT-PCR, or RNA-Seq. The cancer cells used for the determination may be obtained through tumor biopsy or through collection of circulating tumor cells. In certain embodiments, if an antibody-based assay such as flow cytometry or immunohistochemistry is used, ROR1-expressing cancers are any cancers with cells that show anti-ROR1 antibody reactivity greater than that of an isotype control antibody. In certain embodiments, if an RNA-based assay is used, ROR1-expressing cancers are those that show an elevated level of ROR1 RNA compared to a negative control cell or cancer that does not express ROR1.

In certain embodiments, the antibodies and immunoconjugates are for use in treating hematological malignancies. In certain embodiments, the antibodies and immunoconjugates are for use in treating solid tumors. The cancer to be treated may be selected from, e.g., lymphoma, small lymphocytic lymphoma, marginal zone lymphoma, marginal cell B-cell lymphoma, Burkitt's lymphoma, mantle cell lymphoma, diffuse large B-cell lymphoma, a non-Hodgkin lymphoma that has undergone Richter's transformation, chronic lymphocytic leukemia, T cell leukemia, osteosarcoma, renal cell carcinoma, hepatocellular carcinoma, colon cancer, colorectal cancer, breast cancer, epithelial squamous cell cancer, melanoma, myeloma, multiple myeloma, stomach cancer, brain cancer, lung cancer, non-small cell lung cancer, pancreatic cancer, cervical cancer, ovarian cancer, liver cancer, bladder cancer, prostate cancer, testicular cancer, thyroid cancer, and head and neck cancer. In certain embodiments, the cancer to be treated can be a cancer that is refractory to other therapeutics (for example, triple negative breast cancer).

In certain embodiments, the methods for treating cancer described herein comprise treatment with an immunoconjugate of the invention and treatment with an additional therapeutic agent or biologically active molecule. Examples of biologically active molecules include, but are not limited to, peptides, proteins, enzymes, small molecule drugs, prodrugs, carbohydrates, imaging agents, lipids, nucleosides, radionuclides, oligonucleotides, toxins, cells, antibiotics, fungicides, anti-viral agents, anti-inflammatory agents, anti-tumor agents, cardiovascular agents, anti-anxiety agents, hormones, growth factors, steroidal agents, microbially derived toxins, and the like. Further examples of biologically active molecules are those listed above under the heading "Cytotoxic drug moieties."

In certain embodiments, the immunoconjugate and the additional therapeutic agent or biologically active molecule are administered at the same time, e.g., in the same formulation. In certain embodiments, they are administered separately, on the same or different dosing schedules. In some embodiments, the additional therapeutic agent is a vascular endothelial growth factor (VEGF) inhibitor, a Bruton's tyrosine kinase (BTK) inhibitor, an inhibitor of the mammalian target of rapamycin (mTOR), a phosphoinositide 3-kinase (PI3K) inhibitor, a Janus kinase/signal transducers and activators of transcription (Jak/STAT) signaling inhibitor, a B-cell lymphoma 2 (Bcl2) inhibitor, a spleen tyrosine kinase (SYK) inhibitor, a microtubule inhibitor, an epithelial growth factor receptor (EGFR) inhibitor, a poly ADP ribose polymerase (PARP) inhibitor, an anaplastic lymphoma kinase (ALK) inhibitor, a DNA-repair inhibitor, a DNA cross-linker, a nucleoside analog, or an immunomodulatory agent.

In some embodiments, the additional therapeutic agent is a) an antibody such as rituximab (anti-CD20) or bevacizumab (anti-VEGF);
b) a Bruton's tyrosine kinase inhibitor such as acalabrutinib or ibrutinib;
c) an mTOR inhibitor such as sapanisertib, everolimus or BEZ235;

d) a PI3K inhibitor such as idelalisib or buparlisib;
e) a Jak/STAT signaling inhibitor such as ruxolitinib;
f) a Bcl2 inhibitor such as ABT-199/venetoclax, Bcl2i-1, or Bcl2i-2;
g) a SYK inhibitor such as fostamatinib;
h) a microtubule inhibitor such as paclitaxel or vincristine;
i) an EGFR inhibitor such as erlotinib;
j) a PARP inhibitor such as olaparib;
k) an ALK inhibitor such as crizotinib;
l) a DNA-repair inhibitor such as carboplatin;
m) a DNA cross-linker such as oxaliplatin/cisplatin;
n) a nucleoside analog such as gemcitabine; or
o) an immunomodulatory drug (IMiD) such as lenalidomide or pomalidomide.

In a specific embodiment, the additional therapeutic agent is venetoclax.

In certain embodiments, an immunoconjugate of the invention and an additional therapeutic agent or biologically active molecule are used in combination to treat CLL, MCL, or a non-Hodgkin lymphoma that has undergone Richter's transformation. In particular embodiments, the additional therapeutic agent or biologically active molecule is, e.g., ibrutinib, acalabrutinib, venetoclax, Bcl2i-1, Bcl2i-2, everolimus, sapanisertib, or idelalisib.

Additional examples of the additional therapeutic agent are pacritinib, buparlisib, BEZ235, ruxolitinib, fostamatinib, rituximab, lenalidomide, pomalidomide, paclitaxel, vincristine, erlotinib, crizotinib, carboplatin, oxaliplatin/cisplatin, bevacizumab, and gemcitibine.

In certain embodiments, an immunoconjugate of the invention is used in combination with an immune checkpoint modulator that enhances the patient's immune system. For example, the conjugate is used with an immune checkpoint inhibitor such as an antibody or antibody derivative, an antisense oligonucleotide, a small interfering RNA, an aptamer, or a peptide, targeting programmed death-ligand 1 (PD-L1, also known as B7-H1, CD274), programmed death 1 (PD-1), CTLA-4, PD-L2 (B7-DC, CD273), LAG3, TIM3, 2B4, A2aR, B7H1, B7H3, B7H4, BTLA, CD2, CD27, CD28, CD30, CD40, CD70, CD80, CD86, CD137, CD160, CD226, CD276, DR3, GALS, GITR, HAVCR2, HVEM, IDOL IDO2, ICOS (inducible T cell costimulator), KIR, LAIR1, LIGHT, MARCO (macrophage receptor with collagenous structure), PS (phosphatidylserine), OX-40, SLAM, TIGHT, VISTA, VTCN1, or any combination thereof.

It is understood that the immunoconjugates of the invention may be used in a method of treatment as described herein, may be for use in a treatment as described herein, and/or may be for use in the manufacture of a medicament for a treatment as described herein. The invention also provides kits and articles of manufacture comprising the immunoconjugates of the invention as described herein.

4. Pharmaceutical Compositions

In some embodiments, the immunoconjugate of the invention may be comprised in a pharmaceutical composition further comprising one or more pharmaceutically acceptable excipients, carriers, and diluents. For example, the antibodies and immunoconjugates of the invention may be administered suspended in a sterile solution (e.g., a solution comprising 0.9% NaCl). In certain embodiments, the solution further comprises one or more of the following: buffers (e.g., acetate, citrate, histidine, succinate, phosphate, bicarbonate and hydroxymethylaminomethane (Tris) buffers); surfactants (e.g., polysorbate 80 (Tween 80), polysorbate 20 (Tween 20), and poloxamer 188); polyols/disaccharide/polysaccharides (e.g., glucose, dextrose, mannose, mannitol, sorbitol, sucrose, trehalose, and dextran 40); amino acids (e.g., glycine and arginine); antioxidants (e.g., ascorbic acid and methionine); and/or chelating agents (e.g., EDTA and EGTA). Any combination of these excipients is also contemplated. In certain embodiments, the immunoconjugates of the invention are shipped/stored lyophilized and reconstituted before administration. In certain embodiments, lyophilized antibody or immunoconjugate formulations comprise a bulking agent such as mannitol, sorbitol, sucrose, trehalose, and/or dextran 40. The lyophilized formulation can be contained in a vial, such as a glass vial. The immunoconjugates, when formulated, whether reconstituted or not, can be buffered at a certain pH, e.g., less than 7.0 (such as a pH between 4.5 and 6.5, between 4.5 and 6.0, between 4.5 and 5.5, between 4.5 and 5.0, or between 5.0 and 6.0).

The immunoconjugates of the invention, as used herein, encompass pharmaceutically acceptable salts or esters of the conjugates. The pharmaceutically acceptable salts may be formed when an acidic proton present in the polypeptides either is replaced by a metal ion, by way of example an alkali metal ion, an alkaline earth ion, or an aluminum ion; or coordinates with an organic base. In addition, the salt forms of the immunoconjugates can be prepared using salts of the starting materials or intermediates. The immunoconjugates described herein may be prepared as pharmaceutically acceptable acid addition salts (which are a type of a pharmaceutically acceptable salt) by reacting the free base form of the polypeptides described herein with a pharmaceutically acceptable inorganic or organic acid. Alternatively, the immunoconjugates described herein may be prepared as pharmaceutically acceptable base addition salts (which are a type of a pharmaceutically acceptable salt) by reacting the free acid form of amino acids in polypeptides described herein with a pharmaceutically acceptable inorganic or organic base.

Pharmaceutically acceptable salts include, but are not limited to: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; and (2) salts formed when an acidic proton present in the parent compound either is replaced by a metal ion, e.g., an alkali metal ion, an alkaline earth ion, or an aluminum ion; or coordinates with an organic base. Acceptable organic bases include ethanolamine, diethanolamine, triethanolamine, tromethamine, N-methylglucamine, and the like. Acceptable inorganic bases include aluminum hydroxide, calcium hydroxide, potassium hydroxide, sodium carbonate, sodium hydroxide, and the like. The corresponding counterions of the pharmaceutically acceptable salts may be analyzed and identified using various methods including, but not limited to, ion exchange chromatography, ion chromatography, capillary electrophoresis, inductively coupled plasma, atomic absorption spectroscopy, mass spectrometry, or any combination thereof.

In some embodiments, a pharmaceutical composition of the invention includes multiparticulate formulations. In some embodiments, the pharmaceutical composition includes nanoparticle formulations. In some embodiments, nanoparticles comprise cMAP, cyclodextrin, and/or lipids. In some cases, nanoparticles comprise solid lipid nanoparticles, polymeric nanoparticles, self-emulsifying nanoparticles, liposomes, microemulsions, and/or micellar solutions. Additional exemplary nanoparticles include, but are not limited to, paramagnetic nanoparticles, superparamagnetic nanoparticles, metal nanoparticles, fullerene-like materials, inorganic nanotubes, dendrimers (such as with covalently attached metal chelates), nanofibers, nanohorns, nano-onions, nanorods, nanoropes and/or quantum dots. In some embodiments, a nanoparticle is a metal nanoparticle, e.g., a nanoparticle of scandium, titanium, vanadium, chromium, manganese, iron, cobalt, nickel, copper, zinc, yttrium, zirconium, niobium, molybdenum, ruthenium, rhodium, palladium, silver, cadmium, hafnium, tantalum, tungsten, rhenium, osmium, iridium, platinum, gold, gadolinium, aluminum, gallium, indium, tin, thallium, lead, bismuth, magnesium, calcium, strontium, barium, lithium, sodium, potassium, boron, silicon, phosphorus, germanium, arsenic, antimony, and combinations, alloys or oxides thereof.

Any method for administering immunoconjugates accepted in the art may be employed. The pharmaceutical compositions of the invention are typically suitable for parenteral administration. As used herein, "parenteral administration" of a pharmaceutical composition includes any route of administration characterized by physical breaching of a tissue of a subject and administration of the pharmaceutical composition through the breach in the tissue, thus generally resulting in the direct administration into the blood stream, into muscle, or into an internal organ. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal, intravenous, intraarterial, intrathecal, intraventricular, intraurethral, intracranial, intratumoral, and intrasynovial injection or infusions; and kidney dialytic infusion techniques. Regional perfusion is also contemplated. Particular embodiments include the intravenous and subcutaneous routes.

5. Articles of Manufacture and Kits

The present invention also provides articles of manufacture, e.g, kits, comprising a container (e.g., a single-use or multi-use container) containing a pharmaceutical composition of the present immunoconjugate), optionally an additional biologically active molecule (e.g., another therapeutic agent), and instructions for use. The immunoconjugate and additional biologically active molecule can be packaged separately in suitable packing such as a vial or ampule made from non-reactive glass or plastic. In certain embodiments, the vial or ampule holds lyophilized powder comprising the immunoconjugate or additional therapeutic agent or biologically active molecule. In certain embodiments, the vial or ampule holds a concentrated stock (e.g., 2×, 5×, 10× or more) of the immunoconjugate or biologically active molecule. In certain embodiments, the articles of manufacture such as kits include a medical device for administering the immunoconjugate and/or biologically active molecule (e.g., a syringe and a needle); and/or an appropriate diluent (e.g., sterile water and normal saline). The present invention also includes methods for manufacturing said articles.

6. Certain Embodiments

Certain embodiments of the invention are further illustrative below.

1. An immunoconjugate of the formula:

$$\text{Ab-}((\text{L})_m\text{-}(\text{D}))_n$$

or a pharmaceutically acceptable salt thereof, wherein:

i. Ab is an antibody or antigen binding fragment thereof which binds the ROR1 protein;
ii. L is a linker;
iii. D is a drug moiety selected from an anti-tubulin agent, a DNA alkylating agent, a DNA cross-linking agent, a DNA intercalating agent, and an RNA polymerase II inhibitor;
iv. m is 0 or 1; and
v. n is an integer from 1 to 10.

2. An immunoconjugate of the formula:

$$\text{Ab-}((\text{L})_m\text{-}(\text{D}))_n$$

or a pharmaceutically acceptable salt thereof, wherein:

i. Ab is an antibody or antigen binding fragment thereof which binds the ROR1 protein;
ii. L is a cleavable linker;
iii. D is a drug moiety selected from an anti-tubulin agent, a DNA alkylating agent, a DNA cross-linking agent, a DNA intercalating agent, and an RNA polymerase II inhibitor;
iv. m is 0 or 1; and
v. n is an integer from 1 to 10

3. An immunoconjugate of the formula:

$$\text{Ab-}((\text{L})_m\text{-}(\text{D}))_n$$

or a pharmaceutically acceptable salt thereof, wherein:

i. Ab is an antibody or antigen binding fragment thereof which binds the ROR1 protein;
ii. L is a linker, wherein the linker is not attached to a lysine amino acid residue;
iii. D is a drug moiety selected from an anti-tubulin agent, a DNA alkylating agent, a DNA cross-linking agent, a DNA intercalating agent, and an RNA polymerase II inhibitor;
iv. m is 0 or 1; and
v. n is an integer from 1 to 10.

4. The immunoconjugate of any one of embodiments 1-3, wherein D is an anti-tubulin agent.
5. The immunoconjugate of embodiment 4, wherein the anti-tubulin agent comprises an auristatin, a dolastatin, or analog thereof.
6. The immunoconjugate of embodiment 5, wherein the auristatin or dolastatin comprises auristatin E, monomethyl auristatin E (MMAE) or monomethyl auristatin F (MMAF), dimethylvaline-valine-dolaisoleuine-dolaproine-phenylalanine-p-phenylenediamine (AFP), 5-benzoylvaleric acid-auristatin E ester (AEVB), or (AEB).
7. The immunoconjugate of embodiment 6, wherein the auristatin comprises monomethyl auristatin E (MMAE).
8. The immunoconjugate of embodiment 4, wherein the anti-tubulin agent comprises a maytansine, maytansinoid, or analog thereof.

9. The immunoconjugate of embodiment 8, wherein the maytansinoid comprises ansamitocin, mertansine/emtansine (DM1), or ravtansine/soravtansine (DM4).
10. The immunoconjugate of embodiment 9, wherein the maytansinoid comprises mertansine/emtansine (DM1).
11. The immunoconjugate of embodiment 9, wherein the maytansinoid comprises ravtansine/soravtansine (DM4).
12. The immunoconjugate of embodiment 1, wherein D is a DNA alkylating agent.
13. The immunoconjugate of embodiment 12, wherein the DNA alkylating agent comprises duocarmycin.
14. The immunoconjugate of embodiment 1, wherein D is a DNA cross-linking agent.
15. The immunoconjugate of embodiment 14, wherein the DNA cross-linking agent comprises pyrrolobenzodiazepine (PBD).
16. The immunoconjugate of embodiment 1, wherein D is a DNA intercalating agent.
17. The immunoconjugate of embodiment 16, wherein the DNA intercalating agent comprises PNU-159682.
18. The immunoconjugate of embodiment 1, wherein D is an RNA polymerase II inhibitor.
19. The immunoconjugate of embodiment 18, wherein the RNA polymerase II inhibitor comprises α-amanitin.
20. The immunoconjugate of embodiment 1, wherein D is two different drug moieties covalently linked.
21. The immunoconjugate of embodiment 20, wherein D is any two or more of a DNA alkylating agent, a DNA cross-linking agent, a DNA intercalating agent, an RNA polymerase II inhibitor, or an anti-tubulin agent covalently linked to one another.
22. The immunoconjugate of any one of embodiments 1 to 21, wherein the antibody or antigen binding fragment thereof comprises a chimeric, humanized, deimmunized, or human antibody, or antigen binding fragment thereof.
23. The immunoconjugate of any one of embodiments 1 to 22, wherein the antibody or antigen binding fragment comprises a Fab, $F(ab)_2$, or scFv.
24. The immunoconjugate of any one of embodiments 1 to 23, wherein the immunoconjugate further comprises a second antibody or antigen binding fragment thereof, wherein the second antibody or antigen binding fragment thereof specifically binds to an epitope distinct from the antibody or antigen binding fragment.
25. The immunoconjugate of any one of embodiments 1 to 24, wherein the antibody or antigen binding fragment thereof comprises:
   a. a heavy chain CDR1 (HCDR1) amino acid sequence set forth in SEQ ID NO: 7, a heavy chain CDR2 (HCDR2) amino acid sequence set forth in SEQ ID NO: 8, a heavy chain CDR3 (HCDR3) amino acid sequence set forth in SEQ ID NO: 9, a light chain CDR1 (LCDR1) amino acid sequence set forth in SEQ ID NO: 10, a light chain CDR2 (LCDR2) amino acid sequence set forth in SEQ ID NO: 11, and a light chain CDR3 (LCDR3) amino acid sequence set forth in SEQ ID NO: 12;
   b. a HCDR1 amino acid sequence set forth in SEQ ID NO: 27, a HCDR2 amino acid sequence set forth in SEQ ID NO: 28, a HCDR3 amino acid sequence set forth in SEQ ID NO: 29, a LCDR1 amino acid sequence set forth in SEQ ID NO: 30, a LCDR2 amino acid sequence set forth in SEQ ID NO: 31, and a LCDR3 amino acid sequence set forth in SEQ ID NO: 32; or
   c. a HCDR1 amino acid sequence set forth in SEQ ID NO: 37, a HCDR2 amino acid sequence set forth in SEQ ID NO: 38, a HCDR3 amino acid sequence set forth in SEQ ID NO: 39, a LCDR1 amino acid sequence set forth in SEQ ID NO: 40, a LCDR2 amino acid sequence set forth in SEQ ID NO: 41, and a LCDR3 amino acid sequence set forth in SEQ ID NO: 42.
26. The immunoconjugate of any one of embodiments 1 to 24, wherein the antibody or antigen binding fragment thereof comprises: a heavy chain variable region comprising an amino acid sequence at least 80% identical to that set forth in SEQ ID NO: 6, and a light chain variable region comprising an amino acid sequence at least 80% identical to that set forth in SEQ ID NO: 5.
27. The immunoconjugate of any one of embodiments 1 to 26, wherein the antibody binds ROR1 with a $K_D$ of less than about 40 nM.
28. The immunoconjugate of any one of embodiments 1 to 26, wherein the antibody binds ROR1 with a $K_D$ of less than about 1 nM.
29. The immunoconjugate of any one of embodiments 1 to 26, wherein the antibody binds ROR1 with an affinity greater than about 10 times that of antibody D10, wherein antibody D10 comprises an immunoglobulin light chain amino acid sequence set forth in SEQ ID NO: 25, and an immunoglobulin heavy chain amino acid sequence set forth in SEQ ID NO: 26.
30. The immunoconjugate of any one of embodiments 1 to 26, wherein the antibody binds ROR1 with an affinity greater than about 50 times that of antibody D10, wherein antibody D10 comprises an immunoglobulin light chain amino acid sequence set forth in SEQ ID NO: 25, and an immunoglobulin heavy chain amino acid sequence set forth in SEQ ID NO: 26.
31. The immunoconjugate of any one of embodiments 1 to 30, wherein L is selected from a cleavable linker, a non-cleavable linker, a hydrophilic linker, a procharged linker, and a dicarboxylic acid based linker.
32. The immunoconjugate of any one of embodiments 1 to 31, wherein L is selected from 6-maleimidocaproyl (MC), maleimidopropanoyl (MP), valine-citrulline (VC), alanine-phenylalanine (AP), p-aminobenzyloxycarbonyl (PAB), N-succinimidyl 4-(2-pyridylthio) pentanoate (SPP), N-succinimidyl 4-(N-maleimidomethyl) cyclohexane-1-carboxylate (SMCC), N-succinimidyl (4-iodoacetyl) aminobenzoate (SIAB), 6-maleimidocaproyl-valine-citrulline (MC-VC), 6-maleimidocaproyl-valine-citrulline-p-aminobenzyloxycarbonyl (MC-VC-PAB), and N-succinimidyl-1-carboxylate-valine-citrulline-p-aminobenzyloxycarbonyl (SC-VC-PAB).
33. The immunoconjugate of any one of embodiments 1 to 31, wherein L is 6-maleimidocaproyl-valine-citrulline-p-aminobenzyloxycarbonyl (MC-VC-PAB).
34. The immunoconjugate of any one of embodiments 1 to 31, wherein L is N-succinimidyl-1-carboxylate-valine-citrulline-p-aminobenzyloxycarbonyl (SC-VC-PAB).
35. The immunoconjugate of any one of embodiments 1 to 31, wherein L is 6-maleimidocaproyl-valine-citrulline (MC-VC).
36. The immunoconjugate of any one of embodiments 1 to 31, wherein L is N-succinimidyl 4-(N-maleimidomethyl) cyclohexane-1-carboxylate (SMCC).
37. The immunoconjugate of any one of embodiments 1 to 31, wherein Lisa linker of the formula:

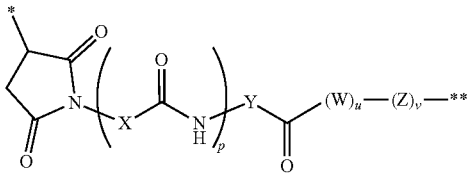

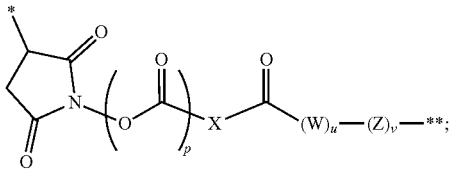

wherein

X is $C_{2-8}$alkyl;

Y is —$(CH_2CH_2O)_qCH_2CH_2$—;

W is an amino acid unit;

Z is

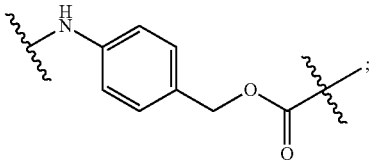

n is 0 or 1;

p is 0 or 1;

q is an integer from 0 to 12;

u is an integer from 0 to 5; and v is 0 or 1; wherein ** indicates the point of attachment to D; and

* indicates the point of attachment to Ab.

38. The immunoconjugate of embodiment 37, wherein X is —$(CH_2)_2$—.
39. The immunoconjugate of embodiment 37, wherein X is —$(CH_2)_3$—.
40. The immunoconjugate of embodiment 37, wherein X is —$(CH_2)_4$—.
41. The immunoconjugate of embodiment 37, wherein X is —$(CH_2)_5$—.
42. The immunoconjugate of any one of embodiments 37 to 41, wherein p is 0.
43. The immunoconjugate of any one of embodiments 37 to 41, wherein p is 1.
44. The immunoconjugate of any one of embodiments 37 to 43, wherein q is an integer from 4 to 8.
45. The immunoconjugate of any one of embodiments 37 to 43, wherein q is 4.
46. The immunoconjugate of any one of embodiments 37 to 43, wherein q is 8.
47. The immunoconjugate of any one of embodiments 37 to 46, wherein n is 0.
48. The immunoconjugate of any one of embodiments 37 to 46, wherein n is 1.
49. The immunoconjugate of any one of embodiments 37 to 48, wherein v is 0.
50. The immunoconjugate of any one of embodiments 37 to 48, wherein v is 1.
51. The immunoconjugate of any one of embodiments 37 to 50, wherein u is an integer from 2 to 4.
52. The immunoconjugate of any one of embodiments 37 to 51, wherein W is selected from alanine, valine, leucine, isoleucine, methionine, phenylalanine, tryptophan, proline, lysine protected or not with acetyl or formyl, arginine, arginine protected or not with tosyl or nitro groups, histidine, ornithine, ornithine protected with acetyl or formyl, and citrulline.
53. The immunoconjugate of any one of embodiments 37 to 52, wherein u is 0.
54. The immunoconjugate of any one of embodiments 1 to 53, further comprising a spacer between L and D.
55. The immunoconjugate of any one of embodiments 1 to 54, wherein the immunoconjugate further comprises at least one additional linker-drug moiety of the formula-q $(L)_m$-$(D))_n)_x$ wherein:
    L is a linker;
    D is a drug moiety selected from an anti-tubulin agent, a DNA alkylating agent, a DNA cross-linking agent, a DNA intercalating agent, or an RNA polymerase II inhibitor;
    m is 0 or 1;
    n is an integer from 1 to 10; and
    x is an integer from 1 to 10.
56. A pharmaceutical composition comprising the immunoconjugate of any one of embodiments 1 to 55 and a pharmaceutically acceptable excipient, diluent, or carrier.
57. The pharmaceutical composition of embodiment 56, wherein the pharmaceutical composition is formulated for intravenous administration.
58. The pharmaceutical composition of embodiment 56, wherein the pharmaceutical composition is formulated for subcutaneous administration.
59. A method of treating cancer comprising administering to an individual in need thereof a therapeutic dose of the immunoconjugate of any one of embodiments 1 to 55 or the pharmaceutical composition of any one of embodiments 56 to 58.
60. Use of the immunoconjugate of any one of embodiments 1 to 55 or the pharmaceutical composition of any one of embodiments 56 to 58 for treating cancer.
61. The method of embodiment 59 or the use of embodiment 60, wherein the cancer expresses ROR1.
62. The method or use of embodiment 61, wherein the cancer is selected from lymphoma, chronic lymphocytic leukemia, small lymphocytic lymphoma, marginal cell B-cell lymphoma, Burkett's lymphoma, renal cell carcinoma, colon cancer, colorectal cancer, breast cancer, epithelial squamous cell cancer, melanoma, myeloma, stomach cancer, brain cancer, lung cancer, pancreatic cancer, cervical cancer, ovarian cancer, liver cancer, bladder cancer, prostate cancer, testicular cancer, thyroid cancer, and head and neck cancer
63. A method of treating an individual with cancer, the method comprising administering to the individual:
    a. the immunoconjugate of any one of embodiments 1 to 55; and
    b. an additional therapeutic agent.
64. The method of embodiment 63, wherein the additional therapeutic agent comprises acalabrutinib, idelalisib, sapanisertib, pacritinib, ABT-199, buparlisib, everolimus, BEZ235, ruxolitinib, fostamatinib, rituximab, lenalidomide, paclitaxel, vincristine, ibrutinib, erlotinib, crizotinib, carboplatin, oxaliplatin/cisplatin, bevacizumab, or gemcitibine.

65. The method of embodiment 63 or 64, wherein the cancer expresses ROR1.

66. The method of embodiment 65, wherein the cancer comprises lymphoma, chronic lymphocytic leukemia, small lymphocytic lymphoma, marginal cell B-cell lymphoma, Burkett's lymphoma, renal cell carcinoma, colon cancer, colorectal cancer, breast cancer, epithelial squamous cell cancer, melanoma, myeloma, stomach cancer, brain cancer, lung cancer, pancreatic cancer, cervical cancer, ovarian cancer, liver cancer, bladder cancer, prostate cancer, testicular cancer, thyroid cancer, and head and neck cancer.

67. The method of any one of embodiments 63 to 66, wherein the immunoconjugate and the additional therapeutic agent are administered separately to the individual with cancer.

68. A pharmaceutical composition comprising the immunoconjugate as described in any one of embodiments 1 to 55 and the additional therapeutic agent as described in embodiment 64.

69. The pharmaceutical composition of embodiment 68, for use in a method of any one of embodiments 63 to 67.

70. A kit comprising the immunoconjugate as described in any one of embodiments 1 to 55 and the additional therapeutic agent as described in embodiment 64, wherein said immunoconjugate and additional therapeutic agent are in suitable packaging.

71. The kit of embodiment 70, for use in a method of any one of embodiments 63 to 67.

Unless the context requires otherwise, throughout the specification and claims, the word "comprise" and variations thereof, such as, "comprises" and "comprising," are to be construed in an open, inclusive sense, that is, as "including, but not limited to." As used in this specification and the appended claims, the singular forms "a," "an," and "the" include plural referents unless the content clearly dictates otherwise. It should also be noted that the term "or" is generally employed in its sense including "and/or" unless the content clearly dictates otherwise. As used herein the term "about" refers to a numerical range that is 10%, 5%, or 1% plus or minus from a stated numerical value within the context of the particular usage. Further, headings provided herein are for convenience only and do not interpret the scope or meaning of the claimed embodiments.

All publications and patents mentioned herein are incorporated herein by reference in their entirety for the purpose of describing and disclosing, for example, the constructs and methodologies that are described in the publications, which might be used in connection with the presently described inventions. The publications discussed herein are provided solely for their disclosure prior to the filing date of the present application. Nothing herein is to be construed as an admission that the inventors of the subject invention are not entitled to antedate such disclosure by virtue of prior invention or for any other reason.

Unless defined otherwise, all technical and scientific terms used herein have the same meaning as commonly understood to one of ordinary skill in the art to which the inventions described herein belong. Any methods, devices, and materials similar or equivalent to those described herein can be used in the practice or testing of the inventions described herein.

EXAMPLES

The following examples illustrate representative embodiments of the present invention and are not meant to be limiting in any way.

Example 1: Synthesis of Exemplary Immunoconjugates

1. Conjugation of Ab1 cysteines in ADC-A, C, and H through P

Conjugation of Ab1 with MC-VC-PAB-MMAE (ADC-A) was performed at multiple scales (2 mg, 30 mg, and 350 mg) with similar results. For the smallest scale, 2 mg Ab1 (10 mg/mL in PBS, pH 6.5) was treated with 2.50 equivalents (eq) of tris(2-carboxyethyl)phosphine (TCEP, 5 mM) in conjugation buffer solution in a water bath at 37° C. for 2 hours. The PBS buffer contained 15.75 mM $Na_2HPO_4$, 34.25 mM $NaH_2PO_4$, 2 mM EDTA, and 50 mM NaCl, at pH 6.5. Subsequently, the reaction was cooled to 4° C. Next, 7 eq MC-VC-PAB-MMAE in N,N-dimethylacetamide (DMA) was added and the mixture was left at 4° C. for an additional 1 hour. The buffer was exchanged with 20 mM histidine, pH 5.5 (MMAE buffer) by using a spin desalting column (40 kD, 0.5 mL). The number of MMAE drug molecules linked per antibody molecule (DAR) was determined using HIC-HPLC, SEC-HPLC, RP-HPLC, and UV/Vis and is summarized in Table 4. Consistent results were obtained at all scales, with DAR ranging from 3.89 to 5.09 on average, depending on the methodology used.

TABLE 4

Characterization of ADC-A

| Scale | Aggregate | Recovery | | DAR | | | |
|---|---|---|---|---|---|---|---|
| (mg) | (%) | (%) | D0* (%) | UV | SEC | HIC | RP |
| 2 | 3.47 | 85.6 | 6.06 | 4.33 | 4.81 | 3.95 | 3.89 |
| 30 | 3.50 | 86.1 | 4.75 | 4.44 | 5.09 | 4.21 | 4.09 |
| 350 | 3.51 | 90.2 | 5.12 | 4.40 | 4.96 | 4.12 | 3.99 |

*D0: unconjugated antibody.

Other linkers and payloads (ADC-C, and ADC-H through ADC-P) were conjugated to Ab1 in a similar fashion, and the resulting DARs are summarized in Table 5.

TABLE 5

Average DAR for Additional ADC Constructs

| Construct | DAR | Methodology |
|---|---|---|
| ADC-C | 6.33 | UV |
| | 6.62 | SEC |
| | 3.97 | HIC |
| | 4.15 | RP |
| | 4.24 | MS |
| ADC-H | 1.98 | UV |
| | 1.93 | SEC |
| ADC-I | 4.1 | SEC/UV |
| ADC-J | 2.1 | HIC |
| ADC-K | 1.9 | PLRP |
| ADC-L | 3.9 | HIC |
| ADC-M | 4.1 | HIC |
| ADC-N | 4.1, 1.9 | PLRP |
| ADC-O | 1.8 | SEC |
| ADC-P | 1.9 | PLRP |

2. Conjugation of Ab1 lysines in ADC-B, E, and F

Ab1 in PBS (pH 6.5) was combined with SC-VC-PAB-MMAE (ADC-E) or SC-VC-PAB-DM1 (ADC-F) in DMA and placed on a rotating platform at 10 rpm at 22° C. for 2-4 hours. For ADC-B, Ab1 in PBS (pH 7.0) was combined with SMCC-DM1 and placed on a rotating platform at 10 rpm at 22° C. for 2-4 hours. Unreacted payload was removed through buffer exchange, using Amicon ultrafiltration (50 kDa, 0.5 mL). ADC-B was exchanged into 20 mM succinic acid (pH 5.0). DAR values were determined using SEC-HPLC, MS, and UV/Vis and are summarized in Table 6. When linker-payload was used at ~11 eq, the DARs approached 4.0 following 4 hours incubation.

TABLE 6

Characterization of ADC-B, ADC-E and ADC-F

| Construct | Scale (mg) | Aggregate (%) | Recovery (%) | D0 (%) | DAR UV | DAR SEC | DAR MS |
|---|---|---|---|---|---|---|---|
| ADC-B | 80 | 2.93 | — | 5.86 | 3.18 | 3.20 | 3.0 |
| ADC-E | 60 | 3.94 | 82.1 | 1.85 | 5.08 | 6.14 | 4.2 |
| ADC-F | 75 | 2.92 | 59.0 | 7.44 | 5.51 | 5.72 | 3.0 |

3. Site-specific conjugation of Ab1 in ADC-Q and R

ADC-Q and ADC-R were synthesized using site-specific conjugation technology (Dennler et al., Bioconjugate Chemistry, 25(3):569-578 (2014) and U.S. Patent Publication 2016/0022833). Ab1 was first deglycosylated by incubation with 6 U/mg protein of N-glycosidase F (PNGase F) overnight at 37° C. The deglycosylated antibody was purified by Protein A chromatography and formulated for the bacterial transglutaminase modification reaction. Next, 10-40 eq of 11-azido-3,6,9-trioxaundecan-1-amine (azido-PEG3-amine) per glutamine was added to 1-5 mg/ml of Ab1 in PBS (pH 7.4) and the reaction was initiated by the addition of 2-6 U/mL of microbial transglutaminase and incubated overnight at 37° C. Subsequently, excess azido-PEG3-amine was removed by Protein A chromatography. Finally, 50-200 μM dibenzylcyclooctyne (DBCO)-containing drug payload (1.25 to 5 mol equiv. per azide group) was added to 20 μM azide-activated Ab1 and incubated at room temperature for 0.5-6 hours, forming Ab1-payload conjugates linked via a triazole moiety. Excess DBCO-containing payload was removed. Characterization of ADCs synthesized in this manner demonstrated DARs of 4.4 for ADC-Q and 2.1 for ADC-R (Table 7).

TABLE 7

Average DAR for Additional ADC Constructs

| Construct | DAR | Methodology |
|---|---|---|
| ADC-Q | 4.4 | HIC |
| ADC-R | 2.1 | PLRP |

Example 2: Antibody and Immunoconjugate Binding to ROR1-Positive Cells

The binding to tumor cells by antibodies Ab1 and 4A5, as well as ADC constructs derived from those antibodies (ADC-A and ADC-T), was evaluated. First, the binding of Ab1 to two ROR1-positive human tumor cell lines representing different cancer types was tested. The Jeko-1 cell line, from mantle cell lymphoma, is a suspension cell line, while the MDA-MB-231 cell line, from triple negative breast cancer, is an adherent cell line. The cell lines have different levels of ROR1 expression, with Jeko-1 cells displaying about 13507 cell surface copies and the MDA-MB-231 cells displaying about 21015 cell surface copies. The Jeko-1 (ATCC Cat. No. CRL-3006) and MDA-MB-231 (ATCC Cat. No. CCL-227) cell lines were purchased from the American Type Culture Collection and were maintained according to the ATCC recommendations.

Jeko-1 cells (FIG. 2A) or MDA-MB-231 cells (FIG. 2B) were incubated with 0, 1, 10, 100, or 1000 ng/mL of Ab1 for 20 minutes on ice. After washing off unbound antibody, the cells were incubated with secondary anti-human IgG antibody labeled with phycoerythrin (PE) for an additional 20 minutes. The amount of PE fluorescence was measured using the BDFACS Verse analyzer and FlowJo V10 software. The PE signal for the highest concentration was used as the maximal binding signal to calculate the % maximal binding. $EC_{50}$ was calculated using GraphPad Prism 7. The receptor binding assay resulted in $EC_{50}$ values of 13.6 ng/ml in Jeko-1 cells and 32.8 ng/ml in MDA-MB-231 cells.

Figure 1:
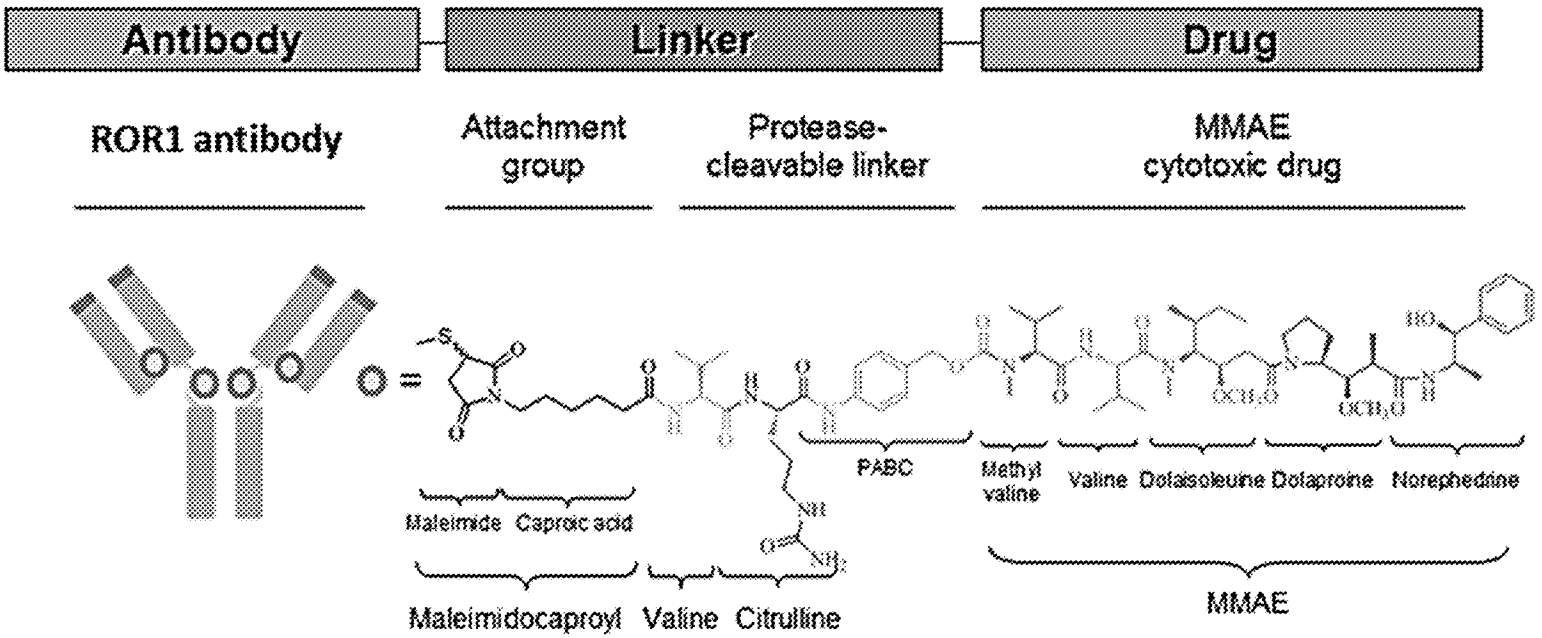
FIG. 1 is a schematic diagram illustrating a non-limiting example of an immunoconjugate of the present disclosure.
Figure 2A:
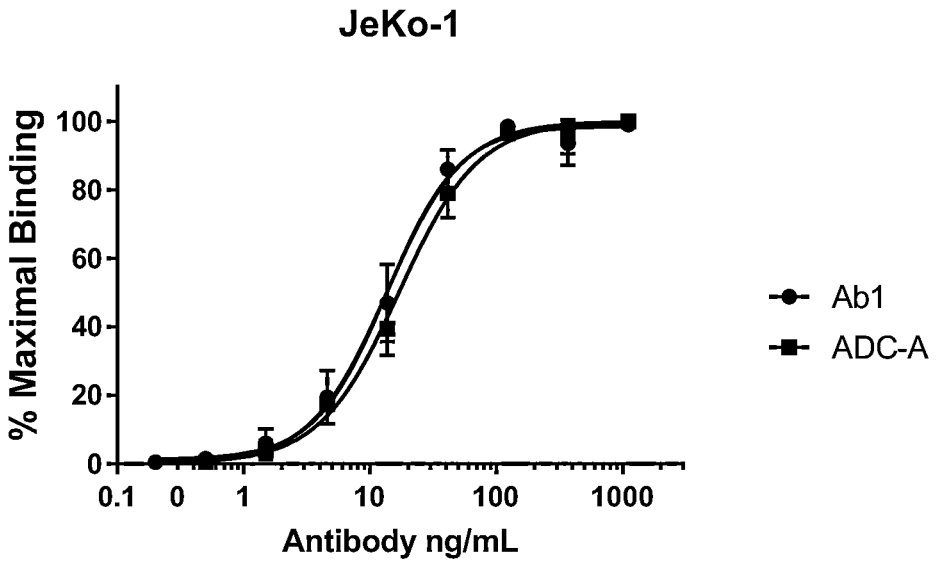
FIGS. 2A and 2B are graphs illustrating the binding of various concentrations of Ab1 and ADC-A to ROR1-positive cells Jeko-1 (2A) and MDA-MB-231 (2B). The $EC_{50}$ values for Ab1 and ADC-A are shown below each graph. The similarity between the $EC_{50}$ values for unconjugated Ab1 and ADC-A demonstrates that drug conjugation had minimal impact on Ab1's binding to the target cells.
Figure 2B:
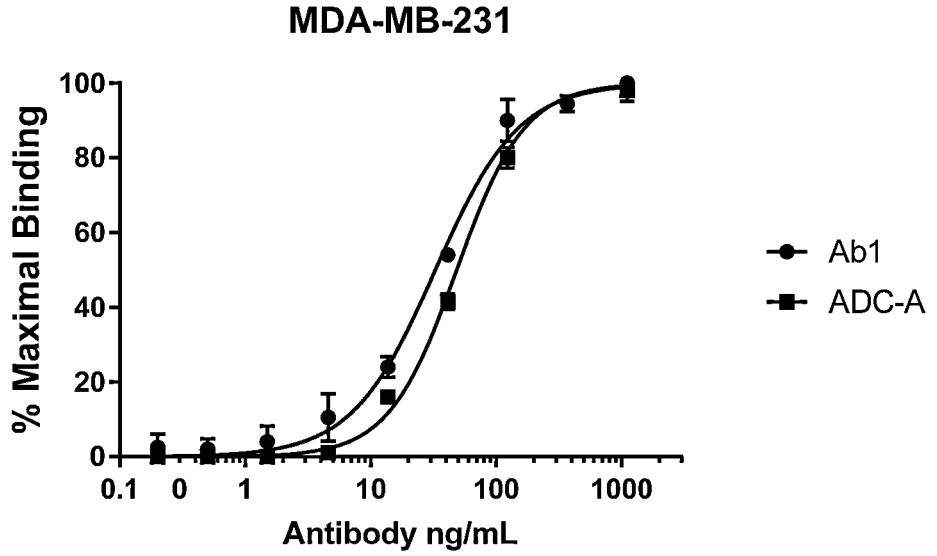
Figure 17:
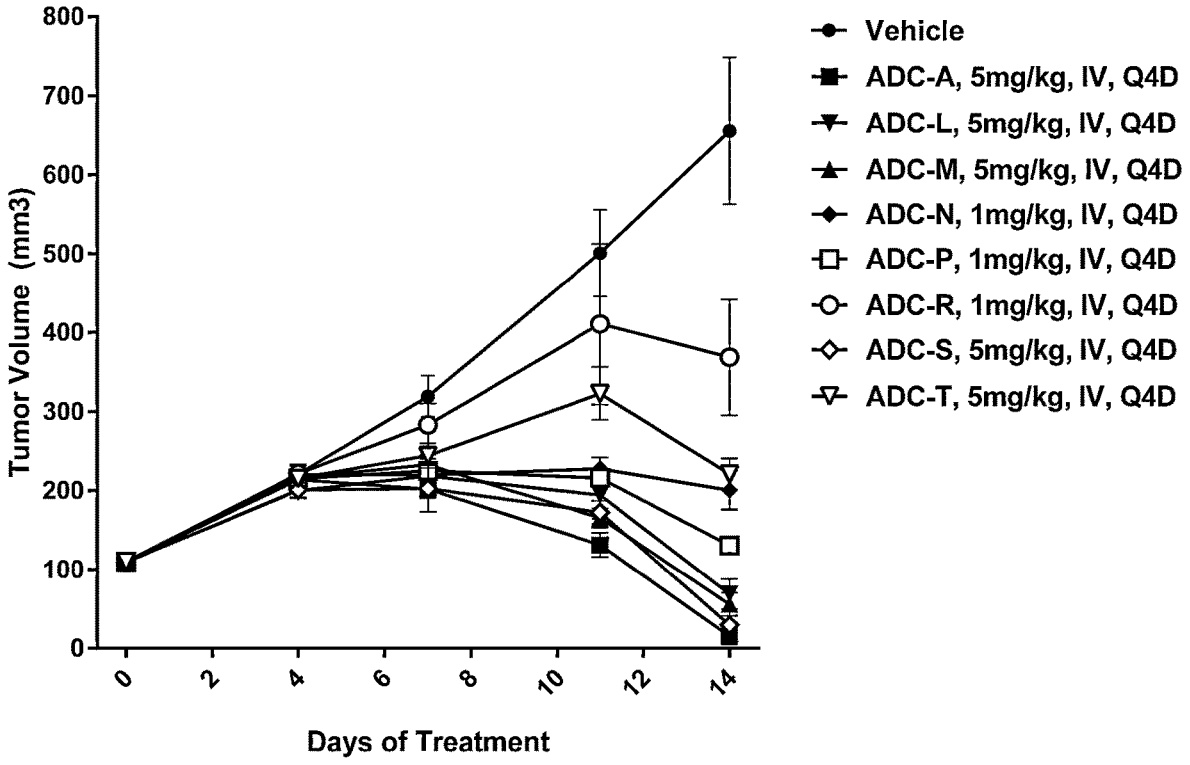
FIG. 17 is a graph illustrating tumor growth inhibition in a Jeko-1 human mantle cell lymphoma xenograft mouse model. Mice were treated with vehicle; 1 mg/kg ADC-N, ADC-P, or ADC-R; or 5 mg/kg ADC-A, ADC-L, ADC-M, ADC-S or ADC-T. Vehicle and ADC constructs were administered IV Q4D. Significant tumor regression was observed in animals treated with ADC-A, ADC-L, ADC-M and ADC-S, while inhibition of tumor growth was observed in animals treated with ADC-N, ADC-P, ADC-R and ADC-T.

Next, the binding of Ab1 was compared to ADC-A (FIGS. 2A and 2B). Binding was compared on both Jeko-1 and MDA-MB-231 cell lines. The binding of ADC-A to Jeko-1 cells (FIG. 2A, squares) and MDA-MB-231 cells (FIG. 2B, squares) was very similar to the binding of the unconjugated, parental antibody Ab1 (FIG. 2A, 17 ng/mL vs. 13.6 ng/mL and FIG. 2B, 48.5 ng/mL vs. 32.8 ng/mL). The similarity between the $EC_{50}$ values of unconjugated Ab1 and ADC-A demonstrates that drug conjugation had minimal impact on Ab1's binding to the target cells.

Figure 3A:
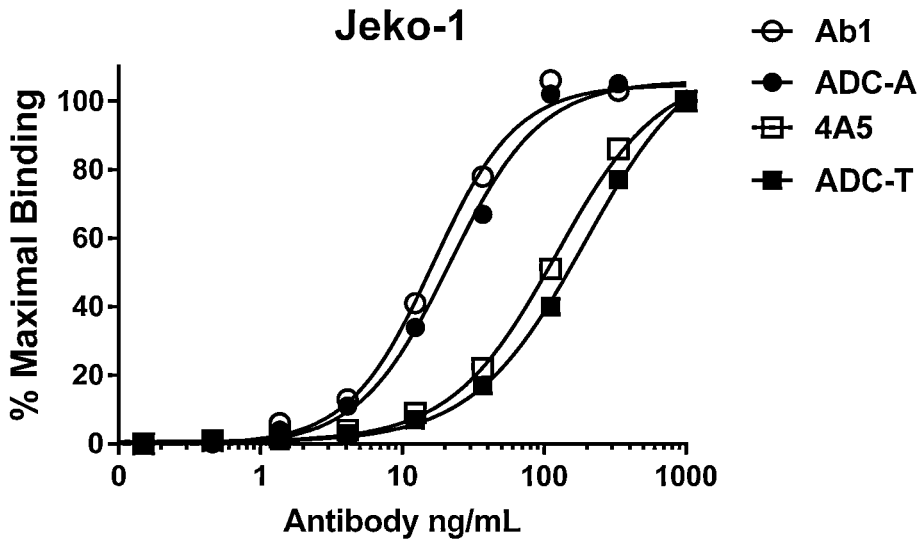
FIGS. 3A and 3B are graphs illustrating the binding of Ab1, 4A5, ADC-A and ADC-T (3A) and Ab1, ADC-A, D10 and ADC-S (3B) to Jeko-1 cells. The $EC_{50}$ values for the antibodies and immunoconjugates are shown below each graph. The similarity between the $EC_{50}$ values of unconjugated antibodies and the corresponding ADC constructs demonstrates that drug conjugation had minimal impact on the antibodies' binding to the target cells. The difference in $EC_{50}$ values between Ab1/ADC-A and D10/ADC-S reflect the higher affinity of Ab1 for ROR1 as compared to D10.

The binding of Ab1 was compared to 4A5, an antibody that binds an epitope on ROR1 distinct from Ab1's epitope (FIG. 3A). Ab1 ($EC_{50}$=16.39 ng/mL; FIG. 3A, open circles) bound Jeko-1 cells with a higher affinity/avidity than did 4A5 ($EC_{50}$=120.6 ng/mL; FIG. 3A, open squares). The binding of the ADC constructs was compared to the corresponding unconjugated parental antibodies (Ab1 versus ADC-A and 4A5 versus ADC-T). ADC-A bound with an $EC_{50}$ of 21.57 ng/mL while ADC-T bound with an $EC_{50}$ of 192.7 ng/mL. The similarity between the $EC_{50}$ values of unconjugated antibodies and the corresponding ADC constructs demonstrates again that drug conjugation had minimal impact on the antibodies' binding to the target cells.

Figure 3B:
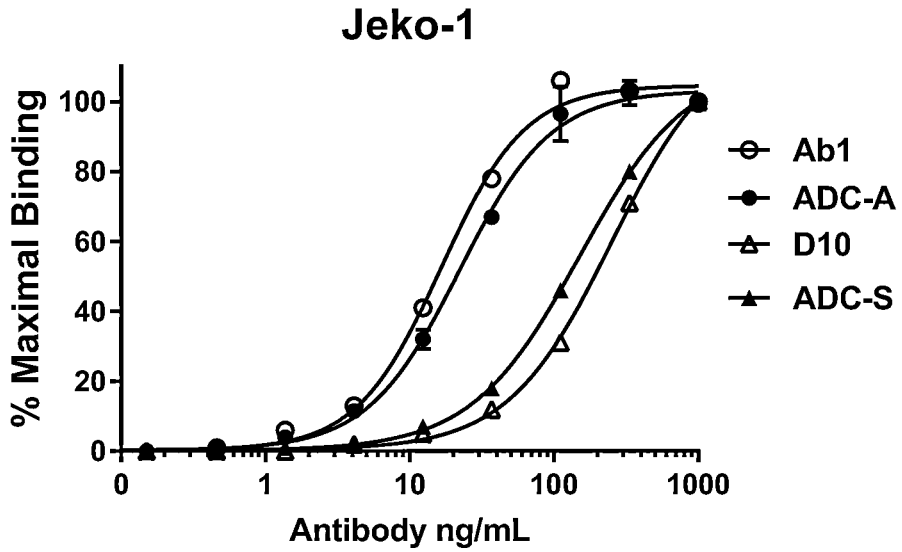

In a different experiment, the binding of Ab1 to Jeko-1 cells was also compared to the binding of D10, a lower affinity antibody that binds the same epitope as Ab1 (FIG. 3B). Ab1 ($EC_{50}$=16.5 ng/mL; FIG. 3B, open circles) bound Jeko-1 cells with a higher affinity/avidity than did D10 ($EC_{50}$=250 ng/mL; FIG. 3B, open triangles). In addition, the binding of the ADC constructs was compared to that of the corresponding unconjugated parental antibodies (Ab1 versus ADC-A and D10 versus ADC-S). ADC-A bound with an $EC_{50}$ of 22.1 ng/mL (FIG. 3B, closed circles) while ADC-S bound with an $EC_{50}$ of 150 ng/mL (FIG. 3B, closed triangles). The similarity between the $EC_{50}$ values of unconjugated antibodies and the corresponding ADC constructs demonstrates again that drug conjugation had minimal impact on the antibodies' binding to the target cells.

In a similar fashion, the binding of all other ADC constructs to ROR1-positive cells was evaluated. All constructs described herein were found to bind ROR1-positive cells.

Example 3: Internalization of ROR1 Antibody and Immunoconjugates

Multiple methods were used to determine antibody internalization. In one approach, internalization was measured using a pulse-chase methodology that quantitates non-internalized, cell surface antibody at 15, 30, 60, 120, and 240 minutes using flow cytometry. Jeko-1 cells were grown and harvested prior to confluency, washed with cold PBS and resuspended at $1\times10^7$ in cold FACS buffer (PBS+2% FBS-Fisher/Gibco Cat. No. 16140071). $1\times10^6$ cells were added to microcentrifuge tubes or wells. Internalization of Ab1 and ADC constructs by the cells was determined at saturating antibody concentrations, using 30 μg/ml for Jeko-1 cells and 100 μg/mL for MDA-MB-231 cells. 10× stock solutions of ADC constructs or Ab1 were prepared (300 μg/ml for use with Jeko-1 cells or 1 mg/ml for use with MDA-MB-231 cells) and 10 μL of sample or buffer control was added to the following (adding additional tubes for each time point):

a) Unstained
b) Secondary antibody only
c) Negative Control hIgG mAb at 30 μg/ml—time 0
d) Positive Control ADC construct or Ab1 at 30 μg/ml—time 0
e) ADC construct or Ab1—time point 1
f) ADC construct or Ab1—time point 2, etc.

Cells and antibody were incubated on ice for 20 minutes, spun at 300×g for 4 minutes, washed twice with 200 μL of FACS buffer, and resuspended in 100 μL of FACS buffer. The samples were incubated at 37° C. for 15, 30, 60, 120, and 240 minutes, as indicated above. Internalization was terminated by transferring the samples to ice. A time course for antibody internalization was generated for each test article as described above, after which antibody remaining on the cell surface was detected using a PE-labeled secondary antibody. Cells were spun at 250×g, washed twice with FACS buffer and resuspended in 100 μL of FACS buffer. The secondary antibody (goat anti-human IgG-PE, Fc-gamma specific—eBiosciences, Cat. No. 12-4998) was diluted 1:2000 (10× stock) in FACS buffer and 10 μL /tube was added to the appropriate tubes. Cells were incubated on ice for 20 minutes, washed twice with FACS buffer and resuspended in 100 μL of fix buffer (4% paraformaldehyde in PBS). Subsequently, FACS analysis was performed. The median fluorescent intensity (MFI) was quantitated and the degree of receptor internalization was determined using the amount of the antibody or ADC present at each time point when compared to the amount present at time=0. The dashed line represents background staining (secondary antibody only).

Figure 4A:
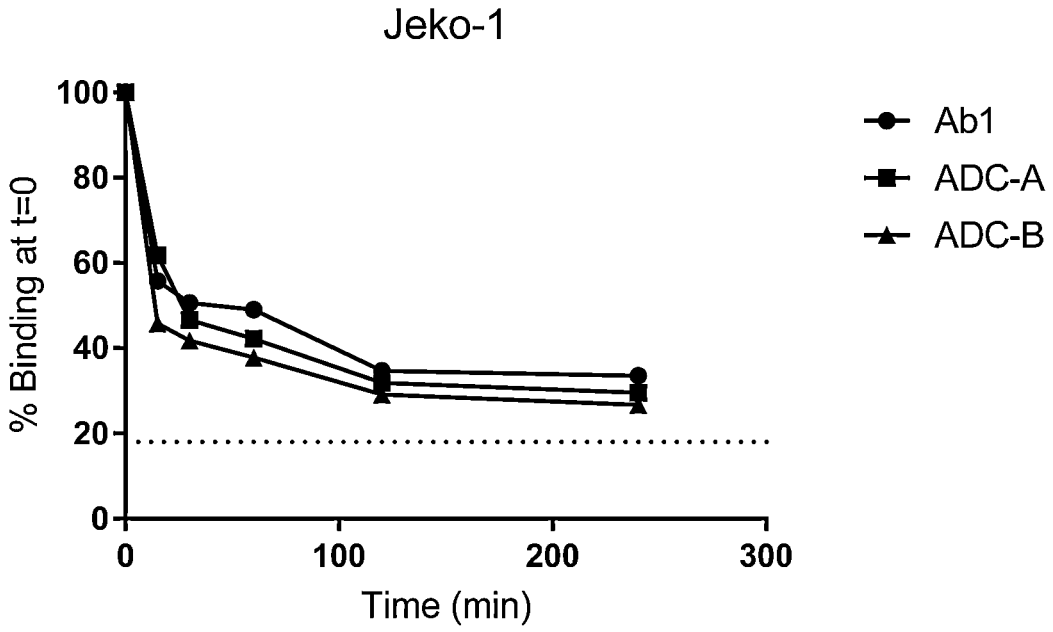
FIGS. 4A and 4B are graphs illustrating the internalization of Ab1, ADC-A, and ADC-B into Jeko-1 cells (4A), and the internalization of Ab1 and ADC-A into MDA-MB-231 cells (4B). The addition of linker and payload to Ab1 did not negatively impact its binding or internalization, as demonstrated with ADC-A and ADC-B.
Figure 4B:
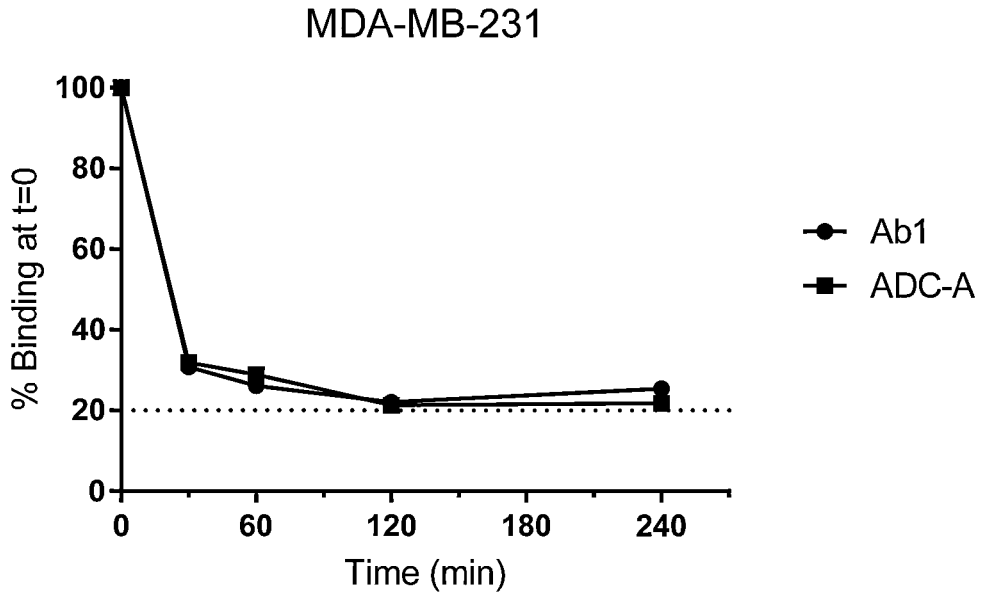

Ab1 bound to and was rapidly internalized by both Jeko-1 (FIG. 4A) and MDA-MB-231 (FIG. 4B) cells. Internalization of 80-90% of the bound antibody was observed in less than 60 minutes for MDA-MB-231 or 120 minutes for Jeko-1. Notably, the addition of linker and payload to Ab1 did not negatively impact binding or internalization, as demonstrated with ADC-A and ADC-B (FIG. 4A, compare ADC-A and ADC-B with Ab1, and FIG. 4B, compare ADC-A with Ab1).

In a similar fashion, the internalization characteristics of other ADC constructs with different linkers and payloads were evaluated using Jeko-1 cells. All of the constructs displayed similar kinetics of internalization compared to Ab1, consistent with the above observation that the linkers and payloads used did not impact the antibody characteristics (data not shown).

We also evaluated the internalization properties of an ADC construct (ADC-T) utilizing a ROR1 antibody (4A5) that recognizes an epitope distinct from Ab1, but with linker and payload chemistries identical to those of ADC-A. ADC-T bound Jeko-1 cells but was internalized at a slower rate and to a lesser extent than did ADC-A (data not shown). These data demonstrate the importance of the antibody and its epitope in determining the internalization properties of the ADC construct.

Figure 5:
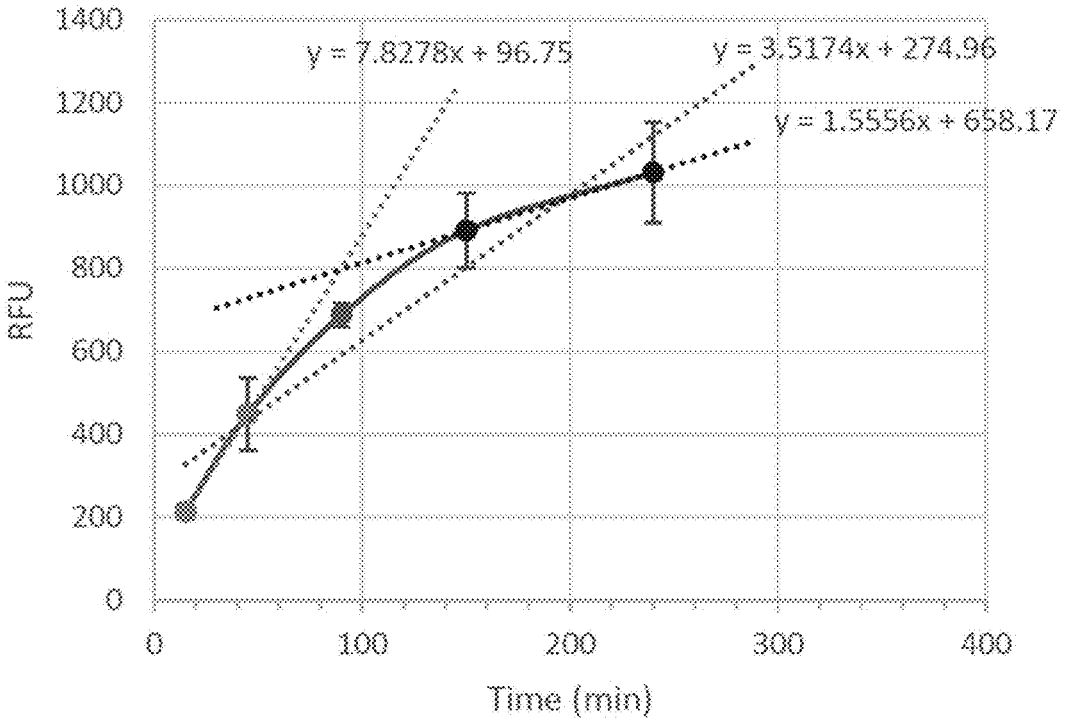
FIG. 5 is a graph illustrating the internalization rate of Ab1 in MDA-MB-231 cells. The graph shows an initially rapid rate, and then a slower rate, of cell surface receptor clearance.

Internalization of Ab1 was also characterized using conventional immunofluorescent staining methods and MDA-MB-231 cells. In this approach, Ab1 was loaded at the cell surface and the cells were subsequently fixed and surface Ab1 was quantitated. In addition, a second sample of the cells was permeabilized and total Ab1 (surface and intracellular) was quantitated. In this protocol, the primary antibody was allowed to incubate without a secondary antibody, eliminating the possibility that the secondary antibody might influence internalization. Surface staining was observed. After permeabilization, clear and distinct punctate intracellular staining of Ab1 was observed. Furthermore, by utilizing a lysosome-specific tracker, it was demonstrated that internalized Ab1 co-localized with the lysosomal pathway. This finding is consistent with a mode of antibody internalization that primarily occurs by the lysosome/endosome pathway. Finally, the rate of internalization was quantitated. When cells were subjected to continuous exposure to Ab1, the initial rate was approximately twice the average rate, and the terminal rate was approximately half the average rate (FIG. 5). This indicates that there is an initial rapid phase of clearing the cell surface receptor followed by a slower process of binding and internalizing receptor that is newly expressed on the cell surface. The newly expressed cell surface receptor may be recycled, expressed from intracellular stores, and/or newly synthesized. The extent and character of co-localization of Ab1 was similar to EGFR, showing substantially lysosomal co-localization after 4 hours.

Example 4: Measurement of Cell Surface ROR1 Expression

Internalization of antibodies was measured using pulse-chase approaches that detected non-internalized, cell surface antibody at various time points (2, 5, 10, 15, 20, 30, 60, 120 and 240 minutes). In this study, in addition to measuring non-internalized cell surface antibody, the expression of ROR1 on the cell surface was quantitated either by (1) re-staining with Ab1 and a secondary antibody or (2) by using a second, labeled anti-ROR1 antibody that recognizes an epitope distinct from that of Ab1.

Figure 6:
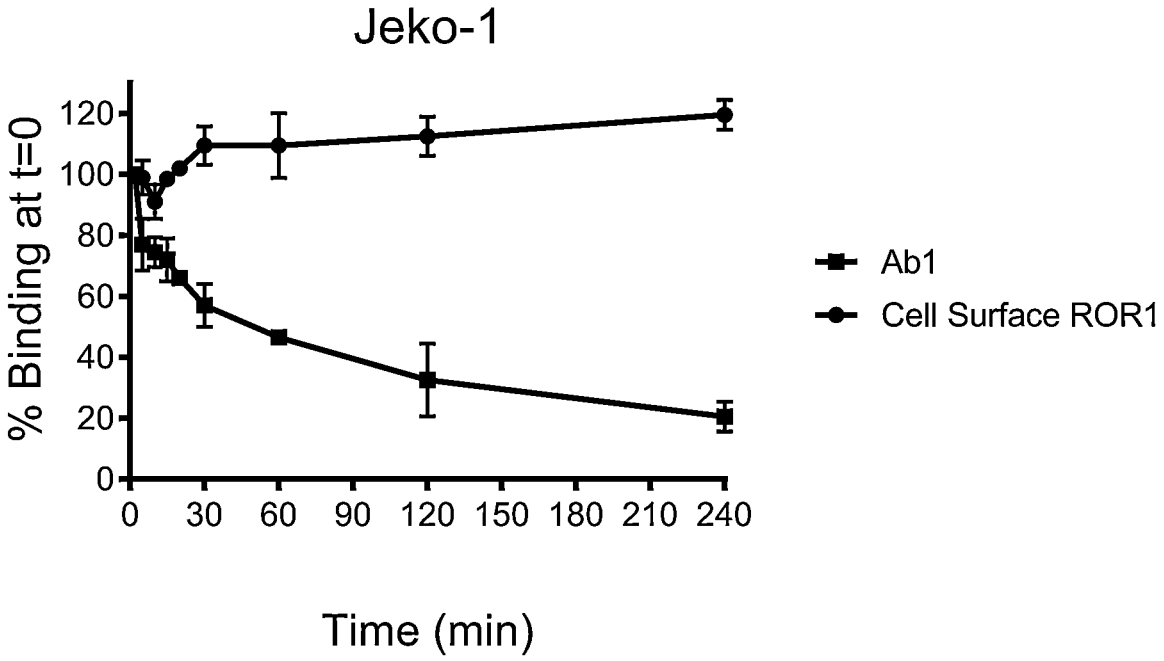
FIG. 6 is a graph illustrating the cell surface expression of ROR1 during Ab1 internalization into Jeko-1 cells. While Ab1 is rapidly internalized, quantitation of cell surface ROR1 shows a small decrease in the first 10 minutes, with subsequent measurements indicating restoration of ROR1 surface expression to initial or slightly higher levels.
Figure 7A:
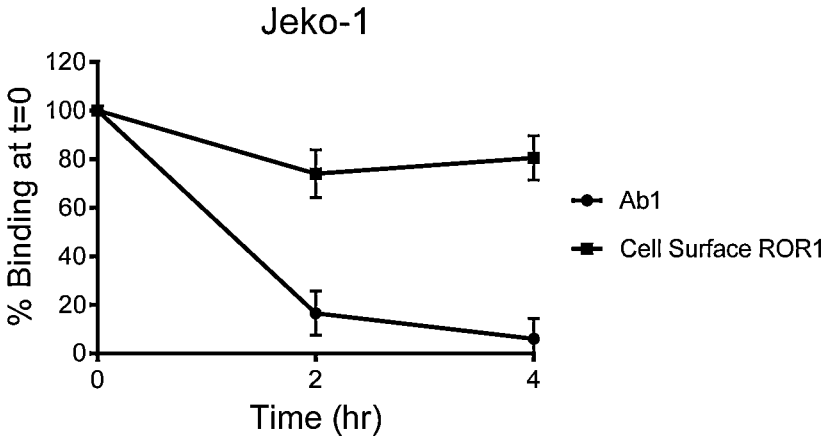
FIGS. 7A-C are graphs illustrating cell surface expression of ROR1 during Ab1 internalization on Jeko-1 cells (7A), MDA-MB-468 cells (7B), and MDA-MB-231 cells (7C).
Figure 7B:
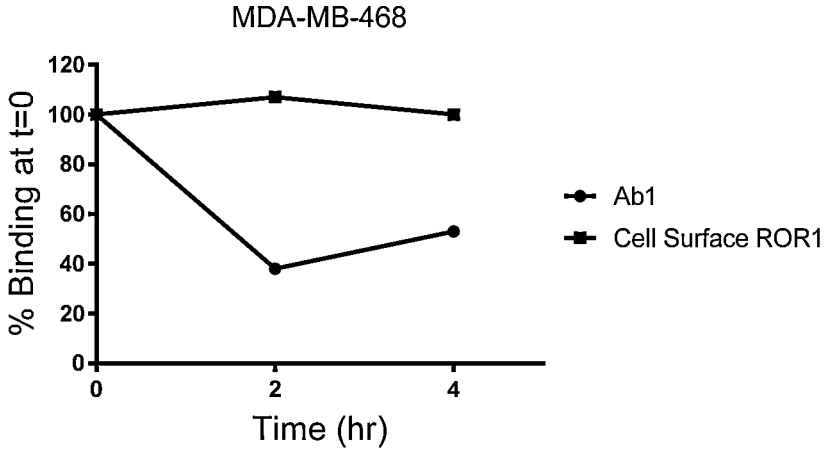
Figure 7C:
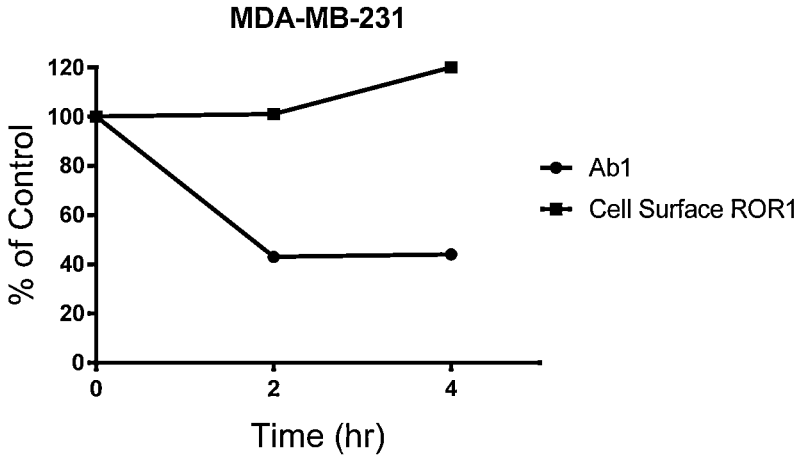
Figure 8A:
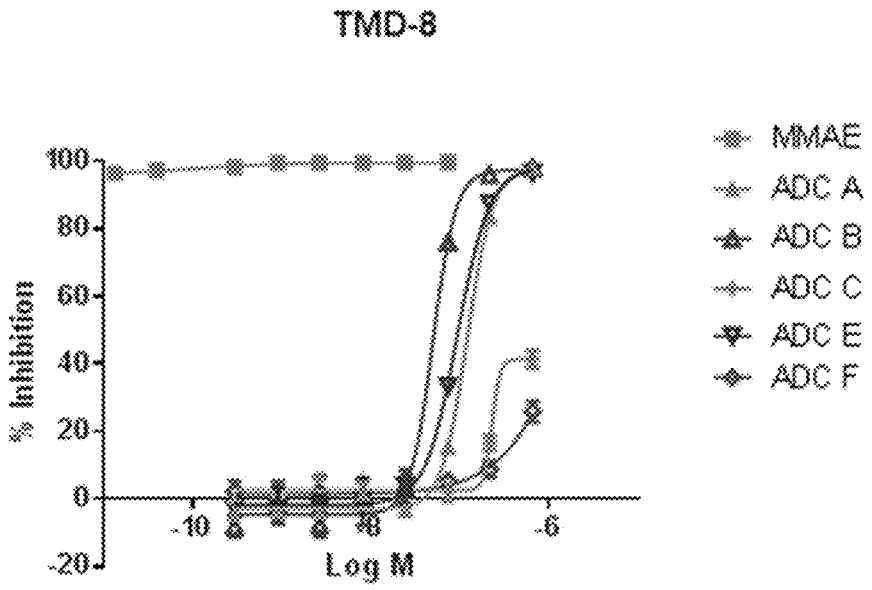
FIGS. 8A-8I are representative $IC_{50}$ plots showing ROR1 binding by immunoconjugates of the present disclosure, as well as unconjugated MMAE, in cancer cell lines TMD-8 (8A), HBL-1 (8B), DOHH2 (8C), MDA-MB-468 (8D), Bt549 (8E), TOV112D (8F), JHOM1 (8G), SKOvr3 (8H), and Mino (81).
Figure 8B:
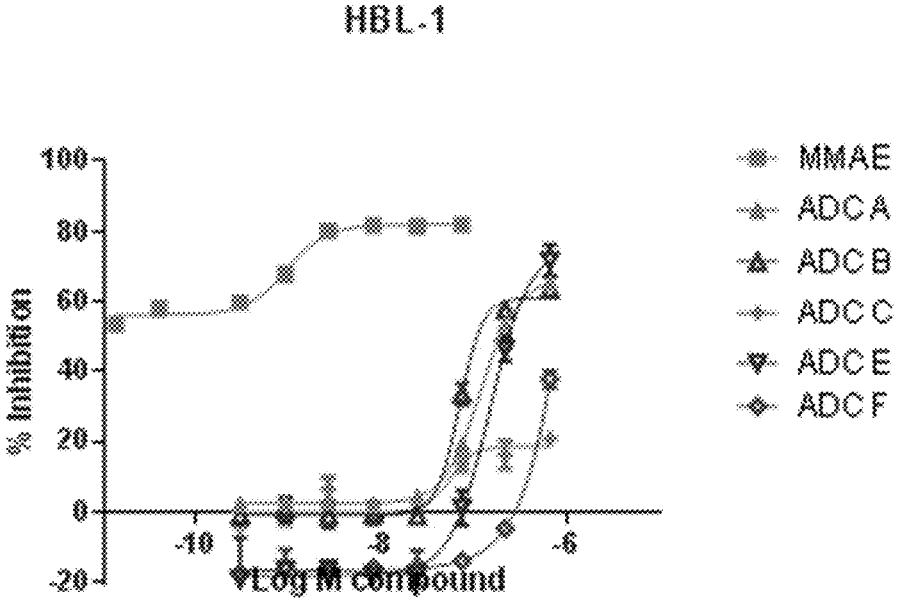
Figure 8C:
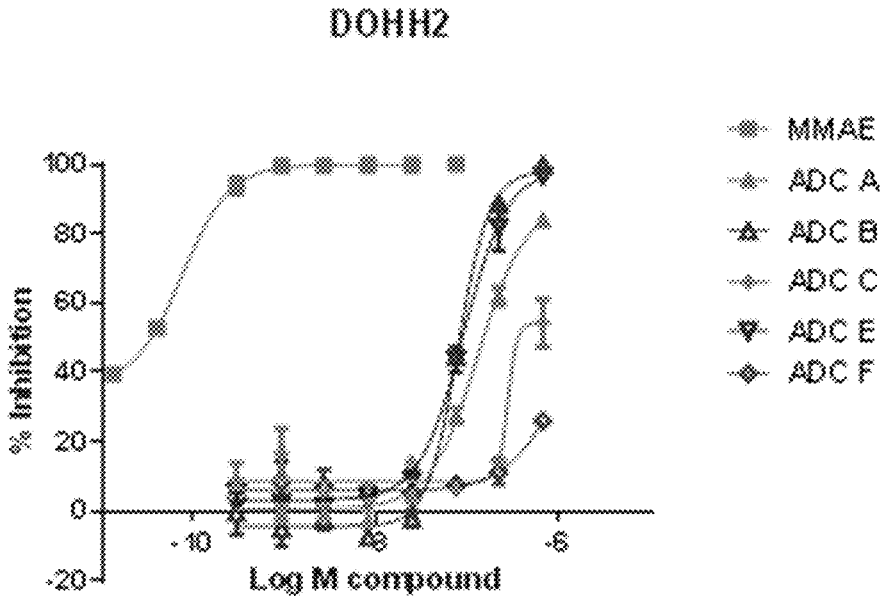
Figure 8D:
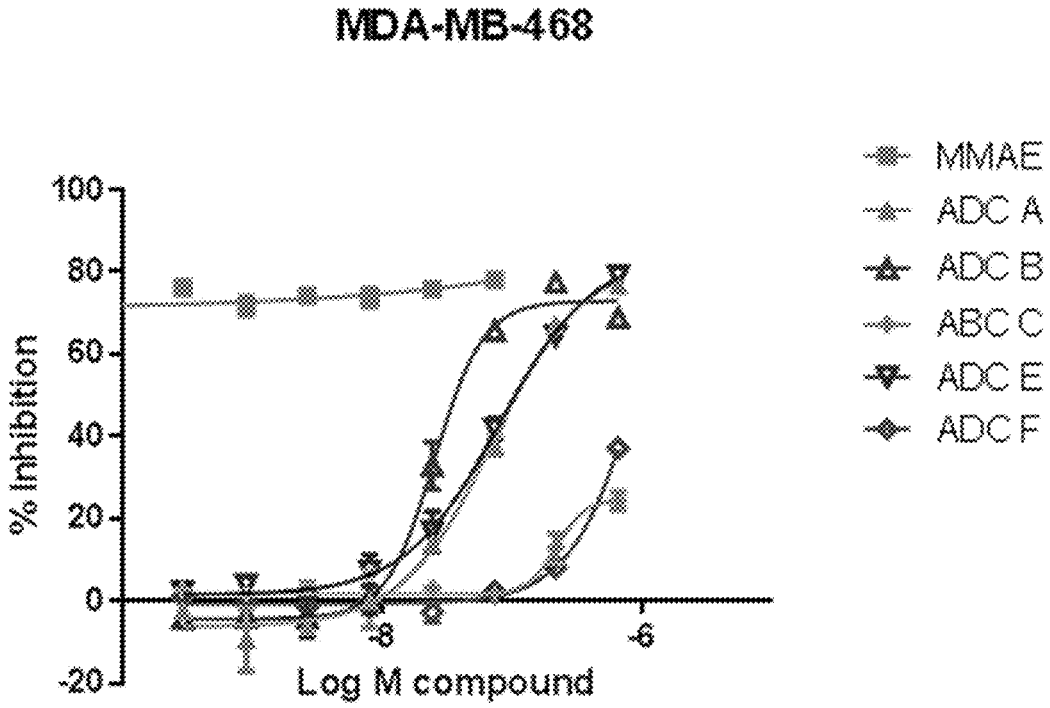
Figure 8E:
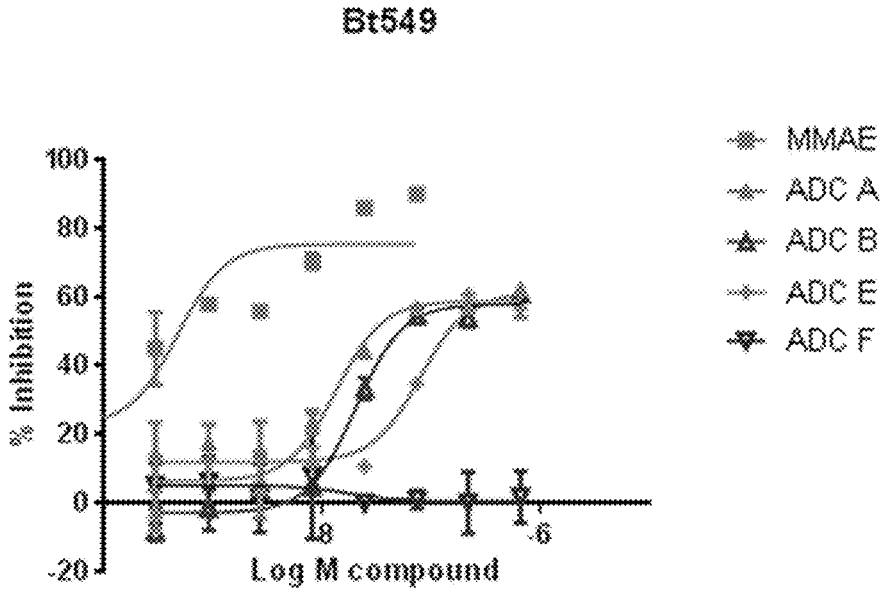
Figure 8F:
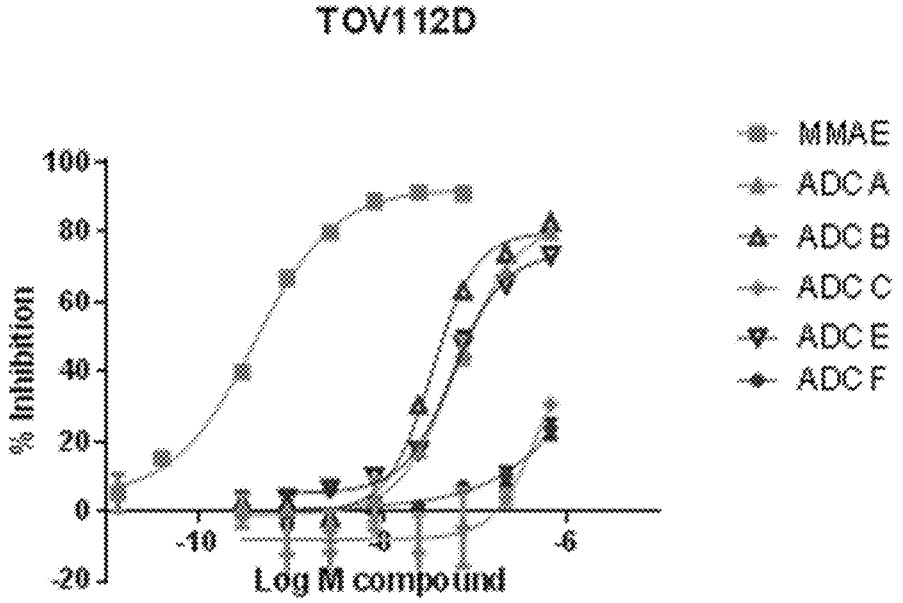
Figure 8G:
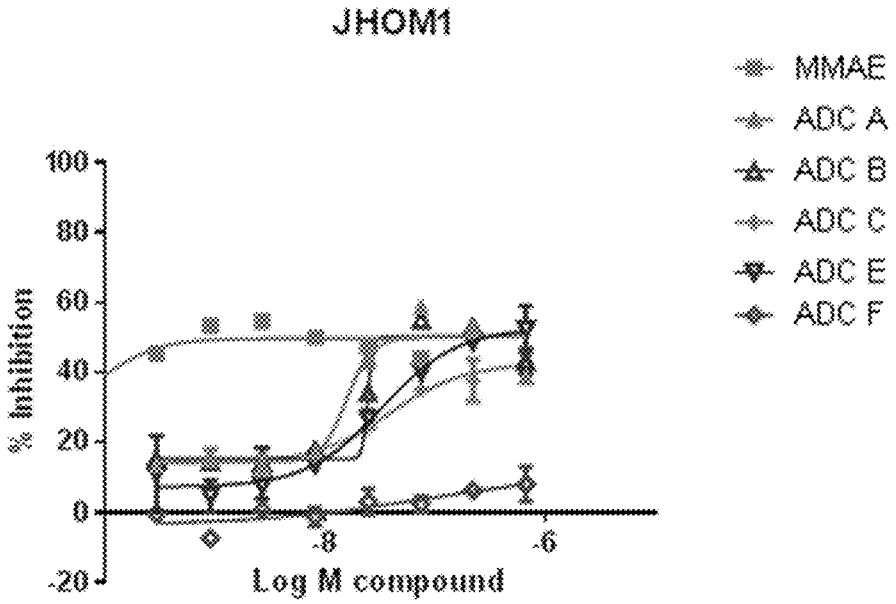
Figure 8H:
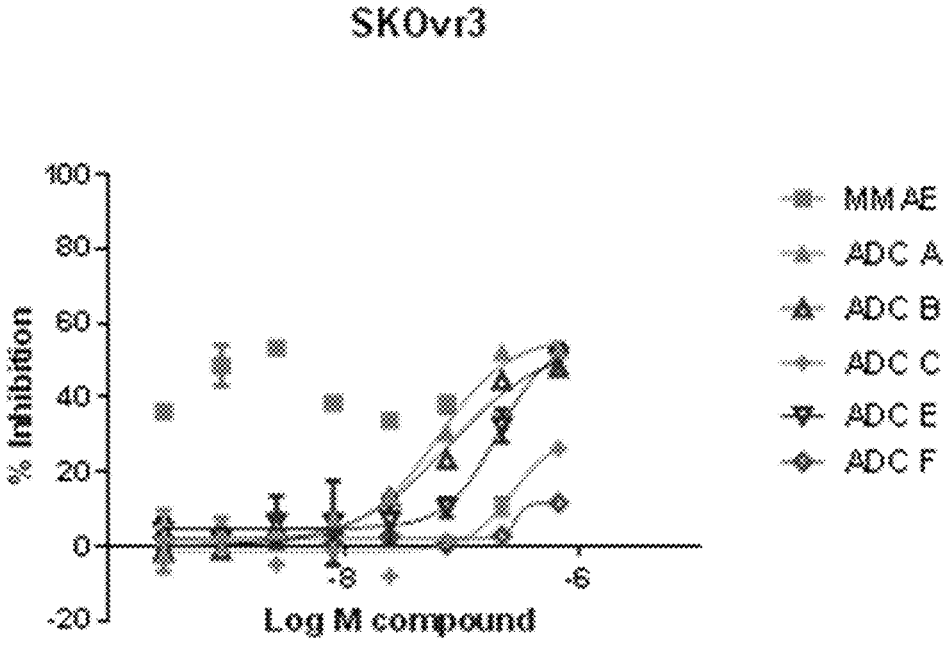
Figure 8I:
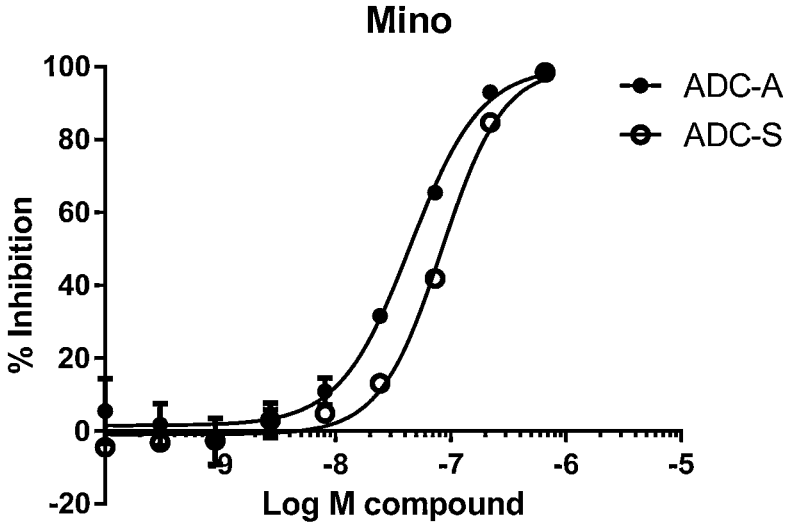

For the first approach, internalization of Ab1 on Jeko-1 cells was performed as described in Example 3 (one sample was processed at each time point to quantitate antibody remaining on the cell surface). Additionally, a second sample at each time point was rapidly re-stained using saturating levels of Ab1 (30 μg/mL) while maintaining the cells on ice. Subsequently, the cells were washed and surface antibody was quantitated using the same secondary antibody used for internalization measurements. As shown previously, Ab1 was rapidly internalized (FIG. 6, squares). By contrast, while quantitation of cell surface ROR1 initially showed a small decrease in the first 10 minutes, subsequent measurements indicated ROR1 surface expression was restored to initial or slightly higher levels (FIG. 6, circles). These data are consistent with recycling of ROR1 to the cell surface dissociated from antibody, or with rapid upregulation of ROR1 through de novo synthesis or trafficking of intracellular stores. This experiment was repeated using Jeko-1 (FIG. 7A), MDA-MB-468 (FIG. 7B), and MDA-MB-231 (FIG. 7C) cells, with similar results.

An alternative approach to measuring cell surface ROR1 expression in conjunction with Ab1 internalization studies was tested. Specifically, cell surface ROR1 expression was quantitated at 0, 0.5, 1, 2, and 4 hours by staining cells directly with a labeled anti-ROR1 antibody that binds an epitope distinct from that of Ab1. ROR1 surface expression on Jeko-1 cells treated with ADC-A, M, N, and P was assessed. Consistent with the results obtained using the previously described approach, ROR1 expression was maintained, or slightly increased, while cells were being treated with Ab1-based ADC constructs (data not shown).

These data indicate that Ab1 and its immunoconjugates may be internalized effectively by ROR1-positive cells. Further, the persistent expression of ROR1 on the cell surface demonstrates that ROR1 is an excellent target for delivering cytotoxic agents to cancer cells through an ADC of the present invention.

Example 5: Potency of Immunoconjugates In Vitro

The ADC-A, B, C, E, and F immunoconjugates, which had different cytotoxic moieties and linker chemistry, were analyzed for this Example. ROR1 binding by these conjugates was tested in cell culture to define the potency of various linker-cytotoxic agent combinations. Three different types of cancer cell lines were tested: B-lymphoma cell-lines TMD-8, HBL-1, and DOHH2; triple negative breast cancer cell lines HCC1187, MDA-MB-468, Bt549; and ovarian cancer cell lines A2008, TOV112D, JHOM1, and SKOvr3.

Cells were cultured in log phase growth and distributed into 96-well plates. Each cell line was plated at a slightly different cell density, ranging from $5\times10^3$ to $50\times10^4$ cells/well. Cells in duplicate were incubated with 3-fold serial dilution of a particular immunoconjugate (10, 3.33, 1.11, 0.37, 0.12, 0.041, 0.014, and 0.0045 μM) for 72 hours at 37° C. and 5% $CO_2$. After treatment, cells were incubated with an equal volume of CellTiter-Glo® reagent (Promega Inc.) for 15 minutes at room temperature and viability was determined by a luminometer. Curves and $EC_{50}$ values were generated in GraphPad Prism using a sigmoidal dose response non-linear regression fit. The data from these experiments are summarized in Table 8. FIGS. 8A-8I show representative $IC_{50}$ plots for all five immunoconjugates tested against the indicated cell lines.

TABLE 8

Cytotoxicity of Exemplary Immunoconjugates in vitro*

| Cancer Type | Cell line | ADC-A | ADC-B | ADC-C | ADC-E | ADC-F |
|---|---|---|---|---|---|---|
| B-cell lymphoma | TMD-8 | 122 | 50 | >1000 | 94.3 | >1000 |
| | HBL-1 | 118 | 70.1 | >1000 | 147 | >1000 |
| | DOHH2 | 129 | 78.3 | >1000 | 89.6 | >1000 |
| Triple negative breast cancer | HCC1187 | 6.8 | 6.2 | >1000 | | >1000 |
| | MDA-MB-468 | 23.5 | 18.8 | >1000 | 80.1 | >1000 |
| | Bt549 | 13.5 | 20.2 | >1000 | 74.4 | >1000 |

TABLE 8-continued

Cytotoxicity of Exemplary Immunoconjugates in vitro*

| Cancer Type | Cell line | ADC-A | ADC-B | ADC-C | ADC-E | ADC-F |
|---|---|---|---|---|---|---|
| Ovarian cancer | A2008 | 125 | 49 | >1000 | | >1000 |
| | TOV112D | 62.4 | 34.2 | >1000 | 57.8 | >1000 |
| | JHOM1 | 15.6 | 24.3 | >1000 | 32.9 | >1000 |
| | SKOvr3 | 62.6 | 78.7 | >1000 | 200.6 | >1000 |

*Data represented as $IC_{50}$ in nM. Empty cells: not done.

Example 6: Additional Data on Potency of Immunoconjugates In Vitro

This Example presented additional data on the potency of the various ADCs in inducing cell death of a variety of cancer cell lines. Cells were grown and distributed into 96-well plates as described in Example 5. Cells in duplicate were incubated with 3-fold serial dilution of a particular immunoconjugate (660, 220, 73.3, 24.4, 8.14, 2.71, 0.91, and 0.3 nM) for 72 hours at 37° C. and 5% $CO_2$. In some experiments, cells were incubated with an immunoconjugate for 96 hours instead of 72 hours (values highlighted with "*"). After treatment, cell viability was determined as described in Example 5. The data from these experiments is summarized in Tables 9.1 through 9.17 below. Cell surface ROR1 expression was assessed by quantitative flow cytometry and ROR1 expression was characterized as MFI>30 or MFI<30 (MFI: mean fluorescent intensity). The data demonstrate that payload-sensitive cancer cells expressing ROR1 responded to a number of the tested ADCs in the cell death assays described herein. While many of the ADC-responsive cancer cells expressed high levels of ROR1 (MFI>30), some cells expressing lower levels of ROR1 (MFI<30) were also sensitive to certain ADCs.

The MEC1 cell line, which is derived from B-chronic lymphocytic leukemia in prolymphocytoid transformation, was transfected with either an expression vector encoding human ROR1 or a control vector, and stable cell lines were created using selection media containing G418. ROR1-transfected MEC1 cells had significantly greater proportions of cells in S/G2/M phase than did control-transfected cells 16 hours after being transferred from serum-free medium to complete growth medium, implying that expression of ROR1 increased the relative proportions of cells undergoing cell division. Consistent with this, $ROR1^+$ MEC1 cells had significantly greater numbers of cells ≥48 hours after being transferred from serum-free medium than did comparably seeded cultures of MEC1 cells that did not express ROR1. Increased levels of p-AKT and p-CREB were also observed in MEC1 cells made to express ROR1 relative to MEC1 cells transfected with control vector.

TABLE 9.1

Cytotoxicity of ADC-A in vitro

| Cell Line | Cancer Type | ADC-A Binding $K_D$ (nM) | ADC-A $EC_{50}$ (nM) | MMAE $EC_{50}$ (nM) | ROR1 Expression |
|---|---|---|---|---|---|
| Mec-vector | CLL | | 558 | 0.5 | MFI < 30 |
| Mec-ROR | CLL | | 208 | 0.6 | MFI > 30 |
| Jeko-1 | MCL | 0.10 | 22.4*, 40.4*, 186.7 | <0.0001 | MFI > 30 |
| Mino | MCL | | 19.5, 27.7* | <0.0001 | MFI > 30 |
| TMD-8 | DLBCL | | 122* | <0.0001 | MFI < 30 |
| HBL-1 | DLBCL | | 118* | <0.0001 | MFI > 30 |

TABLE 9.1-continued

Cytotoxicity of ADC-A in vitro

| Cell Line | Cancer Type | ADC-A Binding $K_D$ (nM) | ADC-A $EC_{50}$ (nM) | MMAE $EC_{50}$ (nM) | ROR1 Expression |
|---|---|---|---|---|---|
| DOHH2 | DLBCL | | 129, 48.3* | 0.007 | MFI > 30 |
| OCI-Ly18 | DLBCL | | 95 | 0.003 | MFI > 30 |
| U2932 | DLBCL | | 176 | 0.006 | MFI < 30 |
| OCI-Ly19 | DLBCL | | 199 | | |
| WSU-DLCL | DLBCL | | 68 | 0.06 | MFI > 30 |
| KMS-PE | MM | | 43.3, 89 | | |
| RPMI-8229 | MM | | 174 | | |
| OPM2 | MM | | 123 | | |
| L363 | MM | | 244 | | |
| NCI-H929 | MM | | 179 | | |
| HCC1187 | TNBC | | 2.3*, 6.8 | <0.0001 | MFI > 30 |
| HCC1806 | TNBC | | 13.4*, 38.1 | <0.0001 | MFI > 30 |
| MDA-MB-468 | TNBC | | 23.4, 21.7*, 82.5, 23.5* | <0.0001 | MFI > 30 |
| MDA-MB-231 | TNBC | 0.32 | 58.4*, 106, 46.7* | <0.0001 | MFI > 30 |
| Bt549 | TNBC | | 13.5 | 0.047 | MFI > 30 |
| Hs578T | TNBC | | 22.9 | <0.0001 | |
| DU4475 | TNBC | | 248 | 2.5 | MFI > 30 |
| HCC1937 | TNBC | | >1,000 | >1,000 | MFI > 30 |
| MCF-7 | Breast | | 198.4*, 289.0, >1000* | <0.0001 | MFI < 30 |
| H1975 | NSCLC | | 9.7 | <0.0001 | MFI > 30 |
| H460 | NSCLC | | 61.5 | <0.0001 | MFI > 30 |
| A549 | NSCLC | | 53.4 | 0.06 | MFI > 30 |
| Hep-G2 | HCC | | >1,000 | >1,000 | |
| A4573 | EWS | | 15.3 | <0.0001 | MFI > 30 |
| SKES | EWS | | 15.3 | 0.03 | MFI > 30 |
| U2OS | OS | | 223 | 1.2 | MFI > 30 |
| HOS | OS | | 126, 148 | 0.06 | MFI > 30 |
| SAOS | OS | | 15.6, 26.3 | 0.05 | MFI > 30 |
| FaDu | HN | | >1,000 | >1,000 | |
| A2008 | Ovarian | | 125 | 0.03 | |
| OvCar4 | Ovarian | | 283 | 24.2 | MFI > 30 |
| TOV112D | Ovarian | | 62.4 | 0.04 | MFI > 30 |
| JHOM1 | Ovarian | | 15.6 | 0.01 | MFI > 30 |
| SKOvr3 | Ovarian | | 62.6 | 0.01 | MFI > 30 |
| ES2 | Ovarian | | 170 | 1.1 | MFI > 30 |
| A2780 | Ovarian | | 64 | 0.08 | MFI > 30 |
| Bx-PC3 | Pancreatic | | 47.4 | 0.04 | MFI > 30 |
| As-PC1 | Pancreatic | | >1,000 | 0.04 | MFI > 30 |
| Ramos | Burkitt's | | 649.8 | <0.0001 | MFI < 30 |

TABLE 9.2

Cytotoxicity of ADC-E in vitro

| Cell Line | Cancer Type | ADC-E $EC_{50}$ (nM) | MMAE $EC_{50}$ (nM) |
|---|---|---|---|
| TMD-8 | DLBCL | 94.3 | <0.0001 |
| HBL-1 | DLBCL | 147 | <0.0001 |
| DOHH2 | DLBCL | 89.6 | 0.007 |
| HCC1187 | TNBC | | <0.0001 |
| MDA-MB-468 | TNBC | 80.1 | <0.0001 |
| Bt549 | TNBC | 74.4 | 0.047 |
| A2008 | Ovarian | | 0.03 |
| TOV112D | Ovarian | 57.8 | 0.04 |
| JHOM1 | Ovarian | 32.9 | 0.01 |
| SKOvr3 | Ovarian | 200.6 | 0.01 |

TABLE 9.3

Cytotoxicity of ADC-B in vitro

| Cell Line | Cancer Type | ADC-B $EC_{50}$ (nM) | DM1 $EC_{50}$ (nM) |
|---|---|---|---|
| TMD-8 | DLBCL | 50 | 1.4 |
| HBL-1 | DLBCL | 70.1 | 9.3 |
| DOHH2 | DLBCL | 78.3 | 1.78 |
| OCI-Ly18 | DLBCL | 40 | |

TABLE 9.3-continued

Cytotoxicity of ADC-B in vitro

| Cell Line | Cancer Type | ADC-B $EC_{50}$ (nM) | DM1 $EC_{50}$ (nM) |
|---|---|---|---|
| U2932 | DLBCL | 53.9 | |
| OCI-Ly19 | DLBCL | 40 | |
| WSU-DLCL | DLBCL | >1,000 | |
| KMS-12PE | MM | 72 | |
| RPMI-8229 | MM | 91 | |
| OPM2 | MM | 108 | |
| L363 | MM | 177 | |
| NCI-H929 | MM | 90 | |
| HCC1187 | TNBC | 6.2, 25.1 | 3.9 |
| HCC1806 | TNBC | 23.1 | |
| MDA-MB-468 | TNBC | 18.8, 70.1 | 15.2 |
| MDA-MB-231 | TNBC | 67.5 | |
| Bt549 | TNBC | 20.2 | 0.047 |
| Hs578T | TNBC | 11.7 | |
| DU4475 | TNBC | 105 | |
| HCC1937 | TNBC | >1,000 | |
| MCF-7 | ER+/PR+/HER2− Breast | >1,000 | |
| A2008 | Ovarian | 49 | |
| OvCar4 | Ovarian | 291 | >1,000 |
| TOV112D | Ovarian | 34.2 | 2.4 |
| JHOM1 | Ovarian | 24.3 | 0.01 |
| SKOvr3 | Ovarian | 78.7 | 9.1 |

TABLE 9.3-continued

Cytotoxicity of ADC-B in vitro

| Cell Line | Cancer Type | ADC-B $EC_{50}$ (nM) | DM1 $EC_{50}$ (nM) |
|---|---|---|---|
| ES2 | Ovarian | 117 | |
| A2780 | Ovarian | 36 | |

TABLE 9.4

Cytotoxicity of ADC-C in vitro

| Cell Line | Cancer Type | ADC-C $EC_{50}$ (nM) | DM1 $EC_{50}$ (nM) |
|---|---|---|---|
| TMD-8 | DLBCL | >1,000 | 1.4 |
| HBL-1 | DLBCL | >1,000 | 9.3 |
| DOHH2 | DLBCL | >1,000 | 1.78 |
| HCC1187 | TNBC | >1,000 | 3.9 |
| MDA-MB-468 | TNBC | >1,000 | 15.2 |
| Bt549 | TNBC | >1,000 | 0.047 |
| A2008 | Ovarian | >1,000 | |
| TOV112D | Ovarian | >1,000 | 2.4 |
| JHOM1 | Ovarian | >1,000 | 0.01 |
| SKOvr3 | Ovarian | >1,000 | 9.1 |

TABLE 9.5

Cytotoxicity of ADC-F in vitro

| Cell Line | Cancer Type | ADC-F $EC_{50}$ (nM) | DM1 $EC_{50}$ (nM) |
|---|---|---|---|
| TMD-8 | DLBCL | >1,000 | 1.4 |
| HBL-1 | DLBCL | >1,000 | 9.3 |
| DOHH2 | DLBCL | >1,000 | 1.78 |
| HCC1187 | TNBC | >1,000 | 3.9 |
| MDA-MB-468 | TNBC | >1,000 | 15.2 |
| Bt549 | TNBC | >1,000 | 0.047 |
| A2008 | Ovarian | >1,000 | |
| TOV112D | Ovarian | >1,000 | 2.4 |
| JHOM1 | Ovarian | >1,000 | 0.01 |
| SKOvr3 | Ovarian | >1,000 | 9.1 |

TABLE 9.6

Cytotoxicity of ADC-H in vitro

| Cell Line | Cancer Type | ADC-H $EC_{50}$ (nM) | Azonafide $EC_{50}$ (nM) |
|---|---|---|---|
| Jeko | MCL | 170 | |
| MDA-MB-231 | TNBC | >1,000 | |
| A549 | NSCLC | >1,000 | >1,000 |
| Hep-3B | HCC | >1,000 | >1,000 |

TABLE 9.7

Cytotoxicity of ADC-I in vitro

| Cell Line | Cancer Type | ADC-I $EC_{50}$ (nM) |
|---|---|---|
| Jeko | MCL | >1000 |
| DOHH2 | DLBCL | >1000 |
| KMS-PE | MM | 266 |
| MDA-MB-468 | TNBC | >1000 |
| MDA-MB-231 | TNBC | >1000 |
| MCF-7 | ER+/PR+/HER2− Breast | >1,000 |
| A549 | NSCLC | >1,000 |
| Hep-G2 | HCC | >1,000 |

TABLE 9.7-continued

Cytotoxicity of ADC-I in vitro

| Cell Line | Cancer Type | ADC-I $EC_{50}$ (nM) |
|---|---|---|
| U2OS | OS | >1,000 |
| FaDu | HN | >1,000 |

TABLE 9.8

Cytotoxicity of ADC-J in vitro

| Cell Line | Cancer Type | ADC-J $EC_{50}$ (nM) |
|---|---|---|
| Jeko | MCL | 59.35 |
| DOHH2 | DLBCL | 5.975 |
| KMS-PE | MM | 362 |
| MDA-MB-468 | TNBC | 146 |
| MDA-MB-231 | TNBC | >1000 |
| MCF-7 | ER+/PR+/HER2− Breast | 268 |
| A549 | NSCLC | >1,000 |
| Hep-G2 | HCC | >1,000 |
| U2OS | OS | >1,000 |
| FaDu | HN | 658.5 |

TABLE 9.9

Cytotoxicity of ADC-K in vitro

| Cell Line | Cancer Type | ADC-K $EC_{50}$ (nM) |
|---|---|---|
| Jeko | MCL | 761.5 |
| DOHH2 | DLBCL | 247 |
| KMS-PE | MM | 1,000 |
| MDA-MB-468 | TNBC | >1000 |
| MDA-MB-231 | TNBC | >1000 |
| MCF-7 | ER+/PR+/HER2− Breast | 363 |
| A549 | NSCLC | >1,000 |
| Hep-G2 | HCC | >1,000 |
| U2OS | OS | >1,000 |
| FaDu | HN | >1,000 |

TABLE 9.10

Cytotoxicity of ADC-L in vitro

| Cell Line | Cancer Type | ADC-L Binding $K_D$ (nM) | ADC-L $EC_{50}$ (nM) | MMAE $EC_{50}$ (nM) |
|---|---|---|---|---|
| Mec-vector | CLL | | 535 | 0.5 |
| Mec-ROR | CLL | | 192 | 0.6 |
| Jeko | MCL | 0.15 | 81.1 | <0.0001 |
| Mino | MCL | | 20.5 | <0.0001 |
| MDA-MB-468 | TNBC | | 141.5 | <0.0001 |
| MCF-7 | ER+/PR+/HER2− Breast | | 232.5* | <0.0001 |

TABLE 9.11

Cytotoxicity of ADC-M in vitro

| Cell Line | Cancer Type | ADC-M Binding $K_D$ (nM) | ADC-M $EC_{50}$ (nM) | MMAE $EC_{50}$ (nM) |
|---|---|---|---|---|
| Mec-vector | CLL | | 569 | 0.5 |
| Mec-ROR | CLL | | 170 | 0.6 |
| Jeko | MCL | 0.12 | 112.3 | <0.0001 |

TABLE 9.11-continued

Cytotoxicity of ADC-M in vitro

| Cell Line | Cancer Type | ADC-M Binding $K_D$ (nM) | ADC-M $EC_{50}$ (nM) | MMAE $EC_{50}$ (nM) |
|---|---|---|---|---|
| Mino | MCL | | 15.8 | <0.0001 |
| MDA-MB-468 | TNBC | | 53.1 | <0.0001 |
| MCF-7 | ER+/PR+/HER2− Breast | | 164.1 | <0.0001 |

TABLE 9.12

Cytotoxicity of ADC-N in vitro

| Cell Line | Cancer Type | ADC-N Binding $K_D$ (nM) | ADC-N $EC_{50}$ (nM) | PNU-159682 $EC_{50}$ (nM) |
|---|---|---|---|---|
| Mec-vector | CLL | | 772 | |
| Mec-ROR | CLL | | 262 | |
| Jeko | MCL | 0.13 | 31.7, 20.3 | |
| Mino | MCL | | 7.7 | |
| DOHH2 | DLBCL | | 3.8 | |
| KMS-PE | MM | | 26.75 | |
| MDA-MB-468 | TNBC | | 4.1, 29.4 | |
| MDA-MB-231 | TNBC | | 71. | 0.005 |
| MCF-7 | ER+/PR+/HER2− Breast | | 78.6 | |
| H460 | NSCLC | | 84.4 | 0.001 |
| A549 | NSCLC | | 30.7 | |
| Hep-G2 | HCC | | 20.8 | |
| U2OS | OS | | 11.25 | |
| FaDu | HN | | 27.05 | |

TABLE 9.13

Cytotoxicity of ADC-O in vitro

| Cell Line | Cancer Type | ADC-O Binding $K_D$ (nM) | ADC-O $EC_{50}$ (nM) | PNU-159682 $EC_{50}$ (nM) |
|---|---|---|---|---|
| Mec-vector | CLL | | 296 | |
| Mec-ROR | CLL | | 116 | |
| Jeko | MCL | 0.12 | 71.7 | |
| Mino | MCL | | 28 | |
| MDA-MB-468 | TNBC | | 85.8 | |
| MDA-MB-231 | TNBC | | 782 | 0.005 |
| MCF-7 | ER+/PR+/HER2− Breast | | 12.65 | |
| H460 | NSCLC | | 365 | 0.002 |

TABLE 9.14

Cytotoxicity of ADC-P in vitro

| Cell Line | Cancer Type | ADC-P Binding $K_D$ (nM) | ADC-P $EC_{50}$ (nM) | PNU-159682 $EC_{50}$ (nM) |
|---|---|---|---|---|
| Mec-vector | CLL | | 30.3 | |
| Mec-ROR | CLL | | 10.4 | |
| Jeko | MCL | 0.11 | 2.4 | |
| Mino | MCL | | 1.2 | |
| MDA-MB-468 | TNBC | | 10.4 | |
| MDA-MB-231 | TNBC | | 24.7 | 0.005 |
| MCF-7 | ER+/PR+/HER2− Breast | | 30.9 | |
| H460 | NSCLC | | 39.6 | 0.001 |

TABLE 9.15

Cytotoxicity of ADC-Q in vitro

| Cell Line | Cancer Type | ADC-Q Binding $K_D$ (nM) | ADC-Q $EC_{50}$ (nM) | MMAE $EC_{50}$ (nM) |
|---|---|---|---|---|
| Jeko | MCL | 0.23 | 265* | <0.0001 |
| Mino | MCL | | 139* | <0.0001 |
| HCC1187 | TNBC | | 5.3* | <0.0001 |
| HCC1806 | TNBC | | 56.1* | <0.0001 |
| MDA-MB-468 | TNBC | | 79.7* | <0.0001 |
| MDA-MB-231 | TNBC | | 167.8* | <0.0001 |
| HCC1937 | TNBC | | >1,000* | >1,000 |
| MCF-7 | ER+/PR+/HER2− Breast | | >1,000* | <0.0001 |
| H1975 | NSCLC | | 26.8* | <0.0001 |
| H460 | NSCLC | | 180.1* | <0.0001 |
| Bx-PC3 | Pancreatic | | 45.6* | 0.04 |

TABLE 9.16

Cytotoxicity of ADC-R in vitro

| Cell Line | Cancer Type | ADC-R Binding $K_D$ (nM) | ADC-R $EC_{50}$ (nM) | PNU-159682 $EC_{50}$ (nM) |
|---|---|---|---|---|
| Mec-vector | CLL | | 183 | |
| Mec-ROR | CLL | | 44.6 | |
| Jeko | MCL | 0.25 | 53.3 | |
| Mino | MCL | | 15 | |
| MDA-MB-468 | TNBC | | 44.3 | |
| MDA-MB-231 | TNBC | | 203 | 0.005 |
| MCF-7 | ER+/PR+/HER2− Breast | | 167* | |
| H460 | NSCLC | | 191 | 0.001 |

TABLE 9.17

Cytotoxicity of ADC-S in vitro

| Cell Line | Cancer Type | ADC-S $EC_{50}$ (nM) | MMAE $EC_{50}$ (nM) |
|---|---|---|---|
| Mino | MCL | 83.3 | <0.0001 |

The data in the tables demonstrate that the tested ADCs are effective against a variety of cancer cell lines with different ROR1 expression levels and different sensitivities to the various payloads.

Example 7: Antigen Dependency of Anti-Proliferative Effects of Exemplary ADCs The studies described in this Example evaluated the dependency of the tested ADCs on ROR1 for their anti-proliferative effects. Jeko-1 cells were cultured in log phase growth prior to experiment setup. For competition experiments, $5\times10^4$ cells were incubated with 100 μg/ml of Ab1 or vehicle control for 2 hours at 37° C. and 5% $CO_2$. Subsequently, 3, 10, and 30 μg/ml of ADC-A was added and the cells were incubated for an additional 72 hours at 37° C. and 5% CO2. Each condition was tested in duplicate. Cell viability was determined as described in Example 5.

Figure 9:
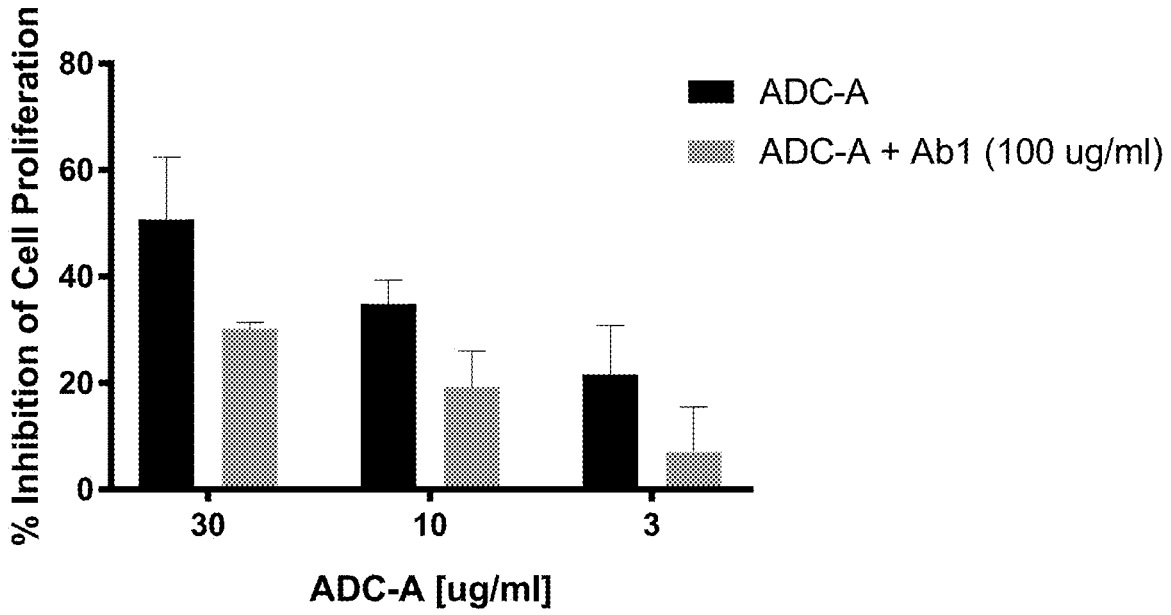
FIG. 9 is a graph illustrating the inhibition of cell proliferation by 3, 10, or 30 μg/mL of ADC-A in Jeko-1 cells, with or without pre-treatment with 100 μg/mL Ab1. ADC-A inhibited cell proliferation in a dose-dependent matter. Pre-incubation of the cells with Ab1 reduced this activity, demonstrating that ADC-A's inhibitory activity on cell proliferation was mediated by the binding of ADC-A to ROR1.
Figure 10:
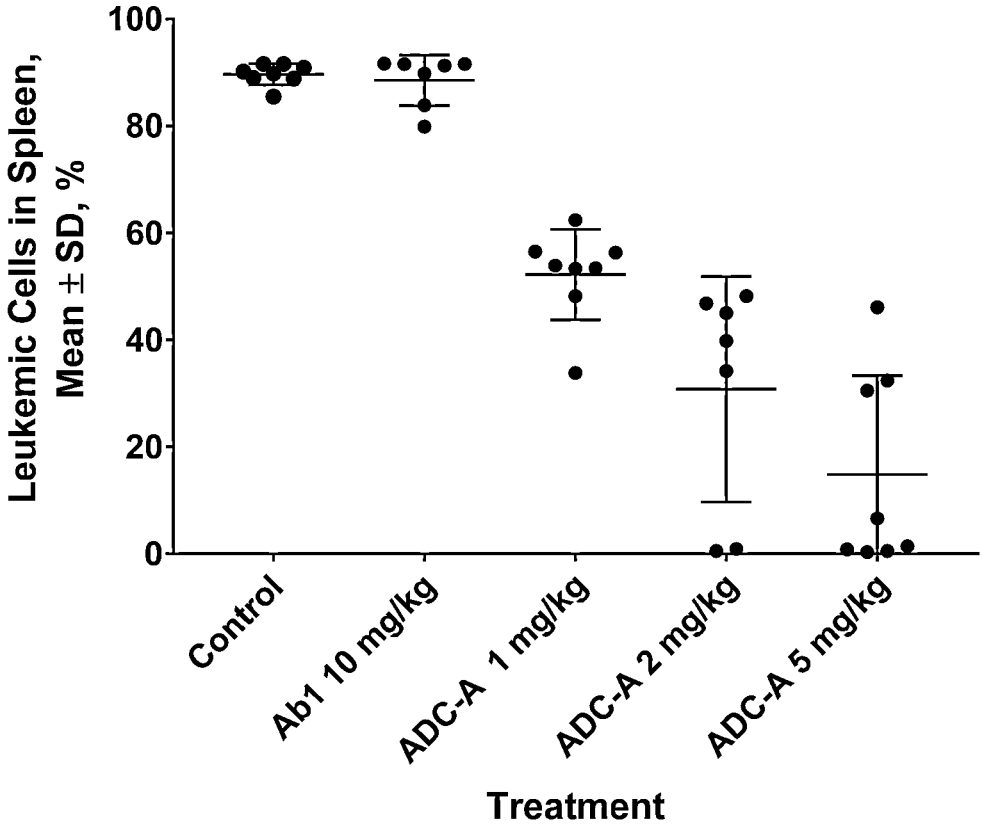
FIG. 10 is a graph illustrating the dose-dependent inhibition of leukemic cell tumor burden in a TCL1-ROR1 chronic lymphocytic leukemia mouse model upon treatment with vehicle, 10 mg/kg Ab1, or 1 mg/kg, 2 mg/kg, or 5 mg/kg ADC-A.
Figure 11:
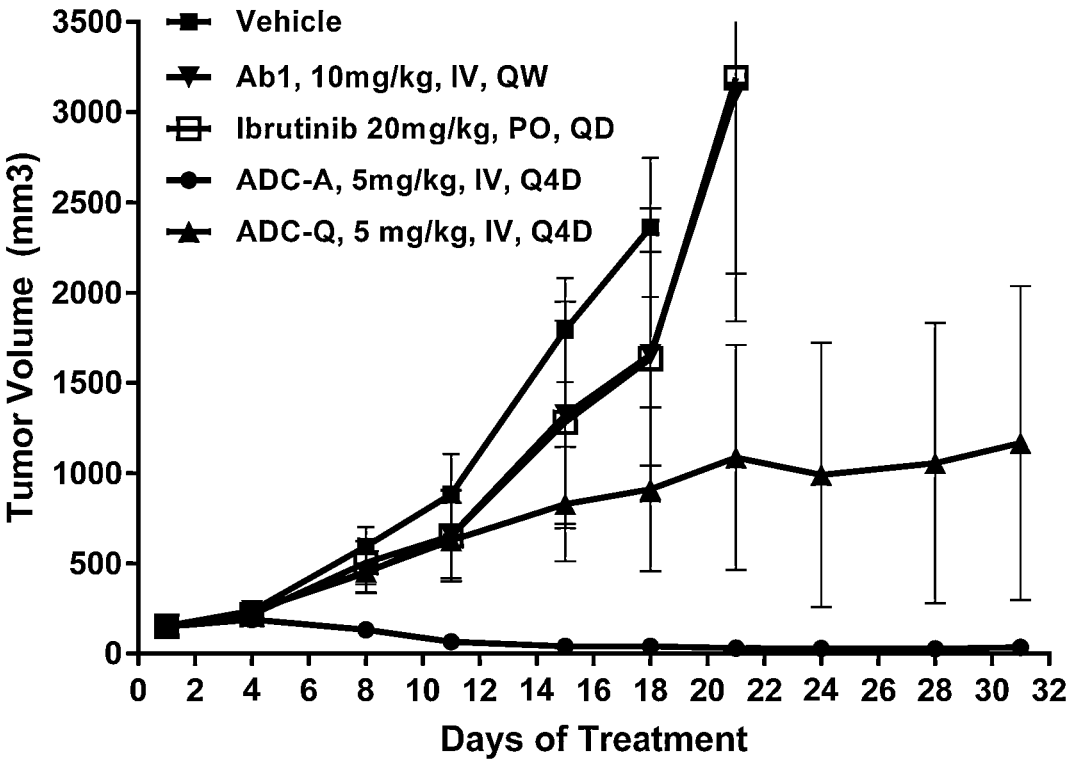
FIG. 11 is a graph illustrating tumor growth inhibition in an MCL xenograft model upon treatment with vehicle, 5 mg/kg ADC-A or ADC-Q intravenously (IV) every four days (Q4D), 10 mg/kg Ab1 IV once per week (QW), or 20 mg/kg ibrutinib per os (PO) every day (QD). ADC-A treatment caused tumor regression.
Figure 12:
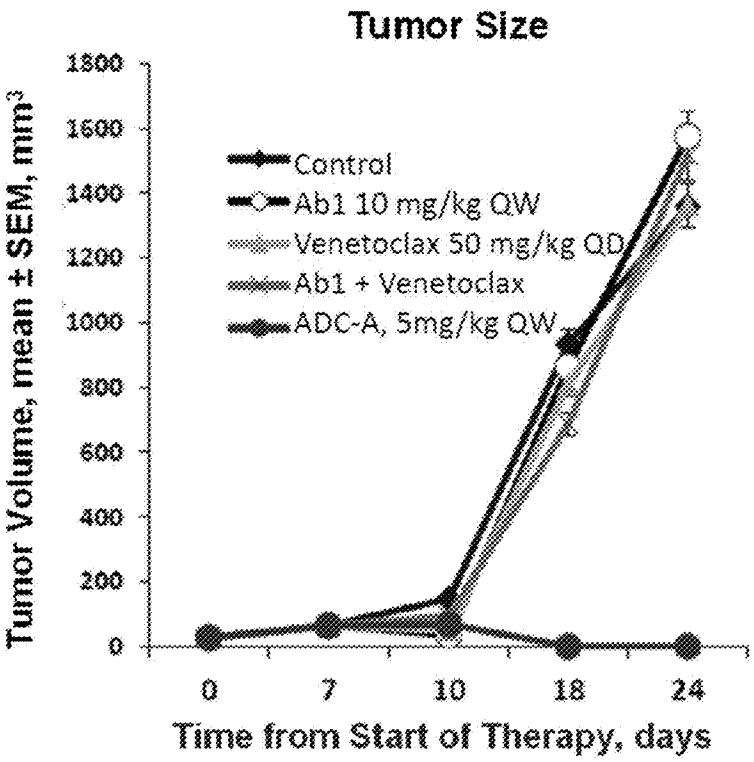
FIG. 12 is a pair of graphs showing ROR1 expression (left panel) and tumor growth inhibition in a DLBCL-GCB xenograft mouse model upon treatment with control, 10 mg/kg QW Ab1, 50 mg/kg venetoclax QD, Ab1+venetoclax, or 5 mg/kg ADC-A QW (right panel). ADC-A treatment resulted in complete tumor regression in all animals treated. Ab1 alone, venetoclax alone, and a combination of Ab1 and venetoclax were ineffective.
Figure 12:
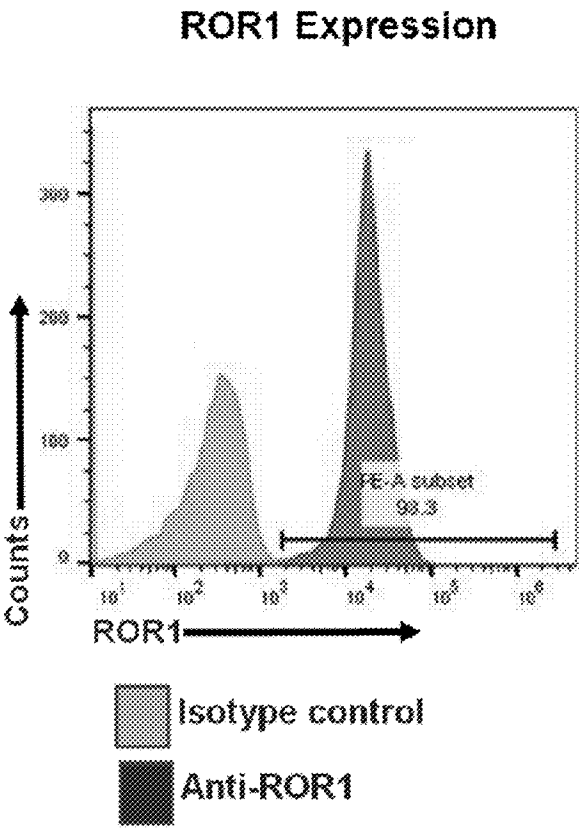

The data show that ADC-A inhibited cell proliferation in a dose-dependent manner (FIG. 9, black bars). Pre-incubation of the cells with the non-conjugated parental antibody Ab1 inhibited this anti-proliferative activity at all ADC-A concentrations tested (FIG. 9, gray bars), demonstrating that the cell killing was mediated by the binding of ADC-A to its target, ROR1.

Example 8: Anti-Tumor Activities of Exemplary Immunoconjugates In Vivo

1. Efficacy of ADC-A in a TCL1×ROR1 CLL Mouse Model

It has been demonstrated that ROR1 interacts with the T-cell leukemia 1 oncogene (TCL1) and enhances leukemogenesis in Em-TCL1 transgenic mice, and treatment with an anti-ROR1 antibody can impair the engraftment of ROR1× TCL1 leukemia cells (Widhopf et al., PNAS 111: 793-798 (2014)). This study evaluated the activity of ADC-A as compared to vehicle and unconjugated Ab1 in the TCL1× ROR1 CLL mouse model. In the study, ROR1×TCL1 leukemia cells were engrafted into mice via tail vein injection, and the injected mice were randomized into five groups, 8 mice/group. The groups were vehicle control, 10 mg/kg Ab1, and 1, 2, and 5 mg/kg ADC-A. The mice were dosed IV weekly for a total of four doses. The results of this study are shown in Table 10 below.

2. Efficacy of ADC-A and ADC-Q in a MCL Xenograft Mouse Model

Jeko-1 (MCL) cells were engrafted subcutaneously into mice, and the engrafted mice were randomized into five groups, 9 mice/group. The groups were vehicle control, 10 mg/kg Ab1, 20 mg/kg ibrutinib, 5 mg/kg ADC-A, and 5 mg/kg ADC-Q. The mice were dosed IV q4d. The results of this study are shown in Table 10 below.

3. Efficacy of ADC-A in a DLBCL-GCB PDX Mouse Model

Germinal center B-cell like diffuse large B-cell lymphoma (DLBCL-GCB) cells were engrafted subcutaneously into mice, and the engrafted mice were randomized into five groups, 6 mice/group. The groups were vehicle control, 10 mg/kg Ab1, 50 mg/kg venetoclax, 10 mg/kg Ab1 plus 50 mg/kg venetoclax, and 5 mg/kg ADC-A. Ab1 and ADC-A were administered IV, qw and venetoclax was administered PO qd. The results of this study are shown in Table 10 below.

4. Efficacy of ADC-A in a ROR1-positive Richter's syndrome PDX Mouse Model

NSG mice were subcutaneously injected in both flank areas with RS9373 cells (patient-derived xenograft or PDX) in a cell suspension in matrigel. When palpable tumors were observed (at approximately 50 $mm^3$), the animals were randomized into three groups, 4 mice/group. The treatment groups were vehicle control, 2.5 mg/kg ADC-A IV q4d, and 5 mg/kg ADC-A IV q4d. The mice received 3 total treatments and tumors were harvested 24 hours after the last treatment. Mean tumor growth inhibition (TGI) was calculated utilizing the following formula:

$$\mathrm{TGI} = \left[1 - \frac{\left(\overline{X}_{Treated_{(Final)}} - \overline{X}_{Treated_{(Day1)}}\right)}{\left(\overline{X}_{Control_{(Final)}} - \overline{X}_{Control_{(Day1)}}\right)}\right] \times 100\%$$

Figure 13:
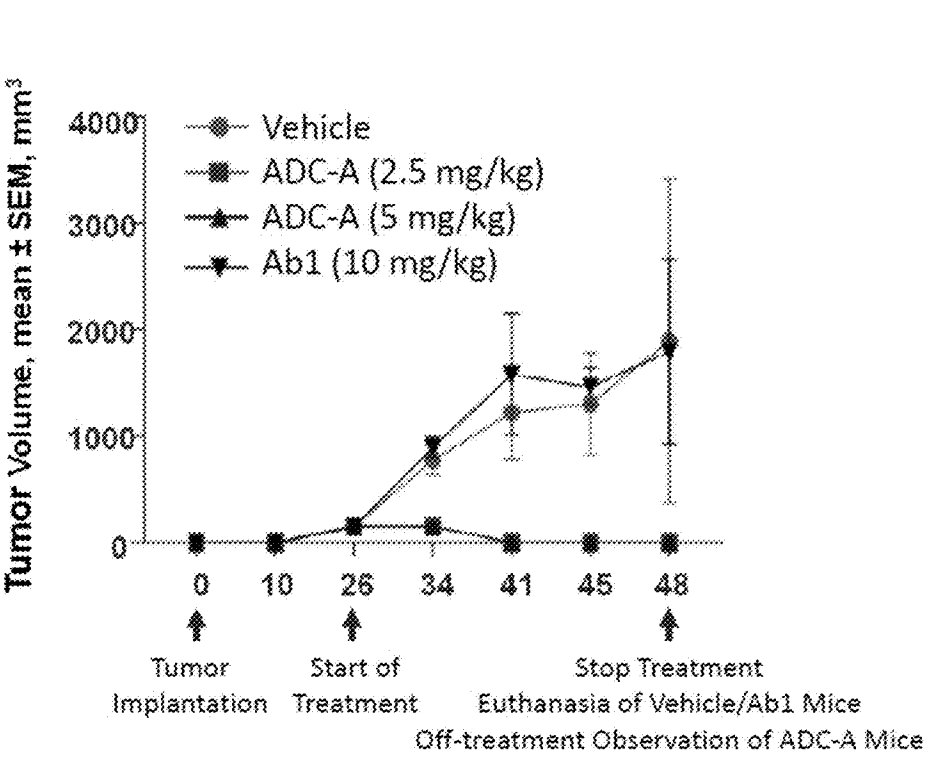
FIG. 13 is a set of graphs showing ROR1 expression (left panel) and inhibition of tumor growth upon treatment with vehicle, 2.5 or 5 mg/kg ADC-A, or 10 mg/kg Ab1 (right panel), in a chemotherapy-resistant Richter's transformation xenograft mouse model. Although only 20-30% of the intra-tumoral cells were ROR1-positive, complete and sustained tumor regressions were observed with 5 mg/kg ADC-A.
Figure 13:
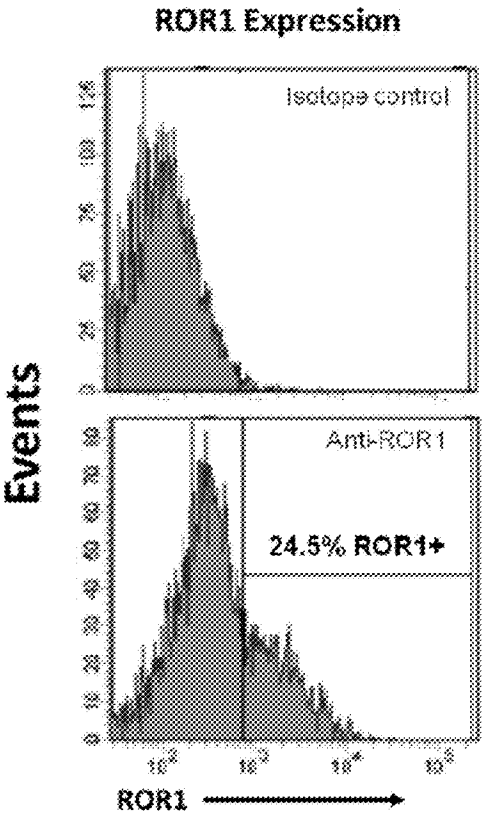
Figure 14:
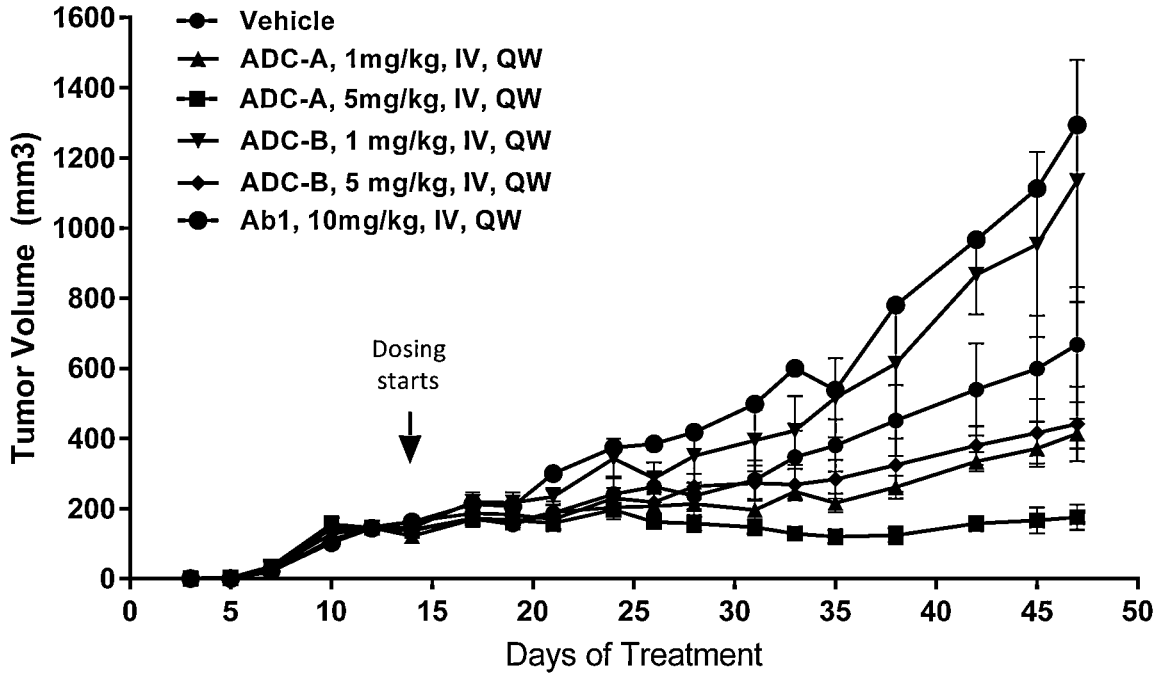
FIG. 14 is a graph illustrating tumor growth inhibition upon treatment with vehicle, 1 or 5 mg/kg ADC-A IV QW, 1 or 5 mg/kg ADC-B IV QW, or 10 mg/kg Ab1 IV QW in a MDA-MB-231 triple negative breast cancer (TNBC) mammary fat pad xenograft mouse model.

With most tumor types, heterogenous ROR1 expression is observed at the intra-tumoral level. Nonetheless, tumor regression was observed in the ADC-A treated groups. In the RS101 PDX model of Richter lymphoma, 20-30% of the cells were ROR1-positive, but complete and sustained regressions were observed (FIG. 13). The results of this study are shown in Table 10 below.

5. Efficacy of ADC-A in a ROR1-Positive Human TNBC Xenograft Model

NCR mice were subcutaneously injected in the mammary fat pad with MDA-MB-231 cells (ROR1-positive human triple negative breast cancer (TNBC) cells) in a cell suspension in matrigel. When palpable tumors were observed (at approximately 250 $mm^3$), the animals were randomized into three different groups, 9 mice/group: vehicle control, 1 mg/kg ADC-A IV qw, and 5 mg/kg ADC-A IV qw. The mice received 5 total treatments and tumors were harvested 24 h after the last treatment. Mean tumor growth inhibition (TGI) was calculated utilizing the above formula. The results of this study are shown in Table 10 below.

6. Efficacy of ADC-A in Two ROR1-Positive Human TNBC PDX Models

Two PDX models displaying different levels of ROR1 expression were selected for this study. ROR1 expression was based on the level of ROR1 staining via IHC of a tissue microarray representing triplicate cores of TNBC PDX models. The mean level of ROR1 expression as assessed by % ROR1-positive cells were 58% and 38% for human TNBC cells BR5011 and BR5015, respectively.

NOD/SCID nude mice were subcutaneously injected with BR5011 or BR5015 cells in the mammary fat pad. When palpable tumors were observed (mean tumor volume approximately 150 $mm^3$ for BR5011 and approximately 250 $mm^3$ for BR5015), animals were randomized into three groups. The groups for the BR5011 PDX model were vehicle control, 1 mg/kg ADC-A IV q4d, and 5 mg/kg ADC-A IV q4d. The groups for the BR5015 PDX model were vehicle control, 1 mg/kg ADC-A IV qw, and 5 mg/kg ADC-A IV qw. Mean TGI was calculated as described above.

Figure 15:
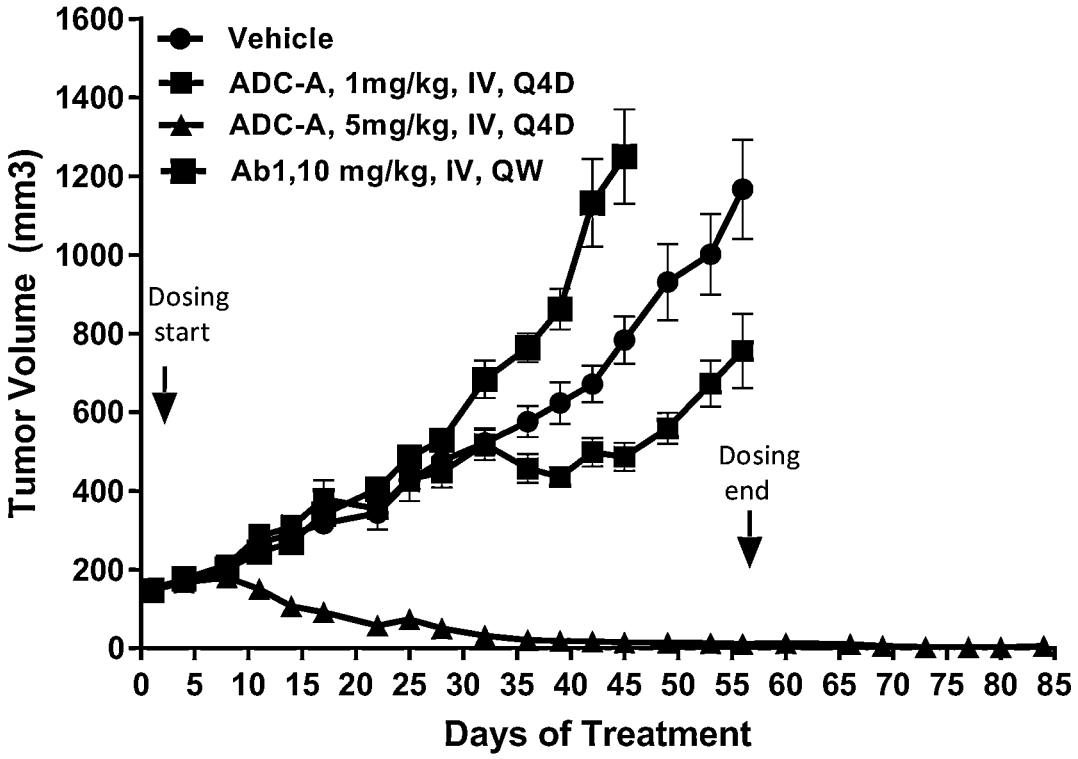
FIG. 15 is a graph illustrating tumor growth inhibition upon treatment with vehicle, 1 or 5 mg/kg ADC-A IV Q4D, or 10 mg/kg Ab1 IV QW in a BR5011 human TNBC xenograft mouse model. Although only 58% of the intra-tumoral cells were ROR1-positive, complete and sustained regressions were observed with 5 mg/kg ADC-A, where tumor regression was maintained for at least 28 days after the last dose.
Figure 16:
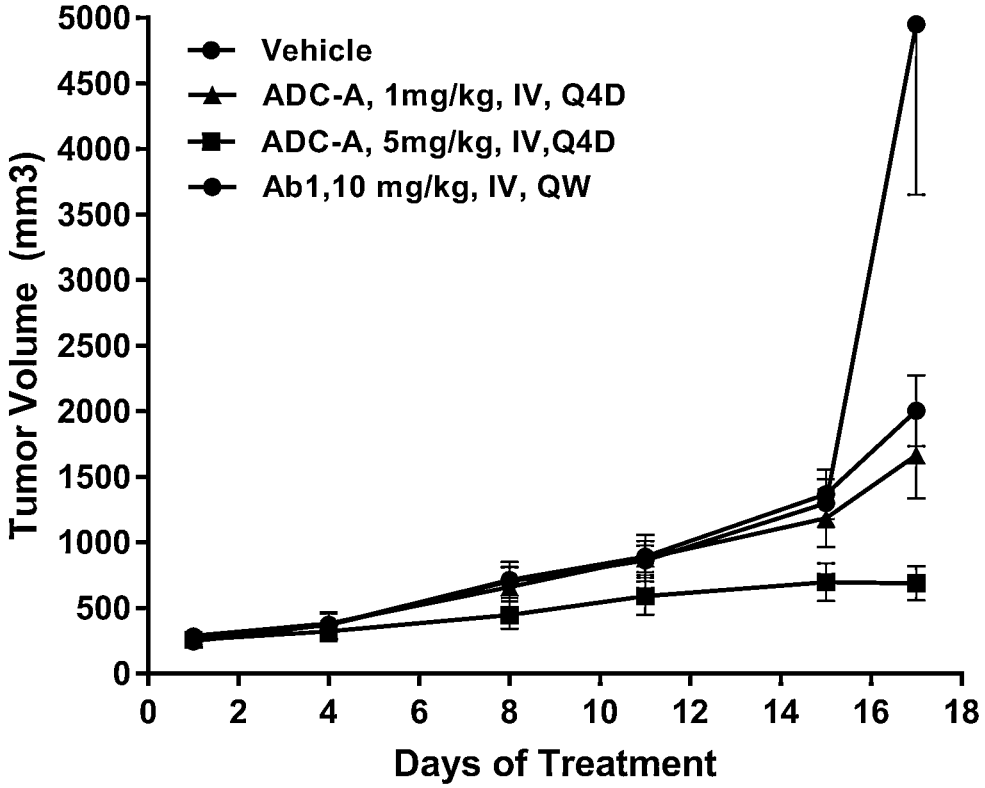
FIG. 16 is a graph illustrating tumor growth inhibition upon treatment with vehicle, 1 or 5 mg/kg ADC-A IV Q4D, or 10 mg/kg Ab1 IV QW in a BR5015 (low ROR1 expression) human TNBC xenograft mouse model. Tumor regression was observed even though only 58% of the intra-tumoral cells were ROR1-positive.

Tumor inhibition and/or regression was observed in the ADC-A treated groups. For example, in the BR5011 TNBC PDX model, which showed ROR1 expression in 58% of the cancer cells, complete and sustained regressions were observed (FIG. 15). The results of this study are shown in Table 10 below.

7. Efficacy of ADC-A, L, M, N, P, R, S and Tin a Jeko-1 Human MCL Xenograft Model Jeko-1 (MCL) cells were engrafted subcutaneously into mice. When tumor size reached 100 $mm^3$, the mice were randomized into nine groups, 9 mice/group. The groups were vehicle control; 1 mg/kg ADC-N, ADC-P or ADC-R; or 5 mg/kg ADC-A, ADC-L, ADC-M, ADC-S, or ADC-T. The mice were dosed IV q4d. The interim results of this study are shown in Table 10 below.

TABLE 10

Results of in vivo Studies with Exemplary Immunoconjugates

| Study | ADC | Animal Model | Duration | Results | FIG. |
|---|---|---|---|---|---|
| 1 | ADC-A | TCL1 × ROR1 leukemia cells | 1 month | ADC-A inhibited leukemic cell tumor burden in a dose-dependent manner (1, 2, and 5 mg/kg). | 10 |

TABLE 10-continued

Results of in vivo Studies with Exemplary Immunoconjugates

| Study | ADC | Animal Model | Duration | Results | FIG. |
|---|---|---|---|---|---|
| 2 | ADC-A<br>ADC-Q | Jeko-1 MCL xenograft | 3 weeks | ADC-A caused tumor regression while ADC-Q caused tumor growth delay. | 11 |
| 3 | ADC-A | DLBCL-GCB PDX | 24 days | ADC-A caused tumor regression (104%) with complete regressions in all animals.<br>Ab1 (unconjugated) alone, venetoclax alone, or Ab1 (unconjugated) + venetoclax were ineffective. | 12 |
| 4 | ADC-A | Chemotherapy-resistant PDX model of Richter transformation | 48 days | 20-30% of the intra-tumoral cells were ROR1-positive, but complete and sustained regressions were observed.<br>ADC-A mean TGI:<br>78% at 2.5 mg/kg;<br>90% at 5 mg/kg. | 13 |
| 5 | ADC-A<br>ADC-B | MDA-MB-231 xenograft | 47 days | ADC-A mean TGI:<br>56.4% at 1 mg/kg;<br>94.2% at 5 mg/kg. | 14 |
| 6 | ADC-A | Human TNBC PDX model, BR5011 | 56 days dosing;<br>84 days observation (5 mg/kg group) | 58% of the intra-tumoral cells were ROR1-positive, but complete and sustained regressions were observed at 5 mg/kg ADC-A.<br>ADC-A mean TGI:<br>40.1% at 1 mg/kg,<br>complete regression at 5 mg/kg.<br>The 5 mg/kg group was monitored for 28 days post last dose and tumor regression was maintained throughout the observation period. | 15 |
| | | Human TNBC PDX, BR5015 (low ROR1 expression) | 17 days | ADC-A mean TGI:<br>22% at 1 mg/kg;<br>75.6% at 5 mg/kg. | 16 |
| 7 | ADC-A<br>ADC-L<br>ADC-M<br>ADC-N<br>ADC-P<br>ADC-R<br>ADC-S<br>ADC-T | Jeko-1 MCL xenograft | Interim results 14 days | Interim analysis at days at 11 and 14 shows that all ADC constructs inhibited tumor growth and all ADC-treated animals demonstrated a reduction in average tumor size at day 14 compared to day 11. This suggests that regression may be observed in all treatment groups by the end of the study (beyond day 14). Animals treated with ADC-A, L, M, and S all displayed significant tumor regression, as shown by the reduction in average tumor size at day 14 compared to pre-treatment at day 0. | 17 |

In vivo studies 1-7 here show that despite the heterogeneity of ROR1 expression within a tumor and varying levels of ROR1 expression across cancer types, treatment with ADC-A resulted in tumor growth inhibition and even sustained, complete regression in a variety of cancers. For example, in the TNBC PDX model that showed expression of ROR1 in 58% of the tumor cells, complete and sustained regressions were observed in all tumors (FIG. 15). Similarly, in the RS101 PDX model of Richter lymphoma, 20-30% of the cells were ROR1-positive, but complete and sustained regressions were observed in all tumors (FIG. 13). These results suggest that the anti-ROR1 immunoconjugates eradicate cancer by not only cytotoxicity to the bound cancer cells, but also bystander toxicity on neighboring cancer cells in the tumor microenvironment, or by upregulating the immune system's anti-cancer effect, or by a combination of these mechanisms. This finding is significant because it indicates that the immunoconjugates of the present invention can be used to treat tumors that have intra-tumoral heterogeneous expression of ROR1.

The present in vivo studies also show that ADC-A was effective in treating drug-resistant cancers. We observed regressions in human tumor xenografts that were resistant to ibrutinib (the Jeko-1 MCL model) or to rituximab-CHOP immunochemotherapy (the Richter transformation model). Since ROR1 is a marker for advanced cancers and that prior chemotherapy appears to increase ROR1 expression, our findings demonstrate the potential of the immunoconjugates of the present invention in treating advanced or aggressive cancers.

8. Further In Vivo Evaluation of ADCs

The in vivo efficacy of the ADCs, e.g., ADC-A, E, F, L, M, N, P, Q, and R may be further evaluated in a ROR1-positive, subcutaneous, human MCL xenograft model using Jeko-1 cells. The animals are dosed IV q4d with vehicle, 1 mg/kg ADC, or 5 mg/kg ADC. Tumor growth and body weights are measured every 2-3 days. Pharmacokinetic analysis of the ADCs of the present invention may be performed to determine standard pharmacokinetic parameters such as antibody C. and half-life.

Example 9: Combination Therapy

The effects of combining ADC-A with other anti-proliferative agents were examined. The initial studies focused on the effects of ADC-A combined with an inhibitor of BTK (ibrutinib, ACP-196/acalabrutinib), Bcl-2 (ABT-199/venetoclax), mTOR (INK128), or PI3K (idelalisib). Additional studies examined the effects of combining ADC-A with two additional Bcl-2 inhibitors, termed Bcl-2i-1 and Bcl-2i-2. Cell lines were tested for both distinct DLBCL subtypes—germinal center B-cell (GCB) and activated B-cell (ABC). The median-effect analysis was used to determine synergism, antagonism, or additivity of inhibition of proliferation of various cell lines treated with ADC-A combined with the anti-proliferative agents. The Combination Index (CI) was determined using the Chou/Talalay equation. The $IC_{50}$ for each compound was determined in a 72 hour CellTiter-Glo® assay. For combination assays, drugs were used at equimolar ratios (i.e., at the ratio of their $IC_{50}$ values). CalcuSyn software (by Biosoft) was used for dose effect analysis. A Combination Index of less than 1.1 indicates the treatments are synergistic; 0.9-1.1 indicates the treatments are additive; and greater than 1.1 indicates that the treatments are antagonistic.

Figure 18A:
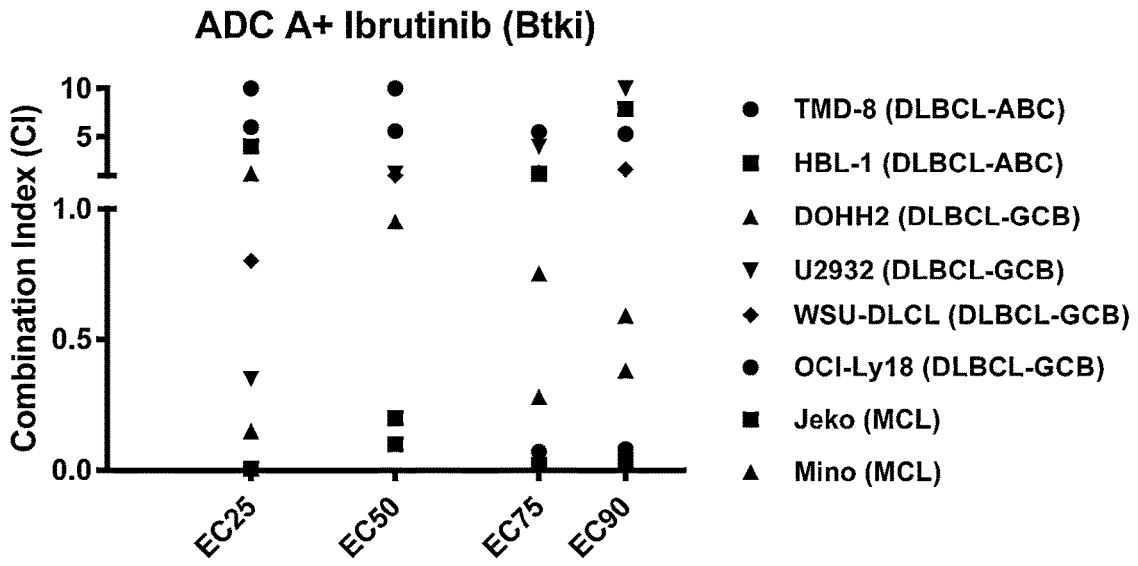
FIGS. 18A and 18B are graphs illustrating the combination index of treatment with ADC-A and BTK inhibitors ibrutinib (18A) or ACP-196/acalabrutinib (18B) in various cell lines. ADC-A displayed a synergistic effect with both ibrutinib and ACP-196/acalabrutinib on inhibition of cell proliferation.
Figure 18B:
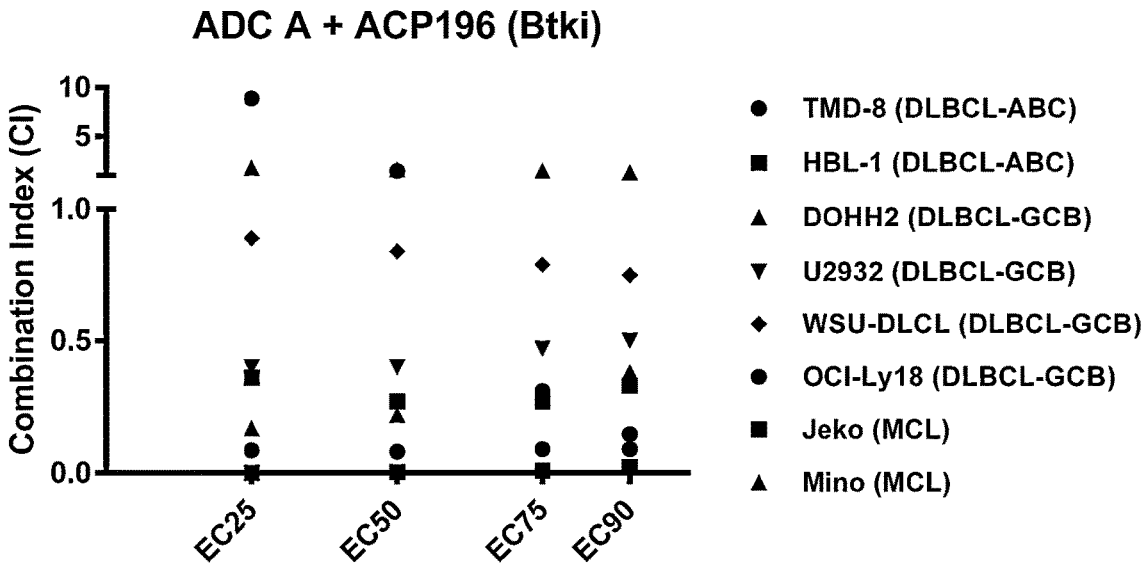
Figure 19A:
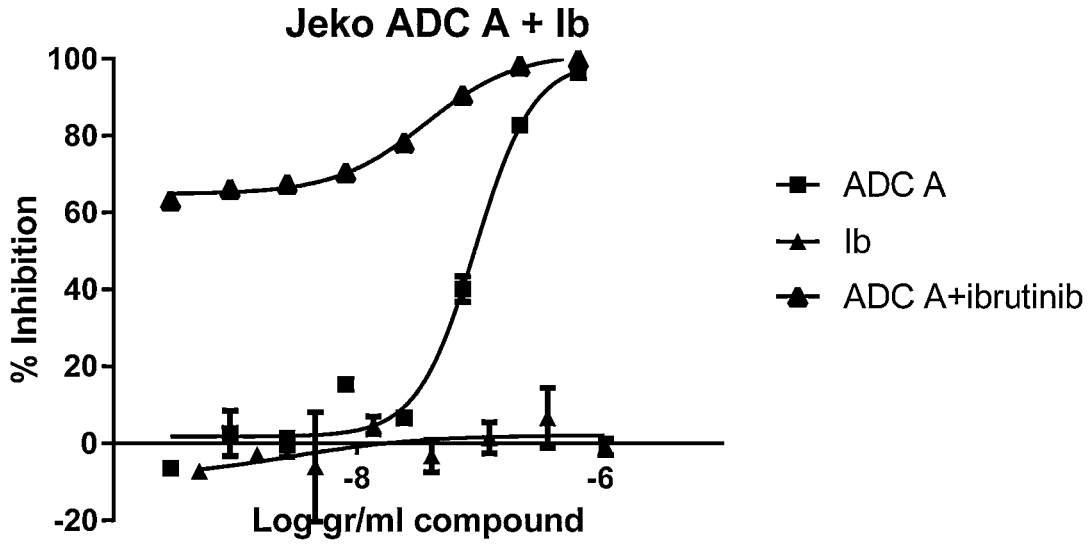
FIGS. 19A and 19B are graphs illustrating inhibition of Jeko-1 cell proliferation upon treatment with ADC-A, ibrutinib ("Ib"), or a combination of ADC-A and ibrutinib (19A); or ADC-A, ACP-196/acalabrutinib ("ACP196" or "196"), or a combination of ADC-A and ACP-196/acalabrutinib (19B).
Figure 19B:
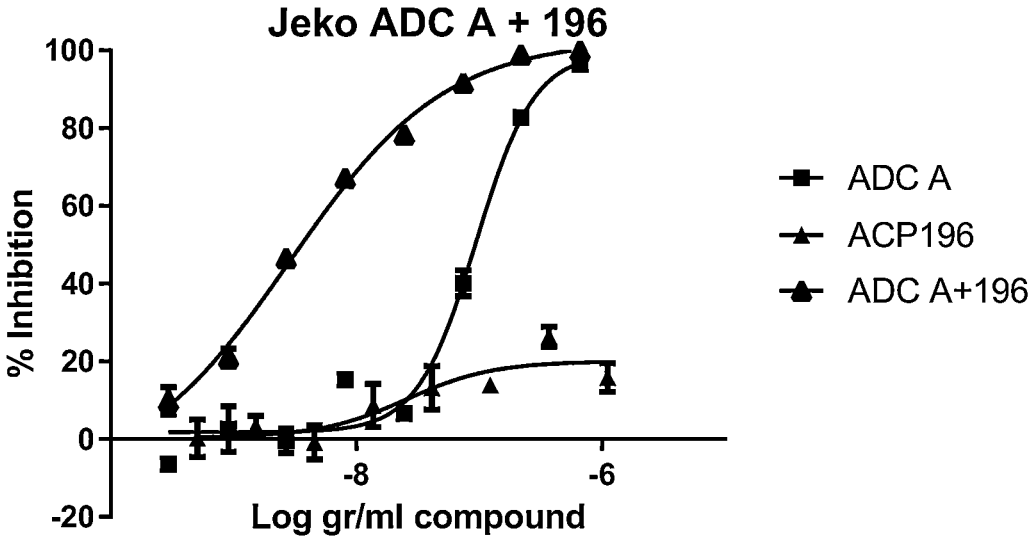

ADC-A displayed a synergistic effect with two different BTK inhibitors, ibrutinib (FIG. 18A) and ACP-196/acalabrutinib (FIG. 18B). The synergistic effect was more pronounced with acalabrutinib and with MCL cell lines. Representative data for ADC-A combined with ibrutinib and acalabrutinib on MCL cell line Jeko-1 are shown in FIGS. 19A and 19B, respectively.

Figure 20A:
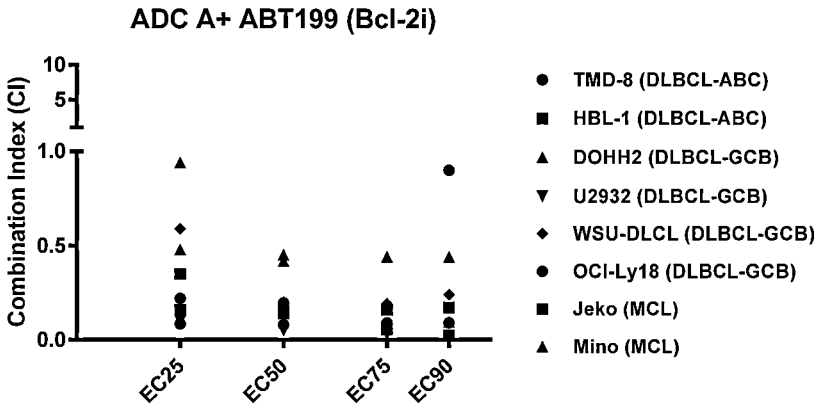
FIGS. 20A-C are graphs illustrating the combination index of treatment with ADC-A and Bcl2 inhibitor ABT-199/venetoclax ("ABT199") in various cell lines (20A), or of ADC-A with Bcl2 inhibitor Bcl2i-1 or Bcl2i-2 in Jeko-1 cells (20B) or Mino cells (20C). ADC-A displayed a synergistic effect with ABT-199 on inhibition of both MCL and DLBCL cell proliferation. ADC-A also displayed a synergistic effect with other Bcl2 inhibitors (Bcl2i-1 and Bcl2i-2)
Figure 20B:
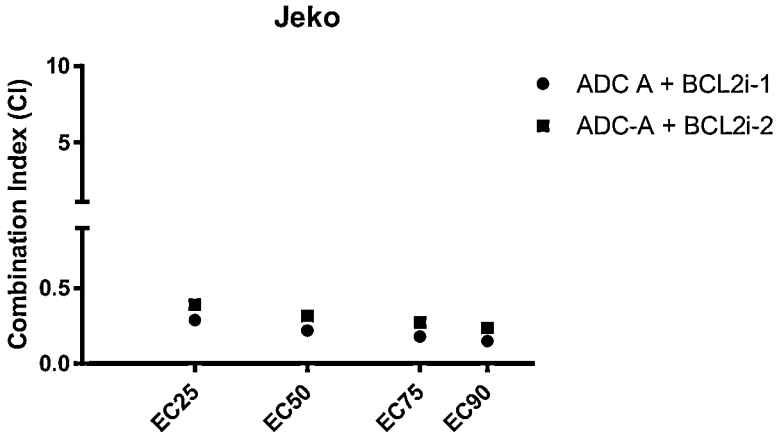
Figure 20C:
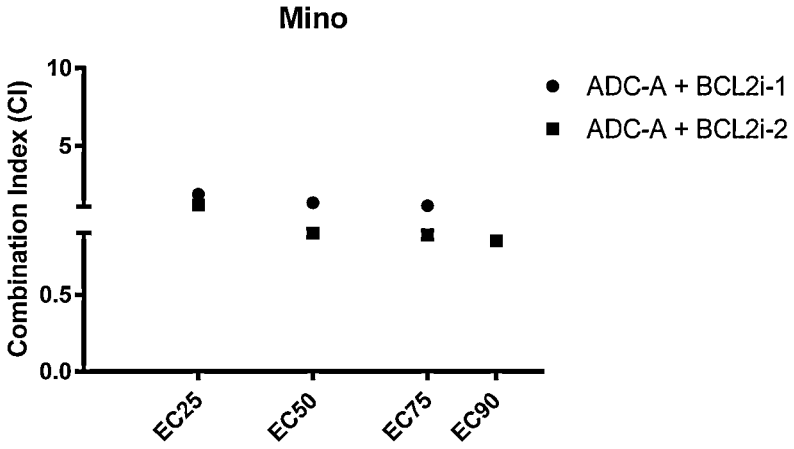

ADC-A also displayed a synergistic effect with Bcl-2 inhibitor ABT-199/venetoclax (FIG. 20A). The synergistic effect was pronounced in both MCL and DLBCL cell lines. The activity of ADC-A combined with additional Bcl2 inhibitors, Bcl2i-1 and Bcl2i-2, was examined on Jeko-1 (FIG. 20B) and Mino (FIG. 20C) cells (both are MCL cell types). ADC-A displayed a synergistic effect with both inhibitors on Jeko-1 cells and an additive effect with both inhibitors on Mino cells. Representative data for ADC-A combined with venetoclax on Jeko-1 are shown in FIG. 21.

ADC-A displayed a synergistic effect with mTOR1/2 inhibitor INK128/sapanisertib (FIG. 22). The synergistic effect was observed on both MCL and DLBCL cell lines. Representative data for ADC-A combined with sapanisertib on Jeko-1 are shown in FIG. 23.

ADC-A displayed a synergistic effect with PI3K inhibitor CAL-101/idelalisib (FIG. 24). The synergistic effect was observed on both MCL and DLBCL cell lines. Representative data for ADC-A combined with idelalisib demonstrating synergistic effects on both subtypes of DLBCL are shown in FIG. 25A (TMD cells, DLBCL-ABC) and FIG. 25B (DOHH2 cells, DLBCL-GCB).

Example 10: Further Evaluation of Combination Therapy

The in vivo efficacy of the ADCs in combination with a Bcl2 inhibitor may be further assessed in a ROR1-positive human MCL xenograft model using Jeko-1 cells or in a PDX model. Both the ADC and the Bcl2 inhibitor are dosed at maximum tolerated and sub-optimal doses, alone and in combination as outlined below, in a repeat dose study. Tumor growth and body weights are measured every 2-3 days.

ADC-A and Bcl2 inhibitor MTD dosing
- 5 mg/kg ADC-A, IV, q4d
- 100 mg/kg venetoclax (ABT-199), weekly ADC-A and Bcl2 inhibitor sub-optimal and combination dosing
- 1 mg/kg ADC-A, IV, q4d
- 2 mg/kg ADC-A, IV, q4d
- 50 mg/kg ABT-199, PO, qd
- 100 mg/kg ABT-199, PO, qd
- 1 mg/kg ADC-A, IV, q4d+50 mg/kg ABT-199, PO, qd
- 2 mg/kg ADC-A, IV, q4d+50 mg/kg ABT-199, PO, qd
- 1 mg/kg ADC-A, IV, q4d+100 mg/kg ABT-199, PO, qd
- 2 mg/kg ADC-A, IV, q4d+100 mg/kg ABT-199, PO, qd Pharmacokinetic analysis is performed to determine standard pharmacokinetic parameters such as antibody $C_{max}$ and half-life.

Example 11: Phase 2 Clinical Study of Anti-ROR1-MMAE Immunoconjugates

The following describes a protocol for a prospective open label Phase 1b/2 clinical trial for anti ROR1-MMAE immunoconjugate therapy.

Inclusion Criteria:
- Eastern Cooperative Oncology Group (ECOG) performance status of 0, 1, or 2
- Histological diagnosis of CLL/SLL or MCL as documented in medical records
- CLL/SLL or MCL has been previously treated and has relapsed after or progressed during prior therapy
- Presence of radiographically measurable lymphadenopathy or extranodal lymphoid malignancy (defined as the presence of ≥1 non-biopsied, non-irradiated lesion that measures ≥2.0 cm in the longest dimension [LD] and ≥1.0 cm in the longest perpendicular dimension [LPD] as assessed by computed tomography [CT] or magnetic resonance imaging [MRI]).
- Current medical need for therapy due to disease-related symptoms, lymphadenopathy, organomegaly, extranodal organ involvement, or progressive disease.
- Completion of all previous therapy (including surgery, radiotherapy, chemotherapy, immunotherapy, or investigational therapy) for the treatment of cancer 1 week before the start of study therapy.
- All acute toxic effects of any prior antitumor therapy resolved to Grade 1 before the start of study therapy (with the exception of alopecia [Grade 1 or 2 permitted], or neurotoxicity [Grade 1 or 2 permitted], or selected laboratory parameters [Grade 1 or Grade 2 permitted with exceptions as noted below]).
- Adequate bone marrow function:
  - a) Absolute neutrophil count (ANC) ≥1.0×109/L (Grade ≤2). b) Platelet count ≥50×109/L (Grade <2). b) Hemoglobin ≥8.0 g/dL (Grade ≤2) maintained for ≥1 week from any prior transfusion.
- Note: Grade ≥3 neutropenia, thrombocytopenia, or anemia is permitted if the abnormality is related to bone marrow involvement with hematological malignancy (as documented by bone marrow biopsy/aspirate obtained since the last prior therapy).

Adequate hepatic profile:

Serum alanine aminotransferase (ALT)≤3×upper limit of normal (ULN) (Grade ≤1).

Serum aspartate aminotransferase (AST)≤3×ULN (Grade ≤1).

Serum bilirubin ≤1.5×ULN (Grade ≤1).

Adequate renal function:

a) Estimated creatinine clearance (eClCR) >45 mL/minute (with eClCR to be calculated by the Cockcroft-Gault formula), or b) Measured creatinine clearance >45 mL/minute (as assessed with a 24-hour urine collection).

Adequate coagulation profile:

Prothrombin time (PT)≤1.5×ULN (Grade ≤1).

Activated partial thromboplastin time (aPTT)≤1.5×ULN (Grade ≤1).

Negative viral serology:

Negative human immunodeficiency virus (HIV) antibody.

Negative hepatitis B surface antigen (HBsAg) and negative hepatitis B core (HBc) antibody or undetectable hepatitis B (HBV) deoxyribonucleic acid (DNA) by quantitative polymerase chain reaction (PCR) testing.

Negative hepatitis C virus (HCV) antibody or negative HCV ribonucleic acid (RNA) by quantitative PCR.

For female subjects of childbearing potential, a negative urine or serum pregnancy test prior to the start of study therapy.

In the judgment of the investigator, participation in the protocol offers an acceptable benefit-to-risk ratio when considering current disease status, medical condition, and the potential benefits and risks of alternative treatments for the subject's cancer.

Willingness and ability of the subject to comply with scheduled visits, drug administration plan, protocol-specified laboratory tests, other study procedures (including all bone marrow biopsy/aspirations and radiographic studies), and study restrictions.

Exclusion Criteria:

Known histological transformation to an aggressive lymphoma (ie, Richter transformation). Note: Biopsy documentation of the absence or presence of transformation is not required.

Known central nervous system malignancy. Note: Central nervous system imaging is only required in subjects with suspected central nervous system malignancy.

History of another malignancy except for the following: adequately treated local basal cell or squamous cell carcinoma of the skin; adequately treated carcinoma in situ without evidence of disease; adequately treated, papillary, noninvasive bladder cancer; other cancer that has been in complete remission for ≥2 years.

Significant cardiovascular disease (eg, myocardial infarction, arterial thromboembolism, cerebrovascular thromboembolism) within 3 months prior to start of study therapy; angina requiring therapy; symptomatic peripheral vascular disease; New York Heart Association Class 3 or 4 congestive heart failure; or uncontrolled Grade ≥3 hypertension (diastolic blood pressure ≥100 mmHg or systolic blood pressure ≥160 mmHg) despite antihypertensive therapy.

Significant screening ECG abnormalities, including unstable cardiac arrhythmia requiring medication, atrial fibrillation/flutter, left bundle branch block, 2nd-degree atrioventricular (AV) block type II, 3rd-degree AV block, Grade ≥2 bradycardia, or corrected QT (QTc) >450 msec (for men) or >470 msec (for women).

Gastrointestinal disease (eg, gastric or intestinal bypass surgery, pancreatic enzyme insufficiency, malabsorption syndrome, symptomatic inflammatory bowel disease, chronic diarrheal illness, bowel obstruction) that might interfere with drug absorption or with interpretation of gastrointestinal AEs.

Ongoing risk for bleeding due to active peptic ulcer disease; bleeding diathesis; or requirement for systemic anticoagulation with an antiplatelet drug (eg, aspirin, triflusal, clopidogrel, prasugrel, ticagrelor, ticlopidine, cilostazol, vorapaxar, dipyridamole); or with heparin, low-molecular-weight heparin or heparin fractions (eg, enoxaparin, dalteparin, fondaparinux) or oral anticoagulants (eg, apixaban, rivaroxaban, dabigatran etexilate, warfarin). Note: Use of heparin or thrombolytic agents for local maintenance or clearance of a central venous catheter is permitted.

Evidence of an ongoing systemic bacterial, fungal, or viral infection (including upper respiratory tract infections) at the time of start of study therapy. Note: Subjects with localized fungal infections of skin or nails are not precluded from participation.

In subjects with prior hematopoietic progenitor cell transplantation, evidence of ongoing graft-versus-host disease (GVHD).

Pregnancy or breastfeeding.

Major surgery within 4 weeks before the start of study therapy.

Prior solid organ transplantation.

Prior anti-ROR1 therapy within 12 weeks prior to the start of study therapy.

Ongoing immunosuppressive therapy, including systemic or enteric corticosteroids. Note:

At Screening, subjects may be using topical or inhaled corticosteroids. During study therapy, use of corticosteroids as prophylaxis for infusion reactions will be minimized. However, subjects may use systemic, enteric, topical or enteric corticosteroids as required for treatment-emergent conditions Primary Outcome Measures:

Phase 1b: Recommended dosing regimen (RDR) [Time Frame: From baseline to 52 weeks] Evaluation of cirmtuzumab dose-pharmacodynamic and pharmacokinetic-pharmacodynamic relationships, and safety.

Phase 2: Complete Response (CR) rate [Time Frame: From randomization to discontinuation of treatment of all study subjects or 72 weeks after accrual of the final subject] Proportion of subjects achieving a CR in accordance with pre-established response criteria for lymphoma (Cheson, J Clin Oncol. 32(27):3059-68 (2014)).

TABLE 11

Exemplary Dosing Regimens

| Arms | Assigned Interventions |
|---|---|
| Phase 1b - dose finding for ROR1-MMAE | Administered IV every 2 weeks for 5 administrations and then every 4 weeks thereafter |
| Phase 1b - dose expansion for ROR1-MMAE | Administered IV every 2 weeks for 3 administrations and then every 4 weeks thereafter |

TABLE 11-continued

| Exemplary Dosing Regimens | |
|---|---|
| Arms | Assigned Interventions |
| Phase 2 - safety and efficacy evaluation for ROR1-MMAE | Administered IV every 2 weeks for 3 administrations and then every 4 weeks thereafter |

Dose finding phase will be conducted by parallel dose comparison at 1.0, 2.0, and 3.0 mg/kg.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention.

The amino acid sequences and nucleotide sequences described herein are listed in Table 12 below.

TABLE 12

| List of Sequences | | |
|---|---|---|
| SIN | Description | SEQUENCE |
| 1 | Human ROR1 fragment | VATNGKEVVS STGVLFVKFG PC |
| 2 | Human ROR1 fragment | EVVSSTGVLF VKFGPC |
| 3 | Ab1 heavy chain | QVQLQESGPGLVKPSQTLSLTCTVSGYAFTAYNIHWVRQAPGQGLEWM<br>GSFDPYDGGSSYNQKFKDRLTISKDTSKNQVVLTMTNMDPVDTATYYC<br>ARGWYYFDYWGHGTLVTVSSASTKGPSVFPLAPSSKSTSGGTAALGCLV<br>KDYFPEPVTVSWNSGALTSGVHTFPAVLQSSGLYSLSSVVTVPSSSLGTQ<br>TYICNVNHKPSNTKVDKKVEPKSCDKTHTCPPCPAPELLGGPSVFLFPPK<br>PKDTLMISRTPEVTCVVVDVSHEDPEVKFNWYVDGVEVHNAKTKPREE<br>QYNSTYRVVSVLTVLHQDWLNGKEYKCKVSNKALPAPIEKTISKAKGQP<br>REPQVYTLPPSRDELTKNQVSLTCLVKGFYPSDIAVEWESNGQPENNYK<br>TTPPVLDSDGSFFLYSKLTVDKSRWQQGNVFSCSVMHEALHNHYTQKSL<br>SLSPGK |
| 4 | Ab1 light chain | DIVMTQTPLSLPVTPGEPASISCRASKSISKYLAWYQQKPGQAPRLLIYSG<br>STLQSGIPPRFSGSGYGTDFTLTINNIESEDAAYYFCQQHDESPYTFGEGT<br>KVEIKRTVAAPSVFIFPPSDEQLKSGTASVVCLLNNFYPREAKVQWKVD<br>NALQSGNSQESVTEQDSKDSTYSLSSTLTLSKADYEKHKVYACEVTHQG<br>LSSPVTKSFNRGEC |
| 5 | Ab1 VH | QVQLQESGPGLVKPSQTLSLTCTVSGYAFTAYNIHWVRQAPGQGLEWM<br>GSFDPYDGGSSYNQKFKDRLTISKDTSKNQVVLTMTNMDPVDTATYYC<br>ARGWYYFDYWGHGTLVTVSS |
| 6 | Ab1 VL | DIVMTQTPLSLPVTPGEPASISCRASKSISKYLAWYQQKPGQAPRLLIYSG<br>STLQSGIPPRFSGSGYGTDFTLTINNIESEDAAYYFCQQHDESPYTFGEGT<br>KVEIK |
| 7 | Ab1 HCDR1 | GYAFTAYN |
| 8 | Ab1 HCDR2 | FDPYDGGS |
| 9 | Ab1 HCDR3 | GWYYFDY |
| 10 | Ab1 LCDR1 | KSISKY |
| 11 | Ab1 LCDR2 | SGS |
| 12 | Ab1 LCDR3 | QQHDESPY |
| 13 | Ab1 VH frag. | SGYAFTAYNIHWVRQ |
| 14 | Ab1 VH frag. | GSFDPYDGGSSYNQKF |
| 15 | Ab1 VH frag. | YYCARGWYYFDYWGHGTLVTVSS |
| 16 | Ab1 VL frag. | CRASKSISKYLAWY |
| 17 | Ab1 VL frag. | LLIYSGSTLQSG |
| 18 | Ab1 VL frag. | CQQHDESPYTFGEGTKVEIK |
| 19 | Ab1 heavy chain coding sequence | AAGCTTACCGCCACCATGGGCTGGAGCTGTATCATCCTCTTCCTGGTG<br>GCGACCGCGACGGGTGTCCACTCCCAGGTGCAGCTCCAGGAGTCCGG<br>CCCCGGGCTTGTGAAGCCGTCACAAACCCTGTCCCTGACGTGCACGG<br>TCTCCGGCTACGCCTTCACGGCCTACAACATACATTGGGTCCGGCAGG<br>CGCCGGGCCAGGGGCTGGAGTGGATGGGTTCCTTCGACCCGTACGAT<br>GGCGGGAGCTCGTACAACCAGAAGTTCAAAGACCGCCTGACGATCTC |

TABLE 12-continued

List of Sequences

| SIN | Description | SEQUENCE |
|---|---|---|
| | | CAAGGACACCTCGAAAAACCAGGTCGTCCTGACCATGACCAACATGG<br>ACCCGGTGGACACGGCGACCTACTATTGCGCCCGCGGCTGGTACTAC<br>TTCGACTACTGGGGCCACGGGACCCTGGTCACCGTGTCTTCCGCTTCG<br>ACCAAGGGCCCCAGCGTCTTCCCGCTCGCGCCCTCCTCGAAGTCCACC<br>TCGGGCGGCACTGCCGCCCTGGGCTGCCTGGTCAAGGACTACTTCCC<br>GGAGCCGGTGACCGTCTCGTGGAACAGCGGGGCACTCACCTCCGGCG<br>TGCACACCTTCCCGGCCGTGCTGCAGTCCTCGGGGCTGTATTCACTCA<br>GCTCGGTCGTCACCGTCCCCTCGTCGTCCCTCGGCACGCAGACGTACA<br>TCTGCAACGTCAACCACAAGCCCTCGAACACCAAGGTGGACAAGAAG<br>GTCGAGCCGAAGTCCTGCGATAAGACCCACACCTGCCCCCCGTGCCC<br>GGCCCCCGAGCTCCTGGGCGGTCCGTCCGTGTTCCTCTTCCCGCCCAA<br>GCCCAAGGACACCCTGATGATCAGCCGCACGCCCGAGGTGACCTGCG<br>TCGTCGTGGACGTCTCCCACGAGGATCCCGAGGTGAAGTTCAACTGG<br>TACGTGGACGGGGTGGAGGTCCACAACGCCAAGACAAAGCCGCGGG<br>AAGAGCAGTACAACTCGACCTACCGCGTCGTCAGCGTGCTGACGGTC<br>CTCCACCAGGACTGGCTGAACGGCAAGGAGTACAAATGCAAGGTGTC<br>CAACAAGGCCCTGCCCGCGCCCATCGAGAAGACCATCTCCAAGGCCA<br>AGGGACAGCCGCGCGAGCCGCAGGTCTACACGCTGCCTCCCTCCCGG<br>GACGAGCTCACGAAGAACCAGGTATCGCTCACCTGCCTCGTGAAGGG<br>CTTCTACCCGAGCGACATCGCCGTCGAGTGGGAGAGCAACGGCCAGC<br>CCGAGAACAACTACAAAACCACGCCGCCGGTCCTCGACTCTGACGGG<br>TCCTTCTTCCTGTACTCCAAGCTGACCGTGGACAAGTCGCGGTGGCAG<br>CAGGGGAACGTGTTCTCGTGCTCGGTCATGCACGAGGCGTTGCACAA<br>CCACTACACCCAGAAGTCACTCTCCCTGAGCCCGGGCAAGTGATAAT<br>CTAGAGTCGGGGCGGCCGGCC |
| 20 | Ab1 light chain coding sequence | AAGCTTACCGCCACCATGGGCTGGTCATGCATCATCCTGTTCCTGGTC<br>GCCACCGCGACGGGGGTCCACAGTGATATCGTCATGACGCAGACGCC<br>GCTGAGCCTCCCGGTGACGCCCGGCGAGCCCGCCAGCATCTCCTGCC<br>GCGCTTCCAAGTCCATCTCGAAGTACCTGGCGTGGTATCAGCAGAAG<br>CCCGGCCAGGCCCCGCGCCTGCTCATCTACTCTGGTTCCACGCTCCAG<br>TCGGGCATCCCGCCCCGGTTCTCGGGTTCGGGATACGGCACCGACTTC<br>ACCCTGACCATCAACAACATCGAGAGCGAAGACGCGGCGTACTACTT<br>CTGCCAGCAGCACGACGAGTCCCCGTACACCTTCGGCGAGGGGACCA<br>AGGTCGAGATCAAGCGTACCGTCGCGGCACCGAGCGTCTTCATCTTC<br>CCCCCGTCCGACGAGCAGCTCAAGTCTGGCACCGCCTCGGTCGTCTGT<br>CTCCTGAACAACTTCTACCCCAGGGAAGCCAAGGTCCAGTGGAAGGT<br>GGACAACGCGCTGCAGTCCGGGAATAGCCAGGAGTCGGTGACGGAG<br>CAGGACTCCAAGGACTCCACGTACTCGCTCTCGTCCACCCTGACCCTC<br>TCCAAGGCGGACTACGAAAAGCACAAGGTCTACGCCTGCGAGGTGAC<br>GCACCAAGGCCTGTCCTCCCCAGTGACCAAGTCGTTCAACCGCGGCG<br>AGTGCTGATAATCTAGAGTCGGGGCGGCCGGCC |
| 21 | Ab1 VH coding sequence 1 | AAGCTTACCGCCACCATGGGCTGGAGCTGTATCATCCTCTTCCTGGTG<br>GCGACCGCGACGGGIGICCACTCCCAGGTGGAGCTCCAGGAGTCCGG<br>CCCCGGGCTTGTGAAGCCGTCACAAACCCTGTCCCTGACGTGCACGG<br>TCTCCGGCTACGCCTTCACGGCCTACAACATACATTGGGTCCGGCAGG<br>CGCCGGGCCAGGGGCTGGAGTGGATGGGTTCCTTCGACCCGTACGAT<br>GGCGGGAGCTCGTACAACCAGAAGTTCAAAGACCGCCTGACGATCTC<br>CAAGGACACCTCGAAAAACCAGGTCGTCCTGACCATGACCAACATGG<br>ACCCGGTGGACACGGCGACCTACTATTGCGCCCGCGGCTGGTACTAC<br>TTCGACTACTGGGGCCACGGGACCCTGGTCACCGTGTCTTCC |
| 22 | Ab1 VL coding sequence 1 | GATATCGTCATGACGCAGACGCCGCTGAGCCTCCCGGTGACGCCCGG<br>CGAGCCCGCCAGCATCTCCTGCCGCGCTTCCAAGTCCATCTCGAAGTA<br>CCTGGCGTGGTATCAGCAGAAGCCCGGCCAGGCCCCGCGCCTGCTCA<br>TCTACTCTGGTTCCACGCTCCAGTCGGGCATCCCGCCCCGGTTCTCGG<br>GTTCGGGATACGGCACCGACTTCACCCTGACCATCAACAACATCGAG<br>AGCGAAGACGCGGCGTACTACTTCTGCCAGCAGCACGACGAGTCCCC<br>GTACACCTTCGGCGAGGGGACCAAGGTCGAGATCAAG |
| 23 | Ab1 VH coding sequence 2 | CAGGTGCAGCTGCAGGAGTCGGGCCCAGGACTGGTGAAGCCTTCACA<br>GACCCTGTCCCTCACCTGCACTGTCTUGGITATGCATICACTGCCTA<br>CAACATACACTGGGTGCGACAGGCCCCTGGACAAGGGCTTGAGTGGA<br>TGGGTTCTTTTGATCCTTACGATGGTGGTAGTAGTTACAACCAGAAGT<br>TCAAGGACAGACTCACCATCTCCAAGGACACCTCCAAAAACCAGGTG<br>GTCCTTACAATGACCAACATGGACCCTGTGGACACAGCCACGTATTA<br>CTGTGCAAGAGGGTGGTACTACTTTGACTACTGGGGCCACGGAACCC<br>TGGTCACCGTCTCCTCA |
| 24 | Ab1 VL coding sequence 2 | GATATTGTGATGACCCAGACTCCACTCTCCCTGCCCGTCACCCCTGGA<br>GAGCCGGCCTCCATCTCCTGCAGGGCAAGTAAGAGCATTAGCAAATA<br>TTTAGCCTGGTACCAGCAGAAACCTGGCCAGGCTCCCAGGCTCCTCAT<br>CTATTCTGGATCCACTTTGCAATCTGGGATCCCACCTCGATTCAGTGG<br>CAGCGGGTATGGAACAGATTTTACCCTCACAATTAATAACATAGAAT |

TABLE 12-continued

List of Sequences

| SIN | Description | SEQUENCE |
|---|---|---|
| | | CTGAGGATGCTGCATATTACTTCTGTCAACAGCATGATGAATCCCCGT<br>ACACGTTCGGCGAGGGGACCAAGGTGGAAATCAAA |
| 25 | D10 VH | QVQLKESGPGLVAPSQTLSITCTVSGFSLTSYGVHWVRQPPGKGLEWLG<br>VIWAGGFTNYNSALKSRLSISKDNSKSQVLLKMTSLQTDDTAMYYCARR<br>GSSYSMDYWGQGTSVIVSS |
| 26 | D10 VL | EIVLSQSPAITAASLGQKVTITCSASSNVSYIHWYQQRSGTSPRPWIYEISK<br>LASGVPVRFSGSGSGTSYSLTISSMEAEDAAIYYCQQWNYPLITFGSGTK<br>LEIQ |
| 27 | D10 HCDR1 | GFSLTSYG |
| 28 | D10 HCDR2 | WAGGFT |
| 29 | D10 HCDR3 | RGSSYSMDY |
| 30 | D10 LCDR1 | SNVSYI |
| 31 | D10 LCDR2 | EIS |
| 32 | D10 LCDR3 | QQWNYPLI |
| 33 | D10 VH coding sequence | CAGGTGCAGCTGAAGGAGTCAGGACCTGGCCTGGTGGCGCCCTCACA<br>GACTCTGTCCATCACTTGCACTGTCTCTGGGTTTTCATTAACCAGTTAT<br>GGTGTACACTGGGTTCGCCAGCCTCCAGGAAAGGGTCTGGAGTGGCT<br>GGGAGTAATATGGGCTGGTGGATTCACAAATTATAATTCGGCTCTCA<br>AGTCCAGACTGAGCATCAGCAAAGACAACTCCAAGAGCCAAGTTCTC<br>TTAAAAATGACCAGTCTGCAAACTGATGACACAGCCATGTACTACTG<br>TGCCAGGAGAGGTAGTTCCTATTCTATGGACTATTGGGGTCAAGGAA<br>CCTCAGTCACCGTCTCCTCA |
| 34 | D10 VL coding sequence | GAAATTGTGCTCTCTCAGTCTCCAGCCATCACAGCTGCATCTCTGGGC<br>CAAAAGGTCACCATCACCTGCAGTGCCAGTTCAAATGTAAGTTACAT<br>CCACTGGTACCAGCAGAGGTCAGGCACCTCCCCCAGACCATGGATTT<br>ATGAAATATCCAAACTGGCTTCTGGAGTCCCAGTTCGCTTCAGTGGCA<br>GTGGGTCTGGGACCTCTTACTCTCTCACAATCAGCAGCATGGAGGCTG<br>AAGATGCTGCCATTTATTATTGTCAGCAGTGGAATTATCCTCTTATCA<br>CGTTCGGCTCGGGGACAAAGTTGGAAATACAA |
| 35 | 4A5 VH | EVKLVESGGGLVKPGGSLKLSCAASGFTFSSYAMSWVRQIPEKRLEWVA<br>SISRGGTTYYPDSVKGRFTISRDNVRNILYLQMSSLRSEDTAMYYCGRYD<br>YDGYYAMDYWGQGTSVTVSS |
| 36 | 4A5 VL | DIKMTQSPSSMYASLGERVTITCKASPDINSYLSWFQQKPGKSPKTLIYRA<br>NRLVDGVPSRFSGGGSGQDYSLTINSLEYEDMGIYYCLQYDEFPYTFGG<br>GTKLEMK |
| 37 | 4A5 HCDR1 | GFTFSSYA |
| 38 | 4A5 HCDR2 | ISRGGTT |
| 39 | 4A5 HCDR3 | YDYDGYYAMDY |
| 40 | 4A5 LCDR1 | PDINSY |
| 41 | 4A5 LCDR2 | RAN |
| 42 | 4A5 LCDR3 | LQYDEFPYT |
| 43 | 4A5 VH coding sequence | GAAGTGAAACTGGTGGAGTCTGGGGGAGGCTTAGTGAAGCCTGGAG<br>GGTCCCTGAAACTCTCCTGTGCAGCCTCTGGATTCACTTTCAGTAGCT<br>ATGCCATGTCTTGGGTTCGCCAGATTCCAGAGAAGAGGCTGGAGTGG<br>GTCGCATCCATTAGTCGTGGTGGTACCACCTACTATCCAGACAGTGTG<br>AAGGGCCGATTCACCATCTCCAGAGATAATGTCAGGAACATCCTGTA<br>CCTGCAAATGAGCAGTCTGAGGTCTGAGGACACGGCCATGTATTACT<br>GTGGAAGATATGATTACGACGGGTACTATGCAATGGACTACTGGGGT<br>CAAGGAACCTCAGTCACCGTCTCCTCA |
| 44 | 4A5 VL coding sequence | GACATCAAGATGACCCAGTCTCCATCTTCCATGTATGCATCTCTAGGA<br>GAGAGAGTCACTATCACTTGCAAGGCGAGTCCGGACATTAATAGCTA<br>TTTAAGCTGGTTCCAGCAGAAACCAGGGAAATCTCCTAAGACCCTGA<br>TCTATCGTGCAAACAGATTGGTTGATGGGGTCCCATCAAGGTTCAGTG<br>GCGGTGGATCTGGGCAAGATTATTCTCTCACCATCAACAGCCTGGAG<br>TATGAAGATATGGGAATTTATTATTGTCTACAGTATGATGAATTTCCG<br>TACACGTTCGGAGGGGGGACCAAGCTGGAAATGAAAC |

TABLE 12-continued

List of Sequences

| SIN | Description | SEQUENCE |
|---|---|---|
| 45 | 99961 VH | EIQLQQSGPVLVKPGASVKVSCKASGYAFTAYNIHWVRQSHGKRLEWIG<br>SFDPYDGGSSYNQKFKDKATLTVDKSSTTAYMHLNSLTSEDSAVYYCAR<br>GWYYFDYWGHGTTLTVSS |
| 46 | 99961 VL | DVQITQSPSYLAASPGETITINCRASKSISKYLAWYQEKPGKTNKLLIYSG<br>STLQSGIPSRFRGSGSGTDFTLTISSLEPEDFAMYYCQQHDESPYTFGEGT<br>KLEIKR |
| 47 | Ab4 heavy chain | QVQLQESGPGLVKPSQTLSLTCTVSGYAFTAYNIHWIRQPPGKGLEWIGS<br>FDPYDGGSSYNQKFKDRLTISKDTSKNQVVLTMTNMDPVDTATYYCAR<br>GWYYFDYWGHGTLVTVSSASTKGPSVFPLAPSSKSTSGGTAALGCLVKD<br>YFPEPVTVSWNSGALTSGVHTFPAVLQSSGLYSLSSVVTVPSSSLGTQTYI<br>CNVNHKPSNTKVDKKVEPKSCDKTHTCPPCPAPELLGGPSVFLFPPKPKD<br>TLMISRTPEVTCVVVDVSHEDPEVKFNWYVDGVEVHNAKTKPREEQYN<br>STYRVVSVLTVLHQDWLNGKEYKCKVSNKALPAPIEKTISKAKGQPREP<br>QVYTLPPSRDELTKNQVSLTCLVKGFYPSDIAVEWESNGQPENNYKTTPP<br>VLDSDGSFFLYSKLTVDKSRWQQGNVFSCSVMHEALHNHYTQKSLSLSP<br>GK |
| 48 | Ab4 VH | QVQLQESGPGLVKPSQTLSLTCTVSGYAFTAYNIHWIRQPPGKGLEWIGS<br>FDPYDGGSSYNQKFKDRLTISKDTSKNQVVLTMTNMDPVDTATYYCAR<br>GWYYFDYWGHGTLVTVSS |
| 49 | Ab4 light chain | DVVMTQSPLSLPVTLGQPASISCRASKSISKYLAWYQQKPGKAPKLLIYS<br>GSTLQSGIPPRFSGSGYGTDFTLTINNIESEDAAYYFCQQHDESPYTFGEG<br>TKVEIKRTVAAPSVFIFPPSDEQLKSGTASVVCLLNNFYPREAKVQWKVD<br>NALQSGNSQESVTEQDSKDSTYSLSSTLTLSKADYEKHKVYACEVTHQG<br>LSSPVTKSFNRGEC |
| 50 | Ab4 VL | DVVMTQSPLSLPVTLGQPASISCRASKSISKYLAWYQQKPGKAPKLLIYS<br>GSTLQSGIPPRFSGSGYGTDFTLTINNIESEDAAYYFCQQHDESPYTFGEG<br>TKVEIK |
| 51 | Ab4 heavy chain coding sequence | CAGGTCCAGCTGCAGGAGTCAGGTCCCGGACTGGTCAAGCCGTCGCA<br>GACGCTGTCCCTCACCTGCACCGTGTCGGGCTACGCCTTCACCGCCTA<br>CAACATCCACTGGATCCGTCAGCCCCCTGGGAAGGGCCTCGAGTGGA<br>TCGGCAGCTTCGACCCGTACGACGGCGGGTCGTCCTACAACCAGAAG<br>TTCAAGGACCGCCTCACCATCAGCAAGGACACCTCCAAGAACCAGGT<br>CGTCCTCACCATGACCAACATGGACCCCGTGGACACCGCCACGTACT<br>ACTGCGCGCGGGGCTGGTACTACTTCGACTACTGGGGGCACGGCACC<br>CTCGTCACGGTCTCGTCGGCGAGCACCAAGGGTCCGAGCGTCTTCCCC<br>CTGGCCCCCTCCAGCAAGTCCACCTCGGGGGGCACCGCCGCCCTGGG<br>CTGCCTGGTCAAGGACTACTTCCCCGAGCCCGTGACCGTGAGCTGGA<br>ACTCCGGCGCCCTCACCAGCGGGGTCCACACCTTCCCGGCGGTCCTGC<br>AGTCATCCGGTCTCTACTCCTTGAGCTCAGTCGTCACCGTCCCGAGCT<br>CCTCCCTCGGAACGCAGACCTACATCTGCAACGTCAACCACAAGCCG<br>TCCAACACCAAGGTCGACAAGAAGGTGGAGCCCAAATCGTGCGACA<br>AGACCCACACCTGCCCGCCGTGCCCCGCCCCGGAACTGCTCGGCGGC<br>CCCTCGGTGTTCCTGTTCCCCCCGAAGCCCAAGGACACCCTCATGATC<br>TCCCGCACCCCCGAGGTCACCTGCGTGGTGGTGGATGTCTCCCACGA<br>GGACCCCGAGGTGAAGTTCAACTGGTACGTGGACGGGGTCGAGGTGC<br>ACAACGCCAAGACCAAGCCCCGAGAGGAACAGTATAACTCGACGTA<br>CCGCGTGGTCAGCGTCCTGACCGTGCTCCACCAGGACTGGCTGAACG<br>GCAAGGAGTACAAGTGCAAGGTCAGCAACAAGGCCCTGCCCGCCCCC<br>ATCGAGAAGACGATCTCCAAGGCGAAGGGGCAGCCGCGCGAGCCGC<br>AGGTCTACACCCTGCCGCCCAGCCGGGACGAGCTCACGAAGAATCAG<br>GTCTCGCTCACCTGCCTCGTCAAGGGTTTCTACCCGTCGGACATCGCG<br>GTCGAATGGGAGTCGAACGGTCAGCCCGAGAATAACTACAAGACGA<br>CCCCGCCCGTCCTGGACTCGGACGGCAGCTTCTTCCTGTACTCGAAGC<br>TGACGGTCGACAAGTCGCGCTGGCAGCAGGGCAACGTCTTCTCGTGC<br>TCGGTGATGCACGAGGCCCTCCACAACCACTACACACAGAAGAGCCT<br>CTCGCTTTCGCCGGGCAAG |
| 52 | Ab4 VH coding sequence | CAGGTCCAGCTGCAGGAGTCAGGTCCCGGACTGGTCAAGCCGTCGCA<br>GACGCTGTCCCTCACCTGCACCGTGTCGGGCTACGCCTTCACCGCCTA<br>CAACATCCACTGGATCCGTCAGCCCCCTGGGAAGGGCCTCGAGTGGA<br>TCGGCAGCTTCGACCCGTACGACGGCGGGTCGTCCTACAACCAGAAG<br>TTCAAGGACCGCCTCACCATCAGCAAGGACACCTCCAAGAACCAGGT<br>CGTCCTCACCATGACCAACATGGACCCCGTGGACACCGCCACGTACT<br>ACTGCGCGCGGGGCTGGTACTACTTCGACTACTGGGGGCACGGCACC<br>CTCGTCACGGTCTCGTCG |
| 53 | Ab4 light chain coding sequence | GACGTCGTGATGACCCAGTCGCCCCTCTCCCTGCCGGTTACCCTGGGC<br>CAGCCCGCCTCCATCAGCTGCCGTGCCTCCAAGTCCATTTCCAAGTAC<br>CTGGCCTGGTACCAGCAGAAGCCGGGGAAGGCCCCAAAGCTCCTCAT |

TABLE 12-continued

List of Sequences

| SIN | Description | SEQUENCE |
|---|---|---|
| | | CTACTCCGGCTCCACCCTCCAGAGCGGCATCCCCCCCCGCTTCAGCGG<br>CTCCGGCTACGGCACCGACTTCACCCTCACCATCAATAACATCGAGTC<br>GGAGGACGCCGCGTACTACTTCTGCCAGCAGCACGACGAATCGCCGT<br>ACACCTTCGGGGAGGGCACCAAGGTGGAGATCAAGAGGACGGTCGC<br>CGCGCCCTCCGTGTTCATCTTCCCCCCCTCGGACGAACAGCTGAAGTC<br>CGGGACCGCCTCCGTCGTCTGCCTCCTCAACAACTTCTACCCGCGCGA<br>GGCCAAGGTGCAGTGGAAGGTCGACAACGCGCTCCAGTCCGGCAACT<br>CCCAGGAGTCGGTGACCGAGCAGGACTCGAAGGACAGTACCTACTCG<br>CTGAGCTCCACACTGACGCTCTCGAAGGCCGACTACGAGAAGCACAA<br>GGTGTACGCATGCGAGGTGACCCACCAGGGGCTGAGCTCGCCGGTGA<br>CTAAGTCGTTCAACAGGGGCGAATGC |
| 54 | Ab4 VL coding sequence | GACGTCGTGATGACCCAGTCGCCCCTCTCCCTGCCGGTTACCCTGGGC<br>CAGCCCGCCTCCATCAGCTGCCGTGCCTCCAAGTCCATTTCCAAGTAC<br>CTGGCCTGGTACCAGCAGAAGCCGGGGAAGGCCCCAAAGCTCCTCAT<br>CTACTCCGGCTCCACCCTCCAGAGCGGCATCCCCCCCCGCTTCAGCGG<br>CTCCGGCTACGGCACCGACTTCACCCTCACCATCAATAACATCGAGTC<br>GGAGGACGCCGCGTACTACTTCTGCCAGCAGCACGACGAATCGCCGT<br>ACACCTTCGGGGAGGGCACCAAGGTGGAGATCAAG |
| 55 | Linker peptide moiety sequence | GGFG |
| 56 | Linker peptide moiety sequence | ALAL |
| 57 | Linker peptide moiety sequence | GFLG |
| 58 | Glutamine tag | LLQGA |
| 59 | Sortase motif | LPxTG |
| 60 | Sortase motif | NPQTN |
| 61 | BirA tag | GFEIDKVWYDLDA |
| 62 | Human $CH_1$ domain plus upper hinge region | ASTKGPSVFPLAPSSKSTSGGTAALGCLVKDYFPEPVTVSWNSGAL<br>TSGVHTFPAVLQSSGLYSLSSVVTVPSSSLGTQTYICNVNHKPSNT<br>KVDKKVEPKSC |
| 63 | Human Kappa constant domain | RTVAAPSVFIFPPSDEQLKSGTASVVCLLNNFYPREAKVQWKVDN<br>ALQSGNSQESVTEQDSKDSTYSLSSTLTLSKADYEKHKVYACEVT<br>HQGLSSPVTKSFNRGEC |
| 64 | Humanized 4A5 scFv | DIQMTQSPSSLSASVGDRVTITCKASPDINSYLSWFQQRPGQSPRRL<br>IYRANRLVDGVPDRFSGSGSGTDFTLKISRVEAEDVGVYYCLQYD<br>EFPYTFGQGTKVEIKGGGGSGSTSGSGKPGSGEGSTKGGGGGSEV<br>QLVQSGAEVKKPGESLRISCKGSGFTFSSYAMSWIRQSPSRGLEWL<br>GSISRGGTTYYPDSVKGRFTISRDNAKNSLYLQMNSLRAEDTAVY<br>YCGRYDYDGYYAMDYWGQGTLVTVSS |
| 65 | Ab1 scFv | DIVMTQTPLSLPVTPGEPASISCRASKSISKYLAWYQQKPGQAPRL<br>LIYSGSTLQSGIPPRFSGSGYGTDFTLTINNIESEDAAYYFCQQHDES<br>PYTFGEGTKVEIKGGGGSGSTSGSGKPGSGEGSTKGGGGGSQVQL<br>QESGPGLVKPSQTLSLTCTVSGYAFTAYNIHWVRQAPGQGLEWM<br>GSFDPYDGGSSYNQKFKDRLTISKDTSKNQVVLTMTNMDPVDTA<br>TYYCARGWYYFDYWGHGTLVTVSS |
| 66 | Ab2 scFv | DVVMTQSPLSLPVTLGQPASISCRASKSISKYLAWYQQKPGKAPK<br>LLIYSGSTLQSGIPPRFSGSGYGTDFTLTINNIESEDAAYYFCQQHD<br>ESPYTFGEGTKVEIKGGGGSGSTSGSGKPGSGEGSTKGGGGGSQV<br>QLQESGPGLVKPSQTLSLTCTVSGYAFTAYNIHWVRQAPGQGLEW<br>MGSFDPYDGGSSYNQKFKDRLTISKDTSKNQVVLTMTNMDPVDT<br>ATYYCARGWYYFDYWGHGTLVTVSS |
| 67 | Ab3 scFv | DIVMTQTPLSLPVTPGEPASISCRASKSISKYLAWYQQKPGQAPRL<br>LIYSGSTLQSGIPPRFSGSGYGTDFTLTINNIESEDAAYYFCQQHDES<br>PYTFGEGTKVEIKGGGGSGSTSGSGKPGSGEGSTKGGGGGSQVQL<br>QESGPGLVKPSQTLSLTCTVSGYAFTAYNIHWIRQPPGKGLEWIGS<br>FDPYDGGSSYNQKFKDRLTISKDTSKNQVVLTMTNMDPVDTATY<br>YCARGWYYFDYWGHGTLVTVSS |

TABLE 12-continued

| List of Sequences | | |
|---|---|---|
| SIN | Description | SEQUENCE |
| 68 | Ab4 scFv | DVVMTQSPLSLPVTLGQPASISCRASKSISKYLAWYQQKPGKAPK LLIYSGSTLQSGIPPRFSGSGYGTDFTLTINNIESEDAAYYFCQQHD ESPYTFGEGTKVEIKGGGGSGSTSGSGKPGSGEGSTKGGGGGSQV QLQESGPGLVKPSQTLSLTCTVSGYAFTAYNIHWIRQPPGKGLEWI GSFDPYDGGSSYNQKFKDRLTISKDTSKNQVVLTMTNMDPVDTA TYYCARGWYYFDYWGHGTLVTVSS |

*SIN SEQ ID NO.

SEQUENCE LISTING

```
<160> NUMBER OF SEQ ID NOS: 68

<210> SEQ ID NO 1
<211> LENGTH: 22
<212> TYPE: PRT
<213> ORGANISM: Homo sapiens

<400> SEQUENCE: 1

Val Ala Thr Asn Gly Lys Glu Val Val Ser Ser Thr Gly Val Leu Phe
1               5                   10                  15

Val Lys Phe Gly Pro Cys
            20


<210> SEQ ID NO 2
<211> LENGTH: 16
<212> TYPE: PRT
<213> ORGANISM: Homo sapiens

<400> SEQUENCE: 2

Glu Val Val Ser Ser Thr Gly Val Leu Phe Val Lys Phe Gly Pro Cys
1               5                   10                  15


<210> SEQ ID NO 3
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Thr Ala Tyr
            20                  25                  30

Asn Ile His Trp Val Arg Gln Ala Pro Gly Gln Gly Leu Glu Trp Met
        35                  40                  45

Gly Ser Phe Asp Pro Tyr Asp Gly Gly Ser Ser Tyr Asn Gln Lys Phe
    50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
            100                 105                 110

Thr Val Ser Ser Ala Ser Thr Lys Gly Pro Ser Val Phe Pro Leu Ala
        115                 120                 125
```

```
Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 4
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Ser Ile Ser Lys Tyr
            20                  25                  30

Leu Ala Trp Tyr Gln Gln Lys Pro Gly Gln Ala Pro Arg Leu Leu Ile
```

```
        35                  40                  45

Tyr Ser Gly Ser Thr Leu Gln Ser Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln His Asp Glu Ser Pro Tyr
                85                  90                  95

Thr Phe Gly Glu Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 5
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ala Phe Thr Ala Tyr
            20                  25                  30

Asn Ile His Trp Val Arg Gln Ala Pro Gly Gln Gly Leu Glu Trp Met
        35                  40                  45

Gly Ser Phe Asp Pro Tyr Asp Gly Gly Ser Ser Tyr Asn Gln Lys Phe
    50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
            100                 105                 110

Thr Val Ser Ser
        115


<210> SEQ ID NO 6
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 6

Asp Ile Val Met Thr Gln Thr Pro Leu Ser Leu Pro Val Thr Pro Gly
1 5 10 15

Glu Pro Ala Ser Ile Ser Cys Arg Ala Ser Lys Ser Ile Ser Lys Tyr
20 25 30

Leu Ala Trp Tyr Gln Gln Lys Pro Gly Gln Ala Pro Arg Leu Leu Ile
35 40 45

Tyr Ser Gly Ser Thr Leu Gln Ser Gly Ile Pro Pro Arg Phe Ser Gly
50 55 60

Ser Gly Tyr Gly Thr Asp Phe Thr Leu Thr Ile Asn Asn Ile Glu Ser
65 70 75 80

Glu Asp Ala Ala Tyr Tyr Phe Cys Gln Gln His Asp Glu Ser Pro Tyr
85 90 95

Thr Phe Gly Glu Gly Thr Lys Val Glu Ile Lys
100 105

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 7

Gly Tyr Ala Phe Thr Ala Tyr Asn
1 5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 8

Phe Asp Pro Tyr Asp Gly Gly Ser
1 5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 9

Gly Trp Tyr Tyr Phe Asp Tyr
1 5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 10

Lys Ser Ile Ser Lys Tyr
1 5

<210> SEQ ID NO 11
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 11

Ser Gly Ser
1

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 12

Gln Gln His Asp Glu Ser Pro Tyr
1 5

<210> SEQ ID NO 13
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 13

Ser Gly Tyr Ala Phe Thr Ala Tyr Asn Ile His Trp Val Arg Gln
1 5 10 15

<210> SEQ ID NO 14
<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 14

Gly Ser Phe Asp Pro Tyr Asp Gly Gly Ser Ser Tyr Asn Gln Lys Phe
1 5 10 15

<210> SEQ ID NO 15
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 15

Tyr Tyr Cys Ala Arg Gly Trp Tyr Tyr Phe Asp Tyr Trp Gly His Gly
1 5 10 15

Thr Leu Val Thr Val Ser Ser
20

<210> SEQ ID NO 16
<211> LENGTH: 14
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 16

Cys Arg Ala Ser Lys Ser Ile Ser Lys Tyr Leu Ala Trp Tyr
1 5 10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 17

Leu Leu Ile Tyr Ser Gly Ser Thr Leu Gln Ser Gly
1 5 10

<210> SEQ ID NO 18
<211> LENGTH: 20
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 18

Cys Gln Gln His Asp Glu Ser Pro Tyr Thr Phe Gly Glu Gly Thr Lys
1 5 10 15

Val Glu Ile Lys
20

<210> SEQ ID NO 19
<211> LENGTH: 1438
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 19 aagcttaccg ccaccatggg ctggagctgt atcatcctct tcctggtggc gaccgcgacg 60 ggtgtccact cccaggtgca gctccaggag tccggccccg ggcttgtgaa gccgtcacaa 120 accctgtccc tgacgtgcac ggtctccggc tacgccttca cggcctacaa catacattgg 180 gtccggcagg cgccgggcca ggggctggag tggatgggtt ccttcgaccc gtacgatggc 240 gggagctcgt acaaccagaa gttcaaagac cgcctgacga tctccaagga cacctcgaaa 300 aaccaggtcg tcctgaccat gaccaacatg gacccggtgg acacggcgac ctactattgc 360 gcccgcggct ggtactactt cgactactgg ggccacggga ccctggtcac cgtgtcttcc 420 gcttcgacca agggccccag cgtcttcccg ctcgcgccct cctcgaagtc cacctcgggc 480 ggcactgccg ccctgggctg cctggtcaag gactacttcc cggagccggt gaccgtctcg 540 tggaacagcg gggcactcac ctccggcgtg cacaccttcc cggccgtgct gcagtcctcg 600 gggctgtatt cactcagctc ggtcgtcacc gtcccctcgt cgtccctcgg cacgcagacg 660 tacatctgca acgtcaacca caagccctcg aacaccaagg tggacaagaa ggtcgagccg 720 aagtcctgcg ataagaccca cacctgcccc ccgtgcccgg cccccgagct cctgggcggt 780 ccgtccgtgt tcctcttccc gcccaagccc aaggacaccc tgatgatcag ccgcacgccc 840 gaggtgacct gcgtcgtcgt ggacgtctcc cacgaggatc ccgaggtgaa gttcaactgg 900 tacgtggacg gggtggaggt ccacaacgcc aagacaaagc cgcgggaaga gcagtacaac 960 tcgacctacc gcgtcgtcag cgtgctgacg gtcctccacc aggactggct gaacggcaag 1020 gagtacaaat gcaaggtgtc caacaaggcc ctgcccgcgc ccatcgagaa gaccatctcc 1080 aaggccaagg gacagccgcg cgagccgcag gtctacacgc tgcctccctc ccgggacgag 1140 ctcacgaaga accaggtatc gctcacctgc ctcgtgaagg gcttctaccc gagcgacatc 1200 gccgtcgagt gggagagcaa cggccagccc gagaacaact acaaaaccac gccgccggtc 1260 ctcgactctg acgggtcctt cttcctgtac tccaagctga ccgtggacaa gtcgcggtgg 1320 cagcagggga acgtgttctc gtgctcggtc atgcacgagg cgttgcacaa ccactacacc 1380 cagaagtcac tctccctgag cccgggcaag tgataatcta gagtcggggc ggccggcc 1438

<210> SEQ ID NO 20
<211> LENGTH: 742
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 20 aagcttaccg ccaccatggg ctggtcatgc atcatcctgt tcctggtcgc caccgcgacg 60 ggggtccaca gtgatatcgt catgacgcag acgccgctga gcctcccggt gacgcccggc 120 gagcccgcca gcatctcctg ccgcgcttcc aagtccatct cgaagtacct ggcgtggtat 180 cagcagaagc ccggccaggc cccgcgcctg ctcatctact ctggttccac gctccagtcg 240 ggcatcccgc cccggttctc gggttcggga tacggcaccg acttcaccct gaccatcaac 300 aacatcgaga gcgaagacgc ggcgtactac ttctgccagc agcacgacga gtccccgtac 360 accttcggcg aggggaccaa ggtcgagatc aagcgtaccg tcgcggcacc gagcgtcttc 420 atcttccccc cgtccgacga gcagctcaag tctggcaccg cctcggtcgt ctgtctcctg 480 aacaacttct accccaggga agccaaggtc cagtggaagg tggacaacgc gctgcagtcc 540 gggaatagcc aggagtcggt gacggagcag gactccaagg actccacgta ctcgctctcg 600 tccaccctga ccctctccaa ggcggactac gaaaagcaca aggtctacgc ctgcgaggtg 660 acgcaccaag gcctgtcctc cccagtgacc aagtcgttca accgcggcga gtgctgataa 720 tctagagtcg gggcggccgg cc 742

<210> SEQ ID NO 21
<211> LENGTH: 420
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 21 aagcttaccg ccaccatggg ctggagctgt atcatcctct tcctggtggc gaccgcgacg 60 ggtgtccact cccaggtgca gctccaggag tccggccccg ggcttgtgaa gccgtcacaa 120 accctgtccc tgacgtgcac ggtctccggc tacgccttca cggcctacaa catacattgg 180 gtccggcagg cgccgggcca ggggctggag tggatgggtt ccttcgaccc gtacgatggc 240 gggagctcgt acaaccagaa gttcaaagac cgcctgacga tctccaagga cacctcgaaa 300 aaccaggtcg tcctgaccat gaccaacatg gacccggtgg acacggcgac ctactattgc 360 gcccgcggct ggtactactt cgactactgg ggccacggga ccctggtcac cgtgtcttcc 420

<210> SEQ ID NO 22
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 22 gatatcgtca tgacgcagac gccgctgagc ctcccggtga cgcccggcga gcccgccagc 60 atctcctgcc gcgcttccaa gtccatctcg aagtacctgg cgtggtatca gcagaagccc 120 ggccaggccc cgcgcctgct catctactct ggttccacgc tccagtcggg catcccgccc 180 cggttctcgg gttcgggata cggcaccgac ttcaccctga ccatcaacaa catcgagagc 240 gaagacgcgg cgtactactt ctgccagcag cacgacgagt ccccgtacac cttcggcgag 300 gggaccaagg tcgagatcaa g 321

<210> SEQ ID NO 23
<211> LENGTH: 348
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 23 caggtgcagc tgcaggagtc gggcccagga ctggtgaagc cttcacagac cctgtccctc 60 acctgcactg tctctggtta tgcattcact gcctacaaca tacactgggt gcgacaggcc 120 cctggacaag ggcttgagtg gatgggttct tttgatcctt acgatggtgg tagtagttac 180 aaccagaagt tcaaggacag actcaccatc tccaaggaca cctccaaaaa ccaggtggtc 240 cttacaatga ccaacatgga ccctgtggac acagccacgt attactgtgc aagagggtgg 300 tactactttg actactgggg ccacggaacc ctggtcaccg tctcctca 348

<210> SEQ ID NO 24
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 24 gatattgtga tgacccagac tccactctcc ctgcccgtca cccctggaga gccggcctcc 60 atctcctgca gggcaagtaa gagcattagc aaatatttag cctggtacca gcagaaacct 120 ggccaggctc ccaggctcct catctattct ggatccactt tgcaatctgg gatcccacct 180 cgattcagtg gcagcgggta tggaacagat tttaccctca caattaataa catagaatct 240 gaggatgctg catattactt ctgtcaacag catgatgaat ccccgtacac gttcggcgag 300 gggaccaagg tggaaatcaa a 321

<210> SEQ ID NO 25
<211> LENGTH: 117
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 25

Gln Val Gln Leu Lys Glu Ser Gly Pro Gly Leu Val Ala Pro Ser Gln
1 5 10 15

Thr Leu Ser Ile Thr Cys Thr Val Ser Gly Phe Ser Leu Thr Ser Tyr
20 25 30

Gly Val His Trp Val Arg Gln Pro Pro Gly Lys Gly Leu Glu Trp Leu
35 40 45

Gly Val Ile Trp Ala Gly Gly Phe Thr Asn Tyr Asn Ser Ala Leu Lys
50 55 60

Ser Arg Leu Ser Ile Ser Lys Asp Asn Ser Lys Ser Gln Val Leu Leu
65 70 75 80

Lys Met Thr Ser Leu Gln Thr Asp Asp Thr Ala Met Tyr Tyr Cys Ala
85 90 95

Arg Arg Gly Ser Ser Tyr Ser Met Asp Tyr Trp Gly Gln Gly Thr Ser
100 105 110

Val Ile Val Ser Ser
115

<210> SEQ ID NO 26
<211> LENGTH: 106
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 26

Glu Ile Val Leu Ser Gln Ser Pro Ala Ile Thr Ala Ala Ser Leu Gly
1 5 10 15

Gln Lys Val Thr Ile Thr Cys Ser Ala Ser Ser Asn Val Ser Tyr Ile
20 25 30

His Trp Tyr Gln Gln Arg Ser Gly Thr Ser Pro Arg Pro Trp Ile Tyr
35 40 45

Glu Ile Ser Lys Leu Ala Ser Gly Val Pro Val Arg Phe Ser Gly Ser
50 55 60

Gly Ser Gly Thr Ser Tyr Ser Leu Thr Ile Ser Ser Met Glu Ala Glu
65 70 75 80

Asp Ala Ala Ile Tyr Tyr Cys Gln Gln Trp Asn Tyr Pro Leu Ile Thr
85 90 95

Phe Gly Ser Gly Thr Lys Leu Glu Ile Gln
100 105

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 27

Gly Phe Ser Leu Thr Ser Tyr Gly
1 5

<210> SEQ ID NO 28
<211> LENGTH: 6
<212> TYPE: PRT
<213> ORGANISM: Artificial Sequence
<220> FEATURE:

<223> OTHER INFORMATION: Description of Artificial Sequence: Synthetic
peptide

<400> SEQUENCE: 28

Trp Ala Gly Gly Phe Thr
1 5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 29

Arg Gly Ser Ser Tyr Ser Met Asp Tyr
1 5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 30

Ser Asn Val Ser Tyr Ile
1 5

<210> SEQ ID NO 31
<211> LENGTH: 3
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 31

Glu Ile Ser
1

<210> SEQ ID NO 32
<211> LENGTH: 8
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 32

Gln Gln Trp Asn Tyr Pro Leu Ile
1 5

<210> SEQ ID NO 33
<211> LENGTH: 351
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 33 caggtgcagc tgaaggagtc aggacctggc ctggtggcgc cctcacagac tctgtccatc 60 acttgcactg tctctgggtt ttcattaacc agttatggtg tacactgggt tcgccagcct 120

```
ccaggaaagg gtctggagtg gctgggagta atatgggctg gtggattcac aaattataat    180

tcggctctca agtccagact gagcatcagc aaagacaact ccaagagcca agttctctta    240

aaaatgacca gtctgcaaac tgatgacaca gccatgtact actgtgccag gagaggtagt    300

tcctattcta tggactattg gggtcaagga acctcagtca ccgtctcctc a             351


<210> SEQ ID NO 34
<211> LENGTH: 318
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 34

gaaattgtgc tctctcagtc tccagccatc acagctgcat ctctgggcca aaaggtcacc     60

atcacctgca gtgccagttc aaatgtaagt tacatccact ggtaccagca gaggtcaggc    120

acctccccca gaccatggat ttatgaaata tccaaactgg cttctggagt cccagttcgc    180

ttcagtggca gtgggtctgg gacctcttac tctctcacaa tcagcagcat ggaggctgaa    240

gatgctgcca tttattattg tcagcagtgg aattatcctc ttatcacgtt cggctcgggg    300

acaaagttgg aaatacaa                                                  318


<210> SEQ ID NO 35
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 35

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Ile Pro Glu Lys Arg Leu Glu Trp Val
        35                  40                  45

Ala Ser Ile Ser Arg Gly Gly Thr Thr Tyr Tyr Pro Asp Ser Val Lys
    50                  55                  60

Gly Arg Phe Thr Ile Ser Arg Asp Asn Val Arg Asn Ile Leu Tyr Leu
65                  70                  75                  80

Gln Met Ser Ser Leu Arg Ser Glu Asp Thr Ala Met Tyr Tyr Cys Gly
                85                  90                  95

Arg Tyr Asp Tyr Asp Gly Tyr Tyr Ala Met Asp Tyr Trp Gly Gln Gly
            100                 105                 110

Thr Ser Val Thr Val Ser Ser
        115


<210> SEQ ID NO 36
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Asp Ile Lys Met Thr Gln Ser Pro Ser Ser Met Tyr Ala Ser Leu Gly
1               5                   10                  15
```

```
Glu Arg Val Thr Ile Thr Cys Lys Ala Ser Pro Asp Ile Asn Ser Tyr
            20                  25                  30

Leu Ser Trp Phe Gln Gln Lys Pro Gly Lys Ser Pro Lys Thr Leu Ile
        35                  40                  45

Tyr Arg Ala Asn Arg Leu Val Asp Gly Val Pro Ser Arg Phe Ser Gly
    50                  55                  60

Gly Gly Ser Gly Gln Asp Tyr Ser Leu Thr Ile Asn Ser Leu Glu Tyr
65                  70                  75                  80

Glu Asp Met Gly Ile Tyr Tyr Cys Leu Gln Tyr Asp Glu Phe Pro Tyr
                85                  90                  95

Thr Phe Gly Gly Gly Thr Lys Leu Glu Met Lys
            100                 105


<210> SEQ ID NO 37
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Phe Thr Phe Ser Ser Tyr Ala
1               5


<210> SEQ ID NO 38
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Ile Ser Arg Gly Gly Thr Thr
1               5


<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Tyr Asp Tyr Asp Gly Tyr Tyr Ala Met Asp Tyr
1               5                   10


<210> SEQ ID NO 40
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Pro Asp Ile Asn Ser Tyr
1               5


<210> SEQ ID NO 41
<211> LENGTH: 3
<212> TYPE: PRT
```

<213> ORGANISM: Artificial Sequence
<220> FEATURE:
<223> OTHER INFORMATION: Description of Artificial Sequence: Synthetic
peptide

<400> SEQUENCE: 41

Arg Ala Asn
1

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 42

Leu Gln Tyr Asp Glu Phe Pro Tyr Thr
1 5

<210> SEQ ID NO 43
<211> LENGTH: 357
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 43 gaagtgaaac tggtggagtc tgggggaggc ttagtgaagc ctggagggtc cctgaaactc 60 tcctgtgcag cctctggatt cactttcagt agctatgcca tgtcttgggt tcgccagatt 120 ccagagaaga ggctggagtg ggtcgcatcc attagtcgtg gtggtaccac ctactatcca 180 gacagtgtga agggccgatt caccatctcc agagataatg tcaggaacat cctgtacctg 240 caaatgagca gtctgaggtc tgaggacacg gccatgtatt actgtggaag atatgattac 300 gacgggtact atgcaatgga ctactggggt caaggaacct cagtcaccgt ctcctca 357

<210> SEQ ID NO 44
<211> LENGTH: 322
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 44 gacatcaaga tgacccagtc tccatcttcc atgtatgcat ctctaggaga gagagtcact 60 atcacttgca aggcgagtcc ggacattaat agctatttaa gctggttcca gcagaaacca 120 gggaaatctc ctaagaccct gatctatcgt gcaaacagat tggttgatgg ggtcccatca 180 aggttcagtg gcggtggatc tgggcaagat tattctctca ccatcaacag cctggagtat 240 gaagatatgg gaatttatta ttgtctacag tatgatgaat ttccgtacac gttcggaggg 300 gggaccaagc tggaaatgaa ac 322

<210> SEQ ID NO 45
<211> LENGTH: 116
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 45

Glu Ile Gln Leu Gln Gln Ser Gly Pro Val Leu Val Lys Pro Gly Ala
1 5 10 15

Ser Val Lys Val Ser Cys Lys Ala Ser Gly Tyr Ala Phe Thr Ala Tyr
20 25 30

Asn Ile His Trp Val Arg Gln Ser His Gly Lys Arg Leu Glu Trp Ile
35 40 45

Gly Ser Phe Asp Pro Tyr Asp Gly Gly Ser Ser Tyr Asn Gln Lys Phe
50 55 60

Lys Asp Lys Ala Thr Leu Thr Val Asp Lys Ser Ser Thr Thr Ala Tyr
65 70 75 80

Met His Leu Asn Ser Leu Thr Ser Glu Asp Ser Ala Val Tyr Tyr Cys
85 90 95

Ala Arg Gly Trp Tyr Tyr Phe Asp Tyr Trp Gly His Gly Thr Thr Leu
100 105 110

Thr Val Ser Ser
115

<210> SEQ ID NO 46
<211> LENGTH: 108
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 46

Asp Val Gln Ile Thr Gln Ser Pro Ser Tyr Leu Ala Ala Ser Pro Gly
1 5 10 15

Glu Thr Ile Thr Ile Asn Cys Arg Ala Ser Lys Ser Ile Ser Lys Tyr
20 25 30

Leu Ala Trp Tyr Gln Glu Lys Pro Gly Lys Thr Asn Lys Leu Leu Ile
35 40 45

Tyr Ser Gly Ser Thr Leu Gln Ser Gly Ile Pro Ser Arg Phe Arg Gly
50 55 60

Ser Gly Ser Gly Thr Asp Phe Thr Leu Thr Ile Ser Ser Leu Glu Pro
65 70 75 80

Glu Asp Phe Ala Met Tyr Tyr Cys Gln Gln His Asp Glu Ser Pro Tyr
85 90 95

Thr Phe Gly Glu Gly Thr Lys Leu Glu Ile Lys Arg
100 105

<210> SEQ ID NO 47
<211> LENGTH: 446
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 47

Gln Val Gln Leu Gln Glu Ser Gly Pro Gly Leu Val Lys Pro Ser Gln
1 5 10 15

Thr Leu Ser Leu Thr Cys Thr Val Ser Gly Tyr Ala Phe Thr Ala Tyr
20 25 30

Asn Ile His Trp Ile Arg Gln Pro Pro Gly Lys Gly Leu Glu Trp Ile
35 40 45

Gly Ser Phe Asp Pro Tyr Asp Gly Gly Ser Ser Tyr Asn Gln Lys Phe

```
    50                  55                  60

Lys Asp Arg Leu Thr Ile Ser Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala Arg Gly Trp Tyr Tyr Phe Asp Tyr Trp Gly His Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445


<210> SEQ ID NO 48
<211> LENGTH: 116
<212> TYPE: PRT
<213> ORGANISM: Artificial Sequence
```

<220> FEATURE:
<223> OTHER INFORMATION: Description of Artificial Sequence: Synthetic
polypeptide

<400> SEQUENCE: 48

Gln Val Gln Leu Gln Glu Ser Gly Pro Gly Leu Val Lys Pro Ser Gln
1 5 10 15

Thr Leu Ser Leu Thr Cys Thr Val Ser Gly Tyr Ala Phe Thr Ala Tyr
20 25 30

Asn Ile His Trp Ile Arg Gln Pro Pro Gly Lys Gly Leu Glu Trp Ile
35 40 45

Gly Ser Phe Asp Pro Tyr Asp Gly Gly Ser Ser Tyr Asn Gln Lys Phe
50 55 60

Lys Asp Arg Leu Thr Ile Ser Lys Asp Thr Ser Lys Asn Gln Val Val
65 70 75 80

Leu Thr Met Thr Asn Met Asp Pro Val Asp Thr Ala Thr Tyr Tyr Cys
85 90 95

Ala Arg Gly Trp Tyr Tyr Phe Asp Tyr Trp Gly His Gly Thr Leu Val
100 105 110

Thr Val Ser Ser
115

<210> SEQ ID NO 49
<211> LENGTH: 214
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 49

Asp Val Val Met Thr Gln Ser Pro Leu Ser Leu Pro Val Thr Leu Gly
1 5 10 15

Gln Pro Ala Ser Ile Ser Cys Arg Ala Ser Lys Ser Ile Ser Lys Tyr
20 25 30

Leu Ala Trp Tyr Gln Gln Lys Pro Gly Lys Ala Pro Lys Leu Leu Ile
35 40 45

Tyr Ser Gly Ser Thr Leu Gln Ser Gly Ile Pro Pro Arg Phe Ser Gly
50 55 60

Ser Gly Tyr Gly Thr Asp Phe Thr Leu Thr Ile Asn Asn Ile Glu Ser
65 70 75 80

Glu Asp Ala Ala Tyr Tyr Phe Cys Gln Gln His Asp Glu Ser Pro Tyr
85 90 95

Thr Phe Gly Glu Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

```
Phe Asn Arg Gly Glu Cys
    210


<210> SEQ ID NO 50
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Asp Val Val Met Thr Gln Ser Pro Leu Ser Leu Pro Val Thr Leu Gly
1               5                   10                  15

Gln Pro Ala Ser Ile Ser Cys Arg Ala Ser Lys Ser Ile Ser Lys Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln His Asp Glu Ser Pro Tyr
                85                  90                  95

Thr Phe Gly Glu Gly Thr Lys Val Glu Ile Lys
            100                 105


<210> SEQ ID NO 51
<211> LENGTH: 1338
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 51

caggtccagc tgcaggagtc aggtcccgga ctggtcaagc cgtcgcagac gctgtccctc     60

acctgcaccg tgtcgggcta cgccttcacc gcctacaaca tccactggat ccgtcagccc    120

cctgggaagg gcctcgagtg gatcggcagc ttcgacccgt acgacggcgg gtcgtcctac    180

aaccagaagt tcaaggaccg cctcaccatc agcaaggaca cctccaagaa ccaggtcgtc    240

ctcaccatga ccaacatgga ccccgtggac accgccacgt actactgcgc gcggggctgg    300

tactacttcg actactgggg gcacggcacc ctcgtcacgg tctcgtcggc gagcaccaag    360

ggtccgagcg tcttccccct ggccccctcc agcaagtcca cctcgggggg caccgccgcc    420

ctgggctgcc tggtcaagga ctacttcccc gagcccgtga ccgtgagctg gaactccggc    480

gccctcacca gcggggtcca caccttcccg gcggtcctgc agtcatccgg tctctactcc    540

ttgagctcag tcgtcaccgt cccgagctcc tccctcggaa cgcagaccta catctgcaac    600

gtcaaccaca agccgtccaa caccaaggtc gacaagaagg tggagcccaa atcgtgcgac    660

aagacccaca cctgcccgcc gtgccccgcc ccggaactgc tcggcggccc ctcggtgttc    720

ctgttccccc cgaagcccaa ggacaccctc atgatctccc gcacccccga ggtcacctgc    780

gtggtggtgg atgtctccca cgaggacccc gaggtgaagt tcaactggta cgtggacggg    840

gtcgaggtgc acaacgccaa gaccaagccc cgagaggaac agtataactc gacgtaccgc    900

gtggtcagcg tcctgaccgt gctccaccag gactggctga acggcaagga gtacaagtgc    960
```

aaggtcagca acaaggccct gcccgccccc atcgagaaga cgatctccaa ggcgaagggg 1020 cagccgcgcg agccgcaggt ctacaccctg ccgcccagcc gggacgagct cacgaagaat 1080 caggtctcgc tcacctgcct cgtcaagggt ttctacccgt cggacatcgc ggtcgaatgg 1140 gagtcgaacg gtcagcccga gaataactac aagacgaccc cgcccgtcct ggactcggac 1200 ggcagcttct tcctgtactc gaagctgacg gtcgacaagt cgcgctggca gcagggcaac 1260 gtcttctcgt gctcggtgat gcacgaggcc ctccacaacc actacacaca gaagagcctc 1320 tcgctttcgc cgggcaag 1338

<210> SEQ ID NO 52
<211> LENGTH: 348
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 52 caggtccagc tgcaggagtc aggtcccgga ctggtcaagc cgtcgcagac gctgtccctc 60 acctgcaccg tgtcgggcta cgccttcacc gcctacaaca tccactggat ccgtcagccc 120 cctgggaagg gcctcgagtg gatcggcagc ttcgacccgt acgacggcgg gtcgtcctac 180 aaccagaagt tcaaggaccg cctcaccatc agcaaggaca cctccaagaa ccaggtcgtc 240 ctcaccatga ccaacatgga ccccgtggac accgccacgt actactgcgc gcggggctgg 300 tactacttcg actactgggg gcacggcacc ctcgtcacgg tctcgtcg 348

<210> SEQ ID NO 53
<211> LENGTH: 642
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 53 gacgtcgtga tgacccagtc gcccctctcc ctgccggtta ccctgggcca gcccgcctcc 60 atcagctgcc gtgcctccaa gtccatttcc aagtacctgg cctggtacca gcagaagccg 120 gggaaggccc caaagctcct catctactcc ggctccaccc tccagagcgg catccccccc 180 cgcttcagcg gctccggcta cggcaccgac ttcaccctca ccatcaataa catcgagtcg 240 gaggacgccg cgtactactt ctgccagcag cacgacgaat cgccgtacac cttcggggag 300 ggcaccaagg tggagatcaa gaggacggtc gccgcgccct ccgtgttcat cttcccccccc 360 tcggacgaac agctgaagtc cgggaccgcc tccgtcgtct gcctcctcaa caacttctac 420 ccgcgcgagg ccaaggtgca gtggaaggtc gacaacgcgc tccagtccgg caactcccag 480 gagtcggtga ccgagcagga ctcgaaggac agtacctact cgctgagctc cacactgacg 540 ctctcgaagg ccgactacga gaagcacaag gtgtacgcat gcgaggtgac ccaccagggg 600 ctgagctcgc cggtgactaa gtcgttcaac aggggcgaat gc 642

<210> SEQ ID NO 54
<211> LENGTH: 321
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 54 gacgtcgtga tgacccagtc gcccctctcc ctgccggtta ccctgggcca gcccgcctcc 60 atcagctgcc gtgcctccaa gtccatttcc aagtacctgg cctggtacca gcagaagccg 120 gggaaggccc caaagctcct catctactcc ggctccaccc tccagagcgg catccccccc 180 cgcttcagcg gctccggcta cggcaccgac ttcaccctca ccatcaataa catcgagtcg 240 gaggacgccg cgtactactt ctgccagcag cacgacgaat cgccgtacac cttcggggag 300 ggcaccaagg tggagatcaa g 321

<210> SEQ ID NO 55
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 55

Gly Gly Phe Gly
1

<210> SEQ ID NO 56
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 56

Ala Leu Ala Leu
1

<210> SEQ ID NO 57
<211> LENGTH: 4
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 57

Gly Phe Leu Gly
1

<210> SEQ ID NO 58
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 58

Leu Leu Gln Gly Ala
1 5

<210> SEQ ID NO 59
<211> LENGTH: 5
<212> TYPE: PRT
<213> ORGANISM: Unknown
<220> FEATURE:
<223> OTHER INFORMATION: Description of Unknown:
sortase motif
<220> FEATURE:

<221> NAME/KEY: MOD_RES
<222> LOCATION: (3)..(3)
<223> OTHER INFORMATION: Any amino acid

<400> SEQUENCE: 59

Leu Pro Xaa Thr Gly
1 5

<210> SEQ ID NO 60
<211> LENGTH: 5
<212> TYPE: PRT
<213> ORGANISM: Unknown
<220> FEATURE:
<223> OTHER INFORMATION: Description of Unknown:
sortase motif

<400> SEQUENCE: 60

Asn Pro Gln Thr Asn
1 5

<210> SEQ ID NO 61
<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 61

Gly Phe Glu Ile Asp Lys Val Trp Tyr Asp Leu Asp Ala
1 5 10

<210> SEQ ID NO 62
<211> LENGTH: 103
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 62

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys
100

<210> SEQ ID NO 63
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 63

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 64
<211> LENGTH: 254
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Lys Ala Ser Pro Asp Ile Asn Ser Tyr
            20                  25                  30

Leu Ser Trp Phe Gln Gln Arg Pro Gly Gln Ser Pro Arg Arg Leu Ile
        35                  40                  45

Tyr Arg Ala Asn Arg Leu Val Asp Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Leu Gln Tyr Asp Glu Phe Pro Tyr
                85                  90                  95

Thr Phe Gly Gln Gly Thr Lys Val Glu Ile Lys Gly Gly Gly Gly Ser
            100                 105                 110

Gly Ser Thr Ser Gly Ser Gly Lys Pro Gly Ser Gly Glu Gly Ser Thr
        115                 120                 125

Lys Gly Gly Gly Gly Gly Ser Glu Val Gln Leu Val Gln Ser Gly Ala
    130                 135                 140

Glu Val Lys Lys Pro Gly Glu Ser Leu Arg Ile Ser Cys Lys Gly Ser
145                 150                 155                 160

Gly Phe Thr Phe Ser Ser Tyr Ala Met Ser Trp Ile Arg Gln Ser Pro
                165                 170                 175

Ser Arg Gly Leu Glu Trp Leu Gly Ser Ile Ser Arg Gly Gly Thr Thr
            180                 185                 190

Tyr Tyr Pro Asp Ser Val Lys Gly Arg Phe Thr Ile Ser Arg Asp Asn
        195                 200                 205

Ala Lys Asn Ser Leu Tyr Leu Gln Met Asn Ser Leu Arg Ala Glu Asp
    210                 215                 220

Thr Ala Val Tyr Tyr Cys Gly Arg Tyr Asp Tyr Asp Gly Tyr Tyr Ala
225                 230                 235                 240

Met Asp Tyr Trp Gly Gln Gly Thr Leu Val Thr Val Ser Ser
```

245 250

<210> SEQ ID NO 65
<211> LENGTH: 251
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 65

Asp Ile Val Met Thr Gln Thr Pro Leu Ser Leu Pro Val Thr Pro Gly
1 5 10 15

Glu Pro Ala Ser Ile Ser Cys Arg Ala Ser Lys Ser Ile Ser Lys Tyr
20 25 30

Leu Ala Trp Tyr Gln Gln Lys Pro Gly Gln Ala Pro Arg Leu Leu Ile
35 40 45

Tyr Ser Gly Ser Thr Leu Gln Ser Gly Ile Pro Pro Arg Phe Ser Gly
50 55 60

Ser Gly Tyr Gly Thr Asp Phe Thr Leu Thr Ile Asn Asn Ile Glu Ser
65 70 75 80

Glu Asp Ala Ala Tyr Tyr Phe Cys Gln Gln His Asp Glu Ser Pro Tyr
85 90 95

Thr Phe Gly Glu Gly Thr Lys Val Glu Ile Lys Gly Gly Gly Gly Ser
100 105 110

Gly Ser Thr Ser Gly Ser Gly Lys Pro Gly Ser Gly Glu Gly Ser Thr
115 120 125

Lys Gly Gly Gly Gly Gly Ser Gln Val Gln Leu Gln Glu Ser Gly Pro
130 135 140

Gly Leu Val Lys Pro Ser Gln Thr Leu Ser Leu Thr Cys Thr Val Ser
145 150 155 160

Gly Tyr Ala Phe Thr Ala Tyr Asn Ile His Trp Val Arg Gln Ala Pro
165 170 175

Gly Gln Gly Leu Glu Trp Met Gly Ser Phe Asp Pro Tyr Asp Gly Gly
180 185 190

Ser Ser Tyr Asn Gln Lys Phe Lys Asp Arg Leu Thr Ile Ser Lys Asp
195 200 205

Thr Ser Lys Asn Gln Val Val Leu Thr Met Thr Asn Met Asp Pro Val
210 215 220

Asp Thr Ala Thr Tyr Tyr Cys Ala Arg Gly Trp Tyr Tyr Phe Asp Tyr
225 230 235 240

Trp Gly His Gly Thr Leu Val Thr Val Ser Ser
245 250

<210> SEQ ID NO 66
<211> LENGTH: 251
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 66

Asp Val Val Met Thr Gln Ser Pro Leu Ser Leu Pro Val Thr Leu Gly
1 5 10 15

Gln Pro Ala Ser Ile Ser Cys Arg Ala Ser Lys Ser Ile Ser Lys Tyr
20 25 30

Leu Ala Trp Tyr Gln Gln Lys Pro Gly Lys Ala Pro Lys Leu Leu Ile

```
        35                  40                  45

Tyr Ser Gly Ser Thr Leu Gln Ser Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln His Asp Glu Ser Pro Tyr
                85                  90                  95

Thr Phe Gly Glu Gly Thr Lys Val Glu Ile Lys Gly Gly Gly Gly Ser
            100                 105                 110

Gly Ser Thr Ser Gly Ser Gly Lys Pro Gly Ser Gly Glu Gly Ser Thr
        115                 120                 125

Lys Gly Gly Gly Gly Gly Ser Gln Val Gln Leu Gln Glu Ser Gly Pro
    130                 135                 140

Gly Leu Val Lys Pro Ser Gln Thr Leu Ser Leu Thr Cys Thr Val Ser
145                 150                 155                 160

Gly Tyr Ala Phe Thr Ala Tyr Asn Ile His Trp Val Arg Gln Ala Pro
                165                 170                 175

Gly Gln Gly Leu Glu Trp Met Gly Ser Phe Asp Pro Tyr Asp Gly Gly
            180                 185                 190

Ser Ser Tyr Asn Gln Lys Phe Lys Asp Arg Leu Thr Ile Ser Lys Asp
        195                 200                 205

Thr Ser Lys Asn Gln Val Val Leu Thr Met Thr Asn Met Asp Pro Val
    210                 215                 220

Asp Thr Ala Thr Tyr Tyr Cys Ala Arg Gly Trp Tyr Tyr Phe Asp Tyr
225                 230                 235                 240

Trp Gly His Gly Thr Leu Val Thr Val Ser Ser
                245                 250


<210> SEQ ID NO 67
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 67

Asp Ile Val Met Thr Gln Thr Pro Leu Ser Leu Pro Val Thr Pro Gly
1               5                   10                  15

Glu Pro Ala Ser Ile Ser Cys Arg Ala Ser Lys Ser Ile Ser Lys Tyr
            20                  25                  30

Leu Ala Trp Tyr Gln Gln Lys Pro Gly Gln Ala Pro Arg Leu Leu Ile
        35                  40                  45

Tyr Ser Gly Ser Thr Leu Gln Ser Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln His Asp Glu Ser Pro Tyr
                85                  90                  95

Thr Phe Gly Glu Gly Thr Lys Val Glu Ile Lys Gly Gly Gly Gly Ser
            100                 105                 110

Gly Ser Thr Ser Gly Ser Gly Lys Pro Gly Ser Gly Glu Gly Ser Thr
        115                 120                 125

Lys Gly Gly Gly Gly Gly Ser Gln Val Gln Leu Gln Glu Ser Gly Pro
    130                 135                 140
```

```
Gly Leu Val Lys Pro Ser Gln Thr Leu Ser Leu Thr Cys Thr Val Ser
145                 150                 155                 160

Gly Tyr Ala Phe Thr Ala Tyr Asn Ile His Trp Ile Arg Gln Pro Pro
                165                 170                 175

Gly Lys Gly Leu Glu Trp Ile Gly Ser Phe Asp Pro Tyr Asp Gly Gly
            180                 185                 190

Ser Ser Tyr Asn Gln Lys Phe Lys Asp Arg Leu Thr Ile Ser Lys Asp
        195                 200                 205

Thr Ser Lys Asn Gln Val Val Leu Thr Met Thr Asn Met Asp Pro Val
    210                 215                 220

Asp Thr Ala Thr Tyr Tyr Cys Ala Arg Gly Trp Tyr Tyr Phe Asp Tyr
225                 230                 235                 240

Trp Gly His Gly Thr Leu Val Thr Val Ser Ser
                245                 250


<210> SEQ ID NO 68
<211> LENGTH: 251
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Asp Val Val Met Thr Gln Ser Pro Leu Ser Leu Pro Val Thr Leu Gly
1               5                   10                  15

Gln Pro Ala Ser Ile Ser Cys Arg Ala Ser Lys Ser Ile Ser Lys Tyr
            20                  25                  30

Leu Ala Trp Tyr Gln Gln Lys Pro Gly Lys Ala Pro Lys Leu Leu Ile
        35                  40                  45

Tyr Ser Gly Ser Thr Leu Gln Ser Gly Ile Pro Pro Arg Phe Ser Gly
    50                  55                  60

Ser Gly Tyr Gly Thr Asp Phe Thr Leu Thr Ile Asn Asn Ile Glu Ser
65                  70                  75                  80

Glu Asp Ala Ala Tyr Tyr Phe Cys Gln Gln His Asp Glu Ser Pro Tyr
                85                  90                  95

Thr Phe Gly Glu Gly Thr Lys Val Glu Ile Lys Gly Gly Gly Gly Ser
            100                 105                 110

Gly Ser Thr Ser Gly Ser Gly Lys Pro Gly Ser Gly Glu Gly Ser Thr
        115                 120                 125

Lys Gly Gly Gly Gly Gly Ser Gln Val Gln Leu Gln Glu Ser Gly Pro
    130                 135                 140

Gly Leu Val Lys Pro Ser Gln Thr Leu Ser Leu Thr Cys Thr Val Ser
145                 150                 155                 160

Gly Tyr Ala Phe Thr Ala Tyr Asn Ile His Trp Ile Arg Gln Pro Pro
                165                 170                 175

Gly Lys Gly Leu Glu Trp Ile Gly Ser Phe Asp Pro Tyr Asp Gly Gly
            180                 185                 190

Ser Ser Tyr Asn Gln Lys Phe Lys Asp Arg Leu Thr Ile Ser Lys Asp
        195                 200                 205

Thr Ser Lys Asn Gln Val Val Leu Thr Met Thr Asn Met Asp Pro Val
    210                 215                 220
```

-continued

```
Asp Thr Ala Thr Tyr Tyr Cys Ala Arg Gly Trp Tyr Tyr Phe Asp Tyr
225                 230                 235                 240

Trp Gly His Gly Thr Leu Val Thr Val Ser Ser
                245                 250
```

What is claimed is:

1. An immunoconjugate [comprising an antibody conjugated to a cytotoxic drug moiety, wherein the $V_H$ and $V_L$ of the antibody comprise the amino acid sequences of SEQ ID NOs: 5 and 6, respectively, and the immunoconjugate is ADC-A, having the structure

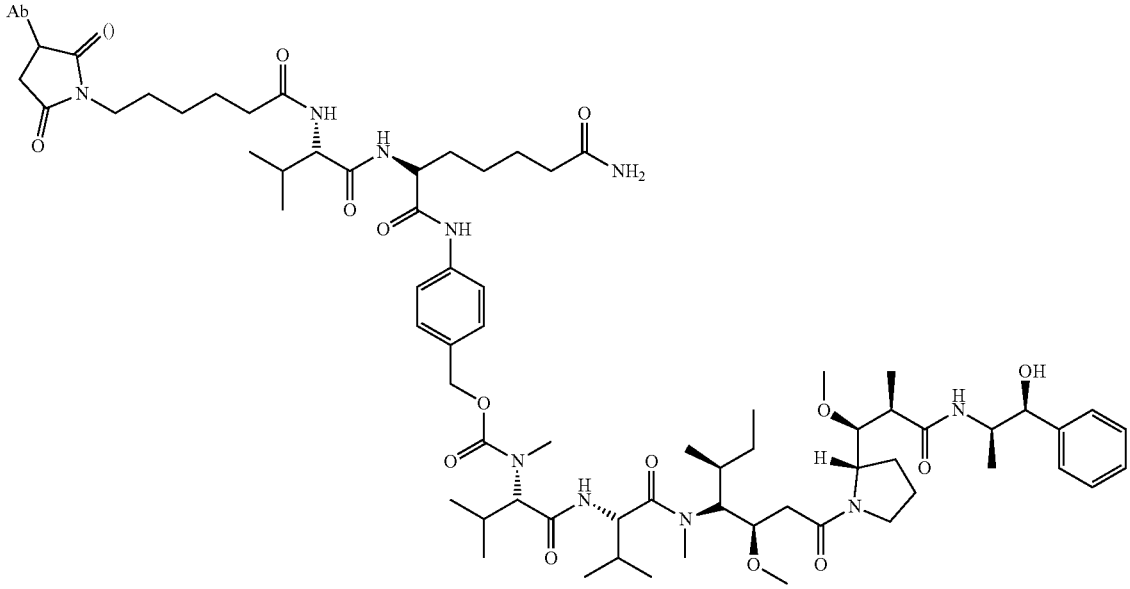

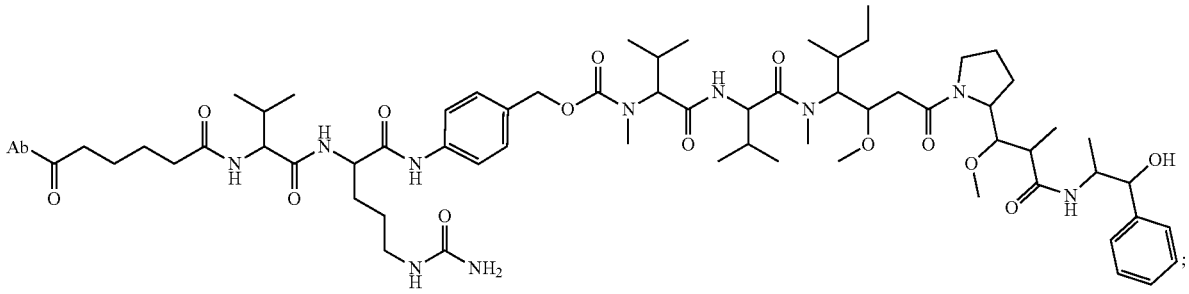

-continued
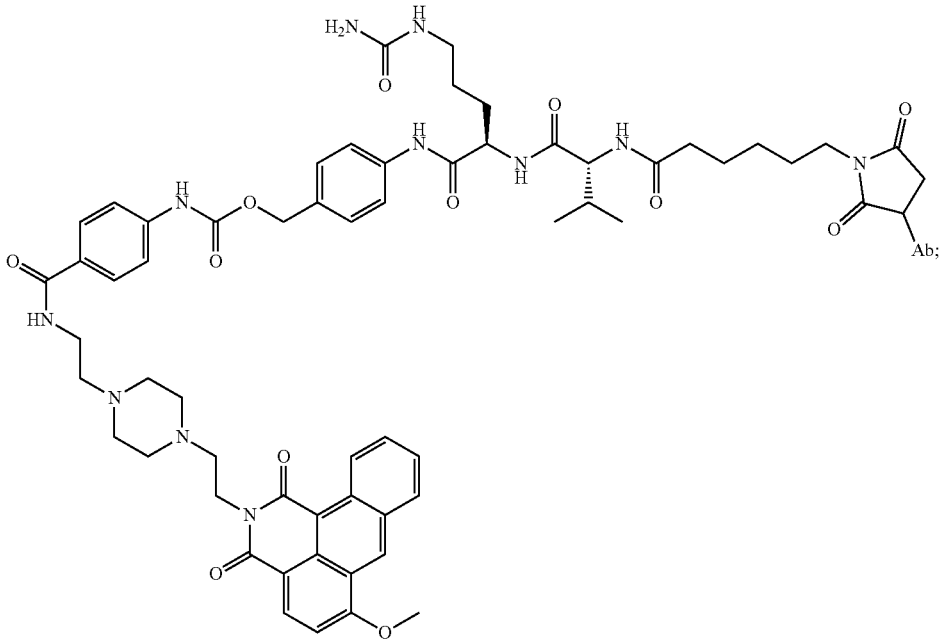
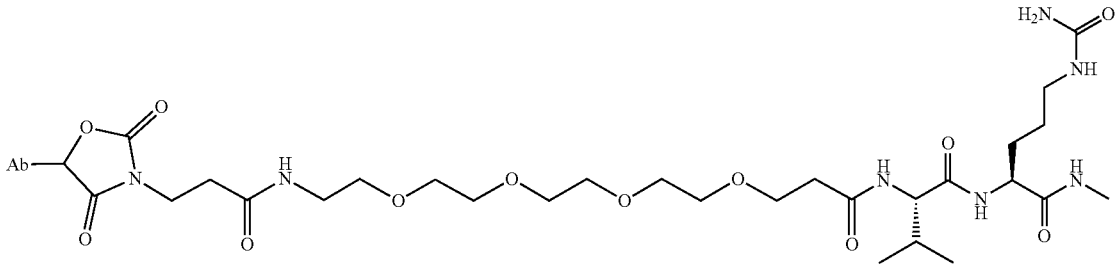
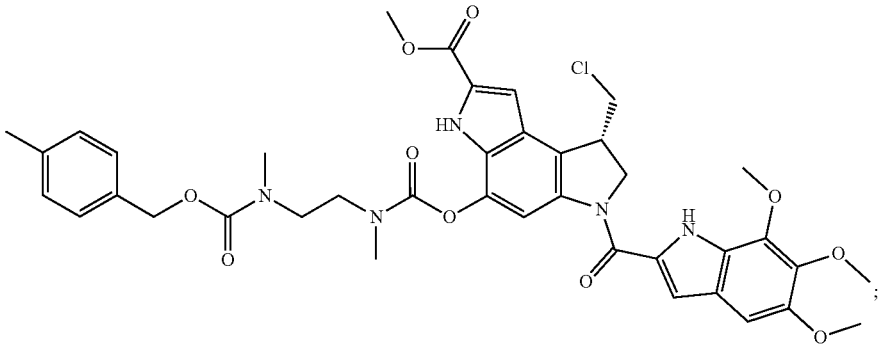
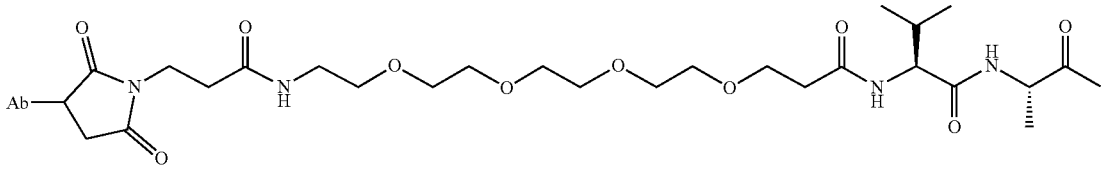
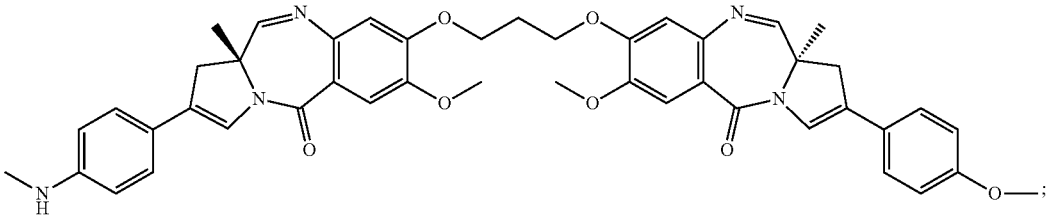

-continued
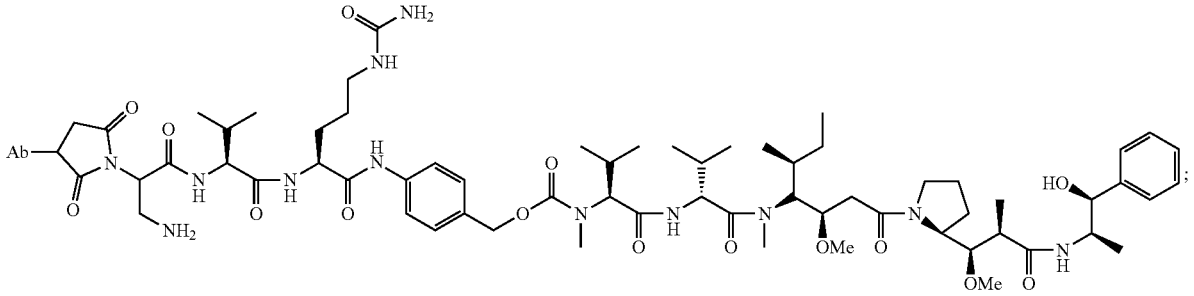
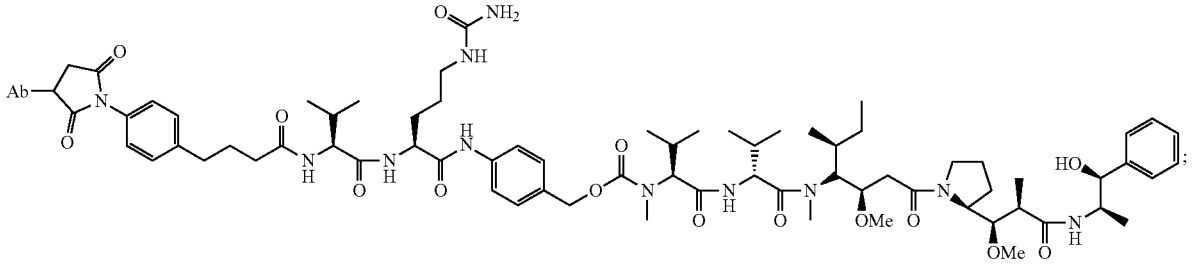
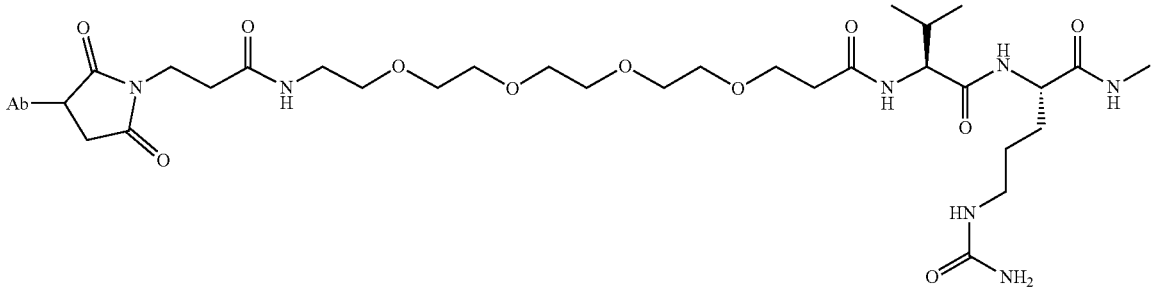
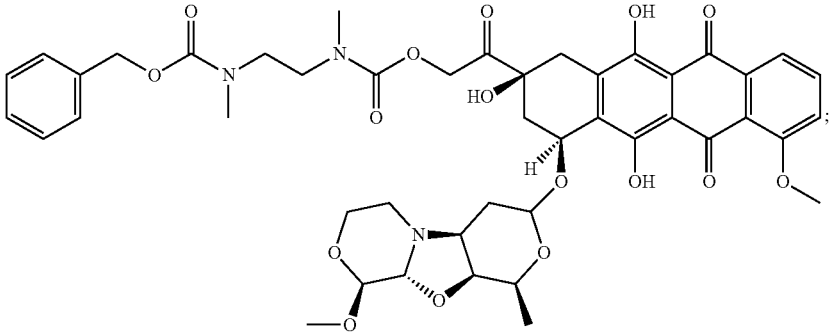
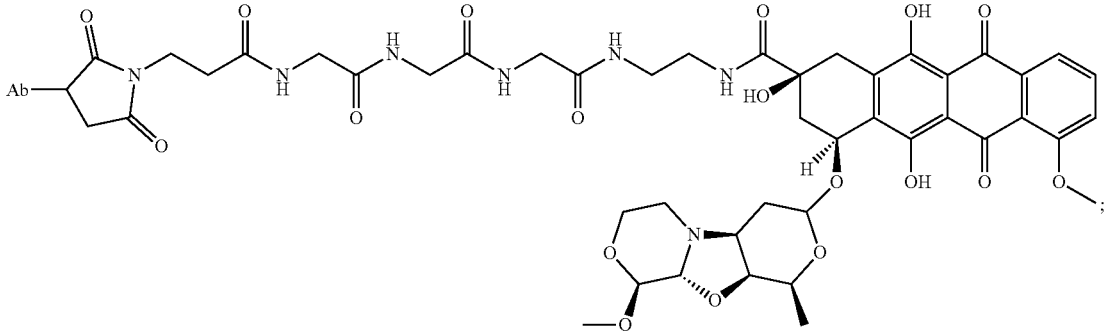

-continued
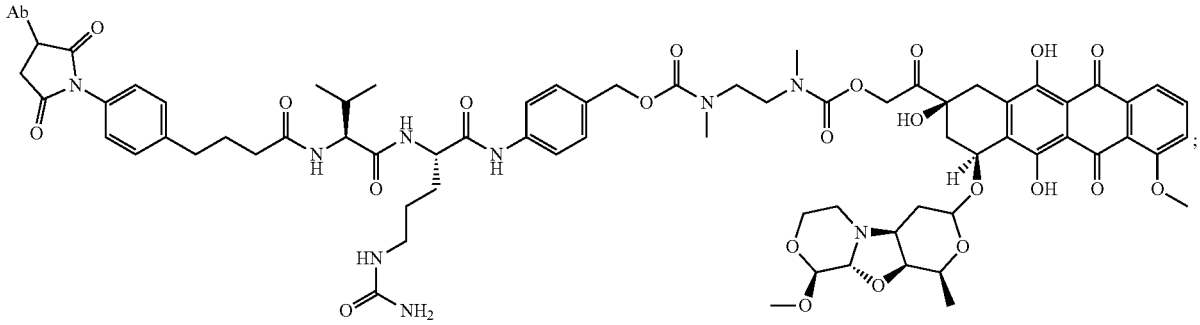
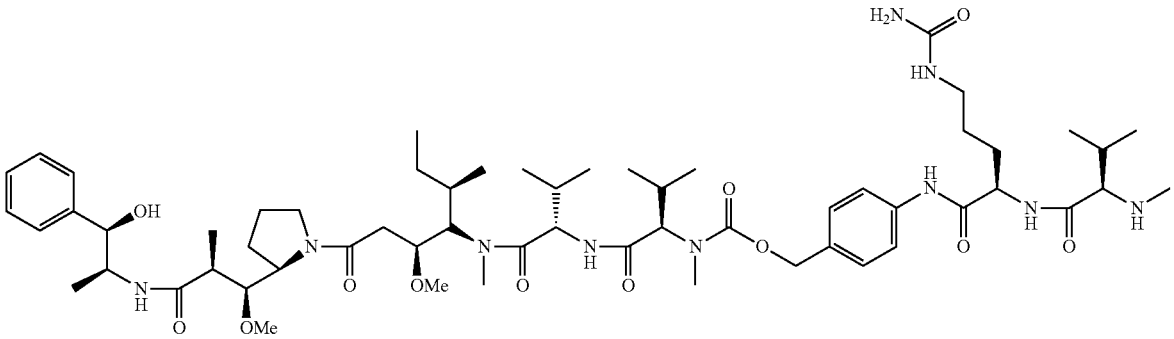
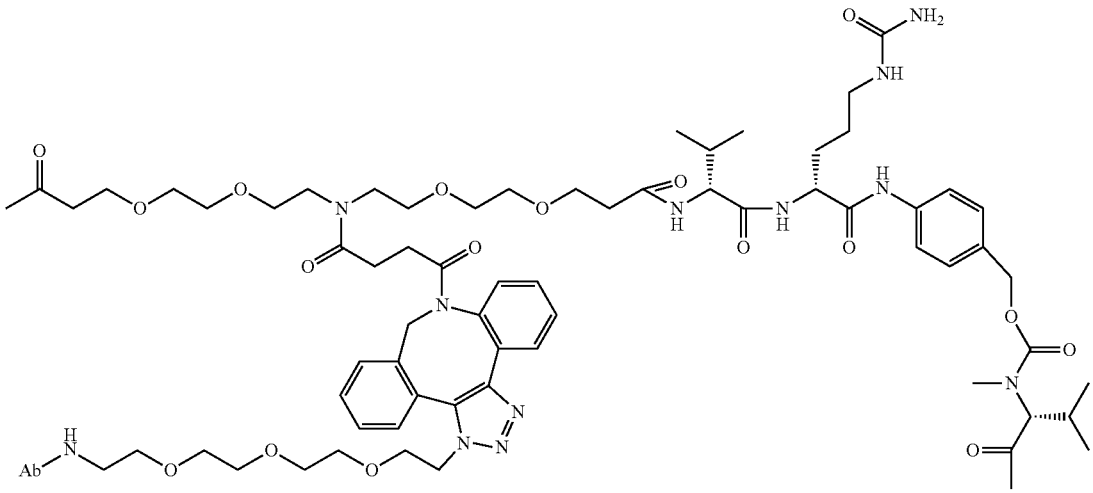

-continued
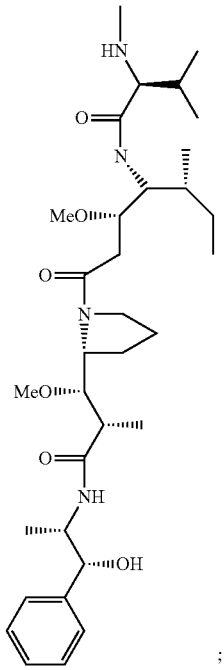
;
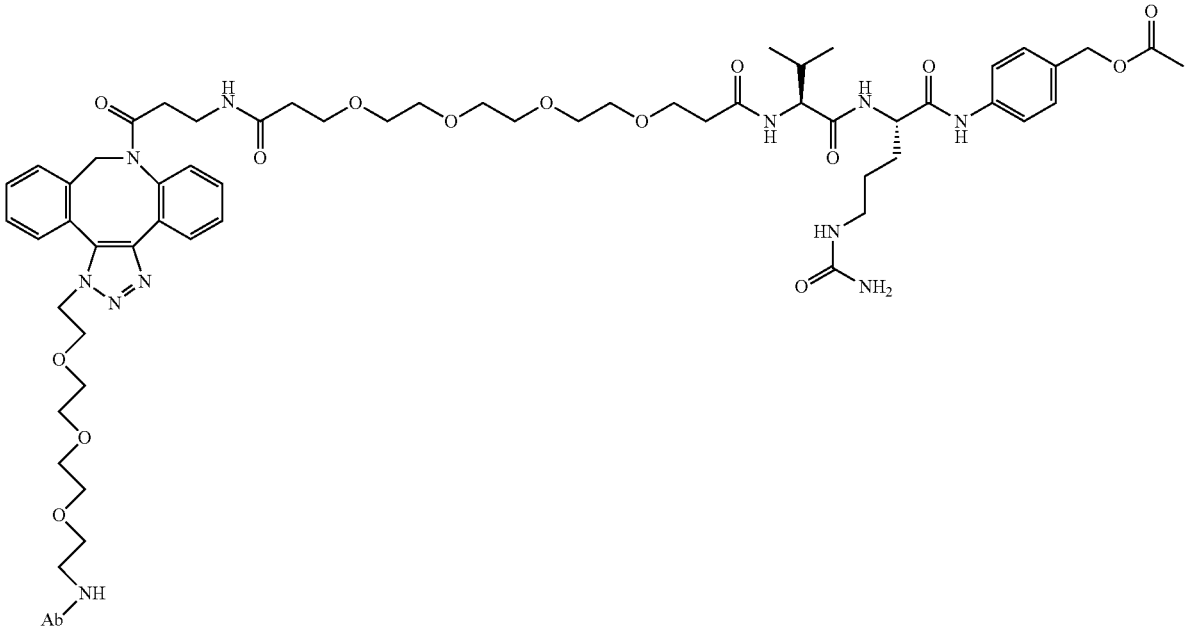
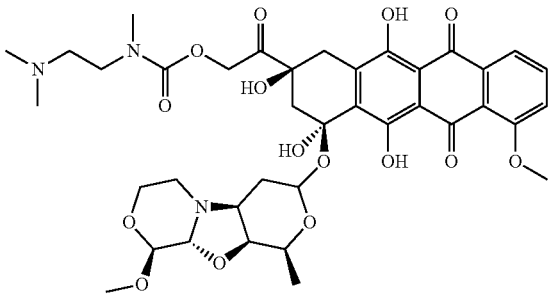
, wherein Ab in the structure is the antibody] *of the formula:*

$Ab\text{-}[(L)_m\text{-}(D)]_n$

*wherein Ab is an antibody that binds to human receptor tyrosine kinase like orphan receptor 1 (ROR1), and wherein*

*Ab comprises:*

(*a*) *a heavy chain variable region* ($V_H$) *comprising an HCDR1 comprising the amino acid sequence of SEQ ID NO: 7, an HCDR2 comprising the amino acid sequence of SEQ ID NO: 8; and an HCDR3 comprising the amino acid sequence of SEQ ID NO: 9, and*

(*b*) *a light chain variable region* ($V_L$) *comprising an LCDRI comprising the amino acid sequence of SEQ ID NO: 10; an LCDR2 comprising the amino acid sequence of SEQ ID NO: 11; and an LCDR3 comprising the amino acid sequence of SEQ ID NO: 12,*

*each occurrence of the group* $-[(L)_m\text{-}(D)]$ *has the structure:*

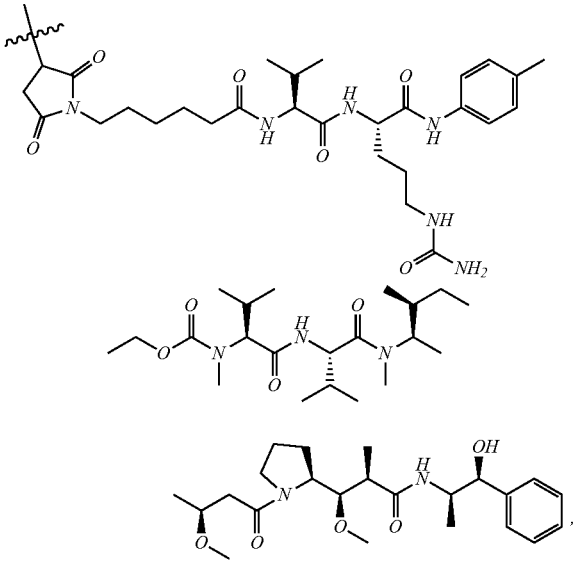

*wherein* ∿∿ *represents the site of attachment to a sulfur atom on a cysteine residue on* [*the antibody*] *Ab; and n is an integer from 1 to 8.*

2. The immunoconjugate of claim 1, wherein the heavy chain and light chain of [the antibody] *Ab* comprise the amino acid sequences of SEQ ID NOs: 3 and 4, respectively.

3. The immunoconjugate of claim 2, wherein [the ratio of the cytotoxic drug moiety to the antibody is 1 to 7] *n is an integer from 1 to 5.*

4. A pharmaceutical composition comprising the immunoconjugate of claim 1 and a pharmaceutically acceptable excipient.

5. The pharmaceutical composition of claim 4, further comprising an additional therapeutic agent selected from the group consisting of a Bruton's tyrosine kinase (BTK) inhibitor, a B-cell lymphoma 2 (Bcl-2) inhibitor, a mammalian target of [rapamycine] *rapamycin* (mTOR) inhibitor, and a phosphoinositide 3-kinase (PI3K) inhibitor.

[6. A method of treating a ROR1-expressing cancer in a patient in need thereof, comprising administering to the patient a therapeutically effective amount of the immunoconjugate of claim 1.]

[7. A method of making the immunoconjugate of claim 1, comprising:

providing an antibody that specifically binds to human receptor tyrosine kinase like orphan receptor 1 (ROR1); and conjugating monomethyl auristatin E (MMAE) to the antibody;

wherein the heavy chain of the antibody comprises the amino acid sequence of SEQ ID NO:5 and the light chain of the antibody comprises the amino acid sequence of SEQ ID NO:6.]

[8. An immunoconjugate comprising an antibody conjugated to a cytotoxic drug moiety wherein the $V_H$ and $V_L$ of the antibody comprise the amino acid sequences of SEQ ID NOs: 5 and 6, respectively, and the immunoconjugate is ADC-E, having the structure

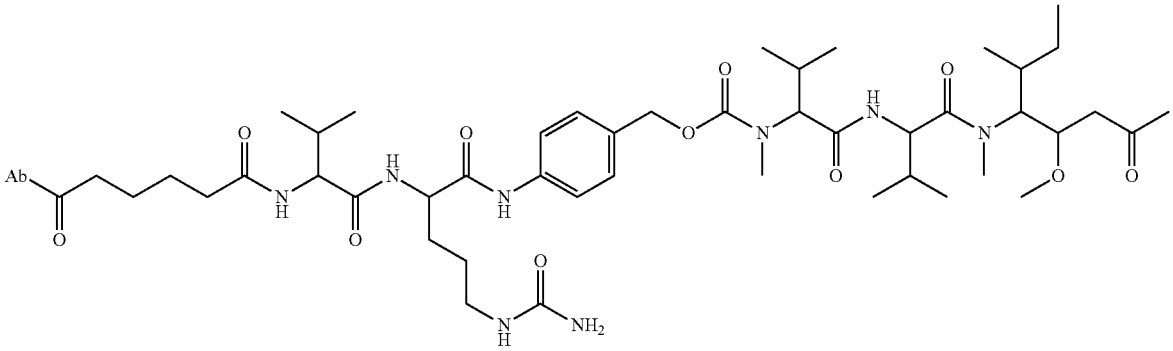

-continued

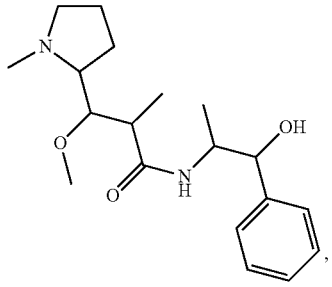

wherein Ab in the structure is the antibody.]

[9. The immunoconjugate of claim 8, wherein the heavy chain and light chain of the antibody comprise the amino acid sequences of SEQ ID NOs: 3 and 4, respectively.]

[10. The immunoconjugate of claim 8, wherein the ratio of the cytoxic drug moiety to the antibody is 1 to 7.]

[11. A pharmaceutical composition comprising the immunoconjugate of claim 8 and a pharmaceutically acceptable excipient.]

[12. The pharmaceutical composition of claim 11, further comprising an additional therapeutic agent selected from the group consisting of a Bruton's tyrosine kinase (BTK) inhibitor, a B-cell lymphoma 2 (Bcl-2) inhibitor, a mammalian target of rapamycine (mTOR) inhibitor, and a phosphoinositide 3-kinase (PI3K) inhibitor.]

[13. A method of treating a ROR1-expressing cancer in a patient in need thereof, comprising administering to the patient a therapeutically effective amount of the immunoconjugate of claim 8.]

[14. A method of making the immunoconjugate of claim 8, comprising:

providing an antibody that specifically binds to human receptor tyrosine kinase like orphan receptor 1 (ROR1); and conjugating monomethyl auristatin E (MMAE) to the antibody;

wherein the heavy chain of the antibody comprises the amino acid sequence of SEQ ID NO:5 and the light chain of the antibody comprises the amino acid sequence of SEQ ID NO:5.]

[15. An immunoconjugate comprising an antibody conjugated to a cytotoxic drug moiety, wherein the $V_H$ and $V_L$ of the antibody comprise the amino acid sequences of SEQ ID NOs: 5 and 6, respectively, and the immunoconjugate is ADC-H, having the structure,

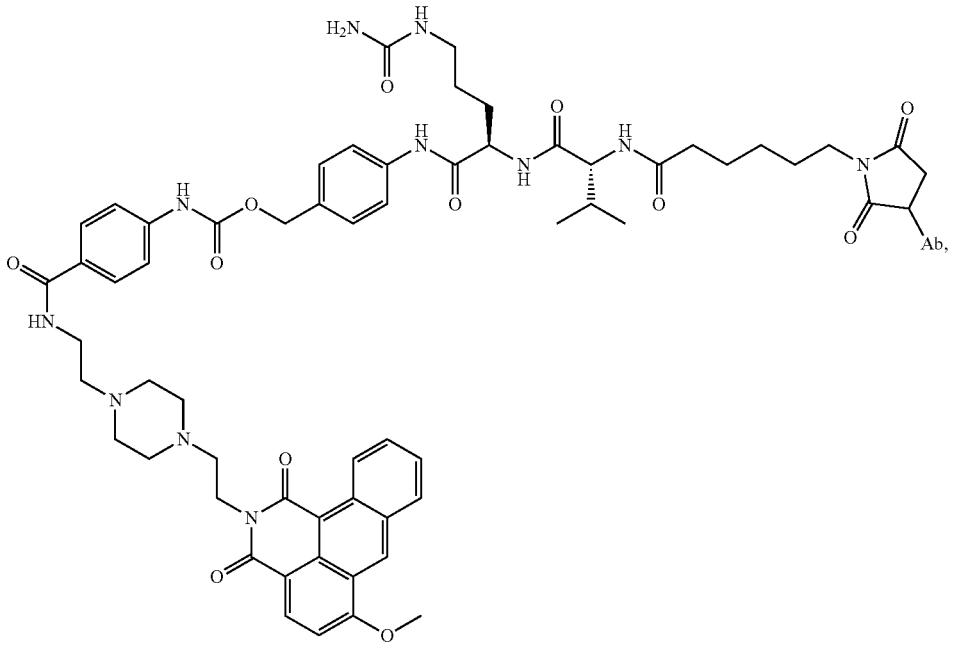

wherein Ab in the structure is the antibody.]

[16. The immunoconjugate of claim 15, wherein the heavy chain and light chain of the antibody comprise the amino acid sequences of SEQ ID NOs: 3 and 4, respectively.]

[17. The immunoconjugate of claim 16, wherein the ratio of the cytotoxic drug moiety to the antibody is 1 to 7.]

[18. A pharmaceutical composition comprising the immunoconjugate of claim 15 and a pharmaceutically acceptable excipient.]

[19. The pharmaceutical composition of claim 18, further comprising an additional therapeutic agent selected from the group consisting of a Bruton'tyrosine kinase (BTK) inhibitor, a B-cell lymphoma 2(Bcl-2) inhibitor, mammalian target of rapamycine (mTOR) inhibitor, and a phosphoinositide 3-kinase (PI3K) inhibitor.]

[20. A method of treating a ROR1-expressing cancer in a patient in need thereof, comprising administering to the patient a therapeutically effective amount of the immunoconjugate of claim 15.]

[21. A method of making the immunoconjugate of claim 15, comprising:

providing an antibody that specifically binds to human receptor tyrosine kinase like orphan receptor 1 (ROR1); and conjugating azonafide to the antibody;

wherein the heavy chain of the antibody comprises the amino acid sequence of SEQ ID NO:5 and the light chain of the antibody comprises the amino acid sequence of SEQ ID NO: 6.]

[22. An immunoconjugate comprising an antibody conjugated to a cytotoxic drug moiety, wherein the $V_H$ and $V_L$ of the antibody comprise the amino acid sequences of SEQ ID NOs: 5 and 6, respectively, and the immunoconjugate is ADC-J, having the structure

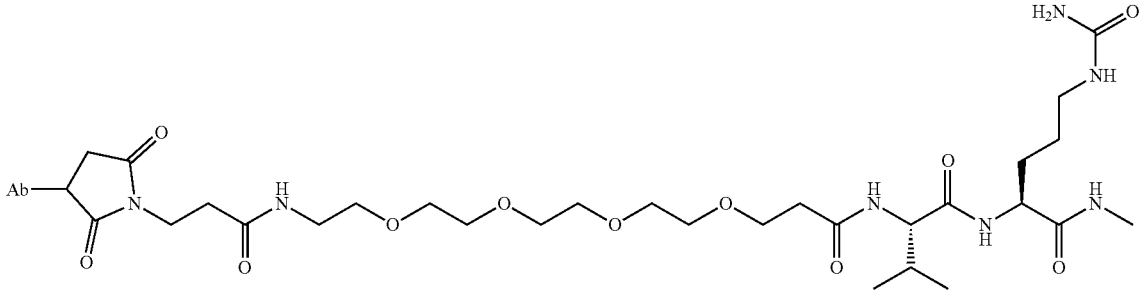

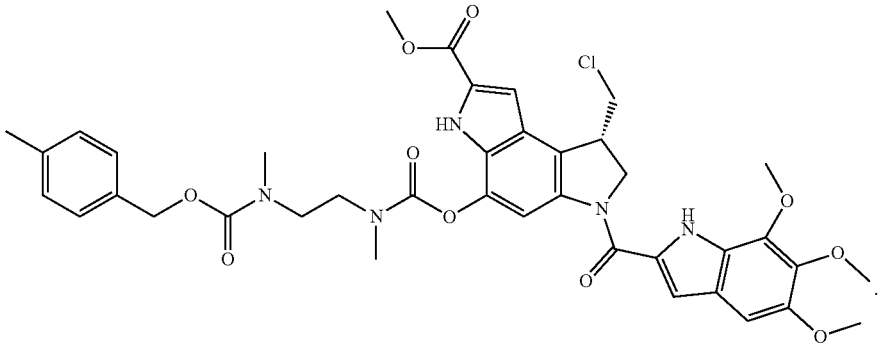

wherein Ab in the structure is the antibody.]

[23. The immunoconjugate of claim 22, wherein the heavy chain and light chain of the antibody comprise the amino acid sequences of SEQ ID NOs: 3 and 4, respectively.]

[24. The immunoconjugate of claim 23, wherein the ratio of the cytotoxic drug moiety to the antibody is 1 to 7.]

[25. A pharmaceutical composition comprising the immunoconjugate of claim 22 and a pharmaceutically acceptable excipient.]

[26. The pharmaceutical composition of claim 25, further comprising an additional therapeutic agent selected from the group consisting of a Bruton's tyrosine kinase (BTK) inhibitor, a B-cell lymphoma 2 (Bcl-2) inhibitor, a mammalian target of rapamycine (MTOR) inhibitor, and a phosphoinositide 3-kinase (PI3K) inhibitor.]

[27. A method of treating a ROR1-expressing cancer in a patient in need thereof, comprising administering to the patient a therapeutically effective amount of the immunoconjugate of claim 22.]

[28. A method of making the immunoconjugate of claim 22, comprising:

providing an antibody that specifically binds to human receptor tyrosine kinase like orphan receptor 1 (ROR1); and conjugating Duocarmycin TM to the antibody;

wherein the heavy chain of the antibody comprises the amino acid sequence of SEQ ID NO:5 and the light chain of the antibody comprises the amino acid sequence of SEQ ID NO:6.]

[29. An immunoconjugate comprising an antibody conjugated to a cytotoxic drug moiety, wherein the $V_H$ and $V_L$ of the antibody comprise the amino acid sequences of SEQ ID NOs: 5 and 6, respectively, and the immunoconjugate is ADC-K, having the structure

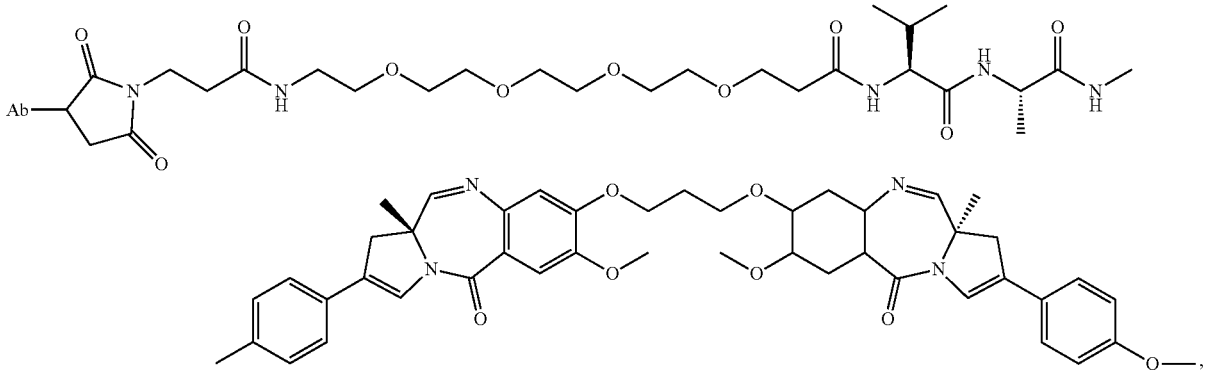

wherein Ab in the structure is the antibody.]

[30. The immunoconjugate of claim 29, wherein the heavy chain and light chain of the antibody comprise the amino acid sequences of SEQ ID NOs: 3 and 4, respectively.]

[31. The immunoconjugate of claim 30, wherein the ratio of the cytotoxic drug moiety to the antibody is 1 to 7.]

[32. A pharmaceutical composition comprising the immunoconjugate of claim 29 and a pharmaceutically acceptable excipient.]

[33. The pharmaceutical composition of claim 32, further comprising an additional therapeutic agent selected from the group consisting of a Bruton's tyrosine kinase (BTK) inhibitor, a B-cell lymphoma 2 (Bcl-2) inhibitor, a mammalian target of rapamycine (mTOR) inhibitor, and a phosphoinositide 3-kinase (PI3K) inhibitor.]

[34. A method of treating a ROR1-expressing cancer in a patient in need thereof, comprising administering to the patient a therapeutically effective amount of the immunoconjugate of claim 29.]

[35. A method of making the immunoconjugate of claim 29, comprising:

providing an antibody that specifically binds to human receptor tyrosine kinase like orphan receptor 1 (ROR1); and conjugating pyrrolobenzodiazepine (PBD) to the antibody;

wherein the heavy chain of the antibody comprises the amino acid sequence of SEQ ID NO:5 and the light chain of the antibody comprises the amino acid sequence of SEQ ID NO:6.]

[36. An immunoconjugate comprising an antibody conjugated to a cytotoxic drug moiety, wherein the $V_H$ and $V_L$ of the antibody comprise the amino acid sequences of SEQ ID NOs: 5 and 6, respectively, and the immunoconjugate is ADC-L, having the structure

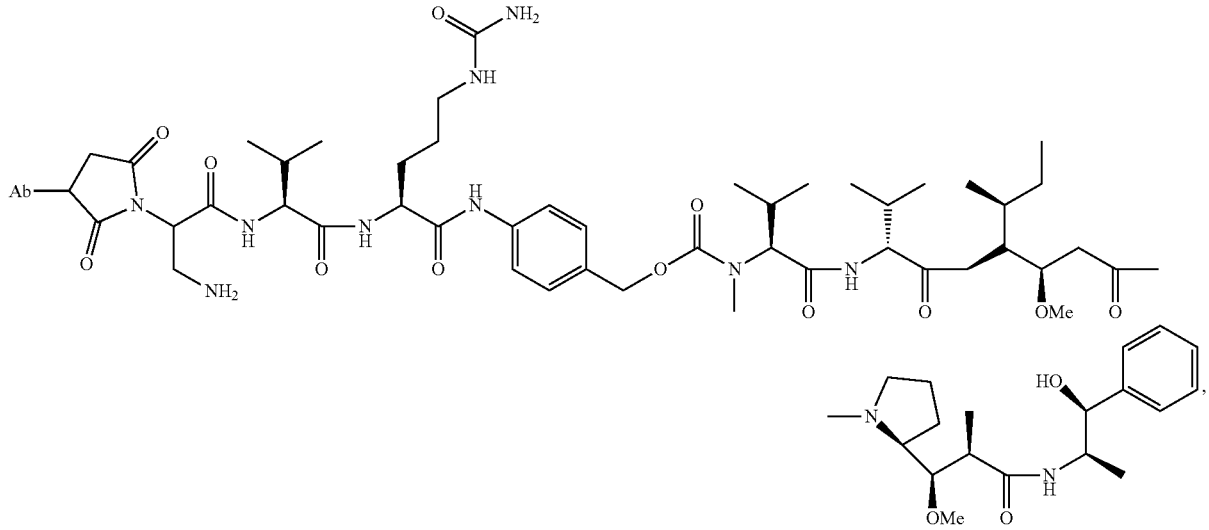

wherein Ab in the structure is the antibody.]

[37. The immunoconjugate of claim 36, wherein the heavy chain and light chain of the antibody comprise the amino acid sequences of SEQ ID NOs: 3 and 4, respectively.]

[38. The immunoconjugate of claim 37, wherein the ratio of the cytotoxic drug moiety to the antibody is 1 to 7.]

[39. A pharmaceutical composition comprising the immunoconjugate of claim 36 and a pharmaceutically acceptable excipient.]

[40. The pharmaceutical composition of claim 39, further comprising an additional therapeutic agent selected from the group consisting of a Bruton's tyrosine kinase (BTK) inhibitor, a B-cell lymphoma 2 (Bcl-2) inhibitor, a mammalian target of rapamycine (mTOR) inhibitor, and a phosphoinositide 3-kinase (PI3K) inhibitor.]

[41. A method of treating a ROR1-expressing cancer in a patient in need thereof, comprising administering to the patient a therapeutically effective amount of the immunoconjugate of claim 36.]

[42. A method of making the immunoconjugate of claim 36, comprising:

providing an antibody that specifically binds to human receptor tyrosine kinase like orphan receptor 1 (ROR1); and conjugating monomethyl auristatin E (MMAE) to the antibody;

wherein the heavy chain of the antibody comprises the amino acid sequence of SEQ ID NO:5 and the light chain of the antibody comprises the amino acid sequence of SEQ ID NO:6.]

[43. An immunoconjugate comprising an antibody conjugated to a cytotoxic drug moiety, wherein the $V_H$ and $V_L$ of the antibody comprise the amino acid sequences of SEQ ID NOs: 5 and 6, respectively, and the immunoconjugate is ADC-M, having the structure

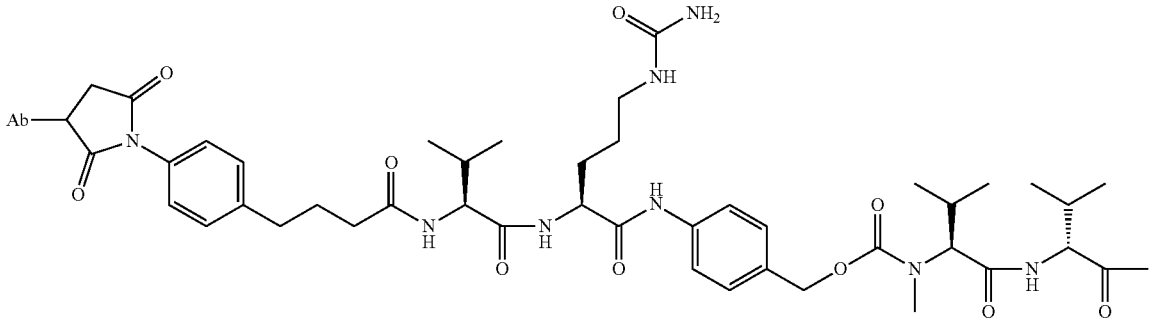

wherein Ab in the structure is the antibody.]

[44. The immunoconjugate of claim 43, wherein the heavy chain and light chain of the antibody comprise the amino acid sequences of SEQ ID NOs: 3 and 4, respectively.]

[45. The immunoconjugate of claim 44, wherein the ratio of the cytotoxic drug moiety to the antibody is 1 to 7.]

[46. A pharmaceutical composition comprising the immunoconjugate of claim 43 and a pharmaceutically acceptable excipient.]

[47. The pharmaceutical composition of claim 46, further comprising an additional therapeutic agent selected from the group consisting of a Bruton's tyrosine kinase (BTK) inhibitor, a B-cell lymphoma 2 (Bcl-2) inhibitor, a mammalian target of rapamycine (mTOR) inhibitor, and a phosphoinositide 3-kinase (PI3K) inhibitor.]

[48. A method of treating a ROR1-expressing cancer in a patient in need thereof, comprising administering to the patient a therapeutically effective amount of the immunoconjugate of claim 43.]

[49. A method of making the immunoconjugate of claim 43, comprising:

providing an antibody that specifically binds to human receptor tyrosine kinase like orphan receptor 1 (ROR1); and conjugating monomethyl auristatin E (MMAE) to the antibody;

wherein the heavy chain of the antibody comprises the amino acid sequence of SEQ ID NO:5 and the light chain of the antibody comprises the amino acid sequence of SEQ ID NO:6.]

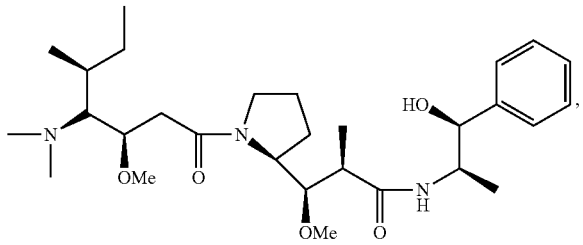

[50. An immunoconjugate comprising an antibody conjugated to a cytotoxic drug moiety, wherein the $V_H$ and $V_L$ of the antibody comprise the amino acid sequences of SEQ ID NOs: 5 and 6, respectively, and the immunoconjugate is ADC-N, having the structure

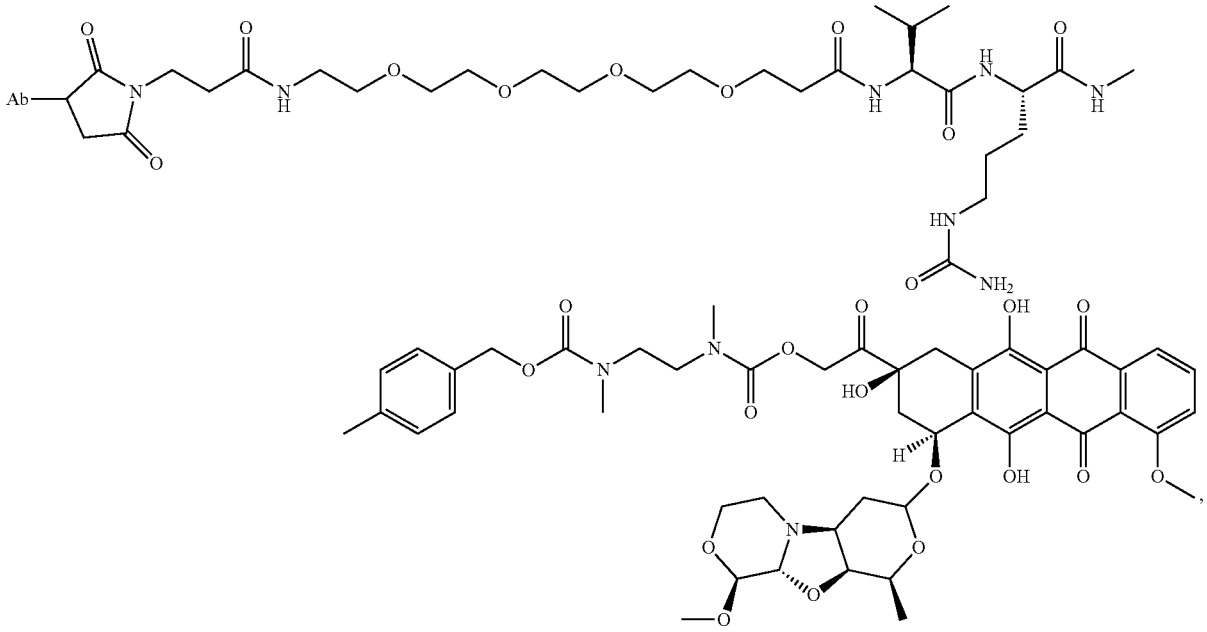

wherein Ab in the structure is the antibody.]

[51. The immunoconjugate of claim 50, wherein the heavy chain and light chain of the antibody comprise the amino acid sequences of SEQ ID NOs: 3 and 4, respectively.]

[52. The immunoconjugate of claim 51, wherein the ratio of the cytotoxic drug moiety to the antibody is 1 to 7.]

[53. A pharmaceutical composition comprising the immunoconjugate of claim 50 and a pharmaceutically acceptable excipient.]

[54. The pharmaceutical composition of claim 53, further comprising an additional therapeutic agent selected from the group consisting of a Bruton's tyrosine kinase (BTK) inhibitor, a B-cell lymphoma 2 (Bcl-2) inhibitor, a mammalian target of rapamycine (mTOR) inhibitor, and a phosphoinositide 3-kinase (PI3K) inhibitor.]

[55. A method of treating a ROR1-expressing cancer in a patient in need thereof, comprising administering to the patient a therapeutically effective amount of the immunoconjugate of claim 50.]

[56. A method of making the immunoconjugate of claim 50, comprising:

providing an antibody that specifically binds to human receptor tyrosine kinase like orphan receptor 1 (ROR1); and conjugating PNU-159682 to the antibody;

wherein the heavy chain of the antibody comprises the amino acid sequence of SEQ ID NO:5 and the light chain of the antibody comprises the amino acid sequence of SEQ ID NO:6.]

[57. An immunoconjugate comprising an antibody conjugated to a cytotoxic drug moiety, wherein the $V_H$ and $V_L$ of the antibody comprise the amino acid sequences of SEQ ID NOs: 5 and 6, respectively, and the immunoconjugate is ADC-O, having the structure

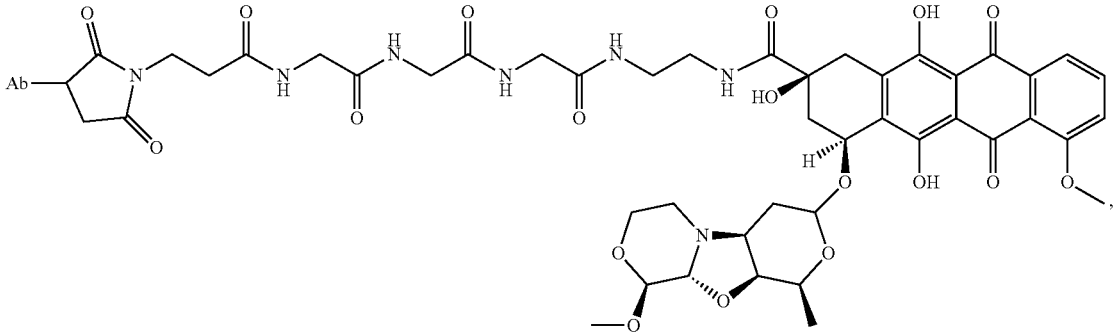

wherein Ab in the structure is the antibody.]

[58. The immunoconjugate of claim 57, wherein the heavy chain and light chain of the antibody comprise the amino acid sequences of SEQ ID NOs: 3 and 4, respectively.]

[59. The immunoconjugate of claim 58, wherein the ratio of the cytotoxic drug moiety to the antibody is 1 to 7.]

[60. A pharmaceutical composition comprising the immunoconjugate of claim 57 and a pharmaceutically acceptable excipient.]

[61. The pharmaceutical composition of claim 60, further comprising an additional therapeutic agent selected from the group consisting of a Bruton's tyrosine kinase (BTK) inhibitor, a B-cell lymphoma 2 (Bcl-2) inhibitor, a mammalian target of rapamycine (mTOR) inhibitor, and a phosphoinositide 3-kinase (PI3K) inhibitor.]

[62. A method of treating a ROR1-expressing cancer in a patient in need thereof, comprising administering to the patient a therapeutically effective amount of the immunoconjugate of claim 57.]

[63. A method of making the immunoconjugate of claim 57, comprising:

providing an antibody that specifically binds to human receptor tyrosine kinase like orphan receptor 1 (ROR1); and conjugating PNU-159682 to the antibody;

wherein the heavy chain of the antibody comprises the amino acid sequence of SEQ ID NO:5 and the light chain of the antibody comprises the amino acid sequence of SEQ ID NO:6.]

[64. An immunoconjugate comprising an antibody conjugated to a cytotoxic drug moiety, wherein the $V_H$ and $V_L$ of the antibody comprise the amino acid sequences of SEQ ID NOs: 5 and 6, respectively, and the immunoconjugate is ADC-P, having the structure

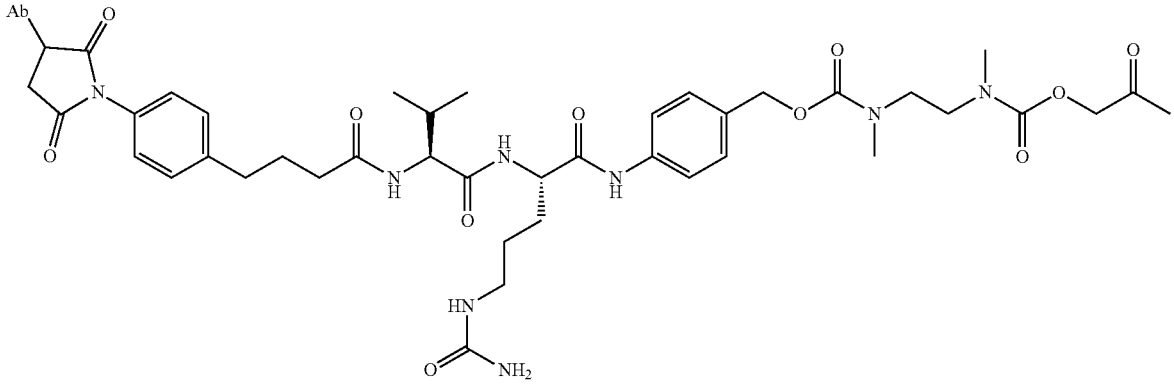

wherein Ab in the structure is the antibody.]

[65. The immunoconjugate of claim 64, wherein the heavy chain and light chain of the antibody comprise the amino acid sequences of SEQ ID NOs: 3 and 4, respectively.]

[66. The immunoconjugate of claim 65, wherein the ratio of the cytotoxic drug moiety to the antibody is 1 to 7.]

[67. A pharmaceutical composition comprising the immunoconjugate of claim 64 and a pharmaceutically acceptable excipient.]

[68. The pharmaceutical composition of claim 67, further comprising an additional therapeutic agent selected from the group consisting of a Bruton's tyrosine kinase (BTK) inhibitor, a B-cell lymphoma 2 (Bcl-2) inhibitor, a mammalian target of rapamycine (mTOR) inhibitor, and a phosphoinositide 3-kinase (PI3K) inhibitor.]

[69. A method of treating a ROR1-expressing cancer in a patient in need thereof, comprising administering to the patient a therapeutically effective amount of the immunoconjugate of claim 64.]

[70. A method of making the immunoconjugate of claim 64, comprising:

providing an antibody that specifically binds to human receptor tyrosine kinase like orphan receptor 1 (ROR1); and conjugating PNU-159682 to the antibody; wherein the heavy chain of the antibody comprises the amino acid sequence of SEQ ID NO:5 and the light chain of the antibody comprises the amino acid sequence of SEQ ID NO:6.]

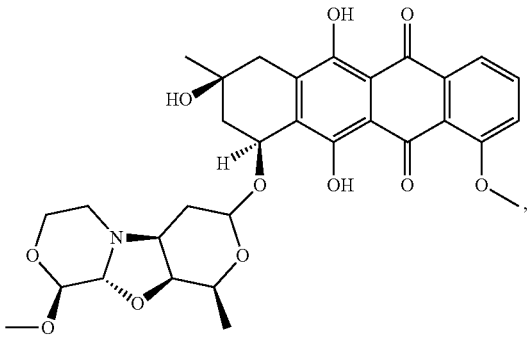

[71. An immunoconjugate comprising an antibody conjugated to a cytotoxic drug moiety, wherein the $V_H$ and $V_L$ of the antibody comprise the amino acid sequences of SEQ ID NOs: 5 and 6, respectively, and the immunoconjugate is ADC-Q, having the structure

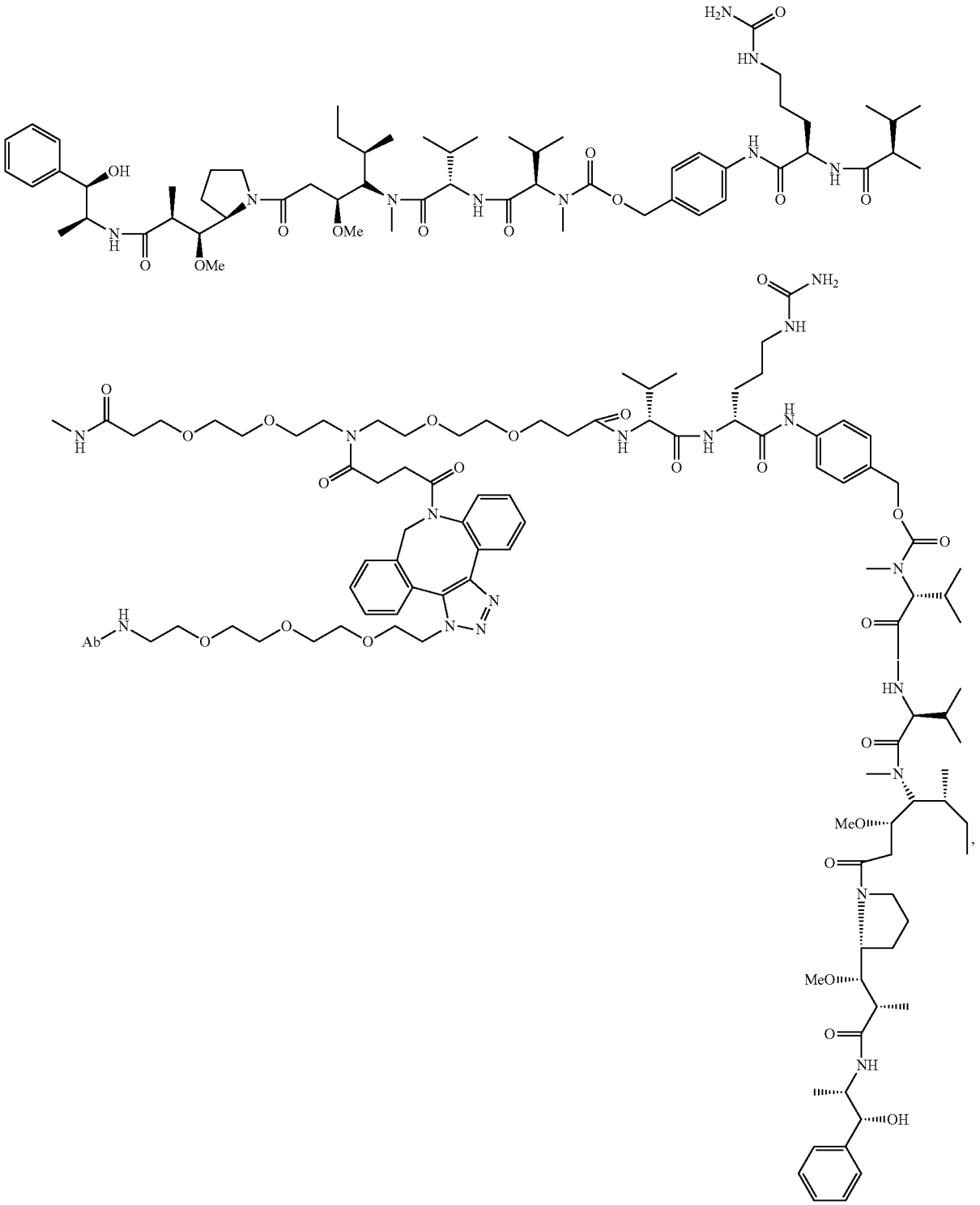

wherein Ab in the structure is the antibody.]

[72. The immunoconjugate of claim 71, wherein the heavy chain and light chain of the antibody comprise the amino acid sequences of SEQ ID NOs: 3 and 4, respectively.]

[73. The immunoconjugate of claim 72, wherein the ratio of the cytotoxic drug moiety to the antibody is 1 to 7.]

[74. A pharmaceutical composition comprising the immunoconjugate of claim 71 and a pharmaceutically acceptable excipient.]

[75. The pharmaceutical composition of claim 74, further comprising an additional therapeutic agent selected from the group consisting of a Bruton's tyrosine kinase (BTK) inhibitor, a B-cell lymphoma 2 (Bcl-2) inhibitor, a mammalian target of rapamycine (mTOR) inhibitor, and a phosphoinositide 3-kinase (PI3K) inhibitor.]

[76. A method of treating a ROR1-expressing cancer in a patient in need thereof, comprising administering to the patient a therapeutically effective amount of the immunoconjugate of claim 71.]

[77. A method of making the immunoconjugate of claim 71, comprising:

providing an antibody that specifically binds to human receptor tyrosine kinase like orphan receptor 1 (ROR1); and conjugating monomethyl auristatin E (MMAE) to the antibody;

wherein the heavy chain of the antibody comprises the amino acid sequence of SEQ ID NO:5 and the light chain of the antibody comprises the amino acid sequence of SEQ ID NO:6.]

[78. An immunoconjugate comprising an antibody conjugated to a cytotoxic drug moiety, wherein the $V_H$ and $V_L$ of the antibody comprise the amino acid sequences of SEQ ID NOs: 5 and 6, respectively, and the immunoconjugate is ADC-R, having the structure

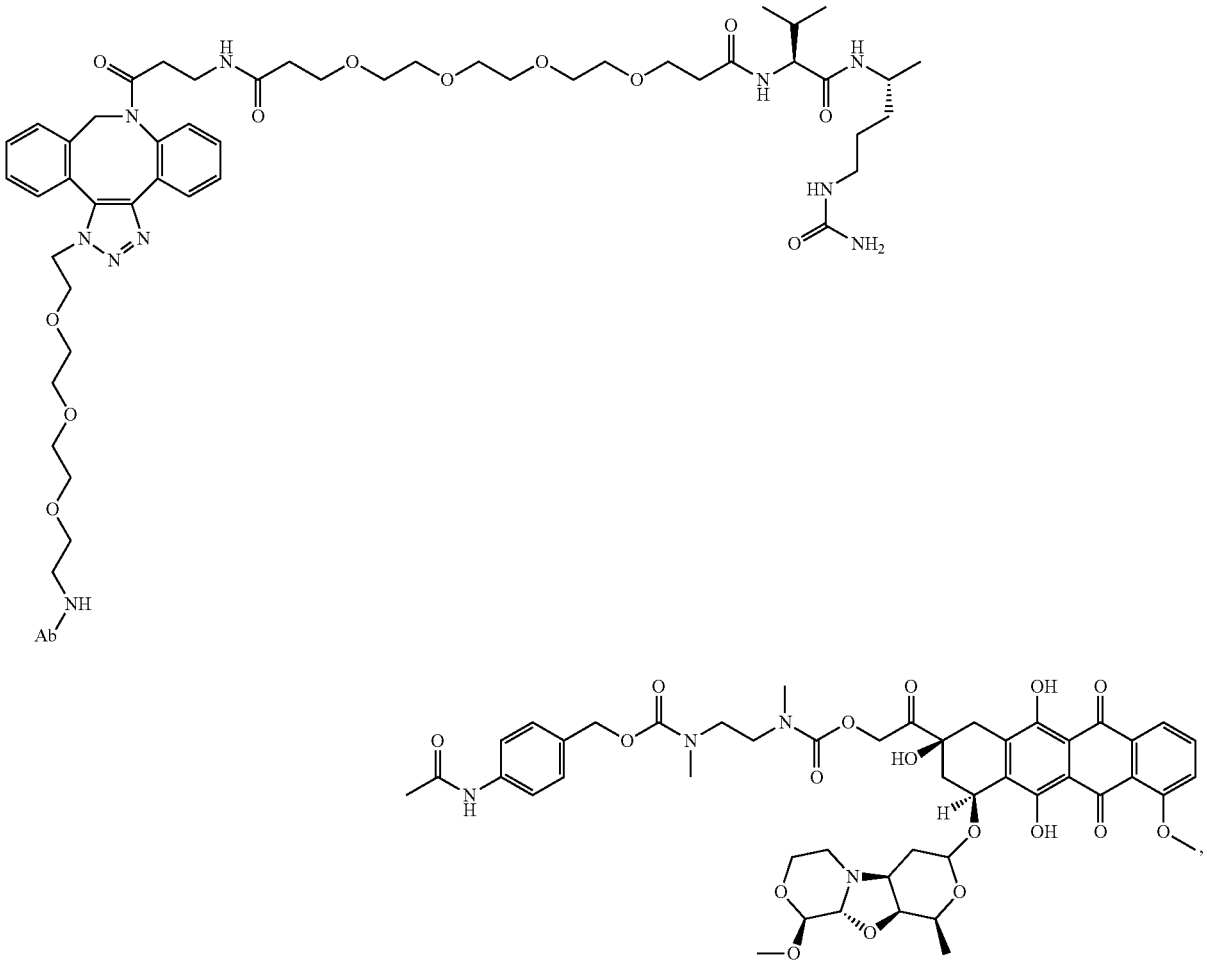

wherein Ab in the structure is the antibody.]

[79. The immunoconjugate of claim 78, wherein the heavy chain and light chain of the antibody comprise the amino acid sequences of SEQ ID NOs: 3 and 4, respectively.]

[80. The immunoconjugate of claim 79, wherein the ratio of the cytotoxic drug moiety to the antibody is 1 to 7.]

[81. A pharmaceutical composition comprising the immunoconjugate of claim 78 and a pharmaceutically acceptable excipient.]

[82. The pharmaceutical composition of claim 81, further comprising an additional therapeutic agent selected from the group consisting of a Bruton's tyrosine kinase (BTK) inhibitor, a B-cell lymphoma 2 (Bcl-2) inhibitor, a mammalian target of rapamycine (mTOR) inhibitor, and a phosphoinositide 3-kinase (PI3K) inhibitor.]

[83. A method of treating a ROR1-expressing cancer in a patient in need thereof, comprising administering to the patient a therapeutically effective amount of the immunoconjugate of claim 78.]

[84. A method of making the immunoconjugate of claim 78, comprising:

providing an antibody that specifically binds to human receptor tyrosine kinase like orphan receptor 1 (ROR1); and conjugating PNU-159682 to the antibody;

wherein the heavy chain of the antibody comprises the amino acid sequence of SEQ ID NO:5 and the light chain of the antibody comprises the amino acid sequence of SEQ ID NO:6.]

*85. The immunoconjugate of claim 3, wherein n is 4.*

*86. The immunoconjugate of claim 1, wherein Ab comprises: a heavy chain comprising an amino acid sequence at least 95% identical to that of SEQ ID NO: 3, and a light chain comprising an amino acid sequence at least 95% identical to that of SEQ ID NO: 4.*

*87. A method of treating a human receptor tyrosine kinase like orphan receptor 1 (ROR1) expressing cancer in a patient in need thereof, comprising administering to the patient a therapeutically effective amount of the immunoconjugate of claim 1.*

*88. A method of making the immunoconjugate of claim 1, comprising the steps:*

*(i) reducing the cysteine residues of Ab of claim 1 by contacting Ab with a reducing agent; and*

*(ii) conjugating one or more thiol groups of the reduced cysteine moieties of the product of step (i) with the maleimide group of the following linker/payload moiety: 6-maleimidocaproyl-valine-citrulline-p-aminobenzyloxycarbonyl-monomethyl auristatin E (MC-VC-PAB-MMAE).*

*89. The method of claim 87, wherein the human receptor tyrosine kinase like orphan receptor 1 (ROR1) expressing cancer is a lymphoma.*

*90. The method of claim 89, wherein the lymphoma is selected from diffuse large β-cell lymphoma (DLBCL), mantle cell lymphoma (MCL), follicular lymphoma (FL), and marginal zone lymphoma (MZL).*

*91. The method of claim 87, further comprising administering to the patient one or more additional therapeutic agents, wherein the one or more additional therapeutic agents are selected from rituximab, cyclophosphamide, vincristine, prednisone, gemcitabine, daunorubicin hydrochloride, and a Bruton's tyrosine kinase (BTK) inhibitor.*

*92. The immunoconjugate of claim 86, wherein Ab comprises: a $V_H$ comprising the amino acid sequence of SEQ ID NO: 5, and a $V_L$ comprising the amino acid sequence of SEQ ID NO: 6.*

*93. A method of making the immunoconjugate of claim 3, comprising the steps:*

*(i) reducing the cysteine residues of Ab of claim 3 by contacting Ab with a reducing agent; and*

*(ii) conjugating one or more thiol groups of the reduced cysteine moieties of the product of step (i) with the maleimide group of the following linker/payload moiety: 6-maleimidocaproyl-valine-citrulline-p-aminobenzyloxycarbonyl-monomethyl auristatin E (MC-VC-PAB-MMAE).*

*94. A method of making the immunoconjugate of claim 86, comprising the steps:*

*(i) reducing the cysteine residues of Ab of claim 86 by contacting Ab with a reducing agent; and*

*(ii) conjugating one or more thiol groups of the reduced cysteine moieties of the product of step (i) with the maleimide group of the following linker/payload moiety: 6-maleimidocaproyl-valine-citrulline-p-aminobenzyloxycarbonyl-monomethyl auristatin E (MC-VC-PAB-MMAE).*

*95. A method of making the immunoconjugate of claim 92, comprising the steps:*

*(i) reducing the cysteine residues of Ab of claim 92 by contacting Ab with a reducing agent; and*

*(ii) conjugating one or more thiol groups of the reduced cysteine moieties of the product of step (i) with the maleimide group of the following linker/payload moiety: 6-maleimidocaproyl-valine-citrulline-p-aminobenzyloxycarbonyl-monomethyl auristatin E (MC-VC-PAB-MMAE).*

*96. The immunoconjugate of claim 86, wherein n is 4.*

*97. The immunoconjugate of claim 92, wherein n is 4.*

*98. The method of claim 90, wherein the lymphoma is diffuse large β-cell lymphoma (DLBCL).*

*99. The method of claim 98, further comprising administering to the patient one or more additional therapeutic agents, wherein the one or more additional therapeutic agents are selected from rituximab, cyclophosphamide, vincristine, prednisone, daunorubicin hydrochloride, and gemcitabine.*

* * * * *